United States Patent
Holder et al.

(10) Patent No.: US 10,494,638 B2
(45) Date of Patent: Dec. 3, 2019

(54) BACTERIOPHAGE RECOMBINATION FOLLOWED BY BLOCKAGE OF NON-RECOMBINANT BACTERIOPHAGE REPLICATION

(71) Applicant: The Charles Stark Draper Laboratory, Inc., Cambridge, MA (US)

(72) Inventors: Jason Holder, Swampscott, MA (US); Connor McBrine, Somerville, MA (US); Miles Rogers, Boston, MA (US); Nicole Billings, Framingham, MA (US); Sarah Gruska, Cambridge, MA (US); Lucas Tilley, Medford, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 69 days.

(21) Appl. No.: 15/893,104

(22) Filed: Feb. 9, 2018

(65) Prior Publication Data

US 2018/0223291 A1    Aug. 9, 2018

Related U.S. Application Data

(60) Provisional application No. 62/456,783, filed on Feb. 9, 2017, provisional application No. 62/515,223, filed on Jun. 5, 2017.

(51) Int. Cl.
| | | |
|---|---|---|
| *C12N 15/70* | (2006.01) | |
| *C12N 15/11* | (2006.01) | |
| *C12N 7/00* | (2006.01) | |
| *C12N 9/96* | (2006.01) | |
| *C12N 9/22* | (2006.01) | |
| *C12N 9/02* | (2006.01) | |
| *C07K 14/005* | (2006.01) | |
| *C12Q 1/70* | (2006.01) | |
| *C12N 15/113* | (2010.01) | |
| *C12N 15/86* | (2006.01) | |
| *C12N 15/90* | (2006.01) | |

(52) U.S. Cl.
CPC ............ *C12N 15/70* (2013.01); *C07K 14/005* (2013.01); *C12N 7/00* (2013.01); *C12N 9/0069* (2013.01); *C12N 9/22* (2013.01); *C12N 9/96* (2013.01); *C12N 15/11* (2013.01); *C12N 15/1131* (2013.01); *C12N 15/86* (2013.01); *C12Q 1/70* (2013.01); *C12N 15/902* (2013.01); *C12N 2310/20* (2017.05); *C12N 2795/10221* (2013.01); *C12N 2795/10243* (2013.01); *C12N 2800/80* (2013.01)

(58) Field of Classification Search
None
See application file for complete search history.

(56) References Cited

U.S. PATENT DOCUMENTS

2015/0184199 A1* 7/2015 Horwitz ............... C12N 15/907
                                                                 435/34
2017/0283779 A1   10/2017 Holder et al.

FOREIGN PATENT DOCUMENTS

WO   WO-2016/100389 A1   6/2016

OTHER PUBLICATIONS

Martel et al., Nucleic Acids Research, 2014, vol. 42, pp. 9504-9513. (Year: 2014).*
Wang et al., BioTechniques vol. 58, 2015, pp. 161-170. (Year: 2015).*
Mosberg et al., Geentics, 186:791-799, 2010 (Year: 2010).*
Box et al., "Functional Analysis of Bacteriophage Immunity through a Type 1-E CRISPR-Cas System in Vibrio cholerae and Its Application in Bacteriophage Genome Engineering", Journal of Bacteriology, vol. 198, No. 3, Nov. 23, 2015 (Nov. 23, 2015), pp. 578-590, XP055385261.
Bryson et al, "Covalent Modification of Bacteriophage T4 DNA Inhibits CRISPR-Cas9", mBio, vol. 6, No. 3, Jun. 16, 2015 (Jun. 16, 2015), pp. e00648-15, XP055323622.
International Search Report and Written Opinion for PCT/US2018/017425 dated May 9, 2018.
International Search Report and Written Opinion for PCT/US2018/017429 dated May 9, 2018.
Kiro et al., "Efficient engineering of a bacteriophage genome using the type 1-E CRISPR-Cas system", RNA Biology, vol. 11, No. 1, Jan. 1, 2014 (Jan. 1, 2014), pp. 42-44, XP055385263.
Office Action on U.S. Appl. No. 15/893,094 dated May 18, 2018.
Sagona et al, "Genetically modified bacteriophages", Integrative Biology, vol. 8, No. 4, Jan. 1, 2016 (Jan. 1, 2016), pp. 465-474, XP055334383.
Schmelcher et al, "Application of bacteriophages for detection of foodborne pathogens", Bacteriophage, vol. 4, No. 2, Feb. 7, 2014 (Feb. 7, 2014), p. e28137, XP055323023.
Yaung et al., "CRISPR/Cas9-Mediated Phage Resistance Is Not Impeded by the DNA Modifications of Phage T4", PLoS ONE, vol. 9, No. 6, Jun. 2, 2014 (Jun. 2, 2014), p. e98811, XP055323625.

* cited by examiner

*Primary Examiner* — Nancy A Treptow
(74) *Attorney, Agent, or Firm* — Foley & Lardner LLP; Christopher J. McKenna

(57) ABSTRACT

The present disclosure provides methods and kits for generating recombinant bacteriophage genomes. Specifically, the present technology provides methods of integrating a heterologous nucleic acid sequence into a bacteriophage DNA genome, and isolating recombinant bacteriophages that express the heterologous nucleic acid sequence.

23 Claims, 48 Drawing Sheets

Specification includes a Sequence Listing.

Figure 1A

```
>AY370674.1 Enterobacteria phage K1-5, complete genome (SEQ ID NO:1)
TCGCCCTCGCCCTCGCCGGGTTGTCCCCATAGGGTGGCCTGAGGGAATCCGTCTTCGACGGGCAGGGCTG
ATGTACTCCTTGTCTAGTACAAGGGAGGCGGAGGGAACGCCTAGGGAGGCCTAGGAATGGCTTAGTGGTG
GACAAGGTGATTACCTTAGTGAAGCCTCTTAGTGCATTCCTGAGGCCATTCAGGGCGTTTATGAGGGATT
GACAGGGTGTGAGGGCGTGGGCTATCTGTTCCTTTGCTCCTCACTTCGTTCGTCGCTGCGGTAGCCTGAT
GTGTACCTTAGGTTATTCCTTGATGGATAGCTTAGGTTAGCCTTAGTGGATTACCTTAGTTAAAGCCTTA
GTGCTTCACTTAGTATCAGCTTAGTAGTGTACCTTAGTAAGTCTTAGTGTCTTCTCTTAGTGATTGCACA
TGCAAGCATGTAAGATGCTAATAGGTCGCGGTCGGCAGACCGCTAAAGAAAGAGAATGGTAATAAGATGC
AGTAGGAGGAACACCAGAAGCCTAGCCAACCTAAGCTATCCTAGCTCTATATCTATTGCTTTTCCTTAGT
CTAACACGTTAGACAACCTATCTTATTCTTAGTGATGGTAACTTAGTGTTGACAAGATAATCTTAGTGTA
ATACTATGCATCACGTAGGCGGTGCTGAGGCACCTAGTAGCCAGCTAGTAAGGCATACGAAGAGACTAGC
GCTTACATTGCTCTTTAACAATTTGCTTAGTGTAACCTATGTATGCCGTGGTTAACTACTTATTGAATGA
GGTATTAACTATGACATTAAATAACCGTGAACTGTCCGTTCTCTTCACTCTGTTGTGCTACATGATTCGT
AACAACGAATTACTTACAGATGATGAGTTAGCCTTGTATCACCGCTTCTTAACGAAGGTTGGACCGATA
CAGTTAATCAATACCGTAACATGATAGATGAGTTGAGGGAGGGTAAATAATGTATCAACATGAGGTATTC
TTTGAATCAGCTAGCGAAGCTATTCGCTTCCGTGATGATATGATGCAAGCTGGTGTAGGCGTTGATGTGT
ATCACTATTTGATAGATTACGACACTGAATATCACCGAGTTACCTTAGTATCTGAGTATGACAACCAAGT
CATTACTGAGTATCTAGGCAGTGAAGATTACGATTACGATGAAGTAATCACGACAAATCTCTAAATTAAC
TGTTGACAGCCACGGCATACAAGGTTACATTAAGCATCAAGACGGCGACGTCTTTAAACATCCCGCTCTT
TAACAATACGGTTTGTGTCTTGATAGGCTAACTAACTAACTAAGGTAATTATCATGAAAGGGTTAATTTG
TGTAGAACGTATGGTCAATGGTAAACTTGAAATATTACCACTGGAAAACCAATCTAGCTTCAAAGAGTGG
TATGGCTGTTTCTCACTGATTTAAGGTAAAGGCTGGCACTAGTCAGCCTATCAAGGCGCAAACCAAGCTC
TTTAACAATTTGGATGGTAGCTTCTTAGTCTGGATAGGTTAAACCTAGGAGATTCTCTTGAGTCTCCTAT
AATGTAACCTAACTAACTAAATGAGGATTAAATCATGGAACGCAATGCTAACGCTTACTACAACCTTCTG
GCTGCAACTGTTGAAGCATTCAACGAGCGTATTCAGTTTGATGAGATTCGCGAAGGTGATGATTACTCTG
ATGCACTACATGAGGTTGTAGACAGCAATGTTCCAGTTTATTACAGCGAAATCTTTACAGTGATGGCTGC
TGATGGTATTGATGTTGATTTTGAGGATGCTGGTTTGATTCCTGACACGAAGGATGTAACCAAGATTCTA
CAAGCTCGCATCTATGAAGCTCTTTATAATGATGTACCAAATGACAGCGATGTAGTTTGGTGTGAAGGCG
AAGAAGAGGAAGAATAAGGATGGAAAAGCAATATAACTTTATCTTTTCAGACGGTGTAACCCTGAAGTGT
TCCCTACGATTCGCACAAATTCGTGAGGAAGTACTAGGCACTACATACAAACTATTTAGCTGACACTATA
AGAGAAGGCTTAACAAGGCGTTACTAAGGTAGCGCCTGATTAAACTTTCACTTACTAGGAGTTGAGATTA
TGAAAACCTTGATTGGATGCTTCTTGTTGGCTTCTCTTGCTCTGGCATTTACCGCTAAAGCTGGTTATGA
CGCTTATAAAGTAGAACAAGCCCAGCAAGACTGGGCAAAAAAAAGTTCAACTTGTGCAGCAAGAGCAAC
ACCTACGAGTACTGCAACAAAACACTAAGACACTTATGGAAAGAGTAACTAGCCTATAGCCCACCTGAGT
GGGCTATGTGATATTTACTTAACACTATATAAGGTGATTACTATGACTACTGAAAACACCCTCGTGTCTG
TCCGTGAAGCTGCAACCGCTGAAATCAAGCAACATTTAGACAATATCGGCACTTCTTACATCAAAGTAGG
GGCTTGTCTGAATGAGTTACGCGGAGACTTTGAAGGTCAAAAAGAGTTTTTAGCCTATGTTGAAGCAGAG
TTTGCCATTAAGAAGGCACAATGTTACAAGCTGATGAGTGTAGCCCGTGTCTTTGAAGGCGATGATCGCT
TTAAAGGCGTGGCGATGCGTGTAATGCTGGCGCTTGTTCCTTTCGCTGATGAAAATATAATCATGGAGAA
GGCCGCAGAACTCGCCGCAAATGGCAAGCTGGACACTAATGCCGTAAACGCCCTGATTGAACCTAAGAAA
GAGTCAAAGGCCGAAACGGTACAATCTAAGGCTGAGACAGTAAAACCGCAGGAGAACGCGACTGAGTCCG
CAGAATCACATGAAATGCAAGCGCCGCAGGTAGTGCCACCCGCGAGCGAGCAGGAGTCCGACGAATCAGC
ACCTTGGGAAGAGGAAAGCAAACCGGAAGCGCCAAAGGCAGCTCCGATGGATAACACGGCTAATACTGAG
AATGCCGCTATTGCTGGTCTGCTGGCACAAATTAAAGCACTGACTGAGCAATTACAGGCAGCCAATGACC
GCATCGCCTCCTTAAGTAGCGCACGCGAAAGCAAGAAGGCATCCGCACCTATGCTGCCGCAGTTCAAATC
TTCCTGCTTCTACGCTCGCTTAGGCTTGAGCGCGGAGGAGGCAACGAAGAAAACAGCAGTTAACAAGGCA
CGCCGCGAACTGGTTAAGCTGGGATACGGTGAAGGCCATGAGGCATGGCCCTTAATCTCTGAGGCAGTAG
AAGAGTTGACTAAGTAACCTTATCGGTGGCATCTTCTTAGGTGTCACCTATTAAGGTTTCTTTCACTAGG
AGTAAACAAGATGCAAGGCCTACACGCTATTCAACTTCAACTTGAAGAAGAAATGTTTAACGGCGGTATC
CGTCGCTTTGAAGCGGACCAACAACGCCAGATTGCATCCGGTAATGAATCAGACACGGCATGGAATCGCC
GCTTATTGTCCGAGTTAATCGCGCCAATGGCTGAAGGTATTCAGGCATACAAGGAAGAGTATGAAGGTAA
```

Figure 1B

AAGAGGCCGTGCACCGCGTGCATTAGCTTTCATTAACTGCGTAGAAAACGAAGTGGCAGCATATATCACG
ATGAAAATCGTTATGGATATGCTGAACACGGATGTAACCTTGCAGGCTATAGCCATGAATGTAGCTGACC
GCATTGAGGACCAAGTACGTTTTAGCAAGCTGGAAGGTCACGCCGCCAAATACTTTGAAAAAGTTAAGAA
GTCACTTAAGGCAAGTAAGACTAAATCATATCGCCATGCGCACAACGTAGCGGTAGTGGCTGAGAAGTCA
GTAGCTGACCGTGACGCTGATTTCTCCCGCTGGGAGGCATGGCCTAAAGACACCTTGCTGCAAATTGGGA
TGACCTTGCTTGAAATCTTAGAGAATAGCGTATTCTTCAACGGGCAACCTGTCTTCCTCCGCACCTTGCG
CACTAATGGCGGCAAACATGGTGTTTACTACCTACAGACTAGTGAACACGTAGGTGAGTGGATAACTGCA
TTCAAAGAGCACGTAGCGCAACTGAGTCCTGCCTATGCTCCTTGCGTCATCCCTCCGCGTCCGTGGGTAT
CACCTTTTAACGGCGGTTTCCACACTGAGAAAGTAGCAAGCCGTATTCGTCTGGTAAAAGGAAACCGCGA
ACACGTCCGCAAGCTGACCAAAAAGCAAATGCCAGAGGTTTACAAGGCTGTTAACGCGTTGCAGGCGACT
AAATGGCAGGTTAACAAGGAAGTTTTACAGGTTGTGGAAGACGTCATCCGTCTAGACCTAGGTTATGGTG
TACCTTCCTTTAAACCACTCATTGACCGCGAGAACAAGCCAGCTAATCCAGTGCCGCTAGAATTTCAGCA
CCTACGGGGCCGTGAACTGAAAGAAATGCTTACGCCGGAACAATGGCAAGCCTTTATCAACTGGAAAGGT
GAATGTACTAAGCTGTACACCGCTGAAACTAAGCGCGGAAGCAAATCGGCGGCAACCGTTCGCATGGTTG
GTCAGGCCCGTAAATATAGCCAGTTCGACGCAATCTACTTCGTGTATGCACTGGACAGCCGCAGCCGCGT
CTACGCGCAATCTAGCACACTCTCACCGCAATCAAATGACTTGGGCAAGGCCTTGCTCCGTTTTACCGAA
GGGCAGCGTCTTGATAGCGCTGAGGCGCTTAAGTGGTTTTTGGTGAACGGGCTAATAACTGGGGTTGGG
ATAAGAAAACTTTTGACGTGCGCACCGCTAACGTGCTGGATAGTGAATTTCAAGACATGTGCCGCGACAT
TGCAGCGGATCCGCTGACCTTCACTCAATGGGTAAATGCCGACTCCCCTTACGGCTTCCTTGCATGGTGC
TTTGAATATGCGCGTTATCTGGATGCACTGGATGAAGGCACGCAAGACCAATTCATGACGCACCTCCCAG
TCCATCAAGATGGTAGTTGTTCTGGTATCCAGCACTACAGTGCTATGCTACGCGATGCAGTAGGTGCGAA
AGCAGTAAACCTTAAGCCCTCTGACTCTCCTCAAGATATTTATGGTGCCGTTGCGCAGGTAGTAATTCAG
AAGAATTATGCATACATGAATGCAGAGGATGCGGAAACCTTCACTTCTGGCAGCGTGACTTTAACAGGTG
CGGAGCTGCGTAGTATGGCTAGTGCGTGGGATATGATAGGAATCACTCGCGGCCTGACCAAAAAGCCCGT
AATGACACTACCTTATGGCAGCACACGTCTAACCTGCCGTGAGTCAGTGATTGATTATATCGTTGATTTA
GAAGAAAAAGAGGCCCAACGGGCTATTGCGGAAGGGCGTACCGCCAATCCTGTACACCCTTTTGATAATG
ACCGTAAAGACAGCCTGACACCTAGCGCAGCTTATAACTATATGACAGCTTTAATCTGGCCTTCTATTTC
GGAAGTGGTTAAAGCCCCTATAGTGGCAATGAAAATGATTCGTCAGCTTGCCCGTTTCGCAGCTAAAAGG
AATGAAGGCTTAGAGTATACCCTGCCTACTGGCTTCATCTTGCAACAAAAGATTATGGCTACTGATATGC
TCCGCGTATCTACTTGCTTGATGGGAGAAATCAAGATGAGTCTACAGATTGAAACAGACGTAGTGGATGA
AACGGCAATGATGGGCGCTGCTGCTCCTAACTTTGTGCATGGTCATGATGCCAGCCACCTTATCTTAACA
GTCTGCGACCTTGTTGATAAAGGGATTACATCTATCGCAGTTATTCATGACTCTTTTGGCACTCATGCAG
GCCGTACAGCCGACCTTCGTGATAGCTTAAGGGCAGAAATGGTGAAGATGTATCAAGGCCGTAATGCACT
GCAAAGCCTGCTAGATGAGCACGAAGAACGCTGGTTAGTTGATACCGGAATACAAGTACCAGAGCAAGGG
GAGTTTGACCTTAACGAAATCTTAGTTTCAGACTATTGCTTCGCATAATATTAATAGGCCATTCCTTCGG
GAGTGGCCTTTCTTTTACCTACTACCTGTAACATTTCATTAACATAAAAGTGTCTCACATGTGAGACTTA
TTTACCGGACACTATAGGATAGCCGTCGGAGACGGGAAAGAAAGGGAAGATAAAGGATATAAAGGAAGTA
ATAGGTATTAAAGGTTATATAGGTTATCTAGGAATACCTATTACCTTCTTCCTTCCTCTTATTACCACTC
AGAGGAAGGGCAGACCTAGGTTGTCTCACATGTGAGACTTCGTATTTACCGGACAGTATAGATAAGATTA
ACTCACTTTGGAGATTTAACCATGCGCAACTTTGAGAAGATGGCCCGTAAAGCTAACCGTTTTGACATGG
AAGAGGGGCAGAAGAAAGGCAAGAAGCTGAATAAGCCTGTCCGTGACCGTGCATCTAAACGCGCTGCGTG
GGAGTTCTAAGTTATGGCTATTATTCAGAATGTACCGTGTCCTGCCTGTCAAAAGAATGGACATGATATT
ACTGGCAACCATCTCATGATATTTGATGATGGTGCCGGCTACTGTAATCGTGGACACTTTCATGATAATG
GTAGACCTTACTATCACAAGCCGGAAGGTGGCATCGAGATAACCGAGTTATCTATTACTGGCAATATCAA
ATATACACCTTCTCAATTCAAAGAAATGGAGAAGGAAGGGAAGATAAGCGACCCTAAATTACGTGCCATC
GCACTTGGTGGTATGCGTATGAAAGACCGTTGGGAGGTCATGAATGAACAAGAAAGGGCAGAGCAAGAAG
CAGAGTGGAAACTTGATGTTGAATGGTTCCTCACGCTTAAGCGTAAGAACCTTGTTTCCAGGCACATTCG
CGGCGACATTTGCGCATTGTATGATGTACGTGTTGGGCACGATGAAGAGGGTAGAGTCTCACGGCATTAC
TATCCGCGCTTCGAAAAAGGTGAGCTAGTAGGCGCTAAGTGTCGCACATTACCTAAAGATTTTAAGTTTG
GTCATTTAGGTAAACTCTTTGGTATGCAAGATCTTTCGGTATGAATACTTTGTCTCACGTGTTAGACAA
GGGAAGACGAAAGGATTGCTTGCTCATTGTCGGCGGCGAACTGGATGCACTAGCAGCGCAGCAGATGCTC
CTTGATTCTGCCAAGGGTACTAAGTGGGAAGGCCAGCCATACCATGTATGGTCTGTCAACAAAGGCGAGT
CTTGCCTTGAAGAGATAGTGCAGAACCGTGAGCATATCGCCCAATTCAAGAAGATTATATGGGGTTTTGA
TGGAGATGAGGTAGGGCAGAAGCAGAATCAGCAAGCGGCTCGCCTGTTTCCTGGTAAATCCTATATCCTT

Figure 1C

```
GAATACCCCTCTGGTTGCAAAGATGCTAACAAGGCATTGATGGCTGGCAAGGCTAAAGAATTTGTAGATG
CATGGTTTAATGCCAAGTCATCTGATGAAGTCTTTGGTAGCCAGATTAAATCTATCGCATCTCAAAGGGA
TAAGCTCAAGGCTGCACGTCCAGAGCAAGGACTGTCATGGCCTTGGCCTAAGCTGAACAAGGTAACGCTA
GGTATTCGTAAGAACCAGCTTATCATTGTAGGTGCAGGGTCTGGTGTAGGTAAGACTGAGTTCCTTCGTG
AAGTAGTTAAGCACCTCATTGAAGAACACGGTGAATCTGTAGGCATCATTTCTACAGAAGACCCGATGGT
CAAGGTGTCCCGTGCTTTTATCGGCAAGTGGATTGATAAGCGTATTGAGTTACCTCCAACCAACGACCCG
AAAGAAGACGGATACCGTGAGGTGTTCGACTATACCGAGGAAGAAGCTAACGCCGCCATTGATTATGTAG
CTGATACAGGTAAGCTGTTTGTAGCTGACCTAGAGGGTGACTATTCGATGGAAAAGGTAGAGCAAACTTG
CCTAGAGTTTGAGGCTATGGGTATTTCTAATATCATCATTGATAACTTAACGGGGATTAAATTAGATGAG
CGTGCTTTTGGTGGGAAGGTTGGTGCACTTGATGAATGCGTCAAGCGGATTGGTACTATCAAAGACCGAC
ACCCGGTTACTATATTCCTTGTATCACACCTTACACGTCCTCCGGCAAACCGTACCCAACACGAAGAAGG
TGGCGAAGTTATCCTTTCTGACTTCCGAGGCTCAGGCGCTATCGGATTCTGGGCATCTTACGCCTTGGGG
ATTGAGCGTAATACAAGAGCTGAAACGCTTGACGAAAGGACTACCACGTACATCTCATGTGTCAAAGACC
GCGACCAAGGTATCTACACTGGAACCAAGGTCATGCTTAAGGGTGACATTCAAACCGGACGTTTAATGGA
ACCACAAGCCCGTACTAAGTCATTTGATACAGGTGAAGCAAGGCAACAAGAAGTACCAGATTTACCGGAT
ACTATAGAAGAGACTACCTTCGATGAAGAAAGTGAGTTCTGATTAGTGTATTTATCAGGCTTGTCTCACA
TGTGAGACAGGCTCTTATTAAGTACATTAAATAACTGGAGATTGATTATGTATAACTTAGTGTTGAATGT
AGGTGACTTTGTACGCAACATCAAGAAAGATTCAAGTCGCTATCTTTGCCGTGGTGTTGTAACCTTTGTA
GGTGAGAACCTGTATTATGTAGAATATCGCAGTGGTGTTAAGCAATATTACCACAAGAAGACAGCACATA
AATATCTTGAAAAGATTGTAGAGATAAACAATCAATGTAAGTGCATACATGATGAGGTTTGCGATAAATG
TGCTCGCCAGATGCTTAAGAATTTCCTAGCTCCTCTTTATTATGGTGCTGGTCCTCAAACACTAGCAGAG
TGCATGGCAGAAAAGAAAACCACACTCAAGAAAGAGCGTCGCAATGTAATCACTGGTAAGACTCAAAGTG
AGATGATTAAGCAATGTGGCACTGCATTAGGTGTTACACAGTTTAATACTCGTGCATTGGGTAAATCCAC
AGGACAAGCTATGGTAAAGATTGGAGAAGCCATGATGCATCCAAATGTACCTGTGCGAATCATGGATGTT
GACCATGCAATCACAGAACAAGGTACGCAACGACGTGTAATTAATAAGCATTTTGCCGACACTATAGAAG
GCATTATTCGTAAGCAAGGGTTGAAAGGTCTTCACATCTTAAATGGTGAAGAATTACTGTACCTACCTAT
CGTTACTGAAGAAACATACGTGAATATCTAAGGAGTTAATCATGACTAAGGTATTAATTTATATGCGTGG
ACCTCATAAATGCTATGCAGTTGTAGCACCAAATGGTGTTAAGCCTTATCGTACTTCAAAAAGATTGGCA
TTAATAGGTGCTAGTAGTAGTGCAAGTTTCCAAATGGAACTTTTTGGTCATTGGACTGAAAGGCAATTCC
GTGAGGATTTTAAAGTCATTGGCAGCTTCATGGTGAAATATGCAGAATAAACATAGTCTTAGAATGTTCG
ATGGTCATGAAAACCTGCAAGCCAAGATTACTAACCAAGCCTTCCTGTTCGCACAGTTAACTATGGCTGA
GGCTAAGAAGAATAGTCTCACTCGTGAACAGGTTATCAAGGAGGCCACTTGGGAACCACACCAAGGTAAA
TATATGGGCCACAAATTAACTGTAACACGCAGTCGATAAGTCAAGGGTTGTCCAACGTGTTGGACAGCCT
TTCATCATATTGATTGGGAGGTATTAAATGACTAAGTTTACTATGCAAGACCTCATTAAATTACGTGATG
AAATAGAATCACCGGAAGTTAATACAGAGTTTCACTACATTGATCCACGAGATAAACGAGAGATTCCTGA
TTATCAGATTGAGACGGAGTTAATGTATGAAGATTATTGATTGGAAGAAGGAAGCAGAAGGCCGTATCCT
AGTGATGGATGCGGAGGCTAAAGGCCTGCTGGGTGCTATCCGCTACGGTCATCGTGAAGATGTACACATT
ATTTGCTGCATGGACTTGCTCACCACTGAGGAGTTCCTCTTCTTCGACCCATATGAGATGCGTGACCCTG
AAGCAAGGGAACACTTGAAAGAGTGGGAAGGCCATCAAGATGGGACCTTGGTTGATGGTGTTAACTTCCT
AAAGCACTGTGAAGCCATCGTCTCACAGAACTTCCTAGGCTATGACGGGCTTCTCTTTGAGAAAGCCTTC
CCTGACATCTGGAAGGGATTTAACTACACCGAGAGGCGCGGCAAGGGCAGACTACGTGCTGACTTGTGTC
CGGTACGCGTCATGGATACGCTGGTCATGAGTCGCCTGTTAAACCCAGATAGACGCCTTCCTCCGCAAGC
ATATGCCAAAGGTATGGGTAACGTTGCCCCTCACTCAATTGAGGCGCACGGCATTCGTATAGGCCGTTAT
AAGCCGGAGAACGAGGATTGGTCTAAACTAACTGACCACATGGTACATCGTGTACGCGAGGACGTGGCGA
TAGGCCGTGACCTATTCCTCTGGCTATTTAACGGAGAATGGACGGAGCACAAACGCCGTGGCGTGAATAA
ACGCACTGGCCTAGGTATTGAGACAGCCTTCCACATGGAGTCCATTGTGACGCTGGAGATGAGCCGTCAG
GCCGAGCGTGGATTCCGTCTGGATATAGATAAAGCATTAGCACGATGCGAGGAATTGGACGCTAAGATTG
ATGAGACAGTCGCAGCGTTCCGTCCGCACATGCCTATGCGTATCAAGTCTAAACCTTTTAAACCGGAAGA
AAAGAATGAAGTATGCCAACGCGCAAATGAGTATGGAGCTAGCAACAATATACCTACTGTCCTTGACCCC
TCTCACTTTCTTCACGCAGAGAGACGAGGAGATCGCAAGACAGTATGGAGTGTCACTACTAAGTCTGGTG
ATTGGTCGGCTAGCGTCAAGAAAGACTTTCCTCACCTTAGAGGAAACCGTAATGACACGCCAAGTGTCAA
GTGGATTGGCGCTTACTCGCCTGTTACTTTCGAAGAGATTCCCTTGGGTAACAGGGATACAGTTAAGCAA
GTGCTCTATGATTATGGATGGAAAGGTGTTGAATTTAACGATACCGAGCAAGCGCATCTCGATGAGCATG
GCGTATTACCCAAGCCTTGGAGTGGGAAGATAAATGAAAAGTCCCTTACTTTATGGCAAGAGAGAGCCGC
```

Figure 1D

```
ACGTGAAGGTAAAACAGTCCCTGATTGGTGCTTGGGTATCGCTGCATGGTACATACTCGTATCCCGTCGT
GGTCAGATCCTCAACCGTGGTGACGTTGAAGCCTTCGACCAGAAGGGGGTGTGGCCTTCGCAAGCTGGTA
TACGAAAGTGTCGCGGCCTTGTACCTGTAGCATTTAACAAGGAGTTAGGAATCAATGCGCAGCAATACTA
CGAAAGGTACGGATGCTGGCCTACGTCAGACAAGGATGACGGAGAATGGCGTGTGCCAGCTATTGCTATT
AGTATTGGAACTTCTACGTTCCGTATGCGTCATCGTAACGTGGTTAATATTCCTGCCCGTGGCTTGTATC
CTTTACGTGATTTATTCATAGCAGGGAAAGGCAAGCTAATCCTTGGTTGTGACGGTGCAGGTCTTGAACT
GCGTGTCCTGTCTCACTTCATGAATGACCCTGAGTACCAAGAGATTGTACTGCACGGTGATATTCATACG
CATAACCAGATGAAGGCTGGTCTTCCTAAGCGTGATATGGCGAAGACATTTATATATGCCTTCCTATATG
GGTCTGGTATAGCTAACCTTGCAGCAGTATGTGGTGTTACTGAGGAAGAAATGGAGGAAGTTGTGGCAAG
ATTTGAGGTTGAACTACCATCTCTTGCACGTCTTCGTGAGAATGTTATCGCACAAGGTAACAAGTTTGGC
TACCTACAAGCACCTGATGGTCATTGGGGTCGCATCCGTATGTCTGGTGGTGAACTTAAAGAACACACTA
TGCTTAACGTACTACTCCAGATGACTGGTTCTCTGTGTATGAAATACGCATTGGTCAGAGCGTTTGCAGT
GATGCGCAAGGAAGGTGTGGCCTTAGATAGCATGGGAAACCCTTGCGGTATAGCTAACGTGCACGATGAA
ATCCAGATGGAAGTCCCTGAAGATGAGGTCTTGTATCTCAACTACGACTTGCCTTTCACCTTAGAAGGGT
TCGAAACAGAGAAGGCTGCTGTGAAAGCAGTGTTCGATGCAGAGGAGAAACGTGTTCATGTGGATTCTGA
AGGACGTATGTGGTCTGCTGCAAATCTCGTTAGTGTTGATGCTGGTGTACTTCATTGCCAGCGTCGTTAT
CACCGTGCAGGGCATATCATTGCCGACGCAATGACCTGGGCGGGTCAGTACCTGAAGATGCGTTGTCCGA
TGGCAGGTGAGTATAAGATTGGTGCAAGTTGGAAGGAAACACACTGATGGACAGGTTTGATATTGTTTGC
CTATTCTCTACCTTCTTTCTTATATTCCTTATGCTTGCTTGCTATGGAAGTATGCGATTAGATATACCTG
ATGAAGAGGAGGGTTACGATTGATGCAGGCATCTTTTATTATTCTTGGAGTCATATTATTTATGGTAGTA
TTCTGGGCTTTCTCTGGCATTGACCCAGATTGTGATGGTAACTACGACTGAGTTATACTCAAGGTCACTT
ACGAGTGGCCTTTATGAATAACTTATTCCTACTTATTTTGTCTAACATGATTTACTGGACACTATAGAAG
GAAAGCATAGGTAATCTAGGTTTATAAGGTAGTATAGGTAATTAAGTAAATATAGGAGATATAAATATGT
CTATGGTAACTACTCTGGTATTCGTGGCTCAATACTTTCGTGGTCTTGCTAATAAGTTCAAGTCCAAGGC
TATCAAAGCTATTGAGGCTCGCATCGAAGCAGTACAGGCAGAGCAAGTTAAAGTTGAAGAACATCGTAGT
TCTCAAATGATTGACTGTCATAACCGCTACTATGCATCTCGTGATGAACTAAATGCACGTCAAGTCAAAG
AGGTAGAAGATATGCTGGCACGTCACCAGCAAGAGCGTGACAGCCTGAAAGCTGAATTTGAAGAGAACAA
GGCATCAATTGCTCTTGTACATCAAGCTGCATCTGACAGTCTGAAGAAAGAGATTGTTATGCTGGAAATC
GAACTGGATAACCTGACCAAATAAGGGGGGTTATGATGGAAGAAGTAATTCAAGCTAAACATGTAGGTA
TTATCTTTCGCGATCTAGAGCAGCGTAAAGTTGCAGGTCATACTCGTCTGGCTAAAGAGGAAGACACCGC
AATCACTACTGTAGAACAAGCAGATGCCTATCGTGGACCAGAGTTCACTCAAGGTGAAACTTGTCACCAA
TTGAGCCTATCAATTTGTGACACTATGGCTATTGTAAATGTGCAAGAAGTCGAAGAGGGTGAGTGTGTCA
GTTACATCTACCCTTTAGATACTATTGCACGCATTAAGGTAATCCATAAGTAATTACTAGACACTATAGA
ACAATAGGTCGGCTTAGTTCGGCCTATGATTGTAAAGTGTTGTTGATGTTGAACCATTGTGCATCTTGCA
CAACCCGATACCGTATAGGGCTTTCTAGTGAGTACATGCTTGTGCTCAGTACAAAGCTAACTGACAATAG
GAGACTAAATAAATGGCACGTGGTGATTTTGATTTTGGTGCTCAGGTTACTAAATCTGAAGGTAAAGTCT
TTAAGAATCCAGAAGTAGGTGATCATGAAGCAGTAATCTCTGGCATCATTCATGTTGGTTCCTTCCAAGA
CATCTTTAAGAAAGGTAATACCACTGAAGTTAAGAAGCCAGCAAACTTTGTTCTGGTTAAGATTGTCCTG
ATGGGTGACGATGACAAGAACGAAGATGGTTCTCGCATGGAACAATGGATGGCTGTGCCTCTGAAGTCTG
GTGATAAGGCAACACTGACTAAGTTCCTGAATGCAGTTGACCCTAAAGAGTTGCTGGGTGGCTTCGATGA
TTTCATTGGTGAATGCCTGACTGCAACGATGGTCGGTTCTGGTGATAAGAATGACGATGGCTCATTCAAG
TATGTTAACTGGAAGGGATTTGGTGGTATGCCGGACAAGCTGAAGAAACTGGTCATTGCTCAGGTTGAAG
AGGAAGGTCTGTCTATGACAGGTCACATTACCTTCGACAAGCTGACCAAAGAAATCCTTGATGACATCCC
AGCCAACTTGGTGCGTCAATACTTCCTGAACGAGACGCCTCGTGGTAAGAACCTGTCTGTTGCTGGTTCT
CACGTAGAAGCAATCATTAAAGCTGCTCGTGAAGAAGACCCAGAATGGAAGAAGGCTAAGAAGAAAGACG
AGGAAGATGCTACCCCAGCTAATCGTAAATCTCTGGATACTGGTGAGTCTGTTCCACAGGAAGTACCTGA
AGCAGAAGATACTCCTGCACCGGAGATGGATGAGGACGCGGAATATTAAGGAGAAAGGATGAAAGTACAA
ATCGTAACCCTGCACTGCAAGAAAGGAATTACAACTCTTGGCGGCAACACTTTTCACTCCTTCTCTGAAG
GGGACACATATGCCGACCTGCACTACATCTGGCGCGACGGACAGCACGTGGTGAACTACAGCGACCCAGC
TACGGGGAAACGCCACGGCGTATCGCTTCCGGCGCATGACATTGCTCAGGTGAACACAGTTTTATAAAGT
CTCACGTGTGAGACAAATCGGTGTCCGGTATTTACTGGACACTATAGAAGAGAAGAATTTTAATCGGCGA
TAATGCCATAACCAACAAAAGGAGAATTTAATATGTTCAAGATTGAAACTATCGTAAACCGTGTTGTTAA
AGGTGCTGCTCTGGTATCCGTTGAGTCTTTCATTATCGTCGATGAAACTGATCAACTGGTAGCTGGTACT
AAGGCTTACGATACCCGTGAAGAAGCTCAGGCTAAGATTGACAGCATGGGTAACTTCGCTGCTGGTCTGG
```

Figure 1E

```
AGTTCGCTCGTGCTTGCTTCCCTGAGCAGGCTGACAAAGCTCAGATTGGTAAGGCTAATATCGTAGCTGA
ATATCTGGATTGGGTTGCTGCTGGTAAACCAGTGAAAGAAGTTAAGGCTGCTGAAGAAGCTGAAGCTCCA
GCAGAAGAAGTAGCTGCACCGGAAACTCCGGTAAGTGAAGAGGAAGAATTTTGATAATAGCAGGTGTTGC
CTCTGTTAGTCCTAGCTGACTATCACGCTCACCTCATCTAATGCCCTGTCTGCCTTAGTGTAGGCAGGGT
CTTTTGCGTAATAGTTATTGGAGAATGAATTATGCCGACTATTGAATCTCGAATTGAACTGGACATTAGC
TACAATGCAATCACCAGACAGTATATTGGGGTTGCCTATGATTACAAAACTGGTGAGAAGCTAGTGGAGG
TGAGACAATGGGATGACTATTGGTTAAGACAGAACCTCCATGATGCGGTGTCCTCCTTCCTGAAGGAGTG
GCCTACATGCGACCAAACTTCGACTTCGGAGCTACAGTATCGGAAGACAATAACCTGTTGCTGTGGCCAA
CTGAAGGTAATCGAATCGCTTTAATAGATGCTGATATGTTACCTTACATCATAGGGTATACAATCAGTGA
TATGACTTATGTACGAGCCACAACTCGTGTTAAGTCAGGGCAAGTCCCCTCAATCAAAGATACACCTGAG
TGTAAGCAAGCGTGTGACCGTGTGAACTCCTTGCTTAACTCTTGGGTGTATGCAGCAGAATGTGATGCAG
CTAAGTTGTTCATGACGAAATCAGAAGCTAACTTCCGTGTCCGCCTAGCATTCACCAAGCCTTATAAAGG
TCAACGTAAGACCGAGAAGCCTCCATTCTTCTATGAATTGCGAGAGCATCTCTTAGAGGTTCACGGTGCA
ATCTTGGCAGATGGAGAGGAAGCAGATGACCTCATGAGTATCGCACAATGGGACAGCCACCGCCGCTTCC
AGCAAGATACAGGTAACGAGTTCCCTATCGGTAGTCCAGAGCATAAAGCATTCTCTGATACTTGCATCGT
TTCCTTGGATAAGGATTTGATGATTGTTCCCGGTTGGCATCTACAGCCGGGTCAAGAGAAGAAATGGGTA
GAGCCTATGGGTTGGCTTGAGCTACGCCGTAAGGCTAATGGGCAAGTCAAAGATCTAAAAGGTGCTGGCC
TCATGTTCCACTATGCACAGATGATTATCGGTGATGATATTGATAACTATGCTGGCATACCAGGTCGTGG
TGCTAAATATGCCTATGATCTTCTCAAAGATTGTAAGACAGAGAAAGAGTTGTACATGGCAGTGCTGGGT
GCTTACAAGGCTAAGTTCGGGCATGGACAAGTTAAAATTAAGAATTACCGAGGTGGTTATCGTATCGGCA
AAGCCTTTGACCTAATGCTTGAGTGTGGTCGCTTATCTCACATGGCAAGATTCAAGGGTGATATATGGCG
AGCCGATAAGAACCCAATCTTGTGGGGAGATGATGCGGAATGGTTAGCAAATTAAAATCATCGGAGGTGG
CAGCTTATAAGAAGGAATTGCTAGATAAGCAAGGATGGAAATGCCCTCTGTGTGGCGGCAGTCTCAAAGC
TGTCACACCTGTAAACCGTGTACTTGACCATGACCATGAGACAGGATTCTGCCGCGCTGTTGTATGCCGA
GGCTGCAATGGTGCGGAAGGGAAGATTAAGGGTGTTATCTCTGGTTATGGTAAGGCTGGTAACAACCGTT
ACTTCCAGCTTCAATGGTTAGAGCGACTATATGAATACTGGAAGTTACATAGTACGCCTCAGACAGATAA
GTTATATCACAAACATCAAACGGAGGCAGAGAAGCGCGAGGCTAAGAACCGTAAGGCACGCCTTGCTTAT
GCAAGAAAGAAGGAGGTTAAAGTTGGGTAAGCTGCGCAGCTTGTACAAAGACTCCGAGGTACTTGATGCA
ATCGAGCAAGCTACCGACGAGAAAGGTAATGTTAACTACAATGAGATGGCACGTGTATTATCGTGTCATA
CTGTGGGTAAGAAGATTACCCGCCAGTTGGCTCGATACTGGCATGGTCAATTCAAGAAGACCAAGAAGAA
TGGTGATTACTACCAGACCCTTCTGCAAGAAGATAAGCGTATCAAAGAAGAGCGTAAGCTCAGGACTCCT
GACCGCTACGAGGATTTGGCTATTGTGCCATTGCCTGACTCGCCTCATCGAAGTGTACTGGTGATCCCTG
ATACTCATGCACCTTATGAGCACCCAGATACCCTAGAGTTCCTTGCAGCCGTGGCAGCACGTTACCGTCC
AGACACAGTGGTACACCTAGGAGATGAGGCAGACAAACATGCCCTGTCATTCCACGATTCGGACCCAAAT
CTGGATAGTGCTGGCATGGAGTTAGAGAAGGCTCGTATCTTCATGCACAAATTGCACAAGATGTTCCCTG
TGATGCGCCTGTGTCACTCTAACCACGGCTCTATGCACTTCCGTAAGGCAAGCGCCAAAGGCATCCCTGT
GCAATACCTGCGCACCTATCGTGAAGTCTTCTTCCCGCAGGGAGGTGGCGACCAGTGGGATTGGCAACAT
ACGCACGTCCTTGAGTTGCCGAATGGTGAACAAGTGGCATTCAAGCATCAACCTGCTGGCTCTGTCCTAG
CAGATGCAGCGCATGAGCGTATGAACCTTGTGTGTGGTCACTTGCACGGTAAGATGTCTGTGGAGTACGC
ACGTAATACACATGAACAGTATTGGGCTGTGCAAGGTGGCTGCTTAATTGATGAGTCATCCCGTGCATTT
GCCTATGGTCGTGAGTCTAAATACAAGCCAGCATTAGGTTGTGTGGTCATTCTGGAGGGTGTGCCTCACA
TTGTCCCGATGCAAACCAATAGCGACAACCGTTGGATTGGCAAGATTTAGTTGACACTATAGAACAAAGG
GCTAGGTAAGACTTTATCGGCTGGCGTATCCAAATGATATTGCACTAGCCCTTGATTGTATAGTGAATGG
AGGATTCAATATGTCACACTATGAATGTAAGAAGTGTCATAAGCGTTATGATTACTGTACTTGTGGTCAA
GAGAAAACATCTTTTAAAGTTGGAGACAAGGTATTTCGTAATGAAAAGATTCGATTCCTTGGAATCAAT
ACTGCAAAGAAGCTGGTATTGACCCTGATAGCCCTGTAACCATAGATGATATTGATGGCATTAACTTGTG
CTTTCGTGAGGTGAGGGGTACAGGTTGGGATTCCAAAAAATTCAAACTTGCATCTGATAAGTTAGACAAC
AATATGGTAATTAAGCCTAAGCACTACGAGTTCTTTGATGGCGTAGAGGCAATCACTATCATTGCCCGCA
GTATGACCGAGAAGCAATTCGCTGGCTATTGCATGGGTAATGCTTTGAAGTACCGTCTACGTGCAGGTAA
GAAGTTCAACACTGAAGAAGACCTGAAGAAAGCAGATTACTACAAAGAGTTATTCCAGAAGCATCGTCAC
GAATGTATTGATGAGGATATTTGATATGAATATCTTTGAGTTCCTAGGTCTTCCAGAAGACCACCGCAAT
CACCCATTCATGCTGGTGAAGCATCGCGGTGAAGTTCCTGAGAAGAAATTAACTTTTCCATGTTATGCAC
AGGTGAAACGAGATGGTATCTTTTCTGCTGTTGTTGTTCGCACTGATGGTGTCGTTGGCATTTTGGTCG
CACTGGTAAGAAATTGGCAAACACTGAAGGACTCGAACAAGCCTTTGCTACCTTTCCGGTTGGCATTTAT
```

Figure 1F

```
CTTGGTGAGCTTCAGTCTATGGCCATTGATATCTACCTTGAGGCAATCTCTGGGGTTGTGAACCCCAATC
GCACTGAGCCACTTGATTTCATAGGCCAGCAGATTAAAGACAACCTGTATATCGACTTCTTCGATATGTT
AACTATTAAGGCATTCCATGATGGATTCACTGATGTTTCTTATCTCAAACGTTACGATGCTTTACATCGT
CGTATCGGCGCTCATCTTAGCGGGTGCAACGCTATCCTTCCTATCACTCCTTGCCATAATGAGCGAGAAG
TTGAAGCGTTTGCGCAAGAGCAAATAGATGCAGGACGTGAGGGTGCTGTATTCAAACTGGACTGCGATTA
TGAAGCAGGACACAAAGGTTATCGTCAGACTAAAGAAGTCCGTAAGGTAACCTATGACCTTACTTGTATT
GGCTTTGAAGAAGGTAAAGGCAAATACAAAGGTAAGGTAGCTAACCTCATTTTCAAATGGAAAGGAGGCA
AGACAATCAAAGCTATGTTAGGTAAGGGGTGGACTCATGCAGATGCAGAGCAGATGTTCCACGACATTAA
ACATGGTGGACGATTGAATGTCATTGGTAAAATCTTTGAAGTCAAAGGTCTTCAGGATTCAAGCAAGGGC
AACATTCGTCTGCCCAAAGCGGGAGAATTAAGACATGACAAAGATGAACCAGATTTCTTTTGATAGCATG
AAGGCAACTCGTGCAGTTGAGGTAGCAGAAGCTATCTTCGAAACTTTATCCTGTGGCATGGAAGTGCCAT
ATACTTTACTTGCTGATGCAGAAGAACTTGGTCTTTCTGTAGAAGCTATCCAAGAGAAGGTTGACGAATT
ATATGGTACAGACGAAGAAGAAACCGACGATTTCATTTGAAGGAATGGAGATGCTTGAGATGATTCTCAA
GCCTTCTTCTCCTAAGGTGACTAAGACTCATGAAGAGTTAATCGTTGATGAAGTTAAGCGTTACATCATG
GATTGTGTCAGAGCACAACTGGTGGTCCAATGATACGTCCAGCCTCCTTCCTAGATATTCCTGAGATTAT
AAACCTTGGGAATAAATATGTGGAAGAGGAAGTCAAGGTTGTAGCCCACCACTCAGCCTCATGGAATGCA
GAACAAAGTGCCATAACCTTTGTGCATCTCTTAATAGAGACCCACCACTCAGCCTCATGGAATGCAGAAC
AAAGTGCACATAACCTTTGTGCATCTCTTAGTAGAGAAGATTTATCCCTATGGGTTGCTGTAGATGAAGG
GCAGATTGTAGGGTTCCTGTGGGCTGGCTATCACGAGTTGGCCCCTTGGACACCTGTAAGAGTTGCCTCT
GACATTCTCTTTTATATTATACCAGAGAGGCGAGGAACACTACTTGGTATGCGTCTCATCAAAGCCCTAA
AGCAATGGGCTAGTGATAATGAATGCTCTGAGGTTCGCCTGTCTATCGCCTCTGGTATTAATGAAGAACG
TGTCGGACGTATGTATAAGCGACTTGGCTTTGAACCGTTTGGCACTGTGTATAACCTGAAGTTCTAAGGA
GATAACATGGGTGTTGTAAAGAAAGCATTTAAGGCTATCGGTCTTGCTCAAGATGCACCACGTATTGAAG
CCAAAGTCCCAGCACAGCAGCTTGAGCGTAAGCCTGAGACTGAAGCTGAAGATATTCAAATTGGTGCAGG
GGATGATGCTACTGCATCTGCAAAAGGTAAGCGTGGCCTTGTCCGTCCGGTAGCTTCTAGCTTGAAGGTG
TAATATGAAACAGAGCATAGATTTGGAGTATGGAGGTAAGCGGTCTAAGATACCTAAGCTATGGGAGAAG
TTCTCCAATAAACGTAGCTCTTTCCTTGATAGGGCGAAGCATTACTCCAAATTAACCTTGCCCTATCTGA
TGAATGACAAAGGTGATAACGAGACTTCGCAGAATGGATGGCAAGGTGTAGGTGCTCAGGCAACCAACCA
TCTAGCCAACAAGCTAGCGCAAGTACTATTCCCTGCACAGCGTTCCTTCTTCCGTGTAGACTTAACTGCA
CAAGGTGAGAAGGTTCTTAATCAGCGTGGCCTGAAGAAGACAGAGCTAGCTACCATCTTCGCTCAAGTGG
AAACACGGGCAATGAAAGAGTTAGAGCAACGTCAATTCCGGCCTGCTGTAGTAGAAGCATTTAAGCATCT
TATTGTTGCTGGCAGCTGTATGCTATACAAGCCGAGCAAAGGTGCAATCAGTGCTATCCCAATGCATCAC
TACGTAGTTAACCGTGATACCAATGGCGACCTGTTAGACATTATCTTGCTACAAGAGAAAGCCTTACGTA
CCTTTGACCCAGCTACACGTGCGGTAGTAGAGGTTGGCCTGAAAGGTAAGAAGTGCAAGGAAGATGACAG
CGTTAAGCTGTACACACATGCTAAGTATCTTGGTGATGGATTTTGGGAACTCAAGCAATCTGCTGATGAT
ATCCCTGTGGGTAAGGTGAGTAAAATCAAATCAGAAAAGCTACCTTTCATCCCATTAACTTGGAAGCGAA
GCTATGGTGAGGATTGGGGTCGACCTCTTGCAGAGGATTACTCCGGTGATTTATTCGTTATCCAATTCTT
ATCTGAAGCGGTTGCCCGTGGTGCTGCGCTGATGGCAGATATCAAGTACCTGATTCGTCCTGGTGCTCAA
ACTGATGTTGACCACTTTGTTAACTCTGGCACTGGTGAGGTTGTCACTGGTGTAGAAGAAGACATCCATA
TTGTACAGTTAGGTAAGTACGCAGACCTCACACCTATTAGCGCGGTTCTAGAGGTATACACTCGCCGTAT
CGGTGTTGTCTTCATGATGGAGACAATGACACGCCGTGACGCCGAACGTGTTACTGCTGTAGAAATCCAG
CGAGATGCGTTAGAGATTGAGCAGAACATGGGTGGTGTATACTCCCTCTTTGCTACTACTATGCAATCGC
CAGTAGCGATGTGGGGTCTGCTGGAGGCAGGGGAGTCCTTCACTAGTGACTTAGTGGACCCTGTGATTAT
CACAGGTATTGAAGCTTTAGGACGCATGGCTGAGTTGGATAAACTGGCTAACTTTGCTCAGTATATGTCA
CTGCCATTACAATGGCCTGAGCCTGTCCTAGCTGCTGTGAAATGGCCTGACTATATGGATTGGGTGCGTG
GTCAAATCTCTGCTGAACTGCCGTTCCTTAAATCGGCTGAAGAGATGGCACAAGAACAGGAAGCACAGAT
GCAAGCACAGCAAGCACAGATGCTTGAAGAAGGTGTGGCTAAGGCCGTGCCGGGTGTAATTCAACAAGAA
CTTAAGGAGGCGTAATGTCTTTCTCATTTACTGAACGTCAACCACTCACCCTACTGCTGAAGAGGGTCC
GGTAGAAACCAAGGAGGTAACAACTGATGCTGCTACTACTGATGCTCCTGCTGACGCTGGCACTTCTGTA
CAAGATGACAATGCTGGTGCACAACCTACTGAAGACACCGGAGGAGAAGCTTCTGGACAGCCTTCAGAAA
AAGGAGACAATGGCGGAGAGAATGGTGAACCTAAGCCAGATGATACCGCGACCGACACTGAGGAAGTGCA
ATACTTCTTCGGAGAACATGAAGTAACAGTAGACATCCCACAGGATGTAACTGACAGCCTTAAAGAGAAA
GGCATTGATGCCAAGCAGGTTGCCAAGGAACTCTATTCCAAAGGTGGCAAGTTTGAACTGTCAGATGCAA
CCAAGCAGAAATTGTATGATGCTTTTGGCAAGTTTGCGGTAGATGCTTACCTATCAGGTCTAAAGGCTCA
```

Figure 1G

```
AAATGAAGCCTTCTTCCTGAAAGAAGCCAACGCAGCTAAAGAGTTGGAAGCAGCTAACACCCAACGCTTC
TCTGATGTTTCTAAGGAAATTGGTGGCGAAGAAGGTTGGTCCCGTCTTGAGGAGTGGGCACTTGAAGCGC
TGTCTGATGACGAACTAATGGCATTCAATGCGGTGATGGAATCTGGCAACCAGTACCTGCAACAATATGC
TGTTCGTGAACTGGAGGGTCGTCGTAAGCAGGCACAGGGGGATGATAAGCCATCCCTGATTGAGCCATCA
GCACCTGCTAAGGCTAATGAAGAGAATGGCCCACTGACGCGAGATCAGTACGTTCAAGCAATCGCAACTC
TTAGCCAGAAGTACGGCAATGACCGTAAAGCTATGGCAGAAGCTCAGGCTAAACTGGACGCCCGTCGCCG
TGCTGGCATGGCTCGCGGTATCTAATTCAGTATTTACTGGACACTATAGAAGGGAGAAAAGTTCTCCCTA
GTTATCAATTTGATTTATAAGGAGATTATAATACATGTCTACACCGAATACTCTGACTAACGTTGCTGTA
TCTGCGTCCGGTGAGGTTGACAGCCTTCTCATTGAGAAGTTTAATGGTAAGGTCAATGAGCAGTACCTGA
AAGGTGAGAACATTCTGTCCTACTTTGATGTACAAACTGTTACTGGCACTAACACAGTGAGCAACAAATA
TTTGGGCGAAACTGAGTTGCAGGTGCTAGCACCGGGTCAGTCCCCTAATGCCACCCCTACTCAGGCGGAT
AAAAACCAGTTGGTAATTGATACCACTGTCATTGCTCGTAACACTGTGGCTCACATCCACGATGTACAAG
GTGACATCGATAGCCTGAAACCAAAACTGGCTATGAACCAAGCCAAGCAACTGAAACGTCTGGAAGACCA
GATGGCAATTCAGCAGATGCTGTTAGGCGGTATTGCTAACACCAAGGCCGAACGTAACAAGCCGCGTGTT
AAAGGGCATGGCTTCTCTATCAACGTTAACGTAACTGAGAGTGAAGCACTGGCTAACCCTCAGTATGTTA
TGGCTGCGGTAGAGTATGCTCTGGAGCAACAGCTTGAGCAGGAAGTGGACATCTCTGATGTAGCTATCAT
GATGCCGTGGAAGTTCTTCAATGCTTTGCGTGATGCAGACCGAATTGTAGATAAGACTTACACTATCAGC
CAGTCTGGTGCAACCATTAATGGCTTCGTTCTCTCTTCTTATAACTGCCCTGTGATCCCGTCTAACCGAT
TCCCTACCTTCGCTCAGGATCAGGCTCACCACCTGTTGTCTAATGAAGATAACGGCTATCGTTATGACCC
TATCGCAGAGATGAATGGTGCAGTTGCTGTTCTGTTCACTTCCGACGCACTGCTGGTGGGTCGTACCATT
GAAGTGACTGGTGACATCTTCTATGAGAAGAAAGAGAAGACTTATTACATTGACACCTTCATGGCTGAGG
GTGCAATCCCTGACCGTTGGGAAGCAGTGTCTGTAGTTACCACTAAACGTGATGCAACTACTGGTGATGC
TGGAGGTCCTGGTGATGATCACGCAACCGTACTGGCTCGTGCACAGCGTAAGGCTGTATATGTCAAAACC
GAAGGTGCTGCGGCTGCATTCTCTGCTGCCCCAGCAGGTATCCAAGCGGAAGACCTTGTAGCGGCGGTAC
GTGCTGTAATGGCAAATGACATTAAGCCGACTGCAATGAAACCTACTGAGTAACACCTATGCCCTATCTA
CCTTGCGTAGGTAGGGTTCTTTTTGTTAGGAGGATTCATGCCTGTAATTAGACAAACCAGTAAATTAGGA
CATATGATGGAAGATGTGGCCTTCCAGATTATTGATAGTAAGCTGGAAGCGGTAAACTTGTGTATGCGAG
CTATTGGTCGTGAGGGTGTGGATTCCCTCGACTCAGGGGACTTGGACGCAGAAGATGCAAGCAAAATGAT
CGACATCGTATCCCAGCGGTTCCAGTACAACAAAGGAGGTGGCTGGTGGTTCAATCGTGAACCAAACTGG
CAACTTGCACCAGACACTAACGGTGAAGTTAATTTACCTAACAACTGCCTAGCAGTATTGCAGTGTTATG
CTTTAGGTGAAAAGAAAGTACCTATGACTATGCGAGCAGGTAAGCTCTACTCTACTTGGAGTCACACCTT
TGATATGCGTAAGCATGTTAATGCTAATGGTATGATTCGTCTTACCTTACTCACCTTACTACCCTACGAG
CATCTACCTACAAGTGTAATGCAGGCTATTGCCTATCAAGCTGCTGTAGAGTTTATTGTGTCTAAGGATG
CAGATCAGACTAAGCTAGCCACTGCGCAGCAGATAGCCACTCAGCTTCTTATGGATGTACAATCTGAGCA
AATGTCACAGAAGCGATTAAACATGCTGGTACATAACCCTACTCAGCGTCAGTTTGGTATCATGGCTGGT
GGCTCTCAGAATGTACCTGCTTACTCTCATTCACCTTATGAGAGTTGGGCGCTCCGTCCGTGGGAGGATC
GTTAATGGAAGTACAAGGTTCATTAGGTAGACAAATCCAAGGGATTAGCCAGCAGCCGCCAGCGGTACGC
TTGGATGGTCAGTGCACAGCTATGGTTAATATGATACCTGATGTAGTGAATGGTACTCAATCACGCATGG
GTACAACTCATATTGCAAAGATACTTGATGCGGGGACTGATGACATGGCTACTCATCATTATCGCAGAGG
TGATGGTGATGAAGAGTATTTCTTCACGTTGAAGAAAGGACAAGTTCCTGAGATATTTGATAAGTATGGG
CGCAAATGTAATGTGACTTCACAAGATGCACCTATGACCTACCTCTCTGAGGTTGTTAATCCAAGGGAAG
ATGTGCAATTCATGACGATAGCTGATGTTACTTTCATGCTTAATCGTAGGAAAGTAGTTAAAGCTAGTAG
CAGGAAGTCACCTAAAGTTGGAAACAAAGCCATTGTGTTTTGTGCGTATGGTCAATATGGTACATCTTAT
TCCATTGTAATTAATGGGGCCAACGCTGCTAGTTTTAAAACACCGGATGGTGGAAGTGCAGACCATGTTG
AACAAATTCGAACTGAACGTATCACTTCTGAATTGTACTCTAAGTTGCAGCAATGGAGCGGTGTGAGTGA
CTATGAAATACAAAGAGACGGTACTAGTATATTTATCGAGAGACGGGATGGTGCTAGCTTTACAATAACA
ACCACCGATGGTGCAAAAGGTAAGGACTTAGTGGCTATCAAGAATAAAGTTAGCTCTACTGACCTACTCC
CTTCTCGTGCGCCTGCTGGTTATAAAGTACAAGTGTGGCCTACTGGCAGCAAACCTGAGTCTCGTTACTG
GCTGCAAGCTGAGCCTAAAGAGGGAAACCTTGTGTCTTGGAAAGAAACAATAGCTGCTGATGTATTACTT
GGGTTTGATAAAGGCACAATGCCTTACATTATTGAACGTACAGATATCATCAACGGCATAGCTCAATTCA
AGATAAGACAAGGTGATTGGGAAGATCGTAAAGTAGGGGATGACTTGACTAACCCTATGCCCTCTTTTAT
TGATGAGGAAGTACCCCAGACAATAGGTGGAATGTTCATGGTGCAGAACCGCCTATGCTTTACAGCAGGT
GAAGCGGTTATTGCTTCTCGTACATCATACTTCTTCGATTTCTTTCGTTATACGGTTATCTCTGCATTGG
CAACTGACCCCTTTGATATTTTCTCAGATGCTAGTGAAGTCTACCAGCTAAAACATGCAGTGACCTTAGA
```

Figure 1H

```
TGGCGCTACCGTGTTGTTCTCTGATAAGTCACAATTCATACTGCCAGGCGATAAGCCTTTAGAGAAGTCA
AATGCACTGCTTAAGCCTGTTACAACATTTGAAGTGAACAATAAAGTGAAGCCAGTAGTAACTGGTGAAT
CGGTAATGTTTGCCACTAATGATGGTTCTTACTCTGGTGTACGAGAGTTCTATACAGACTCTTATAGTGA
CACTAAGAAGGCACAAGCAATCACAAGTCATGTGAATAAACTCATCGAAGGTAACATTACCAACATGGCA
GCAAGCACCAATGTCAACAGGTTACTTGTCACTACCGATAAGTATCGTAACATAATCTACTGCTACGATT
GGTTATGGCAAGGAACAGACCGTGTACAATCAGCATGGCATGTATGGAAGTGGCCTATAGGTACAAAGGT
GCGAGGTATGTTTTATTCTGGTGAATTACTTTACCTGCTCCTTGAGCGAGGAGATGGCGTGTATCTGGAG
AAGATGGACATGGGTGATGCACTAACCTACGGTTTGAATGACCGCATCAGAATGGATAGGCAAGCAGAGT
TAGTCTTCAAGCATTTCAAAGCAGAAGATGAATGGGTATCTGAGCCGCTCCCTTGGGTTCCTACTAACCC
AGAACTTTTAGATTGCATCTTAATCGAGGGTTGGGATTCATATATTGGCGGCTCTTTCTTATTCAAGTAC
AACCCTAGTGACAATACTTTGTCTACAACCTTTGATATGTATGATGACAGCCATGTAAAAGCGAAGGTTA
TTGTTGGTCAGATTTACCCTCAAGAGTTTGAACCTACGCCTGTGGTTATCAGAGACAATCAAGACCGTGT
ATCCTACATTGATGTACCAGTTGTAGGATTGGTTCACCTTAATCTTGACATGTACCCCGATTTCTCCGTA
GAAGTTAAGAATGTGAAGAGTGGTAAAGTACGTAGAGTATTAGCGTCAAACCGTATAGGTGGTGCTCTCA
ATAATACAGTAGGCTATGTTGAACCGAGAGAAGGTGTCTTCAGATTTCCACTGAGAGCTAAGAGCACGGA
TGTTGTTTATCGTATTATTGTAGAGTCACCTCACACATTCCAGCTTCGTGATATTGAGTGGGAAGGGAGC
TACAATCCAACCAAAAGGAGGGTCTAATGGCTATAGGTTCAGCCGTTATGGCTGGTATGTCTTCTATTGG
TAGCATGTTTGCAGGCAGTGGTGCAGCAGCCGCTGCTGGAGGTGCTGCCGCAGGTGGCGGAGGTTTGCTA
GGTTCACTAGGTGGATTCCTAAGTGGCTCTACTGCTGGTTTCTCTAATGCTGGCCTTCTTGGTGCTGGCC
TTCAAGGGTTAGGCTTGATTGGTGATCTATTTGGTGGAAGTGATGAAGCCAAGGCGATGAAGAAAGCACA
AGAAGAGCAATGGCGGCAGCAGCTTATTGCTACACAAGAGGCGTACAAGACAGTGGCAGACGCAGAACGT
TCTGCTGCTAAACAATATCATGCAGATGCAATCAGTAATCAGGCTTCACTGCTACAGCAGCGAGCACAGG
TTGCATTACTTGCTGGGGCTACTGGTACTGGTGGTAATTCTGTGTCCTCTATGCTTAATGACTTAGCAGC
AGATGGCGGCAGGAACCAGAGTACTATCATTGATAACTATGAGAATCAGAAGATTAATTTCACCAACCAG
CTTAAGTCTATCCAACGTGGTGGTCAGATGCAGATGCGTGAGTTTAAGAAGCCTTCTGCTATGAATACCT
TGGTTAAAGGTATTCCAAGTCTGGCATCTGCCTATGTAACTGGTAGTAAGTCTGGCAAGGCATTGGGTAA
AGCCTTAACTGATTCTCGCACATATTCATCTGGAACAAGAGGTATTTAATGGCAATTGAGCGACAAGCAG
TACAAGGTCTGCCACAAGTGCAGGCCACTTCTCCTAATGTCATGACCTTTGCACCTCAACAAGTGGGAGG
TGTGGAGGCTGGCGTGGCTTCTACCTCCGGTAGTAGGTTTATCGAAGACCTTATTCGTGCAGCAAGCAGC
GTGGCTGATGTTACCACTGGTATCCTTAATCAGAAGATTGAGGAAGATAAGGTTGTTCAAATGGAACGGG
CATATAACGGATTAATGCCTTCTGAGGATGCAACTCGTGGTGGCGCTCGTGCTAACATGCTTGTCAAAGC
TCAACTGCTAGCTAATGATGAAGCAGCACGAATGAAAGACATGGCTACTCGTTTCCAAGGAACGGATGAC
GAATGGACACAACTTATGGTTGACTCTCGTAATGAGATGCAGAATAAGCTGTTCCAGCAATACCCTGAGT
TGCAAGGTGACAAAGATACTATGCGTATGGTCACTAATGTCTTCCAAGAACAGCAGCCTCAGATTTGGGC
TACACGAACCCAGCATAAACTTGACCGTGAACAAGCAGACCGTGAGGATACCTTTGACGGGCGAGTGGCT
TCTACTTGGGATTCTAATATTGACCCTGAAGCCTCTGGCTATGCTTTACAGGAACGAATCCGCGAAGGTC
TTACTCAAGGATTACTACCTGAACAGATGTACAAGAAGTTAGTCCAGCGAGCAATTTCACTTGCACAAGG
CGGTGATGTTAGCATGGCTGAAGCCCTGAAGTATGTGAAGGACGATAAGGGTGTTTCTGTTTATGCTAAG
AATCCACAGCTTATCACAGCCATCACTAGTGGTAATGCAGTTTGGGCTAGGAATAATGTAGCTGATGTAA
CTCGTATGTCTTTCGAAGTTAAAGAATCCTACCTTGCAGGTGATTTAACTGATGAAGAATTGTTGGAACG
AGCACAGCACATTAATAATCTGACAGGTAACTCTGTCTTCTCTAATCCAGAACTAGAGGCACTGATGCGC
CAACGGGCTAAGCAGAATGCAGAGCTAGGTGCAATGCAGGATATGCGACGTGAGCTTTACTCCGACCGCC
TGACTGGCTTCCAAGGTAAGACTGATAAAGAGAAGAAGGCTTACATTGATGTTATCAAACAGGATAGCCA
ACTTTATGCAGACCAGCAAATCAAACAACGTGGCTTGGACCCTTACAGTCAAGAGGCTGAAGCTATTCGT
GGTGCAGTGGAAGTGCAGCGCCTGCAATTCATGAACTCCAAAGGCTTAGTGGATGATACCTTTGAGTCTC
GTATCAAAGCCATGGAATCTATGCTATCGCCTGAGCACTTTGCCAAGGGCGAACCACAGGAGTTGATGAC
TATTCGCCAGTTGTGGGAACAGTTACCAGAAGAGAGCCGAGGTGTCTTTGGTGACACGGTGAATGGCTAC
ATGGATAACTACAACACTGCACTACAAATGGGAGAGACACCTTTGCAGGCTGCAAGGTTTGCGCGTAAAG
CACAGCAGAAATTCTCTCGTACTGAGAAGGAAACCAAGAAGTTCAACTCAGCTATTGGAGATGCACTGGA
TGAGGTATCTGGTGCTGGCTGGTTTGATGGTAAAACCGAAGTGTCAGACTTAGGTAAAGCTATTGCGGAA
GAAGAGTTACGAGCTAAGGCCAATATGTTGTGGTCTAGTGGTATGCGTAACATGGATTCCATCAAGAAGG
CTTTAATTACTTGGGGCAATAAACGCTACACTCAATCAGAGGATGCAAAGACTTCCGGTGGCTATTTCAT
TAAAGGTGATTACACTTCTGCATCTGATATGCTTATGTCAGTTGGGAAAGGCGTAAACCCTACCGATGTA
CCTCTGGCGCTTGGTAGGTATGTAGAAACACAGATGCCAGAATTGAAGAAGGAGCTTCAAGAGGGGGAAA
```

Figure 11

```
CTAAAGATGATATATACATTGATTACAATGAACAGAAAGGTACTTTCGTGATTCGTGCTGGTGCAGCAGG
TCGCCCTCTTTCTGGAGTAATCCCTGTAACCTCTTTAGATACCACTTCACTACTAGATTCTGCCTATCAG
AAGAAAGTAGAGGAACGAGATAAAGGCGAGTATGTTCACCCGTATCGTACAGATATTGGTGCACAAGAGC
CTATGCCAGCTAAACCAACTGCCAAAGATATTGGTAAATTTGGACTAGCTAACTTCCTCATGTCTTCTGC
TTTTGCTTCTGGTGAGAATCTGCCTTCTAACTTCGAGATTAACTATCGAGGTAATATGCAACAATTCTAT
GACAAGCTAGCTATGGATGAGAATAAAGATAAAGTTGGCTTTAATAAGGCAACTGGAACCTTTACTCCAT
ATAAAGACGCTCACGGTGAGTCTATCGGTTACGGTCATTTCTTAACGGAAGAAGAGAAGCGAAACGGGTA
TATTAAGATTGGCGATGAACTAGTTCCCTATCGAGGGTCTATGTCTCAGCTTACAGAGAGCAAGGCTCGC
GCTCTTATGGAGCAAGATGCTAAGAAGCATGTGCCTCCTACTCGTGACTGGAAGATTCCGTTTGACCAGA
TGCACCCTGCACAGCAACGTGGCTTGATGGATTTAAGCTACAATTTAGGTAAAGGTGGAATCCAGAACTC
ACCGCGTGCTCTTGCTGCATTCAAAGCTGGTAAGCTTACGGAGGGCTTTATCGAAATGCTGGGCACTGCA
TCAAGTGAAGGTAAGCGTATTCCTGGCCTACTGAAGCGACGCGCTGAGGCATACAATATGGCATCTGCTG
GTGGTGTGCCTAAGATTACCGAAGTGGGAGACTCGTGAAGATGGCTCCATGTGGGTTAGGTTTGGTGGACC
TATGCCAGCAGGTTCTGTCTCGGCATGGACTCATAAACGTATTGGCGCGGATGGTTGGTATCAGGTTTAT
GAGGCTGCACCTACCAAGTTAGCTAAAGATTCTAAGGTAGGTAAAGTTAAGTTGTAGTACCTAACTCAAG
GCTTGTCTCACATGTGAGACAGGTCTTTATGATAGGCACTATGGAGGAATTATGGAACAAGACATTAAGA
CTAATTGGGCTGGATATGTCCAGTCTACTCCTGAGCCGTTTTCTATTGAGGCGGCTCCGGTATCGGCTCC
TACGATACGCCAGCGTAATGAGTTACAAGAGCAAGTTCTTGAAGCTAAAGCTGACGCTGATATCTTAGGT
GCTGTAGGTGCTGCCTTCCAGAATGAGTGGTTGGCATTCGGAGGCAAGCGGTGGTATGACCGTGCCACTG
CTGATTTCACACCTCAACCAGACTTTGAGATACAACCTGAGCAACGTGAAGCACTACGTTTCAAATATGG
TACGGATATGATGCAGACAATCACTGAGGGTGTTCGTTCTGAGGATGAATTGAACTTCCGTATTCAGAAT
GCGGATGAAGACCTTGAGCGCAATAAGCGCATTGCTCAGGCTGGCTGGGTTGGCTCTGTGGCGACGATTG
GCGCTGCTGTGCTTGACCCTGTGGGATGGGTTGCCTCTATTCCAACCGGTGGTGCCGCTAAAGTTGGACT
CGTAGGCCGTGCTGTGCGTGGCGCTATCGCCGCTGGCGTGAGTAATGCCGCTATTGAATCCGTATTGGTC
CAAGGTGACATGACTCGTGATTTAGATGACATTATGGTAGCACTGGGTTCCGGTATGGCTATGGGTGGCG
TTATTGGCGCTGTAGCGCGTGGTAGGGCCACTAAGCTCAGTGAGCAAGGTGATGACAGGGCTGCTAGCAT
TGTGCGCAGTGCAGACGCAGGGGACCGCTATGTTCGTGCTGTTGCCGATGACAGTATCGGTGCGATGCGT
GTTAAGGGCGCAGAGGTTCTCACTGAGGGTGTATTCGATATCTCCAGTAAGAGTGAAGACCTACTGAAAA
CCTTGCAACGAGAAGGTAATGCGATTGATATGACACCTCGCCGTTGGGCTGGAACTATGTCTGCCCTCGG
TACTGTCGTGCACTCATCTAAAGATGCAAGTATCCGAGGCCTTGGTGCTCGTCTGTTTGAATCCCCACAA
GGTCTAGGTATGCAGAAGGCATCTGCTAGTCTTATGCAGAATACTAACTTAAATCGCCTGAAATCTGCTG
ATATGAACCGCTTCAATGATGGGTTTGATTTGTGGCTTAAAGAGAATAATATCAATCCAGTAGCAGGGCA
TACCAACTCTCATTATGTACAGCAATACAATGAAAAGGTGTGGGAGGCAGTGCGTATTGGCATGGATGAG
TCTACACCTAAATCTATCCGCATGGCTGCTGAGGGACAACAGGCTATGTACAGAGAGGCGCTGGCTTTAC
GTCAACGTTCTGGTGAAGCGGGATTTGAAAAGGTAAAAGCCGACAACAAATATATGCCTGATATCTTTGA
TAGTATGAAAGCCAGACGTCAATTCGATATGCACGATAAAGAAGACATCATCGAACTTTTCTCTCGTGCC
TACCAGAATGGCGCTCGTAAGATTCCAAAGGAAGCAGCAGATGAGATTGCACGAGCACAGGTAAATCGCG
TTGCTGATGCTACCTTAACTGGAAAGCTTAGTTTTGAAAAGGCAATGTCAGGTCAGACTAAGGCAGAGTA
TGAAGCTATCATGCGTAAGGCAGGCTTCAGTGATGAAGAAATTGAAAAGATGATAGAAGCTCTGGATAAC
AAAGAAACCAGAGATAACATCTCTAACCGAGCTAAAATGAGTTTAGGATTAGATGTTACTCAAGAATACA
ATGGCATTCGTATGCGTGACTTCATGAATACCAACGTGGAAGAGCTAACAGATAACTATATGAAGGAAGC
AGCAGGTGGCGCTGCATTGGCTCGCCAAGGCTTCTCTACCTATCAGGCTGCACTTAATGCAATTGACCTT
GTAGAGCGAAATGCACGAAACGCGGCTAAGGATAGCAAGGCTAGTTTGGCATTAGATGAAGAGATTCGTC
AGATGCGAGAAGGTCTTCGCCTGATTATGGGCAAGTCGATTGATGCAGACCCACAGGCTATATCTACTAA
GATGATGCGTCGTGGTCGTGATATCACAGGTGTGCTTCGCTTAGGTCAAATGGGCTTCGCACAGCTAGGT
GAACTTGCCAACTTTATGGGTGAATTTGGTATTGCTGCAACTACTATGGCTTTAGGTAAGCAATTCCGCT
TCACCTCTAAGGCGTTGCGTAATGGCGATGGCTTCTTCCGAGATAAGAACTTAGCTGAGGTTGAGAGAAT
GGTGGGGTACATTGGTGAGGATAACTGGCTAACAACTAAGGGTGCACGTCCTGATGAATTTGGTGATGTA
ACCACAGTAAGAGGGATGATGGCTCACTTTGACCAATCCATGAACTCAATACGTCGTGCTCAAACCAACC
TATCACTCTTCCGCATGGCACAGGGTTCTCTGGAGCGAATGACTAATAGGCAAATAGCTTTGTCTTTCAT
TGACCACCTTGAAGGCAAGAAGATTATTCCTCAGAAGAAACTGGAGGAACTTGGTCTTACTCAGGAGTTC
ATGACTAACCTACAGAAGCACTATGATGCTAACTCTAAAGGTTCTGGCTTGCTTGGCTTTGATACAATGC
CTTATGCCATGGGTGAAACTTTAGCTAATGCTATTCGTCGTAAGTCAGGTCTAATCATCCAACGTAACTT
CATTGGTGATGAAGGTATCTGGATGAACAAAGCACTAGGTAAGACATTTGCACAGCTTAAGTCATTCTCT
```

Figure 1J

```
CTTGTATCTGGTGAGAAGCAATTTGGTCGAGGGATTCGCCACGATAAAATTGGTCTTGCTAAGAAGACAG
CTTACGGGTTTGCTTTGGGTTCAATAGTGTATGCGGCAAAAGCCTATGTGAACTCTATTGGGCGAGAAGA
CCAAGATGAATATTTGGAAGAGAAGTTATCGCCTAAAGGGTTGGCCTTTGGTGCAATGGGTATGATGAGT
ACAACTGCTGTATTTAGTCTAGGTGGAGATTTCTTAGGTGGCCTAGGTGTTCTACCTTCCGAACTCATTC
AATCACGCTATGAAGCAGGTTTCCAAAGTAAGGGTCTGATTGACCAAATACCTCTGGTTGGCGTTGGTGC
AGATGCAGTAAATCTGGCTAACTCAATCAAGAAGTATGCAGAAGGTGACACAGAAGGTGTAGATATCGCT
AAGCGAGCACTCCGTCTTGTGCCACTTACCAATATAATAGGTGTCCAAAACGCATTGCGTTATGGCTTAG
ATGAACTGGAGGATTGATGAGTTATACTTTCACAGAACATACAGCCAATGGTACGCAAGTCACCTATCCT
TTTAGCTTTGCTGGTAGGGATAAAGGTTATCTTCGTGCCTCAGATGTGATAGTGGAGTCTCTTCAAGGTA
ACACTTGGATTGAAGTTACATCTGGCTGGCAACTAACTGGCACGCACCAGATTACTTTTGATGTAGCACC
AGTTGCAGGTTTGAAGTTCCGTATTCGAAGGGAAGTACAAAAAGAATATCCATACGCTGAGTTTGACCGT
GGTGTTACCTTGGATATGAAGTCTTTAAATGGTTCTTTCATTCATATACTGGAGATTACACAGGAGTTAC
TTGACGGGTTTTATCCAGAAGGATACTTCATTAAACAGAATGTAAGCTGGGGCGGCAATAAGATTACTGA
TTTGGCTGATGGCACAAATCCGGGAGATGCAGTAAATAAAGGGCAGCTTGATGCCATCGACAAGAAGCAT
ACAGATTGGAACGCCAAACAGGACATTGAGATTGCTGGCCTTAAGGCTGGTATGACTTCTGGTATTGCGC
ACAGAACTGTTCCTTGGTACACGATAGCCCAAGGTGGTGAGATTTCCGTAAAACCACCTTATGAATTTCA
AGATGCACTAGTTTTCCTTAATGGGGTATTGCAGCACCAAATTGTAGGCGCATACTCTATAAGCAACAAC
ACTATCACTTTCGCAGAGCCGCTTGTGGCTGGTACAGAGGTGTATGTGCTGATTGGTAGTCGTGTGGCTA
CATCTGAACCTAATATTCAGTTGGAGTTGAACTTTGACTTAGTAGAAGGCCAACAAGTAGTACAGATTGG
CTCTGCATTTAAGTACATTGAGGTCTACCTTGATGGATTATTACAACCTAAACTTGCTTATCAGGTAGAC
GGTGACATTGTTACTTTCTCAGAAAGAGTACCAGAATGCCGGATGACTGCTAAGATTATCACAGCATAAG
GAGGTGGATGATTAACTCCGAACTGGTAGATAGTGGTGTGAAGCTTGCGCCACCTGCACTCATATCAGG
TGGGTACTTCCTCGGTATCAGTTGGGATAATTGGGTGTTAATAGCAACATTCATTTATACCGTGTTGCAA
ATTGGGGACTGGTTTTATAATAAGTTCAAGATTTGGAGGGAGAAGCGTGAGCGTACACAATAAACATGCA
GCTACAGAGGACGAGGTTGGCATTCTGCATGGTGCTATTACCAAAATCTTCAATAAGAAAGCACAGGCAA
TACTGGACACTATAGAAGAAGACCCTGATGCAGCATTACATTTAGTGTCTGGTAAGGATATTGGTGCGAT
GTGTAAGTGGGTTCTTGATAACGGCATTACCGCCACACCTGCTGCACAGCAGGAAGAGTCCAAGTTATCT
AAGCGCCTCAAGGCTATCCGAGAGGCATCCAGTGGTAAGATAATTCAATTCACTAAGGAGGATTGATGGC
TAAGGCAAGAGAATCACAAGCGGAGGCTCTTGCCAGATGGGAGATGCTACAGGAGTTACAGCAGACCTTT
CCTTACACCGCGGAAGGTTTGCTTCTCTTTGCAGATACAGTTATTCATAACTTAATTGCAGGCAACCCTC
ATCTGATTCGTATGCAGGCGGATATCTTGAAGTTCCTATTTTACGGACACAAGTACCGCCTCATCGAAGC
GCCTCGTGGTATCGCTAAGACAACACTATCAGCAATCTATACGGTATTCCGTATTATTCATGAACCGCAT
AAGCGTATCATGGTTGTGTCCCAAAACGCCAAGCGAGCAGAGGAAATCGCAGGTTGGGTAGTTAAAATCT
TCCGTGGCTTAGACTTTCTTGAGTTTATGCTGCCGGATATCTACGCTGGGGACCGTGCATCCGTTAAGGC
GTTTGAGATTCATTACACCCTACGTGGTAGTGATAAGTCTCCTTCTGTATCCTGTTACTCAATCGAAGCA
GGTATGCAGGGTGCTCGTGCTGATATTATTCTAGCGGATGACGTAGAGTCGATGCAGAATGCTCGTACGG
CAGCGGGCCGTGCCTTGCTTGAGGAGCTGACTAAGGAGTTTGAATCTATCAACCAGTTTGGGGATATCAT
TTACCTTGGTACACCTCAGAACGTAAACTCTATCTACAACAACCTACCTGCTCGTGGTTACTCTGTTCGT
ATCTGGACTGCGCGTTACCCTTCAGTAGAGCAAGAGCAATGTTATGGCGACTTCCTTGCACCTATGATTG
TTCAAGATATGAAGGACAACCCAGCACTTCGCTCAGGGTACGGGTTGGATGGTAATAGTGGTGCACCTTG
TGCCCCTGAAATGTATGATGATGAAGTCCTGATTGAGAAGGAAATCTCTCAGGGTGCTGCTAAGTTCCAG
CTTCAGTTCATGCTTAACACTCGCATGATGGATGCTGACAGATACCCATTACGCCTGAACAATCTAATCT
TCACCTCGTTTGGTACAGAGGAAGTCCCTGTGATGCCTACGTGGAGTAATGATTCCATAAACATCATTGG
TGATGCACCTAAGTATGGTAACAAGCCTACGGATTTCATGTACAGACCTGTAGCTCGCCCATATGAATGG
GGTGCTGTCTCCCGCAAGATTATGTATATTGACCCTGCGGGTGGTAAGAACGGAGATGAGACGGGTG
TAGCCATCGTATTCCTGCACGGCACATTCATTTATGTGTATCAGTGCTTTGGTGTACCTGGCGGATACCG
AGAGTCGTCCCTGAATCGCATTGTGCAGGCCGCAAAGCAGGCGGGTGTTAAAGAGGTATTCATTGAGAAG
AACTTTGGTCATGGCGCGTTTGAGGCGGTAATTAAGCCGTACTTTGAACGAGAGTGGCCTGTAACTCTGG
AAGAGGATTACGCCACCGGACAGAAAGAGTTGCGTATCATTGAGACGCTGGAGCCGCTCATGGCAGCCCA
TAGGCTTATCTTCAATGCAGAGATGGTGAAGTCAGACTTTGAGTCGGTACAGCACTATCCGCTTGAACTA
CGCATGTCCTACAGTCTTTTCAATCAAATGTCGAACATAACGATTGAGAAGAACAGCCTCCGGCACGATG
ACCGCCTAGACGCCCTGTATGGCGCTATACGGCAATTAACTTCTCAGATAGACTATGACGAGGTTACACG
GATTAATCGCCTCAGAGCGCAGGAGATGCGCGATTACATCCATGCTATGAACACACCTCATCTACGCAGG
GCAATGCTATATGGAGATTACGGTACTGAGCGAAGAGTGACCAACACTTCCGTAGCGATGCAGCAGCGAG
```

Figure 1K

```
TTTACGGGCAGAACTACCGAAATAAATCGGCAAGCAGAAATACACTTTCTGCAAGGATTTCAAGGACTTA
TTAATTACTGGACACTATAGAAGGAAGGCCCAGATAATAAGAGAAAATAATAGGTAATATATATATAGGT
TAACCTAGGTTATATAGGTATGCCTTAGTATGGGTGTACTCCTGTACACCCTATTCCTTACTACCTTACT
ATATTTACATAATAGGAGAGAGACAATGGCTAATGATTATAGTAGTCAACCATTAACAGGTAAGTCTAAG
AGAAAGCAGGTACAACCTGTAAGTGAAGAACTAATGCTTCCGGTGCTCAAAAAAGAGGAAGTTAGTAAGA
AAAGCAATGTTATTAATGATGCCACCAAATCAGGTAAACAGAAAGGGGCCATGGTGTGCCTTGAAGTGAA
AGGTGGTGTATTGAAGATTGCTATCGCGGTTGATGGCAAAGAAGATTCAGAGTGGAAGTTAGTAACAGTG
GAACCAACTGTTAACCCAGTTTAAGATAAGGAGGAAGATTACATGGCTAAATATGGTACTACAGGTTCTG
TTACTGGTCAGGCTTTTCGAGTAAAAGCAGTACAAACTATTGCAACGGCAATCCCGATGCCTGTTGTTAA
AGAAGAAGACCTTAAGAGTAAAGACCACCCTATCAACATCAAACATTTATCAGGTAAACAGAAAGGTGCA
ATGGTTGCTCTTGAGAAAGGTGACACAACCTTACATATTGCTGTTGCACGTGGTAGTGAACCCACAGACC
CTTGGGATGTAACTGGTATGGAAAAGGACGCTGTTACTCCAGCAGGGGTATAATAATGCTTAATAAATAC
TTCAAGCGTAAAGAGTTTGCTTGCCGTTGTGGGTGCGGTACATCCACTGTTGATGCTGAATTACTACAGG
TAGTCACAGATGTGCGTGAGCACTTTGGTTCTCCTGTAGTTATCACTTCGGGTCATCGCTGTGCTAAGCA
CAATGCCAATGTAGGTGGCGCTAAGAACTCCATGCATCTTACTGGTAAGGCTGCTGACATTAAAGTGTCT
GGCATATTACCTTCTGAAGTGCATAAGTATCTTACTAGCAAATACCAAGGCAAGTATGGTATAGGTAAGT
ATAACTCCTTCACTCACATCGATGTACGGGATGGTTGTGCGCGATGGTAAGATGTGTTGAATGGTGTGAG
CGTATGGTTGCCCAAGCTGCCGAGGATGGCAACTATGATGACTGGAAGAACTACTCTGACTTGTTAGCTC
AATGGAAAGGGAGATGCAATGAAAAAGCTGTTTAAGTCTAAGAAGGTTGTAGGTGCACTGGTTGCACTTG
TTATTGCTCTTGTTTCTGTAGGTCTTGGTGTAGACCTTGGCTCTGGCACGGAATCCTCTGTGACAGATGT
GGTCTGCCAAGTGATCACCTGTGAATAAGTTTCTAGAAGTTCTGGCAGGTCTTATTGGCCTGCTTGTCTC
TGCTAAGAAGAAACAAGAAGAGAAGGAGGCACAAAGTGAAGCGAATCATGTTAGTGACAACCCTTCTGAT
TGGTTCGCTGACCACTTCCGGGTGTCAGCAGGCGTTACCAGAGAAAGCAATGGTGAAACCTCTGAGGCCG
ACGCTGACGGCAGTTTACGAGGTAGACGATAAGGTCTGCTTTAGTAAGCCTGACGCTACAAAACTTGGTT
TGTACATTCTCTCGCTAGAACGCGGATACAATTAATACATAGCTTTATGTATCAGTGTCTTACGATTTAC
TGGACACTATAGAAGAGGTAAGATAGCGCCGTTCTTTTGAGCGGCCTATTACTAGCCAATCTTCATAGGG
AGGGTTGGAAAGTAATAGGAGATAGCATGGCTAAATTAACCAAACCTAATACTGAAGGAATCTTGCATAA
AGGACAATCTTTGTATGAGTACCTTGATGCGAGAGTTTTAACATCAAAGCCGTTTGGTGCTGCAGGTGAC
GCCACTACTGATGATACGGAGGTTATAGCTGCTTCATTAAACTCTCAGAAAGCTGTCACAGTCTCAGATG
GTGTATTCTCTAGCTCTGGTATTAACAGTAATTACTGTAACTTAGACGGCAGGGGTAGTGGCGTGCTAAG
TCACCGTTCAAGTACAGGTAACTACTTAGTATTTAACAATCTACGTGCAGGTCGCTTAAGTAATATTACG
GTAGAAAGTAATAAGGCGACTGATACAACTCAGGGACAGCAGGTATCCCTTGCTGGTGGAAGTGATGTTA
CTGTAAGTGACGTTAACTTCTCAAACGTTAAAGGTACTGGTTTCAGTTTAATCGCATACCCTAATGATGC
GCCACCTGATGGACTTATGATTAAAGGCATTCGAGGTAGCTATTCCGGCTATGCTACTAATAAGGCAGCC
GGATGCGTACTTGCTGATTCCTCAGTTAACTCCCTCATAGATAACGTCATTGCTAAGAACTACCCTCAGT
TCGGAGCAGTAGAGTTGAAAGGTACAGCCAGTTACAACATAGTCAGTAATGTTATAGGGACAGATTGCCA
GCATGTAACTTACAACGGCACTGAAGGGCCAATAGCTCCTTCTAATAACCTTATCAAGGGGGTGATGGCT
AATAACCCTAAGTATGCAGCGGTTGTTGCAGGCAAAGGAAGTACGAACTTAATCTCAGACGTGCTCGTAG
ATTACTCAACTTCTGATGCTAGGCAGGCTCATGGTGTTACAGTAGAGGGTTCTGATAACGTCATAAATAA
TGTGCTTATGTCAGGATGTGATGGTACTAACTCTTTAGGACAAGGGCAGACTGCTACAATTGCACGCTTT
ATAGGTACAGCTAATAACAACTATGCGTCTGTATTTCCTAGCTACAGTGCTACAGGTGTTATTACTTTCG
AATCCGGCTCTACCCGTAACTTCGTAGAGGTAAAGCACCCTGGCAGGAGAAACGACCTTCTCAGTTCTGC
TAGTACTATTGACGGTGCAGCTACTATTGACGGCACTAGTAATAGTAACGTAGTGCACGCACCTGCCTTA
GGGCAGTACATAGGTAGTATGTCAGGTAGGTTCGAATGGCGGATTAAGTCCATGTCACTCCCTTCAGGCG
TTCTTACTTCTGCTGATAAGTACAGAATGCTTGGAGATGGTGCTGTGTCATTAGCTGTAGGTGGGGGCAC
TTCTTCTCAAGTTCGCCTATTTACTTCTGATGGTACTTCTCGGACAGTGTCCCTCACCAACGGTAACGTG
CGTCTTTCTACCAGTAGCACAGGCTTTTTGCAGTTAGGTGCTGATGCAATGACCCCAGACAGTACTGGTA
CATACGCATTAGGTTCCGCCAGCCGAGCATGGTCTGGCGGTTTTACTCAAGCAGCATTCACTGTTACCTC
AGATGCTCGGTGTAAAACAGAACCTCTTACTATCTCAGATGCCTTACTGGATGCTTGGTCTGAAGTTGAC
TTTGTGCAGTTTCAGTATTTGGATCGTGTTGAGGAGAAGGGTGCAGACTCAGCTAGATGGCACTTCGGTA
TCATCGCTCAGCGAGCTAAGGAGGCTTTCGAACGTCACGGTATAGATGCACATCGCTATGGCTTCTTGTG
CTTCGACAGTTGGGATGATGTATACGAGGAAGATGCCAATGGCTCTCGTAAACTGATTACACCAGCAGGT
TCCCGCTACGGTATTCGTTACGAGGAAGTACTGATATTAGAGGCTGCGTTGATGCGGCGGACTATTAAGC
GTATGCAGGAAGCACTAGCTTCCCTGCCTAAGTAAGCAACAGGCAGTGCGTAAGCACTGCTTTTAGCGCA
```

Figure 1L

```
ACTTTTCTTAAAGGTTATCACGGTGGTAGCCTTTCAGAAAAGGAGGTTACATGATTCAAAGACTAGGTTC
TTCATTAGTTAAATTCAAGAGTAAAATAGCAGGTGCAATCTGGCGTAACTTGGATGACAAGCTCACCGAG
GTTGTATCGCTTAAAGATTTTGGAGCCAAAGGTGATGGTAAGACAAACGACCAAGATGCAGTAAATGCAG
CGATGGCTTCAGGTAAGAGAATTGACGGTGCTGGTGCTACTTACAAAGTATCATCTTTACCTGATATGGA
GCGATTCTATAACACCCGCTTCGTATGGGAACGTTTAGCAGGTCAACCTCTTTACTATGTGAGTAAAGGT
TTTATCAATGGTGAACTATATAAAATCACGGATAACCCTTATTACAATGCTTGGCCTCAAGACAAAGCGT
TTGTATATGAGAACGTGATATATGCACCTTACATGGGTAGTGACCGTCATGGTGTTAGTCGTCTGCATGT
ATCATGGGTTAAGTCTGGTGACGATGGTCAAACATGGTCTACTCCAGAGTGGTTAACTGATCTGCATCCA
GATTACCCTACAGTGAACTATCATTGTATGAGTATGGGTGTATGTCGCAACCGTCTGTTTGCCATGATTG
AAACACGTACTTTAGCCAAGAACAAACTAACCAATTGTGCATTGTGGGATCGCCCTATGTCTCGTAGTCT
GCATCTTACTGGTGGTATCACTAAGGCTGCAAATCAGCAATATGCAACAATACATGTACCAGATCACGGA
CTATTCGTGGGCGATTTTGTTAACTTCTCTAATTCTGCGGTAACAGGTGTATCAGGTGATATGACTGTTG
CAACGGTAATAGATAAGGACAACTTCACGGTTCTTACACCTAACCAGCAGACTTCAGATTTGAATAACGC
TGGAAAGAGTTGGCACATGGGTACTTCTTTCCATAAGTCTCCATGGCGTAAGACAGATCTTGGTCTAATC
CCTAGTGTCACAGAGGTGCATAGCTTTGCTACTATTGATAACAATGGCTTTGTTATGGGCTATCATCAAG
GTGATGTAGCTCCACGAGAAGTTGGTCTTTTCTACTTCCCTGATGCTTTCAATAGCCCATCTAATTATGT
TCGTCGTCAGATACCATCTGAGTATGAACCAGATGCGTCAGAGCCATGCATCAAGTACTATGACGGTGTA
TTATACCTTATCACTCGTGGCACTCTTGGTGACAGACTTGGAAGCTCTTTGCATCGTAGTAGAGATATAG
GTCAGACTTGGGAGTCACTGAGATTTCCACATAATGTTCATCATACTACCCTACCTTTTGCTAAAGTAGG
AGATGACCTTATTATGTTTGGTTCAGAACGTGCAGAAAATGAATGGGAAGCAGGTGCACCAGATGATCGT
TACAAGGCATCTTATCCTCGTACCTTCTATGCACGATTGAATGTAAACAATTGGAATGCAGATGATATTG
AATGGGTTAACATCACAGACCAAATCTATCAAGGTGACATTGTGAACTCTAGTGTAGGTGTAGGTTCGGT
AGTAGTTAAAGACAGCTACATTTACTATATCTTTGGTGGCGAAAACCATTTCAACCCAATGACTTATGGT
GACAACAAAGGTAAAGACCCATTTAAAGGTCATGGACACCCTACTGATATATACTGCTATAAGATGCAGA
TTGCAAATGACAATCGTGTATCTCGTAAGTTTACATATGGTGCAACTCCGGGTCAAGCTATACCTACTTT
CATGGGTACTGATGGAATACGAAATATCCCTGCACCTTTGTATTTCTCAGATAACATTGTTACAGAGGAT
ACTAAAGTTGGACACTTAACACTTAAAGCAAGCACAAGTTCCAATATACGATCTGAAGTGCAGATGGAAG
GTGAATATGGCTTTATTGGCAAGTCTGTTCCAAAGGACAACCCAACTGGTCAACGTTTGATTATTTGTGG
TGGAGAAGAGACTTCGTCCTCTTCAGGTGCACAGATAACTTTGCACGGCTCTAATTCAAGTAAGGCTAAT
CGTATCACTTATAACGGAAATGAGCACCTATTCCAAGGTGCACCAATCATGCCTGCTGTAGATAACCAGT
TTGCTGCTGGTGGACCTAGTAACCGATTCACTACCATCTACCTAGGTAGTGACCCTGTTACAACTTCAGA
TGCTGACCACAAGTACAGTATCTCTAGTATTAATACCAAGGTGTTAAAGGCTTGGAGCAGGGTTGGTTTT
AAACAGTATGGTTTGAATAGTGAAGCAGAGAGGGACCTTGATAGCATACACTTCGGTGTCTTGGCTCAGG
ATATTGTAGCTGCTTTTGAAGCTGAAGGGTTGGATGCCATTAAGTATGAATTGTGTCCTTCGAAGAAGG
TAGGTACGGTGTGAGGTATAGTGAAGTTCTAATACTAGAGGCTGCTTATACTCGTTATCGTTTAGACAAG
TTAGAGGAGATGTATGCCACTAATAAAATCAGTTAAGCAAGCTGCTGTACTCCAGAACACAGAAGAGCTT
ATTCAATCAGGACGTGACCCTAAGCAGGCTTATGCCATTGCCAAGGATGTTCAACGTCGTGCCATGAAGA
AACCTTCTGCATCTTCTGCGTAAGCAGGTTAATATCTTAGTATAAACAAGGGCAGACTTAGGTTTGTCCT
TAGTGTATTCCAAAGGAGGTAACATGCTGAAAGATGGTTGGGTTTCATATGACCCTACAGACCCTAAGAA
TTGGCTACAGGTTATCGCTATAGCTTGTGCAGGTAGCCTATTGGCTGCCCTGATGTATTCATTATGGATG
TACACAAAGTAACCAAAGTCAAAATTTTGATGTAGGCGTGTGTCAGCTCTCGCCCTCGCCCTCGCCGG
GTTGTCCCCATAGGGTGGCCTGAGGGAATCCGTCTTCGACGGGCAGGGCTGATGTACTCCTTGTCTAGTA
CAAGGGAGGCGGAGGGAACGCCTAGGGAGGCCTAGGAATGGCTTAGTGGTGGACAAGGTGATTACCTTAG
TGAAGCCTCTTAGTGCATTCCTGAGGCCATTCAGGGCGTTTATGAGGGATTGACAGGGTGTGAGGGCGTG
GGCTA
```

Figure 2

>K1-5 site sgRNAs 86+89 donor template (homologous recombination substrate) (SEQ ID NO:2)
TGACAGCCACGGCATACAAGGTTACATTAAGCATCAAGACGGCGACGTCTTTAAACATCCCGCTCTTTAACAATAC
GGTTTGTGTCTTGATAGGCTAACTAACTAACTAAGGTAATTATCATGAAAGGGTTAATTTGTGTAGAACGTATGGT
CAATGGTAAACTTGAAATATTACCACTGGAAAACCAATCTAGCTTCAAAGAGTGGTATGGCTGTTTCTCACTGATTT
AAGGTAAAGGCTGGCACTAGTCAGCCTATCAAGGCGCAAACCAAGCTCTTTAACAATTTGGATGGTAGCTTCTTAG
TCTGGATAGGTTAAACCTAGGAGATTCTCTTGAGTCTCCTATAATGTAACCTAACTAACTAAATGAGGATTAAAAG
AGGAGATATACAATGGTTTTTACGCTTGAGGACTTCGTTGGTGACTGGCGTCAAACCGCGGGGTATAATCTTGATC
AGGTCCTGGAGCAGGGCGGAGTTTCGTCCTTATTCCAGAACTTAGGGGTAAGTGTTACGCCGATTCAGCGCATCG
TGCTGAGTGGAGAGAATGGATTGAAAATTGACATTCACGTTATCATTCCGTATGAGGGTTTGAGTGGAGACCAGA
TGGGACAGATTGAAAAGATTTTCAAAGTGGTGTATCCCGTCGATGACCATCACTTTAAAGTAATTCTGCACTATGG
GACCCTTGTGATCGACGGTGTAACGCCAAACATGATTGACTATTTCGGTCGCCCTTACGAAGGTATCGCCGTCTTC
GACGGAAAAAAAATCACTGTCACGGGAACATTATGGAACGGAAATAAAATTATCGACGAACGTCTGATCAATCCT
GATGGAAGCCTGTTATTTCGCGTTACGATCAATGGAGTGACCGGATGGCGTTTATGCGAACGTATTTTGGCTTAAA
GAGGAGATATACAATGGAACGCAACGCAAATGCATATTATAATTTATTAGCAGCTACGGTTGAAGCCTTTAATGAA
CGCATCCAATTCGACGAAATCCGTGAGGGCGACGACTATAGCGACGCCCTTCATGAGGTTGTAGACAGCAATGTT
CCAGTTTATTACAGCGAAATCTTTACAGTGATGGCTGCTGATGGTATTGATGTTGATTTTGAGGATGCTGGTTTGAT
TCCTGACACGAAGGATGTAACCAAGATTCTACAAGCTCGCATCTATGAAGCTCTTTATAATGATGTACCAAATGAC
AGCGATGTAGTTTGGTGTGAAGGCGAAGAAGAGGAAGAATAAGGATGGAAAAGCAATATAACTTTATCTTTTCAG
ACGGTGTAACCCTGAAGTGT

Figure 3

K1-5 site sgRNAs 1112+1122 donor template (homologous recombination substrate) (SEQ ID NO: 3)
ACGTCCAGCCTCCTTCCTAGATATTCCTGAGATTATAAACCTTGGGAATAAATATGTGGAAGAGGAAGTCAAGGTT
GTAGCCCACCACTCAGCCTCATGGAATGCAGAACAAAGTGCCATAACCTTTGTGCATCTCTTAATAGAGACCCACC
ACTCAGCCTCATGGAATGCAGAACAAAGTGCACATAACCTTTGTGCATCTCTTAGTAGAGAAGATTTATCCCTATG
GGTTGCTGTAGATGAAGGGCAGATTGTAGGGTTCCTGTGGGCTGGCTATCACGAGTTGGCCCCTTGGACACCTGT
AAGAGTTGCCTCTGACATTCTCTTTTATATTATACCAGAGAGAAGGGGAACACTACTTGGTATGCGCTTAATTAAG
GCATTGAAACAGTGGGCATCAGATAATGAATGCTCTGAAGTGCGTTTAAGTATTGCAAGTGGCATCAACGAGGAG
CGCGTAGGGCGCATGTACAAACGGCTCGGCTTTGAACCGTTTGGCACTGTGTATAACCTGAAGTTCTAAAGAGGA
GATATACAATGGTTTTTACGCTTGAGGACTTCGTTGGTGACTGGCGTCAAACCGCGGGGTATAATCTTGATCAGGT
CCTGGAGCAGGGCGGAGTTTCGTCCTTATTCCAGAACTTAGGGGTAAGTGTTACGCCGATTCAGCGCATCGTGCT
GAGTGGAGAGAATGGATTGAAAATTGACATTCACGTTATCATTCCGTATGAGGGTTTGAGTGGAGACCAGATGGG
ACAGATTGAAAAGATTTTCAAAGTGGTGTATCCCGTCGATGACCATCACTTTAAAGTAATTCTGCACTATGGGACC
CTTGTGATCGACGGTGTAACGCCAAACATGATTGACTATTTCGGTCGCCCTTACGAAGGTATCGCCGTCTTCGACG
GAAAAAAAATCACTGTCACGGGAACATTATGGAACGGAAATAAAATTATCGACGAACGTCTGATCAATCCTGATG
GAAGCCTGTTATTTCGCGTTACGATCAATGGAGTGACCGGATGGCGTTTATGCGAACGTATTTTGGCTTAAAGAGG
AGATATACAATGGGTGTTGTAAAGAAAGCATTTAAGGCTATCGGTCTTGCTCAAGATGCACCACGTATTGAAGCCA
AAGTCCCAGCACAGCAGCTTGAGCGTAAGCCTGAGACTGAAGCTGAAGATATTCAAATTGGTGCAGGGGATGAT
GCTACTGCATCTGCAAAAGGTAAGCGTGGCCTTGTCCGTCCGGTAGCTTCTAGCTTGAAGGTGTAATATGAAACAG
AGCATAGATTTGGAGTATGGAGGTAAGCGGTCTAAGATACCTAAGCTATGGGAGAAGTTCTCCAATAAACGTAGC
TCTTTCCTTGATAGGGCGAAGCATTACTCCAAATTAACCTTGCCCTATC

Figure 4A

>K1-5 BAR 2.5 (Site specified by sgRNAs 86+89) (SEQ ID NO: 4)
TCGCCCTCGCCCTCGCCGGGTTGTCCCCATAGGGTGGCCTGAGGGAATCCGTCTTCGACGGGCAGGGCTGATGTACTCCTTGTCTAGTACAA
GGGAGGCGGAGGGAACGCCTAGGGAGGCCTAGGAATGGCTTAGTGGTGGACAAGGTGATTACCTTAGTGAAGCCTCTTAGTGCATTCCTGA
GGCCATTCAGGGCGTTTATGAGGGATTGACAGGGTGTGAGGGCGTGGGCTATCTGTTCCTTTGCTCCTCACTTCGTTCGTCGCTGCGGTAGCC
TGATGTGTACCTTAGGTTATTCCTTGATGGATAGCTTAGGTTAGCCTTAGTGGATTACCTTAGTTAAAGCCTTAGTGCTTCACTTAGTATCAGCT
TAGTAGTGTACCTTAGTAAGTCTTAGTGTCTTCTCTTAGTGATTGCACATGCAAGCATGTAAGATGCTAATAGGTCGCGGTCGGCAGACCGCT
AAAGAAAGAGAATGGTAATAAGATGCAGTAGGAGGAACACCAGAAGCCTAGCCAACCTAAGCTATCCTAGCTCTATATCTATTGCTTTTCCTT
AGTCTAACACGTTAGACAACCTATCTTATTCTTAGTGATGGTAACTTAGTGTTGACAAGATAATCTTAGTGTAATACTATGCATCACGTAGGCG
GTGCTGAGGCACCTAGTAGCCAGCTAGTAAGGCATACGAAGAGACTAGCGCTTACATTGCTCTTTAACAATTTGCTTAGTGTAACCTATGTAT
GCCGTGGTTAACTACTTATTGAATGAGGTATTAACTATGACATTAAATAACCGTGAACTGTCCGTTCTCTTCACTCTGTTGTGCTACATGATTCG
TAACAACGAATTACTTACAGATGATGAGTTAGCCTTGTATCACCGCTTTCTTAACGAAGGTTGGACCGATACAGTTAATCAATACCGTAACATG
ATAGATGAGTTGAGGGAGGGTAAATAATGTATCAACATGAGGTATTCTTTGAATCAGCTAGCGAAGCTATTCGCTTCCGTGATGATATGATG
CAAGCTGGTGTAGGCGTTGATGTGTATCACTATTTGATAGATTACGACACTGAATATCACCGAGTTACCTTAGTATCTGAGTATGACAACCAA
GTCATTACTGAGTATCTAGGCAGTGAAGATTACGATTACGATGAAGTAATCACGACAAATCTCTAAATTAACTGTTGACAGCCACGGCATACA
AGGTTACATTAAGCATCAAGACGGCGACGTCTTTAAACATCCCGCTCTTTAACAATACGGTTTGTGTCTTGATAGGCTAACTAACTAACTAAGG
TAATTATCATGAAAGGGTTAATTTGTGTAGAACGTATGGTCAATGGTAAACTTGAAATATTACCACTGGAAAACCAATCTAGCTTCAAAGAGT
GGTATGGCTGTTTCTCACTGATTTAAGGTAAAGGCTGGCACTAGTCAGCCTATCAAGGCGCAAACCAAGCTCTTTAACAATTTGGATGGTAGC
TTCTTAGTCTGGATAGGTTAAACCTAGGAGATTCTCTTGAGTCTCCTATAATGTAACCTAACTAACTAAATGAGGATTAAAAGAGGAGATATA
CAATGGTTTTTACGCTTGAGGACTTCGTTGGTGACTGGCGTCAAACCGCGGGGTATAATCTTGATCAGGTCCTGGAGCAGGGCGGAGTTTCG
TCCTTATTCCAGAACTTAGGGGTAAGTGTTACGCCGATTCAGCGCATCGTGCTGAGTGGAGAGAATGGATTGAAAATTGACATTCACGTTATC
ATTCCGTATGAGGGTTTGAGTGGAGACCAGATGGGACAGATTGAAAAGATTTTCAAAGTGGTGTATCCCGTCGATGACCATCACTTTAAAGT
AATTCTGCACTATGGGACCCTTGTGATCGACGGTGTAACGCCAAACATGATTGACTATTTCGGTCGCCCTTACGAAGGTATCGCCGTCTTCGA
CGGAAAAAAAATCACTGTCACGGGAACATTATGGAACGGAAATAAAATTATCGACGAACGTCTGATCAATCCTGATGGAAGCCTGTTATTTC
GCGTTACGATCAATGGAGTGACCGGATGGCGTTTATGCGAACGTATTTTGGCTTAAAGAGGAGATATACAATGGAACGCAACGCAAATGCAT
ATTATAATTTATTAGCAGCTACGGTTGAAGCCTTTAATGAACGCATCCAATTCGACGAAATCCGTGAGGGCGACGACTATAGCGACGCCCTTC
ATGAGGTTGTAGACAGCAATGTTCCAGTTTATTACAGCGAAATCTTTACAGTGATGGCTGCTGATGGTATTGATGTTGATTTTGAGGATGCTG
GTTTGATTCCTGACACGAAGGATGTAACCAAGATTCTACAAGCTCGCATCTATGAAGCTCTTTATAATGATGTACCAAATGACAGCGATGTAG
TTTGGTGTGAAGGCGAAGAAGAGGAAGAATAAGGATGGAAAAGCAATATAACTTTATCTTTTCAGACGGTGTAACCCTGAAGTGTTCCCTAC
GATTCGCACAAATTCGTGAGGAAGTACTAGGCACTACATACAAACTATTTAGCTGACACTATAAGAGAAGGCTTAACAAGGCGTTACTAAGG
TAGCGCCTGATTAAACTTTCACTTACTAGGAGTTGAGATTATGAAAACCTTGATTGGATGCTTCTTGTTGGCTTCTCTTGCTCTGGCATTTACCG
CTAAAGCTGGTTATGACGCTTATAAAGTAGAACAAGCCCAGCAAGACTGGGCCAAAAAAAGTTCAACTTGTGCAGCAAGAGCAACACCTAC
GAGTACTGCAACAAAACACTAAGACACTTATGGAAAGAGTAACTAGCCTATAGCCCACCTGAGTGGGCTATGTGATATTTACTTAACACTATA
TAAGGTGATTACTATGACTACTGAAAACACCCTCGTGTCTGTCCGTGAAGCTGCAACCGCTGAAATCAAGCAACATTTAGACAATATCGGCAC
TTCTTACATCAAAGTAGGGGCTTGTCTGAATGAGTTACGCGGAGACTTTGAAGGTCAAAAAGAGTTTTTAGCCTATGTTGAAGCAGAGTTTGC
CATTAAGAAGGCACAATGTTACAAGCTGATGAGTGTAGCCCGTGTCTTTGAAGGCGATGATCGCTTTAAAGGCGTGGCGATGCGTGTAATGC
TGGCGCTTGTTCCTTTCGCTGATGAAAATATAATCATGGAGAAGGCCGCAGAACTCGCCGCAAATGGCAAGCTGGACACTAATGCCGTAAAC
GCCCTGATTGAACCTAAGAAAGAGTCAAAGGCCGAAACGGTACAATCTAAGGCTGAGACAGTAAAACCGCAGGAGAACGCGACTGAGTCCG
CAGAATCACATGAAATGCAAGCGCCGCAGGTAGTGCCACCCGCGAGCGAGCAGGAGTCCGACGAATCAGCACCTTGGGAAGAGGAAAGCA
AACCGGAAGCGCAAAGGCAGCTCCGATGGATAACACGGCTAATACTGAGAATGCCGCTATTGCTGGTCTGCTGGCACAAATTAAAGCACTG
ACTGAGCAATTACAGGCAGCCAATGACCGCATCGCCTCCTTAAGTAGCGCACGCGAAAGCAAGAAGGCATCCGCACCTATGCTGCCGCAGTT
CAAATCTTCCTGCTTCTACGCTCGCTTAGGCTTGAGCGCGGAGGAGGCAACGAAGAAAACAGCAGTTAACAAGGCACGCCGCGAACTGGTTA
AGCTGGGATACGGTGAAGGCCATGAGGCATGGCCCTTAATCTCTGAGGCAGTAGAAGAGTTGACTAAGTAACCTTATCGGTGGCATCTTCTT
AGGTGTCACCTATTAAGGTTTCTTTCACTAGGAGTAAACAAGATGCAAGGCCTACACGCTATTCAACTTCAACTTGAAGAAGAAATGTTTAAC
GGCGGTATCCGTCGCTTTGAAGCGGACCAACAACGCCAGATTGCATCCGGTAATGAATCAGACACGGCATGGAATCGCCGCTTATTGTCCGA
GTTAATCGCGCCAATGGCTGAAGGTATTCAGGCATACAAGGAAGAGTATGAAGGTAAAAGAGGCCGTGCACCGCGTGCATTAGCTTTCATTA
ACTGCGTAGAAAACGAAGTGGCAGCATATATCACGATGAAATCGTTATGGATATGCTGAACACGGATGTAACCTTGCAGGCTATAGCCATG
AATGTAGCTGACCGCATTGAGGACCAAGTACGTTTTAGCAAGCTGGAAGGTCACGCCGCCAAATACTTTGAAAAGTTAAGAAGTCACTTAA
GGCAAGTAAGACTAAATCATATCGCCATGCGCACAACGTAGCGGTAGTGGCTGAGAAGTCAGTAGCTGACCGTGACGCTGATTTCTCCCGCT

Figure 4B

```
GGGAGGCATGGCCTAAAGACACCTTGCTGCAAATTGGGATGACCTTGCTTGAAATCTTAGAGAATAGCGTATTCTTCAACGGGCAACCTGTCT
TCCTCCGCACCTTGCGCACTAATGGCGGCAAACATGGTGTTTACTACCTACAGACTAGTGAACACGTAGGTGAGTGGATAACTGCATTCAAAG
AGCACGTAGCGCAACTGAGTCCTGCCTATGCTCCTTGCGTCATCCCTCCGCGTCCGTGGGTATCACCTTTTAACGGCGGTTTCCACACTGAGAA
AGTAGCAAGCCGTATTCGTCTGGTAAAAGGAAACCGCGAACACGTCCGCAAGCTGACCAAAAAGCAAATGCCAGAGGTTTACAAGGCTGTT
AACGCGTTGCAGGCGACTAAATGGCAGGTTAACAAGGAAGTTTTACAGGTTGTGGAAGACGTCATCCGTCTAGACCTAGGTTATGGTGTACC
TTCCTTTAAACCACTCATTGACCGCGAGAACAAGCCAGCTAATCCAGTGCCGCTAGAATTTCAGCACCTACGGGGCCGTGAACTGAAAGAAAT
GCTTACGCCGGAACAATGGCAAGCCTTTATCAACTGGAAAGGTGAATGTACTAAGCTGTACACCGCTGAAACTAAGCGCGGAAGCAAATCGG
CGGCAACCGTTCGCATGGTTGGTCAGGCCCGTAAATATAGCCAGTTCGACGCAATCTACTTCGTGTATGCACTGGACAGCCGCAGCCGCGTCT
ACGCGCAATCTAGCACACTCTCACCGCAATCAAATGACTTGGGCAAGGCCTTGCTCCGTTTTACCGAAGGGCAGCGTCTTGATAGCGCTGAG
GCGCTTAAGTGGTTTTTGGTGAACGGGGCTAATAACTGGGGTTGGGATAAGAAAACTTTTGACGTGCGCACCGCTAACGTGCTGGATAGTGA
ATTTCAAGACATGTGCCGCGACATTGCAGCGGATCCGCTGACCTTCACTCAATGGGTAAATGCCGACTCCCCTTACGGCTTCCTTGCATGGTG
CTTTGAATATGCGCGTTATCTGGATGCACTGGATGAAGGCACGCAAGACCAATTCATGACGCACCTCCCAGTCCATCAAGATGGTAGTTGTTC
TGGTATCCAGCACTACAGTGCTATGCTACGCGATGCAGTAGGTGCGAAAGCAGTAAACCTTAAGCCCTCTGACTCTCCTCAAGATATTTATGG
TGCCGTTGCGCAGGTAGTAATTCAGAAGAATTATGCATACATGAATGCAGAGGATGCGGAAACCTTCACTTCTGGCAGCGTGACTTTAACAG
GTGCGGAGCTGCGTAGTATGGCTAGTGCGTGGGATATGATAGGAATCACTCGCGGCCTGACCAAAAAGCCCGTAATGACACTACCTTATGGC
AGCACACGTCTAACCTGCCGTGAGTCAGTGATTGATTATATCGTTGATTTAGAAGAAAAAGAGGCCCAACGGGCTATTGCGGAAGGGCGTAC
CGCCAATCCTGTACACCCTTTTGATAATGACCGTAAAGACAGCCTGACACCTAGCGCAGCTTATAACTATATGACAGCTTTAATCTGGCCTTCT
ATTTCGGAAGTGGTTAAAGCCCCTATAGTGGCAATGAAAATGATTCGTCAGCTTGCCCGTTTCGCAGCTAAAAGGAATGAAGGCTTAGAGTA
TACCCTGCCTACTGGCTTCATCTTGCAACAAAAGATTATGGCTACTGATATGCTCCGCGTATCTACTTGCTTGATGGGAGAAATCAAGATGAGT
CTACAGATTGAAACAGACGTAGTGGATGAAACGGCAATGATGGGCGCTGCTGCTCCTAACTTTGTGCATGGTCATGATGCCAGCCACCTTATC
TTAACAGTCTGCGACCTTGTTGATAAAGGGATTACATCTATCGCAGTTATTCATGACTCTTTTGGCACTCATGCAGGCCGTACAGCCGACCTTC
GTGATAGCTTAAGGGCAGAAATGGTGAAGATGTATCAAGGCCGTAATGCACTGCAAAGCCTGCTAGATGAGCACGAAGAACGCTGGTTAGT
TGATACCGGAATACAAGTACCAGAGCAAGGGGAGTTTGACCTTAACGAAATCTTAGTTTCAGACTATTGCTTCGCATAATATTAATAGGCCAT
TCCTTCGGGAGTGGCCTTTCTTTTACCTACTACCTGTAACATTTCATTAACATAAAAGTGTCTCACATGTGAGACTTATTTACCGGACACTATAG
GATAGCCGTCGGAGACGGGAAAGAAAGGGAAGATAAAGGATATAAAGGAAGTAATAGGTATTAAAGGTTATATAGGTTATCTAGGAATAC
CTATTACCTTCTTCCTTCCTCTTATTACCACTCAGAGGAAGGGCAGACCTAGGTTGTCTCACATGTGAGACTTCGTATTTACCGGACAGTATAG
ATAAGATTAACTCACTTTGGAGATTTAACCATGCGCAACTTTGAGAAGATGGCCCGTAAAGCTAACCGTTTTGACATGGAAGAGGGGCAGAA
GAAAGGCAAGAAGCTGAATAAGCCTGTCCGTGACCGTGCATCTAAACGCGCTGCGTGGGAGTTCTAAGTTATGGCTATTATTCAGAATGTAC
CGTGTCCTGCCTGTCAAAAGAATGGACATGATATTACTGGCAACCATCTCATGATATTTGATGATGGTGCCGGCTACTGTAATCGTGGACACT
TTCATGATAATGGTAGACCTTACTATCACAAGCCGGAAGGTGGCATCGAGATAACCGAGTTATCTATTACTGGCAATATCAAATATACACCTTC
TCAATTCAAAGAAATGGAGAAGGAAGGGAAGATAAGCGACCCTAAATTACGTGCCATCGCACTTGGTGGTATGCGTATGAAAGACCGTTGG
GAGGTCATGAATGAACAAGAAAGGGCAGAGCAAGAAGCAGAGTGGAAACTTGATGTTGAATGGTTCCTCACGCTTAAGCGTAAGAACCTTG
TTTCCAGGCACATTCGCGGCGACATTTGCGCATTGTATGATGTACGTGTTGGGCACGATGAAGAGGGTAGAGCTCTCACGGCATTACTATCCGC
GCTTCGAAAAAGGTGAGCTAGTAGGCGCTAAGTGTCGCACATTACCTAAAGATTTTAAGTTTGGTCATTTAGGTAAACTCTTTGGTATGCAAG
ATCTTTTCGGTATGAATACTTTGTCTCACGTGTTAGACAAGGGAAGACGAAAGGATTGCTTGCTCATTGTCGGCGGCGAACTGGATGCACTAG
CAGCGCAGCAGATGCTCCTTGATTCTGCCAAGGGTACTAAGTGGGAAGGCCAGCCATACCATGTATGGTCTGTCAACAAAGGCGAGTCTTGC
CTTGAAGAGATAGTGCAGAACCGTGAGCATATCGCCCAATTCAAGAAGATTATATGGGGTTTTGATGGAGATGAGGTAGGGCAGAAGCAGA
ATCAGCAAGCGGCTCGCCTGTTTCCTGGTAAATCCTATATCCTTGAATACCCCTCTGGTTGCAAAGATGCTAACAAGGCATTGATGGCTGGCA
AGGCTAAAGAATTTGTAGATGCATGGTTTAATGCCAAGTCATCTGATGAAGTCTTTGGTAGCCAGATTAAATCTATCGCATCTCAAAGGGATA
AGCTCAAGGCTGCACGTCCAGAGCAAGGACTGTCATGGCCTTGGCCTAAGCTGAACAAGGTAACGCTAGGTATTCGTAAGAACCAGCTTATC
ATTGTAGGTGCAGGGTCTGGTGTAGGTAAGACTGAGTTCCTTCGTGAAGTAGTTAAGCACCTCATTGAAGAACACGGTGAATCTGTAGGCAT
CATTTCTACAGAAGACCCGATGGTCAAGGTGTCCCGTGCTTTTATCGGCAAGTGGATTGATAAGCGTATTGAGTTACCTCCAACCAACGACCC
GAAAGAAGACGGATACCGTGAGGTGTTCGACTATACCGAGGAAGAAGCTAACGCCGCCATTGATTATGTAGCTGATACAGGTAAGCTGTTTG
TAGCTGACCTAGAGGGTGACTATTCGATGGAAAAGGTAGAGCAAACTTGCCTAGAGTTTGAGGCTATGGGTATTTCTAATATCATCATTGATA
ACTTAACGGGGATTAAATTAGATGAGCGTGCTTTTGGTGGGAAGGTTGGTGCACTTGATGAATGCGTCAAGCGGATTGGTACTATCAAAGAC
CGACACCCGGTTACTATATTCCTTGTATCACACCTTACACGTCCTCCGGCAAACCGTACCCAACACGAAGAAGGTGGCGAAGTTATCCTTTCTG
ACTTCCGAGGCTCAGGCGCTATCGGATTCTGGGCATCTTACGCCTTGGGGATTGAGCGTAATACAAGAGCTGAAACGCTTGACGAAAGGACT
ACCACGTACATCTCATGTGTCAAAGACCGCGACCAAGGTATCTACACTGGAACCAAGGTCATGCTTAAGGGTGACATTCAAACCGGACGTTTA
ATGGAACCACAAGCCCGTACTAAGTCATTTGATACAGGTGAAGCAAGGCAACAAGAAGTACCAGATTTACCGGATACTATAGAAGAGACTAC
CTTCGATGAAGAAAGTGAGTTCTGATTAGTGTATTTATCAGGCTTGTCTCACATGTGAGACAGGCTCTTATTAAGTACATTAAATAACTGGAG
ATTGATTATGTATAACTTAGTGTTGAATGTAGGTGACTTTGTACGCAACATCAAGAAAGATTCAAGTCGCTATCTTTGCCGTGGTGTTGTAACC
```

Figure 4C

```
TTTGTAGGTGAGAACCTGTATTATGTAGAATATCGCAGTGGTGTTAAGCAATATTACCACAAGAAGACAGCACATAAATATCTTGAAAAGATT
GTAGAGATAAACAATCAATGTAAGTGCATACATGATGAGGTTTGCGATAAATGTGCTCGCCAGATGCTTAAGAATTTCCTAGCTCCTCTTTATT
ATGGTGCTGGTCCTCAAACACTAGCAGAGTGCATGGCAGAAAAGAAAACCACACTCAAGAAAGAGCGTCGCAATGTAATCACTGGTAAGAC
TCAAAGTGAGATGATTAAGCAATGTGGCACTGCATTAGGTGTTACACAGTTTAATACTCGTGCATTGGGTAAATCCACAGGACAAGCTATGGT
AAAGATTGGAGAAGCCATGATGCATCCAAATGTACCTGTGCGAATCATGGATGTTGACCATGCAATCACAGAACAAGGTACGCAACGACGTG
TAATTAATAAGCATTTTGCCGACACTATAGAAGGCATTATTCGTAAGCAAGGGTTGAAAGGTCTTCACATCTTAAATGGTGAAGAATTACTGT
ACCTACCTATCGTTACTGAAGAAACATACGTGAATATCTAAGGAGTTAATCATGACTAAGGTATTAATTTATATGCGTGGACCTCATAAATGCT
ATGCAGTTGTAGCACCAAATGGTGTTAAGCCTTATCGTACTTCAAAAAGATTGGCATTAATAGGTGCTAGTAGTAGTGCAAGTTTCCAAATGG
AACTTTTTGGTCATTGGACTGAAAGGCAATTCCGTGAGGATTTTAAAGTCATTGGCAGCTTCATGGTGAAATATGCAGAATAAACATAGTCTT
AGAATGTTCGATGGTCATGAAAACCTGCAAGCCAAGATTACTAACCAAGCCTTCCTGTTCGCACAGTTAACTATGGCTGAGGCTAAGAAGAAT
AGTCTCACTCGTGAACAGGTTATCAAGGAGGCCACTTGGGAACCACACCAAGGTAAATATATGGGCCACAAATTAACTGTAACACGCAGTCG
ATAAGTCAAGGGTTGTCCAACGTGTTGGACAGCCTTTCATCATATTGATTGGGAGGTATTAAATGACTAAGTTTACTATGCAAGACCTCATTA
AATTACGTGATGAAATAGAATCACCGGAAGTTAATACAGAGTTTCACTACATTGATCCACGAGATAAACGAGAGATTCCTGATTATCAGATTG
AGACGGAGTTAATGTATGAAGATTATTGATTGGAAGAAGGAAGCAGAAGGCCGTATCCTAGTGATGGATGCGGAGGCTAAAGGCCTGCTGG
GTGCTATCCGCTACGGTCATCGTGAAGATGTACACATTATTTGCTGCATGGACTTGCTCACCACTGAGGAGTTCCTCTTCTTCGACCCATATGA
GATGCGTGACCCTGAAGCAAGGGAACACTTGAAAGAGTGGGAAGGCCATCAAGATGGGACCTTGGTTGATGGTGTTAACTTCCTAAAGCAC
TGTGAAGCCATCGTCTCACAGAACTTCCTAGGCTATGACGGGCTTCTCTTTGAGAAAGCCTTCCCTGACATCTGGAAGGGATTTAACTACACC
GAGAGGCGCGGCAAGGGCAGACTACGTGCTGACTTGTGTCCGGTACGCGTCATGGATACGCTGGTCATGAGTCGCCTGTTAAACCCAGATA
GACGCCTTCCTCCGCAAGCATATGCCAAAGGTATGGGTAACGTTGCCCCTCACTCAATTGAGGCGCACGGCATTCGTATAGGCCGTTATAAGC
CGGAGAACGAGGATTGGTCTAAACTAACTGACCACATGGTACATCGTGTACGCGAGGACGTGGCGATAGGCCGTGACCTATTCCTCTGGCTA
TTTAACGGAGAATGGACGGAGCACAAACGCCGTGGCGTGAATAAACGCACTGGCCTAGGTATTGAGACAGCCTTCCACATGGAGTCCATTGT
GACGCTGGAGATGAGCCGTCAGGCCGACGTGGATTCCGTCTGGATATAGATAAAGCATTAGCACGATGCGAGGAATTGGACGCTAAGATT
GATGAGACAGTCGCAGCGTTCCGTCCGCACATGCCTATGCGTATCAAGTCTAAACCTTTTAAACCGGAAGAAAAGAATGAAGTATGCCAACG
CGCAAATGATGGAGCTAGCAACAATATACCTACTGTCCTTGACCCCTCTCACTTTCTTCACGCAGAGAGACGAGGAGATCGCAAGACAGT
ATGGAGTGTCACTACTAAGTCTGGTGATTGGTCGGCTAGCGTCAAGAAAGACTTTCCTCACCTTAGAGGAAACCGTAATGACACGCCAAGTG
TCAAGTGGATTGGCGCTTACTCGCCTGTTACTTTCGAAGAGATTCCCTTGGGTAACAGGGATACAGTTAAGCAAGTGCTCTATGATTATGGAT
GGAAAGGTGTTGAATTTAACGATACCGAGCAAGCGCATCTCGATGAGCATGGCGTATTACCCAAGCCTTGGAGTGGGAAGATAAATGAAAA
GTCCCTTACTTTATGGCAAGAGAGAGCCGCACGTGAAGGTAAAACAGTCCCTGATTGGTGCTTGGGTATCGCTGCATGGTACATACTCGTATC
CCGTCGTGGTCAGATCCTCAACCGTGGTGACGTTGAAGCCTTCGACCAGAAGGGGGTGTGGCCTTCGCAAGCTGGTATACGAAAGTGTCGCG
GCCTTGTACCTGTAGCATTTAACAAGGAGTTAGGAATCAATGCGCAGCAATACTACGAAAGGTACGGATGCTGGCCTACGTCAGACAAGGAT
GACGGAGAATGGCGTGTGCCAGCTATTGCTATTAGTATTGGAACTTCTACGTTCCGTATGCGTCATCGTAACGTGGTTAATATTCCTGCCCGT
GGCTTGTATCCTTTACGTGATTTATTCATAGCAGGGAAAGGCAAGCTAATCCTTGGTTGTGACGGTGCAGGTCTTGAACTGCGTGTCCTGTCT
CACTTCATGAATGACCCTGAGTACCAAGAGATTGTACTGCACGGTGATATTCATACGCATAACCAGATGAAGGCTGGTCTTCCTAAGCGTGAT
ATGGCGAAGACATTTATATATGCCTTCCTATATGGGTCTGGTATAGCTAACCTTGCAGCAGTATGTGGTGTTACTGAGGAAGAAATGGAGGA
AGTTGTGGCAAGATTTGAGGTTGAACTACCATCTCTTGCACGTCTTCGTGAGAATGTTATCGCACAAGGTAACAAGTTTGGCTACCTACAAGC
ACCTGATGGTCATTGGGGTCGCATCCGTATGTCTGGTGGTGAACTTAAAGAACACACTATGCTTAACGTACTACTCCAGATGACTGGTTCTCT
GTGTATGAAATACGCATTGGTCAGAGCGTTTGCAGTGATGCGCAAGGAAGGTGTGGCCTTAGATAGCATGGGAAACCCTTGCGGTATAGCT
AACGTGCACGATGAAATCCAGATGGAAGTCCCTGAAGATGAGGTCTTGTATCTCAACTACGACTTGCCTTTCACCTTAGAAGGGTTCGAAACA
GAGAAGGCTGCTGTGAAAGCAGTGTTCGATGCAGAGGAGAAACGTGTTCATGTGGATTCTGAAGGACGTATGTGGTCTGCTGCAAATCTCG
TTAGTGTTGATGCTGGTGTACTTCATTGCCAGCGTCGTTATCACCGTGCAGGGCATATCATTGCCGACGCAATGACCTGGGCGGGTCAGTACC
TGAAGATGCGTTGTCCGATGGCAGGTGAGTATAAGATTGGTGCAAGTTGGAAGGAAACACACTGATGGACAGGTTTGATATTGTTTGCCTAT
TCTCTACCTTCTTTCTTATATTCCTTATGCTTGCTTGCTATGGAAGTATGCGATTAGATATACCTGATGAAGAGGAGGGTTACGATTGATGCAG
GCATCTTTTATTATTCTTGGAGTCATATATTTATGGTAGTATTCTGGGCTTTCTCTGGCATTGACCCAGATTGTGATGGTAACTACGACTGAGT
TATACTCAAGGTCACTTACGAGTGGCCTTTATGAATAACTTATTCCTACTTATTTTGTCTAACATGATTTACTGGACACTATAGAAGGAAAGCAT
AGGTAATCTAGGTTTATAAGGTAGTATAGGTAATTAAGTAAATATAGGAGATATAAATATGTCTATGGTAACTACTCTGGTATTCGTGGCTCA
ATACTTTCGTGGTCTTGCTAATAAGTTCAAGTCCAAGGCTATCAAAGCTATTGAGGCTCGCATCGAAGCAGTACAGGCAGAGCAAGTTAAAGT
TGAAGAACATCGTAGTTCTCAAATGATTGACTGTCATAACCGCTACTATGCATCTCGTGATGAACTAAATGCACGTCAAGTCAAAGAGGTAGA
AGATATGCTGGCACGTCACCAGCAAGAGCGTGACAGCCTGAAAGCTGAATTTGAAGAGAACAAGGCATCAATTGCTCTTGTACATCAAGCTG
CATCTGACAGTCTGAAGAAAGAGATTGTTATGCTGGAAATCGAACTGGATAACCTGACCAAATAAGGGGGGGTTATGATGGAAGAAGTAAT
TCAAGCTAAACATGTAGGTATTATCTTTCGCGATCTAGAGCAGCGTAAAGTTGCAGGTCATACTCGTCTGGCTAAAGAGGAAGACACCGCAAT
CACTACTGTAGAACAAGCAGATGCCTATCGTGGACCAGAGTTCACTCAAGGTGAAACTTGTCACCAATTGAGCCTATCAATTTGTGACACTAT
```

Figure 4D

```
GGCTATTGTAAATGTGCAAGAAGTCGAAGAGGGTGAGTGTGTCAGTTACATCTACCCTTTAGATACTATTGCACGCATTAAGGTAATCCATAA
GTAATTACTAGACACTATAGAACAATAGGTCGGCTTAGTTCGGCCTATGATTGTAAAGTGTTGTTGATGTTGAACCATTGTGCATCTTGCACAA
CCCGATACCGTATAGGGCTTTCTAGTGAGTACATGCTTGTGCTCAGTACAAAGCTAACTGACAATAGGAGACTAAATAAATGGCACGTGGTG
ATTTTGATTTTGGTGCTCAGGTTACTAAATCTGAAGGTAAAGTCTTTAAGAATCCAGAAGTAGGTGATCATGAAGCAGTAATCTCTGGCATCA
TTCATGTTGGTTCCTTCCAAGACATCTTTAAGAAAGGTAATACCACTGAAGTTAAGAAGCCAGCAAACTTTGTTCTGGTTAAGATTGTCCTGAT
GGGTGACGATGACAAGAACGAAGATGGTTCTCGCATGGAACAATGGATGGCTGTGCCTCTGAAGTCTGGTGATAAGGCAACACTGACTAAG
TTCCTGAATGCAGTTGACCCTAAAGAGTTGCTGGGTGGCTTCGATGATTTCATTGGTGAATGCCTGACTGCAACGATGGTCGGTTCTGGTGAT
AAGAATGACGATGGCTCATTCAAGTATGTTAACTGGAAGGGATTTGGTGGTATGCCGGACAAGCTGAAGAAACTGGTCATTGCTCAGGTTGA
AGAGGAAGGTCTGTCTATGACAGGTCACATTACCTTCGACAAGCTGACCAAAGAAATCCTTGATGACATCCCAGCCAACTTGGTGCGTCAATA
CTTCCTGAACGAGACGCCTCGTGGTAAGAACCTGTCTGTTGCTGGTTCTCACGTAGAAGCAATCATTAAAGCTGCTCGTGAAGAAGACCCAGA
ATGGAAGAAGGCTAAGAAGAAAGACGAGGAAGATGCTACCCCAGCTAATCGTAAATCTCTGGATACTGGTGAGTCTGTTCCACAGGAAGTA
CCTGAAGCAGAAGATACTCCTGCACCGGAGATGGATGAGGACGCGGAATATTAAGGAGAAAGGATGAAAGTACAAATCGTAACCCTGCACT
GCAAGAAAGGAATTACAACTCTTGGCGGCAACACTTTTCACTCCTTCTCTGAAGGGGACACATATGCCGACCTGCACTACATCTGGCGCGACG
GACAGCACGTGGTGAACTACAGCGACCCAGCTACGGGGAAACGCCACGGCGTATCGCTTCCGGCGCATGACATTGCTCAGGTGAACACAGT
TTTATAAAGTCTCACGTGTGAGACAAATCGGTGTCCGGTATTTACTGGACACTATAGAAGAGAAGAATTTTAATCGGCGATAATGCCATAACC
AACAAAAGGAGAATTTAATATGTTCAAGATTGAAACTATCGTAAACCGTGTTGTTAAAGGTGCTGCTCTGGTATCCGTTGAGTCTTTCATTATC
GTCGATGAAACTGATCAACTGGTAGCTGGTACTAAGGCTTACGATACCCGTGAAGAAGCTCAGGCTAAGATTGACAGCATGGGTAACTTCGC
TGCTGGTCTGGAGTTCGCTCGTGCTTGCTTCCCTGAGCAGGCTGACAAAGCTCAGATTGGTAAGGCTAATATCGTAGCTGAATATCTGGATTG
GGTTGCTGCTGGTAAACCAGTGAAAGAAGTTAAGGCTGCTGAAGAAGCTGAAGCTCCAGCAGAAGAAGTAGCTGCACCGGAAACTCCGGTA
AGTGAAGAGGAAGAATTTTGATAATAGCAGGTGTTGCCTCTGTTAGTCCTAGCTGACTATCACGCTCACCTCATCTAATGCCCTGTCTGCCTTA
GTGTAGGCAGGGTCTTTTGCGTAATAGTTATTGGAGAATGAATTATGCCGACTATTGAATCTCGAATTGAACTGGACATTAGCTACAATGCAA
TCACCAGACAGTATATTGGGGTTGCCTATGATTACAAAACTGGTGAGAAGCTAGTGGAGGTGAGACAATGGGATGACTATTGGTTAAGACA
GAACCTCCATGATGCGGTGTCCTCCTTCCTGAAGGAGTGGCCTACATGCGACCAAACTTCGACTTCGGAGCTACAGTATCGGAAGACAATAAC
CTGTTGCTGTGGCCAACTGAAGGTAATCGAATCGCTTTAATAGATGCTGATATGTTACCTTACATCATAGGGTATACAATCAGTGATATGACTT
ATGTACGAGCCACAACTCGTGTTAAGTCAGGGCAAGTCCCCTCAATCAAAGATACACCTGAGTGTAAGCAAGCGTGTGACCGTGTGAACTCC
TTGCTTAACTCTTGGGTGTATGCAGCAGAATGTGATGCAGCTAAGTTGTTCATGACGAAATCAGAAGCTAACTTCCGTGTCCGCCTAGCATTC
ACCAAGCCTTATAAAGGTCAACGTAAGACCGAGAAGCCTCCATTCTTCTATGAATTGCGAGAGCATCTCTTAGAGGTTCACGGTGCAATCTTG
GCAGATGGAGAGGAAGCAGATGACCTCATGAGTATCGCACAATGGGACAGCCACCGCCGCTTCCAGCAAGATACAGGTAACGAGTTCCCTA
TCGGTAGTCCAGAGCATAAAGCATTCTCTGATACTTGCATCGTTTCCTTGGATAAGGATTTGATGATTGTTCCCGGTTGGCATCTACAGCCGGG
TCAAGAGAAGAAATGGGTAGAGCCTATGGGTTGGCTTGAGGCTAATGGGCAAGTCAAAGATCTAAAAGGTGCTGGCCTC
ATGTTCCACTATGCACAGATGATTATCGGTGATGATATTGATAACTATGCTGGCATACCAGGTCGTGGTGCTAAATATGCCTATGATCTTCTCA
AAGATTGTAAGACAGAGAAAGAGTTGTACATGGCAGTGCTGGGTGCTTACAAGGCTAAGTTCGGGCATGGACAAGTTAAAATTAAGAATTA
CCGAGGTGGTTATCGTATCGGCAAAGCCTTTGACCTAATGCTTGAGTGTGGTCGCTTATCTCACATGGCAAGATTCAAGGGTGATATATGGCG
AGCCGATAAGAACCCAATCTTGTGGGAGATGATGCGGAATGGTTAGCAAATTAAAATCATCGGAGGTGGCAGCTTATAAGAAGGAATTGC
TAGATAAGCAAGGATGGAAATGCCCTCTGTGTGGCGGCAGTCTCAAAGCTGTCACACCTGTAAACCGTGTACTTGACCATGACCATGAGACA
GGATTCTGCCGCGCTGTTGTATGCCGAGGCTGCAATGGTGCGGAAGGGAAGATTAAGGGTGTTATCTCTGGTTATGGTAAGGCTGGTAACA
ACCGTTACTTCCAGCTTCAATGGTTAGAGCGACTATATGAATACTGGAAGTTACATAGTACGCCTCAGACAGATAAGTTATATCACAAACATC
AAACGGAGGCAGAGAAGCGCGAGGCTAAGAACCGTAAGGCACGCCTTGCTTATGCAAGAAAGAAGGAGGTTAAAGTTGGGTAAGCTGCGC
AGCTTGTACAAAGACTCCGAGGTACTTGATGCAATCGAGCAAGCTACCGACGAGAAAGGTAATGTTAACTACAATGAGATGGCACGTGTATT
ATCGTGTCATACTGTGGGTAAGAAGATTACCCGCCAGTTGGCTCGATACTGGCATGGTCAATTCAAGAAGACCAAGAAGAATGGTGATTACT
ACCAGACCCTTCTGCAAGAAGATAAGCGTATCAAAGAAGAGCGTAAGCTCAGGACTCCTGACCGCTACGAGGATTTGGCTATTGTGCCATTG
CCTGACTCGCCTCATCGAAGTGTACTGGTGATCCCTGATACTCATGCACCCTTATGAGCACCCAGATACCCTAGAGTTCCTTGCAGCCGTGGCA
GCACGTTACCGTCCAGACACAGTGGTACACCTAGGAGATGAGGCAGACAAACATGCCCTGTCATTCCACGATTCGGACCCAAATCTGGATAG
TGCTGGCATGGAGTTAGAGAAGGCTCGTATCTTCATGCACAAATTGCACAAGATGTTCCCTGTGATGCGCCTGTGTCACTCTAACCACGGCTC
TATGCACTTCCGTAAGGCAAGCGCCAAAGGCATCCCTGTGCAATACCTGCGCACCTATCGTGAAGTCTTCTTCCCGCAGGGAGGTGGCGACC
AGTGGGATTGGCAACATACGCACGTCCTTGAGTTGCCGAATGGTGAACAAGTGGCATTCAAGCATCAACCTGCTGGCTCTGTCCTAGCAGAT
GCAGCGCATGAGCGTATGAACCTTGTGTGGTCACTTGCACGGTAAGATGTCTGTGGAGTACGCACGTAATACATGAACAGTATTGGGC
TGTGCAAGGTGGCTGCTTAATTGATGAGTCATCCCGTGCATTTGCCTATGGTCGTGAGTCTAAATACAAGCCAGCATTAGGTTGTGTGGTCAT
TCTGGAGGGTGTGCCTCACATTGTCCCGATGCAAACCAATAGCGACAACCGTTGGATTGGCAAGATTTAGTTGACACTATAGAACAAAGGGC
TAGGTAAGACTTTATCGGCTGGCGTATCCAAATGATATTGCACTAGCCCTTGATTGTATAGTGAATGGAGGATTCAATATGTCACACTATGAA
TGTAAGAAGTGTCATAAGCGTTATGATTACTGTACTTGTGGTCAAGAGAAAACATCTTTTAAAGTTGGAGACAAGGTATTTCGTAATGAAAAA
```

Figure 4E

```
GATTCGATTCCTTGGAATCAATACTGCAAAGAAGCTGGTATTGACCCTGATAGCCCTGTAACCATAGATGATATTGATGGCATTAACTTGTGCT
TTCGTGAGGTGAGGGGTACAGGTTGGGATTCCAAAAAATTCAAACTTGCATCTGATAAGTTAGACAACAATATGGTAATTAAGCCTAAGCAC
TACGAGTTCTTTGATGGCGTAGAGGCAATCACTATCATTGCCCGCAGTATGACCGAGAAGCAATTCGCTGGCTATTGCATGGGTAATGCTTTG
AAGTACCGTCTACGTGCAGGTAAGAAGTTCAACACTGAAGAAGACCTGAAGAAAGCAGATTACTACAAAGAGTTATTCCAGAAGCATCGTCA
CGAATGTATTGATGAGGATATTTGATATGAATATCTTTGAGTTCCTAGGTCTTCCAGAAGACCACCGCAATCACCCATTCATGCTGGTGAAGC
ATCGCGGTGAAGTTCCTGAGAAGAAATTAACTTTTCCATGTTATGCACAGGTGAAACGAGATGGTATCTTTTCTGCTGTTGTTGTTCGCACTGA
TGGTGTCGTTGGCATTTTTGGTCGCACTGGTAAGAAATTGGCAAACACTGAAGGACTCGAACAAGCCTTTGCTACCTTTCCGGTTGGCATTTA
TCTTGGTGAGCTTCAGTCTATGGCCATTGATATCTACCTTGAGGCAATCTCTGGGGTTGTGAACCCCAATCGCACTGAGCCACTTGATTTCATA
GGCCAGCAGATTAAAGACAACCTGTATATCGACTTCTTCGATATGTTAACTATTAAGGCATTCCATGATGGATTCACTGATGTTTCTTATCTCA
AACGTTACGATGCTTTACATCGTCGTATCGGCGCTCATCTTAGCGGGTGCAACGCTATCCTTCCTATCACTCCTTGCCATAATGAGCGAGAAGT
TGAAGCGTTTGCGCAAGAGCAAATAGATGCAGGACGTGAGGGTGCTGTATTCAAACTGGACTGCGATTATGAAGCAGGACACAAAGGTTAT
CGTCAGACTAAAGAAGTCCGTAAGGTAACCTATGACCTTACTTGTATTGGCTTTGAAGAAGGTAAAGGCAAATACAAAGGTAAGGTAGCTAA
CCTCATTTTCAAATGGAAAGGAGGCAAGACAATCAAAGCTATGTTAGGTAAGGGGTGGACTCATGCAGATGCAGAGCAGATGTTCCACGAC
ATTAAACATGGTGGACGATTGAATGTCATTGGTAAAATCTTTGAAGTCAAAGGTCTTCAGGATTCAAGCAAGGGCAACATTCGTCTGCCCAAA
GCGGGAGAATTAAGACATGACAAAGATGAACCAGATTTCTTTTGATAGCATGAAGGCAACTCGTGCAGTTGAGGTAGCAGAAGCTATCTTCG
AAACTTTATCCTGTGGCATGGAAGTGCCATATACTTTACTTGCTGATGCAGAAGAACTTGGTCTTTCTGTAGAAGCTATCCAAGAGAAGGTTG
ACGAATTATATGGTACAGACGAAGAAGAAACCGACGATTTCATTTGAAGGAATGGAGATGCTTGAGATGATTCTCAAGCCTTCTTCTCCTAAG
GTGACTAAGACTCATGAAGAGTTAATCGTTGATGAAGTTAAGCGTTACATCATGGATTGTGTCAGAGCACAACTGGTGGTCCAATGATACGT
CCAGCCTCCTTCCTAGATATTCCTGAGATTATAAACCTTGGGAATAAATATGTGGAAGAGGAAGTCAAGGTTGTAGCCCACCACTCAGCCTCA
TGGAATGCAGAACAAAGTGCCATAACCTTTGTGCATCTCTTAATAGAGACCCACCACTCAGCCTCATGGAATGCAGAACAAAGTGCACATAAC
CTTTGTGCATCTCTTAGTAGAGAAGATTTATCCCTATGGGTTGCTGTAGATGAAGGGCAGATTGTAGGGTTCCTGTGGGCTGGCTATCACGAG
TTGGCCCCTTGGACACCTGTAAGAGTTGCCTCTGACATTCTCTTTTATATTATACCAGAGAGGCGAGGAACACTACTTGGTATGCGTCTCATCA
AAGCCCTAAAGCAATGGGCTAGTGATAATGAATGCTCTGAGGTTCGCCTGTCTATCGCCTCTGGTATTAATGAAGAACGTGTCGGACGTATGT
ATAAGCGACTTGGCTTTGAACCGTTTGGCACTGTGTATAACCTGAAGTTCTAAGGAGATAACATGGGTGTTGTAAAGAAAGCATTTAAGGCT
ATCGGTCTTGCTCAAGATGCACCACGTATTGAAGCCAAAGTCCCAGCACAGCAGCTTGAGCGTAAGCCTGAGACTGAAGCTGAAGATATTCA
AATTGGTGCAGGGGATGATGCTACTGCATCTGCAAAAGGTAAGCGTGGCCTTGTCCGTCCGGTAGCTTCTAGCTTGAAGGTGTAATATGAAA
CAGAGCATAGATTTGGAGTATGGAGGTAAGCGGTCTAAGATACCTAAGCTATGGGAGAAGTTCTCCAATAAACGTAGCTCTTTCCTTGATAG
GGCGAAGCATTACTCCAAATTAACCTTGCCCTATCTGATGAATGACAAAGGTGATAACGAGACTTCGCAGAATGGATGGCAAGGTGTAGGTG
CTCAGGCAACCAACCATCTAGCCAACAAGCTAGCGCAAGTACTATTCCCTGCACAGCGTTCCTTCTTCCGTGTAGACTTAACTGCACAAGGTGA
GAAGGTTCTTAATCAGCGTGGCCTGAAGAAGACAGAGCTAGCTACCATCTTCGCTCAAGTGGAAACACGGGCAATGAAAGAGTTAGAGCAA
CGTCAATTCCGGCCTGCTGTAGTAGAAGCATTTAAGCATCTTATTGTTGCTGGCAGCTGTATGCTATACAAGCCGAGCAAAGGTGCAATCAGT
GCTATCCCAATGCATCACTACGTAGTTAACCGTGATACCAATGGCGACCTGTTAGACATTATCTTGCTACAAGAGAAAGCCTTACGTACCTTTG
ACCCAGCTACACGTGCGGTAGTAGAGGTTGGCCTGAAAGGTAAGAAGTGCAAGGAAGATGACAGCGTTAAGCTGTACACACATGCTAAGTA
TCTTGGTGATGGATTTTGGGAACTCAAGCAATCTGCTGATGATATCCCTGTGGGTAAGGTGAGTAAAATCAAATCAGAAAAGCTACCTTTCAT
CCCCATTAACTTGGAAGCGAAGCTATGGTGAGGATTGGGGTCGACCTCTTGCAGAGGATTACTCCGGTGATTTATTCGTTATCCAATTCTTATCT
GAAGCGGTTGCCCGTGGTGCTGCGCTGATGGCAGATATCAAGTACCTGATTCGTCCTGGTGCTCAAACTGATGTTGACCACTTTGTTAACTCT
GGCACTGGTGAGGTTGTCACTGGTGTAGAAGAAGACATCCATATTGTACAGTTAGGTAAGTACGCAGACCTCACACCTATTAGCGCGGTTCT
AGAGGTATACACTCGCCGTATCGGTGTTGTCTTCATGATGGAGACAATGACACGCCGTGACGCCGAACGTGTTACTGCTGTAGAAATCCAGC
GAGATGCGTTAGAGATTGAGCAGAACATGGGTGGTGTATACTCCCTCTTTGCTACTACTATGCAATCGCCAGTAGCGATGTGGGGTCTGCTG
GAGGCAGGGGAGTCCTTCACTAGTGACTTAGTGGACCCTGTGATTATCACAGGTATTGAAGCTTTAGGACGCATGGCTGAGTTGGATAAACT
GGCTAACTTTGCTCAGTATATGTCACTGCCATTACAATGGCCTGAGCCTGTCCTAGCTGCTGTGAAATGGCCTGACTATATGGATTGGGTGCG
TGGTCAAATCTCTGCTGAACTGCCGTTCCTTAAATCGGCTGAAGAGATGGCACAAGAACAGGAAGCACAGATGCAAGCACAGCAAGCACAG
ATGCTTGAAGAAGGTGTGGCTAAGGCCGTGCCGGGTGTAATTCAACAAGAACTTAAGGAGGCGTAATGTCTTTCTCATTTACTGAACCGTCA
ACCACTCACCCTACTGCTGAAGAGGGTCCGGTAGAAACCAAGGAGGTAACAACTGATGCTGCTACTACTGATGCTCCTGCTGACGCTGGCAC
TTCTGTACAAGATGACAATGCTGGTGCACAACCTACTGAAGACACCGGAGGAGAAGCTTCTGGACAGCCTTCAGAAAAAGGAGACAATGGC
GGAGAGAATGGTGAACCTAAGCCAGATGATACCGCGACCGACACTGAGGAAGTGCAATACTTCTTCGGAGAACATGAAGTAACAGTAGACA
TCCCACAGGATGTAACTGACAGCCTTAAAGAGAAAGGCATTGATGCCAAGCAGGTTGCCAAGGAACTCTATTCCAAAGGTGGCAAGTTTGAA
CTGTCAGATGCAACCAAGCAGAAATTGTATGATGCTTTTGGCAAGTTTGCGGTAGATGCTTACCTATCAGGTCTAAAGGCTCAAAATGAAGCC
TTCTTCCTGAAAGAAGCCAACGCAGCTAAAGAGTTGGAAGCAGCTAACACCCAACGCTTCTCTGATGTTTCTAAGGAAATTGGTGGCGAAGA
AGGTTGGTCCCGTCTTGAGGAGTGGGCACTTGAAGCGCTGTCTGATGACGAACTAATGGCATTCAATGCGGTGATGGAATCTGGCAACCAGT
ACCTGCAACAATATGCTGTTCGTGAACTGGAGGGTCGTCGTAAGCAGGCACAGGGGGATGATAAGCCATCCCTGATTGAGCCATCAGCACCT
```

Figure 4F

```
GCTAAGGCTAATGAAGAGAATGGCCCACTGACGCGAGATCAGTACGTTCAAGCAATCGCAACTCTTAGCCAGAAGTACGGCAATGACCGTAA
AGCTATGGCAGAAGCTCAGGCTAAACTGGACGCCCGTCGCCGTGCTGGCATGGCTCGCGGTATCTAATTCAGTATTTACTGGACACTATAGA
AGGGAGAAAAGTTCTCCCTAGTTATCAATTTGATTTATAAGGAGATTATAATACATGTCTACACCGAATACTCTGACTAACGTTGCTGTATCTG
CGTCCGGTGAGGTTGACAGCCTTCTCATTGAGAAGTTTAATGGTAAGGTCAATGAGCAGTACCTGAAAGGTGAGAACATTCTGTCCTACTTTG
ATGTACAAACTGTTACTGGCACTAACACAGTGAGCAACAAATATTTGGGCGAAACTGAGTTGCAGGTGCTAGCACCGGGTCAGTCCCCTAAT
GCCACCCCTACTCAGGCGGATAAAAACCAGTTGGTAATTGATACCACTGTCATTGCTCGTAACACTGTGGCTCACATCCACGATGTACAAGGT
GACATCGATAGCCTGAAACCAAAACTGGCTATGAACCAAGCCAAGCAACTGAAACGTCTGGAAGACCAGATGGCAATTCAGCAGATGCTGTT
AGGCGGTATTGCTAACACCAAGGCCGAACGTAACAAGCCGCGTGTTAAAGGGCATGGCTTCTCTATCAACGTTAACGTAACTGAGAGTGAAG
CACTGGCTAACCCTCAGTATGTTATGGCTGCGGTAGAGTATGCTCTGGAGCAACAGCTTGAGCAGGAAGTGGACATCTCTGATGTAGCTATC
ATGATGCCGTGGAAGTTCTTCAATGCTTTGCGTGATGCAGACCGAATTGTAGATAAGACTTACACTATCAGCCAGTCTGGTGCAACCATTAAT
GGCTTCGTTCTCTCTTCTTATAACTGCCCTGTGATCCCGTCTAACCGATTCCCTACCTTCGCTCAGGATCAGGCTCACCACCTGTTGTCTAATGA
AGATAACGGCTATCGTTATGACCCTATCGCAGAGATGAATGGTGCAGTTGCTGTTCTGTTCACTTCCGACGCACTGCTGGTGGGTCGTACCAT
TGAAGTGACTGGTGACATCTTCTATGAGAAGAAAGAGAAGACTTATTACATTGACACCTTCATGGCTGAGGGTGCAATCCCTGACCGTTGGG
AAGCAGTGTCTGTAGTTACCACTAAACGTGATGCAACTACTGGTGATGCTGGAGGTCCTGGTGATGATCACGCAACCGTACTGGCTCGTGCA
CAGCGTAAGGCTGTATATGTCAAAACCGAAGGTGCTGCGGCTGCATTCTCTGCTGCCCCAGCAGGTATCCAAGCGGAAGACCTTGTAGCGGC
GGTACGTGCTGTAATGGCAAATGACATTAAGCCGACTGCAATGAAACCTACTGAGTAACACCTATGCCCTATCTACCTTGCGTAGGTAGGGTT
CTTTTTGTTAGGAGGATTCATGCCTGTAATTAGACAAACCAGTAAATTAGGACATATGATGGAAGATGTGGCCTTCCAGATTATTGATAGTAA
GCTGGAAGCGGTAAACTTGTGTATGCGAGCTATTGGTCGTGAGGGTGTGGATTCCCTCGACTCAGGGGACTTGGACGCAGAAGATGCAAGC
AAAATGATCGACATCGTATCCCAGCGGTTCCAGTACAACAAAGGAGGTGGCTGGTGGTTCAATCGTGAACCAAACTGGCAACTTGCACCAGA
CACTAACGGTGAAGTTAATTTACCTAACAACTGCCTAGCAGTATTGCAGTGTTATGCTTTAGGTGAAAAGAAAGTACCTATGACTATGCGAGC
AGGTAAGCTCTACTCTACTTGGAGTCACACCTTTGATATGCGTAAGCATGTTAATGCTAATGGTATGATTCGTCTTACCTTACTCACCTTACTAC
CCTACGAGCATCTACCTACAAGTGTAATGCAGGCTATTGCCTATCAAGCTGCTGTAGAGTTTATTGTGTCTAAGGATGCAGATCAGACTAAGC
TAGCCACTGCGCAGCAGATAGCCACTCAGCTTCTTATGGATGTACAATCTGAGCAAATGTCACAGAAGCGATTAAACATGCTGGTACATAACC
CTACTCAGCGTCAGTTTGGTATCATGGCTGGTGGCTCTCAGAATGTACCTGCTTACTCTCATTCACCTTATGAGAGTTGGGCGCTCCGTCCGTG
GGAGGATCGTTAATGGAAGTACAAGGTTCATTAGGTAGACAAATCCAAGGGATTAGCCAGCAGCCGCCAGCGGTACGCTTGGATGGTCAGT
GCACAGCTATGGTTAATATGATACCTGATGTAGTGAATGGTACTCAATCACGCATGGGTACAACTCATATTGCAAAGATACTTGATCGGGG
ACTGATGACATGGCTACTCATCATTATCGCAGAGGTGATGGTGATGAAGAGTATTTCTTCACGTTGAAGAAAGGACAAGTTCCTGAGATATTT
GATAAGTATGGGCGCAAATGTAATGTGACTTCACAAGATGCACCTATGACCTACCTCTCTGGAGGTTGTTAATCCAAGGGAAGATGTGCAATTC
ATGACGATAGCTGATGTTACTTTCATGCTTAATCGTAGGAAAGTAGTTAAAGCTAGTAGCAGGAAGTCACCTAAAGTTGGAAACAAAGCCATT
GTGTTTTGTGCGTATGGTCAATATGGTACATCTTATTCCATTGTAATTAATGGGGCCAACGCTGCTAGTTTTAAAACACCGGATGGTGGAAGT
GCAGACCATGTTGAACAAATTCGAACTGAACGTATCACTTCTGAATTGTACTCTAAGTTGCAGCAATGGAGCGGTGTGAGTGACTATGAAATA
CAAAGAGACGGTACTAGTATATTTATCGAGAGACGGGATGGTGCTAGCTTTACAATAACAACCACCGATGGTGCAAAAGGTAAGGACTTAGT
GGCTATCAAGAATAAAGTTAGCTCTACTGACCTACTCCCTTCTCGTGCGCCTGCTGGTTATAAAGTACAAGTGTGGCCTACTGGCAGCAAACC
TGAGTCTCGTTACTGGCTGCAAGCTGAGCCTAAAGAGGGAAACCTTGTGTCTTGGAAAGAAACAATAGCTGCTGATGTATTACTTGGGTTTG
ATAAAGGCACAATGCCTTACATTATTGAACGTACAGATATCATCAACGGCATAGCTCAATTCAAGATAAGACAAGGTGATTGGGAAGATCGT
AAAGTAGGGGATGACTTGACTAACCCTATGCCCTCTTTTATTGATGAGGAAGTACCCCAGACAATAGGTGGAATGTTCATGGTGCAGAACCG
CCTATGCTTTACAGCAGGTGAAGCGGTTATTGCTTCTCGTACATCATACTTCTTCGATTTCTTTCGTTATACGGTTATCTCTGCATTGGCAACTG
ACCCCTTTGATATTTTCTCAGATGCTAGTGAAGTCTACCAGCTAAAACATGCAGTGACCTTAGATGGCGCTACCGTGTTGTTCTCTGATAAGTC
ACAATTCATACTGCCAGGCGATAAGCCTTTAGAGAAGTCAAATGCACTGCTTAAGCCTGTTACAACATTTGAAGTGAACAATAAAGTGAAGCC
AGTAGTAACTGGTGAATCGGTAATGTTTGCCACTAATGATGGTTCTTACTCTGGTGTACGAGAGTTCTATACAGACTCTTATAGTGACACTAA
GAAGGCACAAGCAATCACAAGTCATGTGAATAAACTCATCGAAGGTAACATTACCAACATGGCAGCAAGCACCAATGTCAACAGGTTACTTG
TCACTACCGATAAGTATCGTAACATAATCTACTGCTACGATTGGTTATGGCAAGGAACAGACCGTGTACAATCAGCATGGCATGTATGGAAGT
GGCCTATAGGTACAAAGGTGCGAGGTATGTTTTATTCTGGTGAATTACTTTACCTGCTCCTTGAGCGAGGAGATGGCGTGTATCTGGAGAAG
ATGGACATGGGTGATGCACTAACCTACGGTTTGAATGACCGCATCAGAATGGATAGGCAAGCAGAGTTAGTCTTCAAGCATTTCAAAGCAGA
AGATGAATGGGTATCTGAGCCGCTCCCTTGGGTTCCTACTAACCCAGAACTTTTAGATTGCATCTTAATCGAGGGTTGGGATTCATATATTGGC
GGCTCTTTCTTATTCAAGTACAACCCTAGTGACAATACTTTGTCTACAACCTTTGATATGTATGATGACAGCCATGTAAAAGCGAAGGTTATTG
TTGGTCAGATTTACCCTCAAGAGTTTGAACCTACGCCTGTGGTTATCAGAGACAATCAAGACCGTGTATCCTACATTGATGTACCAGTTGTAG
GATTGGTTCACCTTAATCTTGACATGTACCCCGATTTCTCCGTAGAAGTTAAGAATGTGAAGAGTGGTAAAGTACGTAGAGTATTAGCGTCAA
ACCGTATAGGTGGTGCTCTCAATAATACAGTAGGCTATGTTGAACCGAGAGAAGGTGTCTTCAGATTTCCACTGAGAGCTAAGAGCACGGAT
GTTGTTTATCGTATTATTGTAGAGTCACCTCACACATTCCAGCTTCGTGATATTGAGTGGGAAGGGAGCTACAATCCAACCAAAAGGAGGGTC
TAATGGCTATAGGTTCAGCCGTTATGGCTGGTATGTCTTCTATTGGTAGCATGTTTGCAGGCAGTGGTGCAGCAGCCGCTGCTGGAGGTGCT
```

Figure 4G

```
GCCGCAGGTGGCGGAGGTTTGCTAGGTTCACTAGGTGGATTCCTAAGTGGCTCTACTGCTGGTTTCTCTAATGCTGGCCTTCTTGGTGCTGGC
CTTCAAGGGTTAGGCTTGATTGGTGATCTATTTGGTGGAAGTGATGAAGCCAAGGCGATGAAGAAAGCACAAGAAGAGCAATGGCGGCAGC
AGCTTATTGCTACACAAGAGGCGTACAAGACAGTGGCAGACGCAGAACGTTCTGCTGCTAAACAATATCATGCAGATGCAATCAGTAATCAG
GCTTCACTGCTACAGCAGCGAGCACAGGTTGCATTACTTGCTGGGGCTACTGGTACTGGTGGTAATTCTGTGTCCTCTATGCTTAATGACTTA
GCAGCAGATGGCGGCAGGAACCAGAGTACTATCATTGATAACTATGAGAATCAGAAGATTAATTTCACCAACCAGCTTAAGTCTATCCAACGT
GGTGGTCAGATGCAGATGCGTGAGTTTAAGAAGCCTTCTGCTATGAATACCTTGGTTAAAGGTATTCCAAGTCTGGCATCTGCCTATGTAACT
GGTAGTAAGTCTGGCAAGGCATTGGGTAAAGCCTTAACTGATTCTCGCACATATTCATCTGGAACAAGAGGTATTTAATGGCAATTGAGCGA
CAAGCAGTACAAGGTCTGCCACAAGTGCAGGCCACTTCTCCTAATGTCATGACCTTTGCACCTCAACAAGTGGGAGGTGTGGAGGCTGGCGT
GGCTTCTACCTCCGGTAGTAGGTTTATCGAAGACCTTATTCGTGCAGCAAGCAGCGTGGCTGATGTTACCACTGGTATCCTTAATCAGAAGAT
TGAGGAAGATAAGGTTGTTCAAATGGAACGGGCATATAACGGATTAATGCCTTCTGAGGATGCAACTCGTGGTGGCGCTCGTGCTAACATGC
TTGTCAAAGCTCAACTGCTAGCTAATGATGAAGCAGCACGAATGAAAGACATGGCTACTCGTTTCCAAGGAACGGATGACGAATGGACACAA
CTTATGGTTGACTCTCGTAATGAGATGCAGAATAAGCTGTTCCAGCAATACCCTGAGTTGCAAGGTGACAAAGATACTATGCGTATGGTCACT
AATGTCTTCCAAGAACAGCAGCCTCAGATTTGGGCTACACGAACCCAGCATAAACTTGACCGTGAACAAGCAGACCGTGAGGATACCTTTGA
CGGGCGAGTGGCTTCTACTTGGGATTCTAATATTGACCCTGAAGCCTCTGGCTATGCTTTACAGGAACGAATCCGCGAAGGTCTTACTCAAGG
ATTACTACCTGAACAGATGTACAAGAAGTTAGTCCAGCGAGCAATTTCACTTGCACAAGGCGGTGATGTTAGCATGGCTGAAGCCCTGAAGT
ATGTGAAGGACGATAAGGGTGTTTCTGTTTATGCTAAGAATCCACAGCTTATCACAGCCATCACTAGTGGTAATGCAGTTTGGGCTAGGAATA
ATGTAGCTGATGTAACTCGTATGTCTTTCGAAGTTAAAGAATCCTACCTTGCAGGTGATTTAACTGATGAAGAATTGTTGGAACGAGCACAGC
ACATTAATAATCTGACAGGTAACTCTGTCTTCTCTAATCCAGAACTAGAGGCACTGATGCGCCAACGGGCTAAGCAGAATGCAGAGCTAGGT
GCAATGCAGGATATGCGACGTGAGCTTTACTCCGACCGCCTGACTGGCTTCCAAGGTAAGACTGATAAAGAGAAGAAGGCTTACATTGATGT
TATCAAACAGGATAGCCAACTTTATGCAGACCAGCAAATCAAACAACGTGGCTTGGACCCTTACAGTCAAGAGGCTGAAGCTATTCGTGGTG
CAGTGGAAGTGCAGCGCCTGCAATTCATGAACTCCAAAGGCTTAGTGGATGATACCTTTGAGTCTCGTATCAAAGCCATGGAATCTATGCTAT
CGCCTGAGCACTTTGCCAAGGGCGAACCACAGGAGTTGATGACTATTCGCCAGTTGTGGGAACAGTTACCAGAAGAGAGCCGAGGTGTCTTT
GGTGACACGGTGAATGGCTACATGGATAACTACAACACTGCACTACAAATGGGAGAGACACCTTTGCAGGCTGCAAGGTTTGCGCGTAAAG
CACAGCAGAAATTCTCTCGTACTGAGAAGGAAACCAAGAAGTTCAACTCAGCTATTGGAGATGCACTGGATGAGGTATCTGGTGCTGGCTGG
TTTGATGGTAAAACCGAAGTGTCAGACTTAGGTAAAGCTATTGCGGAAGAAGAGTTACGAGCTAAGGCCAATATGTTGTGGTCTAGTGGTAT
GCGTAACATGGATTCCATCAAGAAGGCTTTAATTACTTGGGGCAATAAACGCTACACTCAATCAGAGGATGCAAAGACTTCCGGTGGCTATTT
CATTAAAGGTGATTACACTTCTGCATCTGATATGCTTATGTCAGTTGGGAAAGGCGTAAACCCTACCGATGTACCTCTGGCGCTTGGTAGGTA
TGTAGAAACACAGATGCCAGAATTGAAGAAGGAGCTTCAAGAGGGGAAACTAAAGATGATATATACATTGATTACAATGAACAGAAAGGT
ACTTTCGTGATTCGTGCTGGTGCAGCAGGTCGCCCTCTTTCTGGAGTAATCCCTGTAACCTCTTTAGATACCACTTCACTACTAGATTCTGCCTA
TCAGAAGAAAGTAGAGGAACGAGATAAAGGCGAGTATGTTCACCCGTATCGTACAGATATTGGTGCACAAGAGCCTATGCCAGCTAAACCA
ACTGCCAAAGATATTGGTAAATTTGGACTAGCTAACTTCCTCATGTCTTCTGCTTTTGCTTCTGGTGAGAATCTGCCTTCTAACTTCGAGATTAA
CTATCGAGGTAATATGCAACAATTCTATGACAAGCTAGCTATGGATGAGAATAAAGATAAAGTTGGCTTTAATAAGGCAACTGGAACCTTTAC
TCCATATAAAGACGCTCACGGTGAGTCTATCGGTTACGGTCATTTCTTAACGGAAGAAGAGAAGCGAAACGGGTATATTAAGATTGGCGATG
AACTAGTTCCCTATCGAGGGTCTATGTCTCAGCTTACAGAGAGCAAGGCTCGCGCTCTTATGGAGCAAGATGCTAAGAAGCATGTGCCTCCTA
CTCGTGACTGGAAGATTCCGTTTGACCAGATGCACCCTGCACAGCAACGTGGCTTGATGGATTTAAGCTACAATTTAGGTAAAGGTGGAATCC
AGAACTCACCGCGTGCTCTTGCTGCATTCAAAGCTGGTAAGCTTACGGAGGGCTTTATCGAAATGCTGGGCACTGCATCAAGTGAAGGTAAG
CGTATTCCTGGCCTACTGAAGCGACGCGCTGAGGCATACAATATGGCATCTGCTGGTGGTGTGCCTAAGATTACCGAAGTGGAGACTCGTGA
AGATGGCTCCATGTGGGTTAGGTTTGGTGGACCTATGCCAGCAGGTTCTGTCTCGGCATGGACTCATAAACGTATTGGCGCGGATGGTTGGT
ATCAGGTTTATGAGGCTGCACCTACCAAGTTAGCTAAAGATTCTAAGGTAGGTAAAGTTAAGTTGTAGTACCTAACTCAAGGCTTGTCTCACA
TGTGAGACAGGTCTTTATGATAGGCACTATGGAGGAATTATGGAACAAGACATTAAGACTAATTGGGCTGGATATGTCCAGTCTACTCCTGA
GCCGTTTTCTATTGAGGCGGCTCCGGTATCGGTCCTACGATACGCCAGCGTAATGAGTTACAAGAGCAAGTTCTTGAAGCTAAAGCTGACGC
TGATATCTTAGGTGCTGTAGGTGCTGCCTTCCAGAATGAGTGGTTGGCATTCGGAGGCAAGCGGTGGTATGACCGTGCCACTGCTGATTTCA
CACCTCAACCAGACTTTGAGATACAACCTGAGCAACGTGAAGCACTACGTTTCAAATATGGTACGGATATGATGCAGACAATCACTGAGGGT
GTTCGTTCTGAGGATGAATTGAACTTCCGTATTCAGAATGCGGATGAAGACCTTGAGCGCAATAAGCGCATTGCTCAGGCTGGCTGGGTTGG
CTCTGTGGCGACGATTGGCGCTGCTGTGCTTGACCCTGTGGGATGGGTTGCCTCTATTCCAACCGGTGGTGCCGCTAAAGTTGGACTCGTAG
GCCGTGCTGTGCGTGGCGCTATCGCCGCTGGCGTGAGTAATGCCGCTATTGAATCCGTATTGGTCCAAGGTGACATGACTCGTGATTTAGAT
GACATTATGGTAGCACTGGGTTCCGGTATGGCTATGGGTGGCGTTATTGGCGCTGTAGCGCGTGGTAGGGCCACTAAGCTCAGTGAGCAAG
GTGATGACAGGGCTGCTAGCATTGTGCGCAGTGCAGACGCAGGGGACCGCTATGTTCGTGCTGTTGCCGATGACAGTATCGGTGCGATGCG
TGTTAAGGGCGCAGAGGTTCTCACTGAGGGTGTATTCGATATCTCCAGTAAGAGTGAAGACCTACTGAAAACCTTGCAACGAGAAGGTAATG
CGATTGATATGACACCTCGCCGTTGGGCTGGAACTATGTCTGCCCTCGGTACTGTCGTGCACTCATCTAAAGATGCAAGTATCCGAGGCCTTG
GTGCTCGTCTGTTTGAATCCCCACAAGGTCTAGGTATGCAGAAGGCATCTGCTAGTCTTATGCAGAATACTAACTTAAATCGCCTGAAATCTGC
```

Figure 4H

```
TGATATGAACCGCTTCAATGATGGGTTTGATTTGTGGCTTAAAGAGAATAATATCAATCCAGTAGCAGGGCATACCAACTCTCATTATGTACA
GCAATACAATGAAAAGGTGTGGGAGGCAGTGCGTATTGGCATGGATGAGTCTACACCTAAATCTATCCGCATGGCTGCTGAGGGACAACAG
GCTATGTACAGAGAGGCGCTGGCTTTACGTCAACGTTCTGGTGAAGCGGGATTTGAAAAGGTAAAAGCCGACAACAAATATATGCCTGATAT
CTTTGATAGTATGAAAGCCAGACGTCAATTCGATATGCACGATAAAGAAGACATCATCGAACTTTTCTCTCGTGCCTACCAGAATGGCGCTCG
TAAGATTCCAAAGGAAGCAGCAGATGAGATTGCACGAGCACAGGTAAATCGCGTTGCTGATGCTACCTTAACTGGAAAGCTTAGTTTTGAAA
AGGCAATGTCAGGTCAGACTAAGGCAGAGTATGAAGCTATCATGCGTAAGGCAGGCTTCAGTGATGAAGAAATTGAAAAGATGATAGAAGC
TCTGGATAACAAAGAAACCAGAGATAACATCTCTAACCGAGCTAAAATGAGTTTAGGATTAGATGTTACTCAAGAATACAATGGCATTCGTAT
GCGTGACTTCATGAATACCAACGTGGAAGAGCTAACAGATAACTATATGAAGGAAGCAGCAGGTGGCGCTGCATTGGCTCGCCAAGGCTTCT
CTACCTATCAGGCTGCACTTAATGCAATTGACCTTGTAGAGCGAAATGCACGAAACGCGGCTAAGGATAGCAAGGCTAGTTTGGCATTAGAT
GAAGAGATTCGTCAGATGCGAGAAGGTCTTCGCCTGATTATGGGCAAGTCGATTGATGCAGACCCACAGGCTATATCTACTAAGATGATGCG
TCGTGGTCGTGATATCACAGGTGTGCTTCGCTTAGGTCAAATGGGCTTCGCACAGCTAGGTGAACTTGCCAACTTTATGGGTGAATTTGGTAT
TGCTGCAACTACTATGGCTTTAGGTAAGCAATTCCGCTTCACCTCTAAGGCGTTGCGTAATGGCGATGGCTTCTTCCGAGATAAGAACTTAGCT
GAGGTTGAGAGAATGGTGGGGTACATTGGTGAGGATAACTGGCTAACAACTAAGGGTGCACGTCCTGATGAATTTGGTGATGTAACCACAG
TAAGAGGGATGATGGCTCACTTTGACCAATCCATGAACTCAATACGTCGTGCTCAAACCAACCTATCACTCTTCCGCATGGCACAGGGTTCTCT
GGAGCGAATGACTAATAGGCAAATAGCTTTGTCTTTCATTGACCACCTTGAAGGCAAGAAGATTATTCCTCAGAAGAAACTGGAGGAACTTG
GTCTTACTCAGGAGTTCATGACTAACCTACAGAAGCACTATGATGCTAACTCTAAAGGTTCTGGCTTGCTTGGCTTTGATACAATGCCTTATGC
CATGGGTGAAACTTTAGCTAATGCTATTCGTCGTAAGTCAGGTCTAATCATCCAACGTAACTTCATTGGTGATGAAGGTATCTGGATGAACAA
AGCACTAGGTAAGACATTTGCACAGCTTAAGTCATTCTCTCTTGTATCTGGTGAGAAGCAATTTGGTCGAGGGATTCGCCACGATAAAATTGG
TCTTGCTAAGAAGACAGCTTACGGGTTTGCTTTGGGTTCAATAGTGTATGCGGCAAAAGCCTATGTGAACTCTATTGGGCGAGAAGACCAAG
ATGAATATTTGGAAGAGAAGTTATCGCCTAAAGGGTTGGCCTTTGGTGCAATGGGTATGATGAGTACAACTGCTGTATTTAGTCTAGGTGGA
GATTTCTTAGGTGGCCTAGGTGTTCTACCTTCCGAACTCATTCAATCACGCTATGAAGCAGGTTTCCAAAGTAAGGGTCTGATTGACCAAATAC
CTCTCGGTTGGCGTTGGTGCAGATGCAGTAAATCTGGCTAACTCAATCAAGAAGTATGCAGAAGGTGACACAGAAGGTGTAGATATCGCTAAG
CGAGCACTCCGTCTTGTGCCACTTACCAATATAATAGGTGTCCAAAACGCATTGCGTTATGGCTTAGATGAACTGGAGGATTGATGAGTTATA
CTTTCACAGAACATACAGCCAATGGTACGCAAGTCACCTATCCTTTTAGCTTTGCTGGTAGGGATAAAGGTTATCTTCGTGCCTCAGATGTGAT
AGTGGAGTCTCTTCAAGGTAACACTTGGATTGAAGTTACATCTGGCTGGCAACTAACTGGCACGCACCAGATTACTTTTGATGTAGCACCAGT
TGCAGGTTTGAAGTTCCGTATTCGAAGGGAAGTACAAAAAGAATATCCATACGCTGAGTTTGACCGTGGTGTTACCTTGGATATGAAGTCTTT
AAATGGTTCTTTCATTCATATACTGGAGATTACACAGGAGTTACTTGACGGGTTTTATCCAGAAGGATACTTCATTAAACAGAATGTAAGCTG
GGGCGGCAATAAGATTACTGATTTGGCTGATGGCACAAATCCGGGAGATGCAGTAAATAAAGGGCAGCTTGATGCCATCGACAAGAAGCAT
ACAGATTGGAACGCCAAACAGGACATTGAGATTGCTGGCCTTAAGGCTGGTATGACTTCTGGTATTGCGCACAGAACTGTTCCTTGGTACAC
GATAGCCCAAGGTGGTGAGATTTCCGTAAAACCACCTTATGAATTTCAAGATGCACTAGTTTTCCTTAATGGGGTATTGCAGCACCAAATTGT
AGGCGCATACTCTATAAGCAACAACACTATCACTTTCGCAGAGCCGCTTGTGGCTGGTACAGAGGTGTATGTGCTGATTGGTAGTCGTGTGG
CTACATCTGAACCTAATATTCAGTTGGAGTTGAACTTTGACTTAGTAGAAGGCCAACAAGTAGTACAGATTGGCTCTGCATTTAAGTACATTG
AGGTCTACCTTGATGGATTATTACAACCTAAACTTGCTTATCAGGTAGACGGTGACATTGTTACTTTCTCAGAAAGAGTACCAGAATGCCGGA
TGACTGCTAAGATTATCACAGCATAAGGAGGTGGGATGATTAACTCCGAACTGGTAGATAGTGGTGTGAAGCTTGCGCCACCTGCACTCATA
TCAGGTGGGTACTTCCTCGGTATCAGTTGGGATAATTGGGTGTTAATAGCAACATTCATTTATACCGTGTTGCAAATTGGGGACTGGTTTTAT
AATAAGTTCAAGATTTGGAGGGGAGAAGCGTGAGCGTACACAATAAACATGCAGCTACAGAGGACGAGGTTGGCATTCTGCATGGTGCTATT
ACCAAAATCTTCAATAAGAAAGCACAGGCAATACTGGACACTATAGAAGAAGACCCTGATGCAGCATTACATTTAGTGTCTGGTAAGGATATT
GGTGCGATGTGTAAGTGGGTTCTTGATAACGGCATTACCGCCACACCTGCTGCACAGCAGGAAGAGTCCAAGTTATCTAAGCGCCTCAAGGC
TATCCGAGAGGCATCCAGTGGTAAGATAATTCAATTCACTAAGGAGGATTGATGGCTAAGGCAAGAGAATCACAAGCGGAGGCTCTTGCCA
GATGGGAGATGCTACAGGAGTTACAGCAGACCTTTCCTTACACCGCGGAAGGTTTGCTTCTCTTTGCAGATACAGTTATTCATAACTTAATTGC
AGGCAACCCTCATCTGATTCGTATGCAGGCGGATATCTTGAAGTTCCTATTTTACGGACACAAGTACCGCCTCATCGAAGCGCCTCGTGGTAT
CGCTAAGACAACACTATCAGCAATCTATACGGTATTCCGTATTATTCATGAACCGCATAAGCGTATCATGGTTGTGTCCCAAAACGCCAAGCG
AGCAGAGGAAATCGCAGGTTGGGTAGTTAAAATCTTCCGTGGCTTAGACTTTCTTGAGTTTATGCTGCCGGATATCTACGCTGGGGACCGTGC
ATCCGTTAAGGCGTTTGAGATTCATTACACCCTACGTGGTAGTGATAAGTCTCCTTCTGTATCCTGTTACTCAATCGAAGCAGGTATGCAGGGT
GCTCGTGCTGATATTATTCTAGCGGATGACGTAGAGTCGATGCAGAATGCTCGTACGGCAGCGGGCCGTGCCTTGCTTGAGGAGCTGACTAA
GGAGTTTGAATCTATCAACCAGTTTGGGGATATCATTTACCTTGGTACACCTCAGAACGTAAACTCTATCTACAACAACCTACCTGCTCGTGGT
TACTCTGTTCGTATCTGGACTGCGCGTTACCCTTCAGTAGAGCAAGAGCAATGTTATGGCGACTTCCTTGCACCTATGATTGTTCAAGATATGA
AGGACAACCCAGCACTTCGCTCAGGGTACGGGTTGGATGGTAATAGTGGTGCACCTTGTGCCCCTGAAATGTATGATGATGAAGTCCTGATT
GAGAAGGAAATCTCTCAGGGTGCTGCTAAGTTCCAGCTTCAGTTCATGCTTAACACTCGCATGATGGATGCTGACAGATACCCATTACGCCTG
AACAATCTAATCTTCACCTCGTTTGGTACAGAGGAAGTCCCTGTGATGCCTACGTGGAGTAATGATTCCATAAACATCATTGGTGATGCACCTA
AGTATGGTAACAAGCCTACGGATTTCATGTACAGACCTGTAGCTCGCCCATATGAATGGGGTGCTGTCTCCCGCAAGATTATGTATATTGACC
```

Figure 4I

CTGCGGGTGGTGGTAAGAACGGAGATGAGACGGGTGTAGCCATCGTATTCCTGCACGGCACATTCATTTATGTGTATCAGTGCTTTGGTGTA
CCTGGCGGATACCGAGAGTCGTCCCTGAATCGCATTGTGCAGGCCGCAAAGCAGGCGGGTGTTAAAGAGGTATTCATTGAGAAGAACTTTG
GTCATGGCGCGTTTGAGGCGGTAATTAAGCCGTACTTTGAACGAGAGTGGCCTGTAACTCTGGAAGAGGATTACGCCACCGGACAGAAAGA
GTTGCGTATCATTGAGACGCTGGAGCCGCTCATGGCAGCCCATAGGCTTATCTTCAATGCAGAGATGGTGAAGTCAGACTTTGAGTCGGTAC
AGCACTATCCGCTTGAACTACGCATGTCCTACAGTCTTTTCAATCAAATGTCGAACATAACGATTGAGAAGAACAGCCTCCGGCACGATGACC
GCCTAGACGCCCTGTATGGCGCTATACGGCAATTAACTTCTCAGATAGACTATGACGAGGTTACACGGATTAATCGCCTCAGAGCGCAGGAG
ATGCGCGATTACATCCATGCTATGAACACACCTCATCTACGCAGGGCAATGCTATATGGAGATTACGGTACTGAGCGAAGAGTGACCAACAC
TTCCGTAGCGATGCAGCAGCGAGTTTACGGGCAGAACTACCGAAATAAATCGGCAAGCAGAAATACACTTTCTGCAAGGATTTCAAGGACTT
ATTAATTACTGGACACTATAGAAGGAAGGCCCAGATAATAAGAGAAAATAATAGGTAATATATATATAGGTTAACCTAGGTTATATAGGTAT
GCCTTAGTATGGGTGTACTCCTGTACACCCTATTCCTTACTACCTTACTATATTTACATAATAGGAGAGAGACAATGGCTAATGATTATAGTAG
TCAACCATTAACAGGTAAGTCTAAGAGAAAGCAGGTACAACCTGTAAGTGAAGAACTAATGCTTCCGGTGCTCAAAAAAGAGGAAGTTAGTA
AGAAAAGCAATGTTATTAATGATGCCACCAAATCAGGTAAACAGAAAGGGGCCATGGTGTGCCTTGAAGTGAAAGGTGGTGTATTGAAGAT
TGCTATCGCGGTTGATGGCAAAGAAGATTCAGAGTGGAAGTTAGTAACAGTGGAACCAACTGTTAACCCAGTTTAAGATAAGGAGGAAGAT
TACATGGCTAAATATGGTACTACAGGTTCTGTTACTGGTCAGGCTTTTCGAGTAAAAGCAGTACAAACTATTGCAACGGCAATCCCGATGCCT
GTTGTTAAAGAAGAAGACCTTAAGAGTAAAGACCACCCTATCAACATCAAACATTTATCAGGTAAACAGAAAGGTGCAATGGTTGCTCTTGA
GAAAGGTGACACAACCTTACATATTGCTGTTGCACGTGGTAGTGAACCCACAGACCCTTGGGATGTAACTGGTATGGAAAAGGACGCTGTTA
CTCCAGCAGGGGTATAATAATGCTTAATAAATACTTCAAGCGTAAAGAGTTTGCTTGCCGTTGTGGGTGCGGTACATCCACTGTTGATGCTGA
ATTACTACAGGTAGTCACAGATGTGCGTGAGCACTTTGGTTCTCCTGTAGTTATCACTTCGGGTCATCGCTGTGCTAAGCACAATGCCAATGTA
GGTGGCGCTAAGAACTCCATGCATCTTACTGGTAAGGCTGCTGACATTAAAGTGTCTGGCATATTACCTTCTGAAGTGCATAAGTATCTTACTA
GCAAATACCAAGGCAAGTATGGTATAGGTAAGTATAACTCCTTCACTCACATCGATGTACGGGATGGTTGTGCGCGATGGTAAGATGTGTTG
AATGGTGTGAGCGTATGGTTGCCCAAGCTGCCGAGGATGGCAACTATGATGACTGGAAGAACTACTCTGACTTGTTAGCTCAATGGAAAGG
GAGATGCAATGAAAAAGCTGTTTAAGTCTAAGAAGGTTGTAGGTGCACTGGTTGCACTTGTTATTGCTCTTGTTTCTGTAGGTCTTGGTGTAG
ACCTTGGCTCTGGCACGGAATCCTCTGTGACAGATGTGGTCTGCCAAGTGATCACCTGTGAATAAGTTTCTAGAAGTTCTGGCAGGTCTTATT
GGCCTGCTTGTCTCTGCTAAGAAGAAACAAGAAGAGAAGGAGGCACAAAGTGAAGCGAATCATGTTAGTGACAACCCTTCTGATTGGTTCGC
TGACCACTTCCGGGTGTCAGCAGGCGTTACCAGAGAAAGCAATGGTGAAACCTCTGAGGCCGACGCTGACGGCAGTTTACGAGGTAGACGA
TAAGGTCTGCTTTAGTAAGCCTGACGCTACAAAACTTGGTTTGTACATTCTCTCGCTAGAACGCGGATACAATTAATACATAGCTTTATGTATC
AGTGTCTTACGATTTACTGGACACTATAGAAGAGGTAAGATAGCGCCGTTCTTTTGAGCGGCCTATTACTAGCCAATCTTCATAGGGAGGGTT
GGAAAGTAATAGGAGATAGCATGGCTAAATTAACCAAACCTAATACTGAAGGAATCTTGCATAAAGGACAATCTTTGTATGAGTACCTTGAT
GCGAGAGTTTTAACATCAAAGCCGTTTGGTGCTGCAGGTGACGCCACTACTGATGATACGGAGGTTATAGCTGCTTCATTAAACTCTCAGAAA
GCTGTCACAGTCTCAGATGGTGTATTCTCTAGCTCTGGTATTAACAGTAATTACTGTAACTTAGACGGCAGGGGTAGTGGCGTGCTAAGTCAC
CGTTCAAGTACAGGTAACTACTTAGTATTTAACAATCTACGTGCAGGTCGCTTAAGTAATATTACGGTAGAAAGTAATAAGGCGACTGATACA
ACTCAGGGACAGCAGGTATCCCTTGCTGGTGGAAGTGATGTTACTGTAAGTGACGTTAACTTCTCAAACGTTAAAGGTACTGGTTTCAGTTTA
ATCGCATACCCTAATGATGCGCCACCTGATGGACTTATGATTAAAGGCATTCGAGGTAGCTATTCCGGCTATGCTACTAATAAGGCAGCCGGA
TGCGTACTTGCTGATTCCTCAGTTAACTCCCTCATAGATAACGTCATTGCTAAGAACTACCCTCAGTTCGGAGCAGTAGAGTTGAAAGGTACA
GCCAGTTACAACATAGTCAGTAATGTTATAGGGACAGATTGCCAGCATGTAACTTACAACGGCACTGAAGGGCCAATAGCTCCTTCTAATAAC
CTTATCAAGGGGTGATGGCTAATAACCCTAAGTATGCAGCGGTTGTTGCAGGCAAAGGAAGTACGAACTTAATCTCAGACGTGCTCGTAGA
TTACTCAACTTCTGATGCTAGGCAGGCTCATGGTGTTACAGTAGAGGGTTCTGATAACGTCATAAATAATGTGCTTATGTCAGGATGTGATGG
TACTAACTCTTTAGGACAAGGGCAGACTGCTACAATTGCACGCTTTATAGGTACAGCTAATAACAACTATGCGTCTGTATTTCCTAGCTACAGT
GCTACAGGTGTTATTACTTTCGAATCCGGCTCTACCCGTAACTTCGTAGAGGTAAAGCACCCTGGCAGGAGAAACGACCTTCTCAGTTCTGCT
AGTACTATTGACGGTGCAGCTACTATTGACGGCACTAGTAATAGTAACGTAGTGCACGCACCTGCCTTAGGGCAGTACATAGGTAGTATGTC
AGGTAGGTTCGAATGGCGGATTAAGTCCATGTCACTCCCTTCAGGCGTTCTTACTTCTGCTGATAAGTACAGAATGCTTGGAGATGGTGCTGT
GTCATTAGCTGTAGGTGGGGGCACTTCTTCTCAAGTTCGCCTATTTACTTCTGATGGTACTTCTCGGACAGTGTCCCTCACCAACGGTAACGTG
CGTCTTTCTACCAGTAGCACAGGCTTTTTGCAGTTAGGTGCTGATGCAATGACCCCAGACAGTACTGGTACATACGCATTAGGTTCCGCCAGC
CGAGCATGGTCTGGCGGTTTTACTCAAGCAGCATTCACTGTTACCTCAGATGCTCGGTGTAAAACAGAACCTCTTACTATCTCAGATGCCTTAC
TGGATGCTTGGTCTGAAGTTGACTTTGTGCAGTTTCAGTATTTGGATCGTGTTGAGGAGAAGGGTGCAGACTCAGCTAGATGGCACTTCGGT
ATCATCGCTCAGCGAGCTAAGGAGGCTTTCGAACGTCACGGTATAGATGCACATCGCTATGGCTTCTTGTGCTTCGACAGTTGGGATGATGTA
TACGAGGAAGATGCCAATGGCTCTCGTAAACTGATTACACCACCAGGTTCCCGCTACGGTATTCGTTACGAGGAAGTACTGCTGATATTAGAGGC
TGCGTTGATGCGGCGGACTATTAAGCGTATGCAGGAAGCACTAGCTTCCCTGCCTAAGTAAGCAACAGGCAGTGCGTAAGCACTGCTTTTAG
CGCAACTTTTCTTAAAGGTTATCACGGTGGTAGCCTTTCAGAAAAGGAGGTTACATGATTCAAAGACTAGGTTCTTCATTAGTTAAATTCAAGA
GTAAAATAGCAGGTGCAATCTGGCGTAACTTGGATGACAAGCTCACCGAGGTTGTATCGCTTAAAGATTTTGGAGCCAAAGGTGATGGTAAG
ACAAACGACCAAGATGCAGTAAATGCAGCGATGGCTTCAGGTAAGAGAATTGACGGTGCTGGTGCTACTTACAAAGTATCATCTTTACCTGA

Figure 4J

```
TATGGAGCGATTCTATAACACCCGCTTCGTATGGGAACGTTTAGCAGGTCAACCTCTTTACTATGTGAGTAAAGGTTTTATCAATGGTGAACTA
TATAAAATCACGGATAACCCTTATTACAATGCTTGGCCTCAAGACAAAGCGTTTGTATATGAGAACGTGATATATGCACCTTACATGGGTAGT
GACCGTCATGGTGTTAGTCGTCTGCATGTATCATGGGTTAAGTCTGGTGACGATGGTCAAACATGGTCTACTCCAGAGTGGTTAACTGATCTG
CATCCAGATTACCCTACAGTGAACTATCATTGTATGAGTATGGGTGTATGTCGCAACCGTCTGTTTGCCATGATTGAAACACGTACTTTAGCCA
AGAACAAACTAACCAATTGTGCATTGTGGGATCGCCCTATGTCTCGTAGTCTGCATCTTACTGGTGGTATCACTAAGGCTGCAAATCAGCAAT
ATGCAACAATACATGTACCAGATCACGGACTATTCGTGGGCGATTTTGTTAACTTCTCTAATTCTGCGGTAACAGGTGTATCAGGTGATATGA
CTGTTGCAACGGTAATAGATAAGGACAACTTCACGGTTCTTACACCTAACCAGCAGACTTCAGATTTGAATAACGCTGGAAAGAGTTGGCACA
TGGGTACTTCTTTCCATAAGTCTCCATGGCGTAAGACAGATCTTGGTCTAATCCCTAGTGTCACAGAGGTGCATAGCTTTGCTACTATTGATAA
CAATGGCTTTGTTATGGGCTATCATCAAGGTGATGTAGCTCCACGAGAAGTTGGTCTTTTCTACTTCCCTGATGCTTTCAATAGCCCATCTAATT
ATGTTCGTCGTCAGATACCATCTGAGTATGAACCAGATGCGTCAGAGCCATGCATCAAGTACTATGACGGTGTATTATACCTTATCACTCGTG
GCACTCTTGGTGACAGACTTGGAAGCTCTTTGCATCGTAGTAGAGATATAGGTCAGACTTGGGAGTCACTGAGATTTCCACATAATGTTCATC
ATACTACCCTACCTTTTGCTAAAGTAGGAGATGACCTTATTATGTTTGGTTCAGAACGTGCAGAAAATGAATGGGAAGCAGGTGCACCAGAT
GATCGTTACAAGGCATCTTATCCTCGTACCTTCTATGCACGATTGAATGTAAACAATTGGAATGCAGATGATATTGAATGGGTTAACATCACA
GACCAAATCTATCAAGGTGACATTGTGAACTCTAGTGTAGGTGTAGGTTCGGTAGTAGTTAAAGACAGCTACATTTACTATATCTTTGGTGGC
GAAAACCATTTCAACCCAATGACTTATGGTGACAACAAAGGTAAAGACCCATTTAAAGGTCATGGACACCCTACTGATATATACTGCTATAAG
ATGCAGATTGCAAATGACAATCGTGTATCTCGTAAGTTTACATATGGTGCAACTCCGGGTCAAGCTATACCTACTTTCATGGGTACTGATGGA
ATACGAAATATCCCTGCACCTTTGTATTTCTCAGATAACATTGTTACAGAGGATACTAAAGTTGGACACTTAACACTTAAAGCAAGCACAAGTT
CCAATATACGATCTGAAGTGCAGATGGAAGGTGAATATGGCTTTATTGGCAAGTCTGTTCCAAAGGACAACCCAACTGGTCAACGTTTGATTA
TTTGTGGTGGAGAAGAGACTTCGTCCTCTTCAGGTGCACAGATAACTTTGCACGGCTCTAATTCAAGTAAGGCTAATCGTATCACTTATAACG
GAAATGAGCACCTATTCCAAGGTGCACCAATCATGCCTGCTGTAGATAACCAGTTTGCTGCTGGTGGACCTAGTAACCGATTCACTACCATCT
ACCTAGGTAGTGACCCTGTTACAACTTCAGATGCTGACCACAAGTACAGTATCTCTAGTATTAATACCAAGGTGTTAAAGGCTTGGAGCAGGG
TTGGTTTTAAACAGTATGGTTTGAATAGTGAAGCAGAGAGGGACCTTGATAGCATACACTTCGGTGTCTTGGCTCAGGATATTGTAGCTGCTT
TTGAAGCTGAAGGGTTGGATGCCATTAAGTATGGAATTGTGTCCTTCGAAGAAGGTAGGTACGGTGAGGTATAGTGAAGTTCTAATACTA
GAGGCTGCTTATACTCGTTATCGTTTAGACAAGTTAGAGGAGATGTATGCCACTAATAAAATCAGTTAAGCAAGCTGCTGTACTCCAGAACAC
AGAAGAGCTTATTCAATCAGGACGTGACCCTAAGCAGGCTTATGCCATTGCCAAGGATGTTCAACGTCGTGCCATGAAGAAACCTTCTGCATC
TTCTGCGTAAGCAGGTTAATATCTTAGTATAAACAAGGGCAGACTTAGGTTTGTCCTTAGTGTATTCCAAAGGAGGTAACATGCTGAAAGATG
GTTGGGTTTCATATGACCCTACAGACCCTAAGAATTGGCTACAGGTTATCGCTATAGCTTGTGCAGGTAGCCTATTGGCTGCCCTGATGTATTC
ATTATGGATGTACACAAAGTAACCAAAGTCAAAATTTTGATGTAGGCGTGTGTCAGCTCTCTCGCCCTCGCCCTCGCCGGGTTGTCCCCATAG
GGTGGCCTGAGGGAATCCGTCTTCGACGGGCAGGGCTGATGTACTCCTTGTCTAGTACAAGGGAGGCGGAGGGAACGCCTAGGGAGGCCT
AGGAATGGCTTAGTGGTGGACAAGGTGATTACCTTAGTGAAGCCTCTTAGTGCATTCCTGAGGCCATTCAGGGCGTTTATGAGGGATTGACA
GGGTGTGAGGGCGTGGGCTA
```

Figure 5A

>K1-5 BAR 2.5 (Site specified by sgRNAs 1112+1122) (SEQ ID NO: 5)
TCGCCCTCGCCCTCGCCGGGTTGTCCCCATAGGGTGGCCTGAGGGAATCCGTCTTCGACGGGCAGGGCTGATGTACTCCTTGTCTAGTACAA
GGGAGGCGGAGGGAACGCCTAGGGAGGCCTAGGAATGGCTTAGTGGTGGACAAGGTGATTACCTTAGTGAAGCCTCTTAGTGCATTCCTGA
GGCCATTCAGGGCGTTTATGAGGGATTGACAGGGTGTGAGGGCGTGGGCTATCTGTTCCTTTGCTCCTCACTTCGTTCGTCGCTGCGGTAGCC
TGATGTGTACCTTAGGTTATTCCTTGATGGATAGCTTAGGTTAGCCTTAGTGGATTACCTTAGTTAAAGCCTTAGTGCTTCACTTAGTATCAGCT
TAGTAGTGTACCTTAGTAAGTCTTAGTGTCTTCTCTTAGTGATTGCACATGCAAGCATGTAAGATGCTAATAGGTCGCGGTCGGCAGACCGCT
AAAGAAAGAGAATGGTAATAAGATGCAGTAGGAGGAACACCAGAAGCCTAGCCAACCTAAGCTATCCTAGCTCTATATCTATTGCTTTTCCTT
AGTCTAACACGTTAGACAACCTATCTTATTCTTAGTGATGGTAACTTAGTGTTGACAAGATAATCTTAGTGTAATACTATGCATCACGTAGGCG
GTGCTGAGGCACCTAGTAGCCAGCTAGTAAGGCATACGAAGAGACTAGCGCTTACATTGCTCTTTAACAATTTGCTTAGTGTAACCTATGTAT
GCCGTGGTTAACTACTTATTGAATGAGGTATTAACTATGACATTAAATAACCGTGAACTGTCCGTTCTCTTCACTCTGTTGTGCTACATGATTCG
TAACAACGAATTACTTACAGATGATGAGTTAGCCTTGTATCACCGCTTTCTTAACGAAGGTTGGACCGATACAGTTAATCAATACCGTAACATG
ATAGATGAGTTGAGGGAGGGTAAATAATGTATCAACATGAGGTATTCTTTGAATCAGCTAGCGAAGCTATTCGCTTCCGTGATGATATGATG
CAAGCTGGTGTAGGCGTTGATGTGTATCACTATTTGATAGATTACGACACTGAATATCACCGAGTTACCTTAGTATCTGAGTATGACAACCAA
GTCATTACTGAGTATCTAGGCAGTGAAGATTACGATTACGATGAAGTAATCACGACAAATCTCTAAATTAACTGTTGACAGCCACGGCATACA
AGGTTACATTAAGCATCAAGACGGCGACGTCTTTAAACATCCCGCTCTTTAACAATACGGTTTGTGTCTTGATAGGCTAACTAACTAACTAAGG
TAATTATCATGAAAGGGTTAATTTGTGTAGAACGTATGGTCAATGGTAAACTTGAAATATTACCACTGGAAAACCAATCTAGCTTCAAAGAGT
GGTATGGCTGTTTCTCACTGATTTAAGGTAAAGGCTGGCACTAGTCAGCCTATCAAGGCGCAAACCAAGCTCTTTAACAATTTGGATGGTAGC
TTCTTAGTCTGGATAGGTTAAACCTAGGAGATTCTCTTGAGTCTCCTATAATGTAACCTAACTAACTAAATGAGGATTAAATCATGGAACGCAA
TGCTAACGCTTACTACAACCTTCTGGCTGCAACTGTTGAAGCATTCAACGAGCGTATTCAGTTTGATGAGATTCGCGAAGGTGATGATTACTCT
GATGCACTACATGAGGTTGTAGACAGCAATGTTCCAGTTTATTACAGCGAAATCTTTACAGTGATGGCTGCTGATGGTATTGATGTTGATTTT
GAGGATGCTGGTTTGATTCCTGACACGAAGGATGTAACCAAGATTCTACAAGCTCGCATCTATGAAGCTCTTTATAATGATGTACCAAATGAC
AGCGATGTAGTTTGGTGTGAAGGCGAAGAAGAGGAAGAATAAGGATGGAAAAGCAATATAACTTTATCTTTTCAGACGGTGTAACCCTGAA
GTGTTCCCTACGATTCGCACAAATTCGTGAGGAAGTACTAGGCACTACATACAAACTATTTAGCTGACACTATAAGAGAAGGCTTAACAAGGC
GTTACTAAGGTAGCGCCTGATTAAACTTTCACTTACTAGGAGTTGAGATTATGAAAACCTTGATTGGATGCTTCTTGTTGGCTTCTCTTGCTCT
GGCATTTACCGCTAAAGCTGGTTATGACGCTTATAAAGTAGAACAAGCCCAGCAAGACTGGGCCAAAAAAAGTTCAACTTGTGCAGCAAGA
GCAACACCTACGAGTACTGCAACAAAACACTAAGCACTTATGGAAAGAGTAACTAGCCTATAGCCCACCTGAGTGGGCTATGTGATATTTAC
TTAACACTATATAAGGTGATTACTATGACTACTGAAAACACCCTCGTGTCTGTCCGTGAAGCTGCAACCGCTGAAATCAAGCAACATTTAGAC
AATATCGGCACTTCTTACATCAAAGTAGGGGCTTGTCTGAATGAGTTACGCGGAGACTTTGAAGGTCAAAAAGAGTTTTTAGCCTATGTTGAA
GCAGAGTTTGCCATTAAGAAGGCACAATGTTACAAGCTGATGAGTGTAGCCCGTGTCTTTGAAGGCGATGATCGCTTTAAAGGCGTGGCGAT
GCGTGTAATGCTGGCGCTTGTTCCTTTCGCTGATGAAAATATAATCATGGAGAAGGCCGCAGAACTCGCCGCAAATGGCAAGCTGGACACTA
ATGCCGTAAACGCCCTGATTGAACCTAAGAAAGAGTCAAAGGCCGAAACGGTACAATCTAAGGCTGAGACAGTAAAACCGCAGGAGAACGC
GACTGAGTCCGCAGAATCACATGAAATGCAAGCGCCGCAGGTAGTGCCACCCGCGAGCGAGCAGGAGTCCGACGAATCAGCACCTTGGGAA
GAGGAAAGCAAACCGGAAGCGCCAAAGGCAGCTCCGATGGATAACACGGCTAATACTGAGAATGCCGCTATTGCTGGTCTGCTGGCACAAA
TTAAAGCACTGACTGAGCAATTACAGGCAGCCAATGACCGCATCGCCTCCTTAAGTAGCGCACGCGAAAGCAAGAAGGCATCCGCACCTATG
CTGCCGCAGTTCAAATCTTCCTGCTTCTACGCTCGCTTAGGCTTGAGCGCGGAGGAGGCAACGAAGAAAACAGCAGTTAACAAGGCACGCCG
CGAACTGGTTAAGCTGGGATACGGTGAAGGCCATGAGGCATGGCCCTTAATCTCTGAGGCAGTAGAAGAGTTGACTAAGTAACCTTATCGGT
GGCATCTTCTTAGGTGTCACCTATTAAGGTTTCTTTCACTAGGAGTAAACAAGATGCAAGGCCTACACGCTATTCAACTTCAACTTGAAGAAGA
AATGTTTAACGGCGGTATCCGTCGCTTTGAAGCGGACCAACAACGCCAGATTGCATCCGGTAATGAATCAGACACGGCATGGAATCGCCGCT
TATTGTCCGAGTTAATCGCGCCAATGGCTGAAGGTATTCAGGCATACAAGGAAGAGTATGAAGGTAAAAGAGGCCGTGCACCGCGTGCATT
AGCTTTCATTAACTGCGTAGAAAACGAAGTGGCAGCATATATCACGATGAAAATCGTTATGGATATGCTGAACACGGATGTAACCTTGCAGG
CTATAGCCATGAATGTAGCTGACCGCATTGAGGACCAAGTACGTTTAGCAAGCTGGAAGGTCACGCCGCCAAATACTTTGAAAAAGTTAAG
AAGTCACTTAAGGCAAGTAAGACTAAATCATATCGCCATGCGCACAACGTAGCGGTAGTGGCTGAGAAGTCAGTAGCTGACCGTGACGCTGA
TTTCTCCCGCTGGGAGGCATGGCCTAAAGACACCTTGCTGCAAATTGGGATGACCTTGCTTGAAATCTTAGAGAATAGCGTATTCTTCAACGG
GCAACCTGTCTTCCTCCGCACCTTGCGCACTAATGGCGGCAAACATGGTGTTTACTACCTACAGACTAGTGAACACGTAGGTGAGTGGATAAC
TGCATTCAAAGAGCACGTAGCGCAACTGAGTCCTGCCTATGCTCCTTGCGTCATCCCTCCGCGTCCGTGGGTATCACCTTTTAACGGCGGTTTC
CACACTGAGAAAGTAGCAAGCCGTATTCGTCTGGTAAAAGGAAACCGCGAACACGTCCGCAAGCTGACCAAAAAGCAAATGCCAGAGGTTT
ACAAGGCTGTTAACGCGTTGCAGGCGACTAAATGGCAGGTTAACAAGGAAGTTTTACAGGTTGTGGAAGACGTCATCCGTCTAGACCTAGGT
TATGGTGTACCTTCCTTTAAACCACTCATTGACCGCGAGAACAAGCCAGCTAATCCAGTGCCGCTAGAATTTCAGCACCTACGGGGCCGTGAA
CTGAAAGAAATGCTTACGCCGGAACAATGGCAAGCCTTTATCAACTGGAAAGGTGAATGTACTAAGCTGTACACCGCTGAAACTAAGCGCGG

Figure 5B

```
AAGCAAATCGGCGGCAACCGTTCGCATGGTTGGTCAGGCCCGTAAATATAGCCAGTTCGACGCAATCTACTTCGTGTATGCACTGGACAGCC
GCAGCCGCGTCTACGCGCAATCTAGCACACTCTCACCGCAATCAAATGACTTGGGCAAGGCCTTGCTCCGTTTTACCGAAGGGCAGCGTCTTG
ATAGCGCTGAGGCGCTTAAGTGGTTTTTGGTGAACGGGGCTAATAACTGGGGTTGGGATAAGAAAACTTTTGACGTGCGCACCGCTAACGTG
CTGGATAGTGAATTTCAAGACATGTGCCGCGACATTGCAGCGGATCCGCTGACCTTCACTCAATGGGTAAATGCCGACTCCCCTTACGGCTTC
CTTGCATGGTGCTTTGAATATGCGCGTTATCTGGATGCACTGGATGAAGGCACGCAAGACCAATTCATGACGCACCTCCCAGTCCATCAAGAT
GGTAGTTGTTCTGGTATCCAGCACTACAGTGCTATGCTACGCGATGCAGTAGGTGCGAAAGCAGTAAACCTTAAGCCCTCTGACTCTCCTCAA
GATATTTATGGTGCCGTTGCGCAGGTAGTAATTCAGAAGAATTATGCATACATGAATGCAGAGGATGCGGAAACCTTCACTTCTGGCAGCGT
GACTTTAACAGGTGCGGAGCTGCGTAGTATGGCTAGTGCGTGGGATATGATAGGAATCACTCGCGGCCTGACCAAAAAGCCCGTAATGACA
CTACCTTATGGCAGCACACGTCTAACCTGCCGTGAGTCAGTGATTGATTATATCGTTGATTTAGAAGAAAAAGAGGCCCAACGGGCTATTGCG
GAAGGGCGTACCGCCAATCCTGTACACCCTTTTGATAATGACCGTAAAGACAGCCTGACACCTAGCGCAGCTTATAACTATATGACAGCTTTA
ATCTGGCCTTCTATTTCGGAAGTGGTTAAAGCCCCTATAGTGGCAATGAAAATGATTCGTCAGCTTGCCCGTTTCGCAGCTAAAAGGAATGAA
GGCTTAGAGTATACCCTGCCTACTGGCTTCATCTTGCAACAAAAGATTATGGCTACTGATATGCTCCGCGTATCTACTTGCTTGATGGGAGAAA
TCAAGATGAGTCTACAGATTGAAACAGACGTAGTGGATGAAACGGCAATGATGGGCGCTGCTGCTCCTAACTTTGTGCATGGTCATGATGCC
AGCCACCTTATCTTAACAGTCTGCGACCTTGTTGATAAAGGGATTACATCTATCGCAGTTATTCATGACTCTTTTGGCACTCATGCAGGCCGTA
CAGCCGACCTTCGTGATAGCTTAAGGGCAGAAATGGTGAAGATGTATCAAGGCCGTAATGCACTGCAAAGCCTGCTAGATGAGCACGAAGA
ACGCTGGTTAGTTGATACCGGAATACAAGTACCAGAGCAAGGGGAGTTTGACCTTAACGAAATCTTAGTTTCAGACTATTGCTTCGCATAATA
TTAATAGGCCATTCCTTCGGGAGTGGCCTTTCTTTTACCTACTACCTGTAACATTTCATTAACATAAAAGTGTCTCACATGTGAGACTTATTTAC
CGGACACTATAGGATAGCCGTCGGAGACGGGAAAGAAAGGGAAGATAAAGGATATAAAGGAAGTAATAGGTATTAAAGGTTATATAGGTT
ATCTAGGAATACCTATTACCTTCTTCCTTCCTCTTATTACCACTCAGAGGAAGGGCAGACCTAGGTTGTCTCACATGTGAGACTTCGTATTTACC
GGACAGTATAGATAAGATTAACTCACTTTGGAGATTTAACCATGCGCAACTTTGAGAAGATGGCCCGTAAAGCTAACCGTTTTGACATGGAA
GAGGGGCAGAAGAAAGGCAAGAAGCTGAATAAGCCTGTCCGTGACCGTGCATCTAAACGCGCTGCGTGGGAGTTCTAAGTTATGGCTATTA
TTCAGAATGTACCGTGTCCTGCCTGTCAAAAGAATGGACATGATATTACTGGCAACCATCTCATGATATTTGATGATGGTGCCGGCTACTGTA
ATCGTGGACACTTTCATGATAATGGTAGACCTTACTATCACAAGCCGGAAGGTGGCATCGAGATAACCGAGTTATCTATTACTGGCAATATCA
AATATACACCTTCTCAATTCAAAGAAATGGAGAAGGAAGGGAAGATAAGCGACCCTAAATTACGTGCCATCGCACTTGGTGGTATGCGTATG
AAAGACCGTTGGGAGGTCATGAATGAACAAGAAAGGGCAGAGCAAGCAAGACAGAGTGGAAACTTGATGTTGAATGGTTCCTCACGCTTAAGC
GTAAGAACCTTGTTTCCAGGCACATTCGCGGCGACATTTGCGCATTGTATGATGTACGTGTTGGGCACGATGAAGAGGGTAGAGTCTCACGG
CATTACTATCCGCGCTTCGAAAAAGGTGAGCTAGTAGGCGCTAAGTGTCGCACATTACCTAAAGATTTTAAGTTTGGTCATTTAGGTAAACTCT
TTGGTATGCAAGATCTTTTCGGTATGAATACTTTGTCTCACGTGTTAGACAAGGGAAGACGAAAGGATTGCTTGCTCATTGTCGGCGGCGAAC
TGGATGCACTAGCAGCGCAGCAGATGCTCCTTGATTCTGCCAAGGGTACTAAGTGGGAAGGCCAGCCATACCATGTATGGTCTGTCAACAAA
GGCGAGTCTTGCCTTGAAGAGATAGTGCAGAACCGTGAGCATATCGCCCAATTCAAGAAGATTATATGGGGTTTTGATGGAGATGAGGTAG
GGCAGAAGCAGAATCAGCAAGCGGCTCGCCTGTTTCCTGGTAAATCCTATATCCTTGAATACCCCTCTGGTTGCAAAGATGCTAACAAGGCAT
TGATGGCTGGCAAGGCTAAAGAATTTGTAGATGCATGGTTTAATGCCAAGTCATCTGATGAAGTCTTTGGTAGCCAGATTAAATCTATCGCAT
CTCAAAGGGATAAGCTCAAGGCTGCACGTCCAGAGCAAGGACTGTCATGGCCTTGGCCTAAGCTGAACAAGGTAACGCTAGGTATTCGTAAG
AACCAGCTTATCATTGTAGGTGCAGGGTCTGGTGTAGGTAAGACTGAGTTCCTTCGTGAAGTAGTTAAGCACCTCATTGAAGAACACGGTGA
ATCTGTAGGCATCATTTCTACAGAAGACCCGATGGTCAAGGTGTCCCGTGCTTTTATCGGCAAGTGGATTGATAAGCGTATTGAGTTACCTCC
AACCAACGACCCGAAAGAAGACGGATACCGTGAGGTGTTCGACTATACCGAGGAAGAAGCTAACGCCGCCATTGATTATGTAGCTGATACA
GGTAAGCTGTTTGTAGCTGACCTAGAGGGTGACTATTCGATGGAAAAGGTAGAGCAAACTTGCCTAGAGTTTGAGGCTATGGGTATTTCTAA
TATCATCATTGATAACTTAACGGGGATTAAATTAGATGAGCGTGCTTTTGGTGGGAAGGTTGGTGCACTTGATGAATGCGTCAAGCGGATTG
GTACTATCAAAGACCGACACCCGGTTACTATATTCCTTGTATCACACCTTACACGTCCTCCGGCAAACCGTACCCAACACGAAGAAGGTGGCG
AAGTTATCCTTTCTGACTTCCGAGGCTCAGGCGCTATCGGATTCTGGGCATCTTACGCCTTGGGGATTGAGCGTAATACAAGAGCTGAAACGC
TTGACGAAAGGACTACCACGTACATCTCATGTGTCAAAGACCGCGACCAAGGTATCTACACTGGAACCAAGGTCATGCTTAAGGGTGACATT
CAAACCGGACGTTAATGGAACCACAAGCCCGTACTAAGTCATTTGATACAGGTGAAGCAAGGCAACAAGAAGTACCAGATTTACCGGATAC
TATAGAAGAGACTACCTTCGATGAAGAAAGTGAGTTCTGATTAGTGTATTTATCAGGCTTGTCTCACATGTGAGACAGGCTCTTATTAAGTAC
ATTAAATAACTGGAGATTGATTATGTATAACTTAGTGTTGAATGTAGGTGACTTTGTACGCAACATCAAGAAAGATTCAAGTCGCTATCTTTGC
CGTGGTGTTGTAACCTTTGTAGGTGAGAACCTGTATTATGTAGAATATCGCAGTGGTGTTAAGCAATATTACCACAAGAAGACAGCACATAAA
TATCTTGAAAAGATTGTAGAGATAAACAATCAATGTAAGTGCATACATGATGAGGTTTGCGATAAATGTGCTCGCCAGATGCTTAAGAATTTC
CTAGCTCCTCTTTATTATGGTGCTGGTCCTCAAACACTAGCAGAGTGCATGGCAGAAAAGAAAACCACACTCAAGAAAGAGCGTCGCAATGT
AATCACTGGTAAGACTCAAAGTGAGATGATTAAGCAATGTGGCACTGCATTAGGTGTTACACAGTTTAATACTCGTGCATTGGGTAAATCCAC
AGGACAAGCTATGGTAAAGATTGGAGAAGCCATGATGCATCCAAATGTACCTGTGCGAATCATGGATGTTGACCATGCAATCACAGAACAAG
GTACGCAACGACGTGTAATTAATAAGCATTTTGCCGACACTATAGAAGGCATTATTCGTAAGCAAGGGTTGAAAGGTCTTCACATCTTAAATG
GTGAAGAATTACTGTACCTACCTATCGTTACTGAAGAAACATACGTGAATATCTAAGGAGTTAATCATGACTAAGGTATTAATTTATATGCGT
```

Figure 5C

```
GGACCTCATAAATGCTATGCAGTTGTAGCACCAAATGGTGTTAAGCCTTATCGTACTTCAAAAAGATTGGCATTAATAGGTGCTAGTAGTAGT
GCAAGTTTCCAAATGGAACTTTTTGGTCATTGGACTGAAAGGCAATTCCGTGAGGATTTTAAAGTCATTGGCAGCTTCATGGTGAAATATGCA
GAATAAACATAGTCTTAGAATGTTCGATGGTCATGAAAACCTGCAAGCCAAGATTACTAACCAAGCCTTCCTGTTCGCACAGTTAACTATGGC
TGAGGCTAAGAAGAATAGTCTCACTCGTGAACAGGTTATCAAGGAGGCCACTTGGGAACCACACCAAGGTAAATATATGGGCCACAAATTAA
CTGTAACACGCAGTCGATAAGTCAAGGGTTGTCCAACGTGTTGGACAGCCTTTCATCATATTGATTGGGAGGTATTAAATGACTAAGTTTACT
ATGCAAGACCTCATTAAATTACGTGATGAAATAGAATCACCGGAAGTTAATACAGAGTTTCACTACATTGATCCACGAGATAAACGAGAGATT
CCTGATTATCAGATTGAGACGGAGTTAATGTATGAAGATTATTGATTGGAAGAAGGAAGCAGAAGGCCGTATCCTAGTGATGGATGCGGAG
GCTAAAGGCCTGCTGGGTGCTATCCGCTACGGTCATCGTGAAGATGTACACATTATTTGCTGCATGGACTTGCTCACCACTGAGGAGTTCCTC
TTCTTCGACCCATATGAGATGCGTGACCCTGAAGCAAGGGAACACTTGAAAGAGTGGGAAGGCCATCAAGATGGGACCTTGGTTGATGGTG
TTAACTTCCTAAAGCACTGTGAAGCCATCGTCTCACAGAACTTCCTAGGCTATGACGGGCTTCTCTTTGAGAAAGCCTTCCCTGACATCTGGAA
GGGATTTAACTACACCGAGAGGCGCGGCAAGGGCAGACTACGTGCTGACTTGTGTCCGGTACGCGTCATGGATACGCTGGTCATGAGTCGC
CTGTTAAACCCAGATAGACGCCTTCCTCCGCAAGCATATGCCAAAGGTATGGGTAACGTTGCCCCTCACTCAATTGAGGCGCACGGCATTCGT
ATAGGCCGTTATAAGCCGGAGAACGAGGATTGGTCTAAACTAACTGACCACATGGTACATCGTGTACGCGAGGACGTGGCGATAGGCCGTG
ACCTATTCCTCTGGCTATTTAACGGAGAATGGACGGAGCACAAACGCCGTGGCGTGAATAAACGCACTGGCCTAGGTATTGAGACAGCCTTC
CACATGGAGTCCATTGTGACGCTGGAGATGAGCCGTCAGGCCGAGCGTGGATTCCGTCTGGATATAGATAAAGCATTAGCACGATGCGAGG
AATTGGACGCTAAGATTGATGAGACAGTCGCAGCGTTCCGTCCGCACATGCCTATGCGTATCAAGTCTAAACCTTTTAAACCGGAAGAAAAG
AATGAAGTATGCCAACGCGCAAATGAGTATGGAGCTAGCAACAATATACCTACTGTCCTTGACCCCTCTCACTTTCTTCACGCAGAGAGACGA
GGAGATCGCAAGACAGTATGGAGTGTCACTACTAAGTCTGGTGATTGGTCGGCTAGCGTCAAGAAAGACTTTCCTCACCTTAGAGGAAACCG
TAATGACACGCCAAGTGTCAAGTGGATTGGCGCTTACTCGCCTGTTACTTTCGAAGAGATTCCCTTGGGTAACAGGGATACAGTTAAGCAAGT
GCTCTATGATTATGGATGGAAAGGTGTTGAATTTAACGATACCGAGCAAGCGCATCTCGATGAGCATGGCGTATTACCCAAGCCTTGGAGTG
GGAAGATAAATGAAAAGTCCCTTACTTTATGGCAAGAGAGAGCCGCACGTGAAGGTAAAACAGTCCCTGATTGGTGCTTGGGTATCGCTGCA
TGGTACATACTCGTATCCCGTCGTGGTCAGATCCTCAACCGTGGTGACGTTGAAGCCTTCGACCAGAAGGGGGTGTGGCCTTCGCAAGCTGG
TATACGAAAGTGTCGCGGCCTTGTACCTGTAGCATTTAACAAGGAGTTAGGAATCAATGCGCAGCAATACTACGAAAGGTACGGATGCTGGC
CTACGTCAGACAAGGATGACGGAGAATGGCGTGTGCCAGCTATTGCTATTAGTATTGGAACTTCTACGTTCCGTATGCGTCATCGTAACGTGG
TTAATATTCCTGCCCGTGGCTTGTATCCTTTACGTGATTTATTCATAGCAGGGAAAGGCAAGCTAATCCTTGGTTGTGACGGTGCAGGTCTTGA
ACTGCGTGTCCTGTCTCACTTCATGAATGACCCTGAGTACCAAGAGATTGTACTGCACGGTGATATTCATACGCATAACCAGATGAAGGCTGG
TCTTCCTAAGCGTGATATGGCGAAGACATTTATATATGCCTTCCTATATGGGTCTGGTATAGCTAACCTTGCAGCAGTATGTGGTGTTACTGAG
GAAGAAATGGAGGAAGTTGTGGCAAGATTTGAGGTTGAACTACCATCTCTTGCACGTCTTCGTGAGAATGTTATCGCACAAGGTAACAAGTT
TGGCTACCTACAAGCACCTGATGGTCATTGGGGTCGCATCCGTATGTCTGGTGGTGAACTTAAAGAACACACTATGCTTAACGTACTACTCCA
GATGACTGGTTCTCTGTGTATGAAATACGCATTGGTCAGAGCGTTTGCAGTGATGCGCAAGGAAGGTGTGGCCTTAGATAGCATGGGAAACC
CTTGCGGTATAGCTAACGTGCACGATGAAATCCAGATGGAAGTCCCTGAAGATGAGGTCTTGTATCTCAACTACGACTTGCCTTTCACCTTAG
AAGGGTTCGAAACAGAGAAGGCTGCTGTGAAAGCAGTGTTCGATGCAGAGGAGAAACGTGTTCATGTGGATTCTGAAGGACGTATGTGGTC
TGCTGCAAATCTCGTTAGTGTTGATGCTGGTGTACTTCATTGCCAGCGTCGTTATCACCGTGCAGGGCATATCATTGCCGACGCAATGACCTG
GGCGGGTCAGTACCTGAAGATGCGTTGTCCGATGGCAGGTGAGTATAAGATTGGTGCAAGTTGGAAGGAAACACACTGATGGACAGGTTTG
ATATTGTTTGCCTATTCTCTACCTTCTTTCTTATATTCCTTATGCTTGCTTGCTATGGAAGTATGCGATTAGATATACCTGATGAAGAGGAGGGT
TACGATTGATGCAGGCATCTTTTATTATTCTTGGAGTCATATTATTTATGGTAGTATTCTGGGCTTTCTCTGGCATTGACCCAGATTGTGATGGT
AACTACGACTGAGTTATACTCAAGGTCACTTACGAGTGGCCTTTATGAATAACTTATTCCTACTTATTTTGTCTAACATGATTTACTGGACACTA
TAGAAGGAAAGCATAGGTAATCTAGGTTTATAAGGTAGTATAGGTAATTAAGTAAATATAGGAGATATAAATATGTCTATGGTAACTACTCTG
GTATTCGTGGCTCAATACTTTCGTGGTCTTGCTAATAAGTTCAAGTCCAAGGCTATCAAAGCTATTGAGGCTCGCATCGAAGCAGTACAGGCA
GAGCAAGTTAAAGTTGAAGAACATCGTAGTTCTCAAATGATTGACTGTCATAACCGCTACTATGCATCTCGTGATGAACTAAATGCACGTCAA
GTCAAAGAGGTAGAAGATATGCTGGCACGTCACCAGCAAGAGCGTGACAGCCTGAAAGCTGAATTTGAAGAGAACAAGGCATCAATTGCTC
TTGTACATCAAGCTGCATCTGACAGTCTGAAGAAAGAGATTGTTATGCTGGAAATCGAACTGGATAACCTGACCAAATAAGGGGGGGTTATG
ATGGAAGAAGTAATTCAAGCTAAACATGTAGGTATTATCTTTCGCGATCTAGAGCAGCGTAAAGTTGCAGGTCATACTCGTCTGGCTAAAGA
GGAAGACACCGCAATCACTACTGTAGAACAAGCAGATGCCTATCGTGGACCAGAGTTCACTCAAGGTGAAACTTGTCACCAATTGAGCCTAT
CAATTTGTGACACTATGGCTATTGTAAATGTGCAAGAAGTCGAAGAGGGTGAGTGTGTCAGTTACATCTACCCTTTAGATACTATTGCACGCA
TTAAGGTAATCCATAAGTAATTACTAGACACTATAGAACAATAGGTCGGCTTAGTTCGGCCTATGATTGTAAAGTGTTGTTGATGTTGAACCA
TTGTGCATCTTGCACAACCCGATACCGTATAGGGCTTTCTAGTGAGTACATGCTTGTGCTCAGTACAAAGCTAACTGACAATAGGAGACTAAA
TAAATGGCACGTGGTGATTTTGATTTTGGTGCTCAGGTTACTAAATCTGAAGGTAAAGTCTTTAAGAATCCAGAAGTAGGTGATCATGAAGCA
GTAATCTCTGGCATCATTCATGTTGGTTCCTTCCAAGACATCTTTAAGAAAGGTAATACCACTGAAGTTAAGAAGCCAGCAAACTTTGTTCTGG
TTAAGATTGTCCTGATGGGTGACGATGACAAGAACGAAGATGGTTCTCGCATGGAACAATGGATGGCTGTGCCTCTGAAGTCTGGTGATAAG
GCAACACTGACTAAGTTCCTGAATGCAGTTGACCCTAAAGAGTTGCTGGGTGGCTTCGATGATTTCATTGGTGAATGCCTGACTGCAACGATG
```

Figure 5D

```
GTCGGTTCTGGTGATAAGAATGACGATGGCTCATTCAAGTATGTTAACTGGAAGGGATTTGGTGGTATGCCGGACAAGCTGAAGAAACTGGT
CATTGCTCAGGTTGAAGAGGAAGGTCTGTCTATGACAGGTCACATTACCTTCGACAAGCTGACCAAAGAAATCCTTGATGACATCCCAGCCAA
CTTGGTGCGTCAATACTTCCTGAACGAGACGCCTCGTGGTAAGAACCTGTCTGTTGCTGGTTCTCACGTAGAAGCAATCATTAAAGCTGCTCG
TGAAGAAGACCCAGAATGGAAGAAGGCTAAGAAGAAAGACGAGGAAGATGCTACCCCAGCTAATCGTAAATCTCTGGATACTGGTGAGTCT
GTTCCACAGGAAGTACCTGAAGCAGAAGATACTCCTGCACCGGAGATGGATGAGGACGCGGAATATTAAGGAGAAAGGATGAAAGTACAA
ATCGTAACCCTGCACTGCAAGAAAGGAATTACAACTCTTGGCGGCAACACTTTTCACTCCTTCTCTGAAGGGGACACATATGCCGACCTGCAC
TACATCTGGCGCGACGGACAGCACGTGGTGAACTACAGCGACCCAGCTACGGGGAAACGCCACGGCGTATCGCTTCCGGCGCATGACATTG
CTCAGGTGAACACAGTTTTATAAAGTCTCACGTGTGAGACAAATCGGTGTCCGGTATTTACTGGACACTATAGAAGAGAAGAATTTTAATCGG
CGATAATGCCATAACCAACAAAAGGAGAATTTAATATGTTCAAGATTGAAACTATCGTAAACCGTGTTGTTAAAGGTGCTGCTCTGGTATCCG
TTGAGTCTTTCATTATCGTCGATGAAACTGATCAACTGGTAGCTGGTACTAAGGCTTACGATACCCGTGAAGAAGCTCAGGCTAAGATTGACA
GCATGGGTAACTTCGCTGCTGGTCTGGAGTTCGCTCGTGCTTGCTTCCCTGAGCAGGCTGACAAAGCTCAGATTGGTAAGGCTAATATCGTAG
CTGAATATCTGGATTGGGTTGCTGCTGGTAAACCAGTGAAAGAAGTTAAGGCTGCTGAAGAAGCTGAAGCTCCAGCAGAAGAAGTAGCTGC
ACCGGAAACTCCGGTAAGTGAAGAGGAAGAATTTTGATAATAGCAGGTGTTGCCTCTGTTAGTCCTAGCTGACTATCACGCTCACCTCATCTA
ATGCCCTGTCTGCCTTAGTGTAGGCAGGGTCTTTTGCGTAATAGTTATTGGAGAATGAATTATGCCGACTATTGAATCTCGAATTGAACTGGA
CATTAGCTACAATGCAATCACCAGACAGTATATTGGGGTTGCCTATGATTACAAAACTGGTGAGAAGCTAGTGGAGGTGAGACAATGGGATG
ACTATTGGTTAAGACAGAACCTCCATGATGCGGTGTCCTCCTTCCTGAAGGAGTGGCCTACATGCGACCAAACTTCGACTTCGGAGCTACAGT
ATCGGAAGACAATAACCTGTTGCTGTGGCCAACTGAAGGTAATCGAATCGCTTTAATAGATGCTGATATGTTACCTTACATCATAGGGTATAC
AATCAGTGATATGACTTATGTACGAGCCACAACTCGTGTTAAGTCAGGGCAAGTCCCCTCAATCAAAGATACACCTGAGTGTAAGCAAGCGT
GTGACCGTGTGAACTCCTTGCTTAACTCTTGGGTGTATGCAGCAGAATGTGATGCAGCTAAGTTGTTCATGACGAAATCAGAAGCTAACTTCC
GTGTCCGCCTAGCATTCACCAAGCCTTATAAAGGTCAACGTAAGACCGAGAAGCCTCCATTCTTCTATGAATTGCGAGAGCATCTCTTAGAGG
TTCACGGTGCAATCTTGGCAGATGGAGAGGAAGCAGATGACCTCATGAGTATCGCACAATGGGACAGCCACCGCCGCTTCCAGCAAGATACA
GGTAACGAGTTCCCTATCGGTAGTCCAGAGCATAAAGCATTCTCTGATACTTGCATCGTTTCCTTGGATAAGGATTTGATGATTGTTCCCGGTT
GGCATCTACAGCCGGGTCAAGAGAAGAAATGGGTAGAGCCTATGGGTTGGCTTGAGCTACGCCGTAAGGCTAATGGGCAAGTCAAAGATCT
AAAAGGTGCTGGCCTCATGTTCCACTATGCACAGATGATTATCGGTGATGATATTGATAACTATGCTGGCATACCAGGTCGTGGTGCTAAATA
TGCCTATGATCTTCTCAAAGATTGTAAGACAGAGAAAGAGTTGTACATGGCAGTGCTGGGTGCTTACAAGGCTAAGTTCGGGCATGGACAAG
TTAAAATTAAGAATTACCGAGGTGGTTATCGTATCGGCAAAGCCTTTGACCTAATGCTTGAGTGTGGTCGCTTATCTCACATGGCAAGATTCA
AGGGTGATATATGGCGAGCCGATAAGAACCCAATCTTGTGGGGAGATGATGCGGAATGGTTAGCAAATTAAAATCATCGGAGGTGGCAGCT
TATAAGAAGGAATTGCTAGATAAGCAAGGATGGAAATGCCCTCTGTGTGGCGGCAGTCTCAAAGCTGTCACACCTGTAAACCGTGTACTTGA
CCATGACCATGAGACAGGATTCTGCCGCGCTGTTGTATGCCGAGGCTGCAATGGTGCGGAAGGGAAGATTAAGGGTGTTATCTCTGGTTATG
GTAAGGCTGGTAACAACCGTTACTTCCAGCTTCAATGGTTAGAGCGACTATATGAATACTGGAAGTTACATAGTACGCCTCAGACAGATAAGT
TATATCACAAACATCAAACGGAGGCAGAGAAGCGCGAGGCTAAGAACCGTAAGGCACGCCTTGCTTATGCAAGAAAGAAGGAGGTTAAAGT
TGGGTAAGCTGCGCAGCTTGTACAAAGACTCCGAGGTACTTGATGCAATCGAGCAAGCTACCGACGAGAAAGGTAATGTTAACTACAATGAG
ATGGCACGTGTATTATCGTGTCATACTGTGGGTAAGAAGATTACCCGCCAGTTGGCTCGATACTGGCATGGTCAATTCAAGAAGACCAAGAA
GAATGGTGATTACTACCAGACCCTTCTGCAAGAAGATAAGCGTATCAAGAAGAGCGTAAGCTCAGGACTCCTGACCGCTACGAGGATTTGG
CTATTGTGCCATTGCCTGACTCGCCTCATCGAAGTGTACTGGTGATCCCTGATACTCATGCACCTTATGAGCACCCAGATACCCTAGAGTTCCT
TGCAGCCGTGGCAGCACGTTACCGTCCAGACACAGTGGTACACCTAGGAGATGAGGCAGACAAACATGCCCTGTCATTCCACGATTCGGACC
CAAATCTGGATAGTGCTGGCATGGAGTTAGAGAAGGCTCGTATCTTCATGCACAAATTGCACAAGATGTTCCCTGTGATGCGCCTGTGTCACT
CTAACCACGGCTCTATGCACTTCCGTAAGGCAAGCGCCAAAGGCATCCCTGTGCAATACCTGCGCACCTATCGTGAAGTCTTCTTCCCGCAGG
GAGGTGGCGACCAGTGGGATTGGCAACATACGCACGTCCTTGAGTTGCCGAATGGTGAACAAGTGGCATTCAAGCATCAACCTGCTGGCTCT
GTCCTAGCAGATGCAGCGCATGAGCGTATGAACCTTGTGTGTGGTCACTTGCACGGTAAGATGTCTGTGGAGTACGCACGTAATACACATGA
ACAGTATTGGGCTGTGCAAGGTGGCTGCTTAATTGATGAGTCATCCCGTGCATTTGCCTATGGTCGTGAGTCTAAATACAAGCCAGCATTAGG
TTGTGTGGTCATTCTGGAGGGTGTGCCTCACATTGTCCCGATGCAAACCAATAGCGACAACCGTTGGATTGGCAAGATTTAGTTGACACTATA
GAACAAAGGGCTAGGTAAGACTTTATCGGCTGGCGTATCCAAATGATATTGCACTAGCCCTTGATTGTATAGTGAATGGAGGATTCAATATGT
CACACTATGAATGTAAGAAGTGTCATAAGCGTTATGATTACTGTACTTGTGGTCAAGAGAAAACATCTTTTAAAGTTGGAGACAAGGTATTTC
GTAATGAAAAAGATTCGATTCCTTGGAATCAATACTGCAAAGAAGCTGGTATTGACCCTGATAGCCCTGTAACCATAGATGATATTGATGGCA
TTAACTTGTGCTTTCGTGAGGTGAGGGGTACAGGTTGGGATTCCAAAAAATTCAAACTTGCATCTGATAAGTTAGACAACAATATGGTAATTA
AGCCTAAGCACTACGAGTTCTTTGATGGCGTAGAGGCAATCACTATCATTGCCCGCCAGTATGACCGAGAAGCAATTCGCTGGCTATTGCATGG
GTAATGCTTTGAAGTACCGTCTACGTGCAGGTAAGAAGTTCAACACTGAAGAAGACCTGAAGAAAGCAGATTACTACAAAGAGTTATTCCAG
AAGCATCGTCACGAATGTATTGATGAGGATATTTGATATGAATATCTTTGAGTTCCTAGGTCTTCCAGAAGACCACCGCAATCACCCATTCATG
CTGGTGAAGCATCGCGGTGAAGTTCCTGAGAAGAAATTAACTTTTCCATGTTATGCACAGGTGAAACGAGATGGTATCTTTTCTGCTGTTGTT
GTTCGCACTGATGGTGTCGTTGGCATTTTTGGTCGCACTGGTAAGAAATTGGCAAACACTGAAGGACTCGAACAAGCCTTTGCTACCTTTCCG
```

Figure 5E

```
GTTGGCATTTATCTTGGTGAGCTTCAGTCTATGGCCATTGATATCTACCTTGAGGCAATCTCTGGGGTTGTGAACCCCAATCGCACTGAGCCAC
TTGATTTCATAGGCCAGCAGATTAAAGACAACCTGTATATCGACTTCTTCGATATGTTAACTATTAAGGCATTCCATGATGGATTCACTGATGT
TTCTTATCTCAAACGTTACGATGCTTTACATCGTCGTATCGGCGCTCATCTTAGCGGGTGCAACGCTATCCTTCCTATCACTCCTTGCCATAATG
AGCGAGAAGTTGAAGCGTTTGCGCAAGAGCAAATAGATGCAGGACGTGAGGGTGCTGTATTCAAACTGGACTGCGATTATGAAGCAGGACA
CAAAGGTTATCGTCAGACTAAAGAAGTCCGTAAGGTAACCTATGACCTTACTTGTATTGGCTTTGAAGAAGGTAAAGGCAAATACAAAGGTA
AGGTAGCTAACCTCATTTTCAAATGGAAAGGAGGCAAGACAATCAAAGCTATGTTAGGTAAGGGGTGGACTCATGCAGATGCAGAGCAGAT
GTTCCACGACATTAAACATGGTGGACGATTGAATGTCATTGGTAAAATCTTTGAAGTCAAAGGTCTTCAGGATTCAAGCAAGGGCAACATTCG
TCTGCCCAAAGCGGGAGAATTAAGACATGACAAAGATGAACCAGATTTCTTTTGATAGCATGAAGGCAACTCGTGCAGTTGAGGTAGCAGAA
GCTATCTTCGAAACTTTATCCTGTGGCATGGAAGTGCCATATACTTTACTTGCTGATGCAGAAGAACTTGGTCTTTCTGTAGAAGCTATCCAAG
AGAAGGTTGACGAATTATATGGTACAGACGAAGAAGAAACCGACGATTTCATTTGAAGGAATGGAGATGCTTGAGATGATTCTCAAGCCTTC
TTCTCCTAAGGTGACTAAGACTCATGAAGAGTTAATCGTTGATGAAGTTAAGCGTTACATCATGGATTGTGTCAGAGCACAACTGGTGGTCCA
ATGATACGTCCAGCCTCCTTCCTAGATATTCCTGAGATTATAAACCTTGGGAATAAATATGTGGAAGAGGAAGTCAAGGTTGTAGCCCACCAC
TCAGCCTCATGGAATGCAGAACAAAGTGCCATAACCTTTGTGCATCTCTTAATAGAGACCCACCACTCAGCCTCATGGAATGCAGAACAAAGT
GCACATAACCTTTGTGCATCTCTTAGTAGAGAAGATTTATCCCTATGGGTTGCTGTAGATGAAGGCAGATTGTAGGGTTCCTGTGGGCTGGC
TATCACGAGTTGGCCCCTTGGACACCTGTAAGAGTTGCCTCTGACATTCTCTTTTATATTATACCAGAGAGAAGGGGAACACTACTTGGTATGC
GCTTAATTAAGGCATTGAAACAGTGGGCATCAGATAATGAATGCTCTGAAGTGCGTTTAAGTATTGCAAGTGGCATCAACGAGGAGCGCGTA
GGGCGCATGTACAAACGGCTCGGCTTTGAACCGTTTGGCACTGTGTATAACCTGAAGTTCTAAAGAGGAGATATACAATGGTTTTTACGCTTG
AGGACTTCGTTGGTGACTGGCGTCAAACCGCGGGGTATAATCTTGATCAGGTCCTGGAGCAGGGCGGAGTTTCGTCCTTATTCCAGAACTTA
GGGGTAAGTGTTACGCCGATTCAGCGCATCGTGCTGAGTGGAGAGAATGGATTGAAAATTGACATTCACGTTATCATTCCGTATGAGGGTTT
GAGTGGAGACCAGATGGGACAGATTGAAAAGATTTTCAAAGTGGTGTATCCCGTCGATGACCATCACTTTAAAGTAATTCTGCACTATGGGA
CCCTTGTGATCGACGGTGTAACGCCAAACATGATTGACTATTTCGGTCGCCCTTACGAAGGTATCGCCGTCTTCGACGGAAAAAAAATCACTG
TCACGGGAACATTATGGAACGGAAATAAAATTATCGACGAACGTCTGATCAATCCTGATGGAAGCCTGTTATTTCGCGTTACGATCAATGGAG
TGACCGGATGGCGTTTATGCGAACGTATTTTGGCTTAAAGAGGAGATATACAATGGGTGTTGTAAAGAAAGCATTTAAGGCTATCGGTCTTG
CTCAAGATGCACCACGTATTGAAGCCAAAGTCCCAGCACAGCAGCTTGAGCGTAAGCCTGAGACTGAAGCTGAAGATATTCAAATTGGTGCA
GGGGATGATGCTACTGCATCTGCAAAAGGTAAGCGTGGCCTTGTCCGTCCGGTAGCTTCTAGCTTGAAGGTGTAATATGAAACAGAGCATAG
ATTTGGAGTATGGAGGTAAGCGGTCTAAGATACCTAAGCTATGGGAGAAGTTCTCCAATAAACGTAGCTCTTTCCTTGATAGGGCGAAGCAT
TACTCCAAATTAACCTTGCCCTATCTGATGAATGACAAAGGTGATAACGAGACTTCGCAGAATGGATGGCAAGGTGTAGGTGCTCAGGCAAC
CAACCATCTAGCCAACAAGCTAGCGCAAGTACTATTCCCTGCACAGCGTTCCTTCTTCCGTGTAGACTTAACTGCACAAGGTGAGAAGGTTCTT
AATCAGCGTGGCCTGAAGAAGACAGAGCTAGCTACCATCTTCGCTCAAGTGGAAACACGGGCAATGAAAGAGTTAGAGCAACGTCAATTCC
GGCCTGCTGTAGTAGAAGCATTTAAGCATCTTATTGTTGCTGGCAGCTGTATGCTATACAAGCCGAGCAAAGGTGCAATCAGTGCTATCCCAA
TGCATCACTACGTAGTTAACCGTGATACCAATGGCGACCTGTTAGACATTATCTTGCTACAAGAGAAAGCCTTACGTACCTTTGACCCAGCTAC
ACGTGCGGTAGTAGAGGTTGGCCTGAAAGGTAAGAAGTGCAAGGAAGATGACAGCGTTAAGCTGTACACACATGCTAAGTATCTTGGTGAT
GGATTTTGGGAACTCAAGCAATCTGCTGATGATATCCCTGTGGGTAAGGTGAGTAAAATCAAATCAGAAAAGCTACCTTTCATCCCATTAACT
TGGAAGCGAAGCTATGGTGAGGATTGGGGTCGACCTCTTGCAGAGGATTACTCCGGTGATTTATTCGTTATCCAATTCTTATCTGAAGCGGTT
GCCCGTGGTGCTGCGCTGATGGCAGATATCAAGTACCTGATTCGTCCTGGTGCTCAAACTGATGTTGACCACTTTGTTAACTCTGGCACTGGT
GAGGTTGTCACTGGTGTAGAAGAAGACATCCATATTGTACAGTTAGGTAAGTACGCAGACCTCACACCTATTAGCGCGGTTCTAGAGGTATA
CACTCGCCGTATCGGTGTTGTCTTCATGATGGAGACAATGACACGCCGTGACGCCGAACGTGTTACTGCTGTAGAAATCCAGCGAGATGCGT
TAGAGATTGAGCAGAACATGGGTGGTGTATACTCCCTCTTTGCTACTACTATGCAATCGCCAGTAGCGATGTGGGGTCTGCTGGAGGCAGGG
GAGTCCTTCACTAGTGACTTAGTGGACCCTGTGATTATCACAGGTATTGAAGCTTTAGGACGCATGGCTGAGTTGGATAAACTGGCTAACTTT
GCTCAGTATATGTCACTGCCATTACAATGGCCTGAGCCTGTCCTAGCTGCTGTGAAATGGCCTGACTATATGGATTGGGTGCGTGGTCAAATC
TCTGCTGAACTGCCGTTCCTTAAATCGGCTGAAGAGATGGCACAAGAACAGGAAGCACAGATGCAAGCACAGCAAGCACAGATGCTTGAAG
AAGGTGTGGCTAAGGCCGTGCCGGGTGTAATTCAACAAGAACTTAAGGAGGCGTAATGTCTTTCTCATTTACTGAACCGTCAACCACTCACCC
TACTGCTGAAGAGGGTCCGGTAGAAACCAAGGAGGTAACAACTGATGCTGCTACTACTGATGCTCCTGCTGACGCTGGCACTTCTGTACAAG
ATGACAATGCTGGTGCACAACCTACTGAAGACACCGGAGGAGAAGCTTCTGGACAGCCTTCAGAAAAAGGAGACAATGGCGGAGAGAATG
GTGAACCTAAGCCAGATGATACCGCGACCGACACTGAGGAAGTGCAATACTTCTTCGGAGAACATGAAGTAACAGTAGACATCCCACAGGAT
GTAACTGACAGCCTTAAAGAGAAAGGCATTGATGCCAAGCAGGTTGCCAAGGAACTCTATTCCAAAGGTGGCAAGTTTGAACTGTCAGATGC
AACCAAGCAGAAATTGTATGATGCTTTTGGCAAGTTTGCGGTAGATGCTTACCTATCAGGTCTAAAGGCTCAAAATGAAGCCTTCTTCCTGAA
AGAAGCCAACGCAGCTAAAGAGTTGGAAGCAGCTAACACCCAACGCTTCTCTGATGTTTCTAAGGAAATTGGTGGCGAAGAAGGTTGGTCCC
GTCTTGAGGAGTGGGCACTTGAAGCGCTGTCTGATGACGAACTAATGGCATTCAATGCGGTGATGGAATCTGGCAACCAGTACCTGCAACAA
TATGCTGTTCGTGAACTGGAGGGTCGTCGTAAGCAGGCACAGGGGATGATAAGCCATCCCTGATTGAGCCATCAGCACCTGCTAAGGCTAA
TGAAGAGAATGGCCCACTGACGCGAGATCAGTACGTTCAAGCAATCGCAACTCTTAGCCAGAAGTACGGCAATGACCGTAAAGCTATGGCA
```

Figure 5F

```
GAAGCTCAGGCTAAACTGGACGCCCGTCGCCGTGCTGGCATGGCTCGCGGTATCTAATTCAGTATTTACTGGACACTATAGAAGGGAGAAAA
GTTCTCCCTAGTTATCAATTTGATTTATAAGGAGATTATAATACATGTCTACACCGAATACTCTGACTAACGTTGCTGTATCTGCGTCCGGTGA
GGTTGACAGCCTTCTCATTGAGAAGTTTAATGGTAAGGTCAATGAGCAGTACCTGAAAGGTGAGAACATTCTGTCCTACTTTGATGTACAAAC
TGTTACTGGCACTAACACAGTGAGCAACAAATATTTGGGCGAAACTGAGTTGCAGGTGCTAGCACCGGGTCAGTCCCCTAATGCCACCCCTAC
TCAGGCGGATAAAAACCAGTTGGTAATTGATACCACTGTCATTGCTCGTAACACTGTGGCTCACATCCACGATGTACAAGGTGACATCGATAG
CCTGAAACCAAAACTGGCTATGAACCAAGCCAAGCAACTGAAACGTCTGGAAGACCAGATGGCAATTCAGCAGATGCTGTTAGGCGGTATTG
CTAACACCAAGGCCGAACGTAACAAGCCGCGTGTTAAAGGGCATGGCTTCTCTATCAACGTTAACGTAACTGAGAGTGAAGCACTGGCTAAC
CCTCAGTATGTTATGGCTGCGGTAGAGTATGCTCTGGAGCAACAGCTTGAGCAGGAAGTGGACATCTCTGATGTAGCTATCATGATGCCGTG
GAAGTTCTTCAATGCTTTGCGTGATGCAGACCGAATTGTAGATAAGACTTACACTATCAGCCAGTCTGGTGCAACCATTAATGGCTTCGTTCTC
TCTTCTTATAACTGCCCTGTGATCCCGTCTAACCGATTCCCTACCTTCGCTCAGGATCAGGCTCACCACCTGTTGTCTAATGAAGATAACGGCTA
TCGTTATGACCCTATCGCAGAGATGAATGGTGCAGTTGCTGTTCTGTTCACTTCCGACGCACTGCTGGTGGGTCGTACCATTGAAGTGACTGG
TGACATCTTCTATGAGAAGAAAGAGAAGACTTATTACATTGACACCTTCATGGCTGAGGGTGCAATCCCTGACCGTTGGGAAGCAGTGTCTGT
AGTTACCACTAAACGTGATGCAACTACTGGTGATGCTGGAGGTCCTGGTGATGATCACGCAACCGTACTGGCTCGTGCACAGCGTAAGGCTG
TATATGTCAAAACCGAAGGTGCTGCGGCTGCATTCTCTGCTGCCCCAGCAGGTATCCAAGCGGAAGACCTTGTAGCGGCGGTACGTGCTGTA
ATGGCAAATGACATTAAGCCGACTGCAATGAAACCTACTGAGTAACACCTATGCCCTATCTACCTTGCGTAGGTAGGGTTCTTTTTGTTAGGA
GGATTCATGCCTGTAATTAGACAAACCAGTAAATTAGGACATATGATGGAAGATGTGGCCTTCCAGATTATTGATAGTAAGCTGGAAGCGGT
AAACTTGTGTATGCGAGCTATTGGTCGTGAGGGTGTGGATTCCCTCGACTCAGGGGACTTGGACGCAGAAGATGCAAGCAAAATGATCGAC
ATCGTATCCCAGCGGTTCCAGTACAACAAAGGAGGTGGCTGGTGGTTCAATCGTGAACCAAACTGGCAACTTGCACCAGACACTAACGGTGA
AGTTAATTTACCTAACAACTGCCTAGCAGTATTGCAGTGTTATGCTTTAGGTGAAAAGAAAGTACCTATGACTATGCGAGCAGGTAAGCTCTA
CTCTACTTGGAGTCACACCTTTGATATGCGTAAGCATGTTAATGCTAATGGTATGATTCGTCTTACCTTACTCACCTTACTACCCTACGAGCATC
TACCTACAAGTGTAATGCAGGCTATTGCCTATCAAGCTGCTGTAGAGTTTATTGTGTCTAAGGATGCAGATCAGACTAAGCTAGCCACTGCGC
AGCAGATAGCCACTCAGCTTCTTATGGATGTACAATCTGAGCAAATGTCACAGAAGCGATTAAACATGCTGGTACATAACCCTACTCAGCGTC
AGTTTGGTATCATGGCTGGTGGCTCTCAGAATGTACCTGCTTACTCTCATTCACCTTATGAGAGTTGGGCGCTCCGTCCGTGGGAGGATCGTT
AATGGAAGTACAAGGTTCATTAGGTAGACAAATCCAAGGGATTAGCCAGCAGCCGCCAGCGGTACGCTTGGATGGTCAGTGCACAGCTATG
GTTAATATGATACCTGATGTAGTGAATGGTACTCAATCACGCATGGGTACAACTCATATTGCAAAGATACTTGATGCGGGGACTGATGACATG
GCTACTCATCATTATCGCAGAGGTGATGGTGATGAAGAGTATTTCTTCACGTTGAAGAAAGGACAAGTTCCTGAGATATTTGATAAGTATGG
GCGCAAATGTAATGTGACTTCACAAGATGCACCTATGACCTACCTCTCTGAGGTTGTTAATCCAAGGGAAGATGTGCAATTCATGACGATAGC
TGATGTTACTTTCATGCTTAATCGTAGGAAAGTAGTTAAAGCTAGTAGCAGGAAGTCACCTAAAGTTGGAAACAAAGCCATTGTGTTTTGTGC
GTATGGTCAATATGGTACATCTTATTCCATTGTAATTAATGGGGCCAACGCTGCTAGTTTTAAAACACCGGATGGTGGAAGTGCAGACCATGT
TGAACAAATTCGAACTGAACGTATCACTTCTGAATTGTACTCTAAGTTGCAGCAATGGAGCGGTGTGAGTGACTATGAAATACAAAGAGACG
GTACTAGTATATTTATCGAGAGACGGGATGGTGCTAGCTTTACAATAACAACCACCGATGGTGCAAAAGGTAAGGACTTAGTGGCTATCAAG
AATAAAGTTAGCTCTACTGACCTACTCCCTTCTCGTGCGCCTGCTGGTTATAAAGTACAAGTGTGGCCTACTGGCAGCAAACCTGAGTCTCGTT
ACTGGCTGCAAGCTGAGCCTAAAGAGGGAAACCTTGTGTCTTGGAAAGAAACAATAGCTGCTGATGTATTACTTGGGTTTGATAAAGGCACA
ATGCCTTACATTATTGAACGTACAGATATCATCAACGGCATAGCTCAATTCAAGATAAGACAAGGTGATTGGGAAGATCGTAAAGTAGGGGA
TGACTTGACTAACCCTATGCCCTCTTTTATTGATGAGGAAGTACCCCAGACAATAGGTGGAATGTTCATGGTGCAGAACCGCCTATGCTTTACA
GCAGGTGAAGCGGTTATTGCTTCTCGTACATCATACTTCTTCGATTTCTTTCGTTATACGGTTATCTCTGCATTGGCAACTGACCCCTTTGATAT
TTTCTCAGATGCTAGTGAAGTCTACCAGCTAAAACATGCAGTGACCTTAGATGGCGCTACCGTGTTGTTCTCTGATAAGTCACAATTCATACTG
CCAGGCGATAAGCCTTTAGAGAAGTCAAATGCACTGCTTAAGCCTGTTACAACATTTGAAGTGAACAATAAAGTGAAGCCAGTAGTAACTGG
TGAATCGGTAATGTTTGCCACTAATGATGGTTCTTACTCTGGTGTACGAGAGTTCTATACAGACTCTTATAGTGACACTAAGAAGGCACAAGC
AATCACAAGTCATGTGAATAAACTCATCGAAGGTAACATTACCAACATGGCAGCAAGCACCAATGTCAACAGGTTACTTGTCACTACCGATAA
GTATCGTAACATAATCTACTGCTACGATTGGTTATGGCAAGGAACAGACCGTGTACAATCAGCATGGCATGTATGGAAGTGGCCTATAGGTA
CAAAGGTGCGAGGTATGTTTTATTCTGGTGAATTACTTTACCTGCTCCTTGAGCGAGGAGATGGCGTGTATCTGGAGAAGATGGACATGGGT
GATGCACTAACCTACGGTTTGAATGACCGCATCAGAATGGATAGGCAAGCAGAGTTAGTCTTCAAGCATTTCAAAGCAGAAGATGAATGGGT
ATCTGAGCCGCTCCCTTGGGTTCCTACTAACCCAGAACTTTTAGATTGCATCTTAATCGAGGGTTGGGATTCATATATTGGCGGCTCTTTCTTAT
TCAAGTACAACCCTAGTGACAATACTTTGTCTACAACCTTTGATATGTATGATGACAGCCATGTAAAAGCGAAGGTTATTGTTGGTCAGATTTA
CCCTCAAGAGTTTGAACCTACGCCTGTGGTTATCAGAGACAATCAAGACCGTGTATCCTACATTGATGTACCAGTTGTAGGATTGGTTCACCTT
AATCTTGACATGTACCCCGATTTCTCCGTAGAAGTTAAGAATGTGAAGAGTGGTAAAGTACGTAGAGTATTAGCGTCAAACCGTATAGGTGG
TGCTCTCAATAATACAGTAGGCTATGTTGAACCGAGAGAAGGTGTCTTCAGATTTCCACTGAGAGCTAAGAGCACGGATGTTGTTTATCGTAT
TATTGTAGAGTCACCTCACACATTCCAGCTTCGTGATATTGAGTGGGAAGGGAGCTACAATCCAACCAAAAGGAGGGTCTAATGGCTATAGG
TTCAGCCGTTATGGCTGGTATGTCTTCTATTGGTAGCATGTTTGCAGGCAGTGGTGCAGCAGCCGCTGCTGGAGGTGCTGCCGCAGGTGGCG
GAGGTTTGCTAGGTTCACTAGGTGGATTCCTAAGTGGCTCTACTGCTGGTTTCTCTAATGCTGGCCTTCTTGGTGCTGGCCTTCAAGGGTTAG
```

Figure 5G

```
GCTTGATTGGTGATCTATTTGGTGGAAGTGATGAAGCCAAGGCGATGAAGAAAGCACAAGAAGAGCAATGGCGGCAGCAGCTTATTGCTAC
ACAAGAGGCGTACAAGACAGTGGCAGACGCAGAACGTTCTGCTGCTAAACAATATCATGCAGATGCAATCAGTAATCAGGCTTCACTGCTAC
AGCAGCGAGCACAGGTTGCATTACTTGCTGGGGCTACTGGTACTGGTGGTAATTCTGTGTCCTCTATGCTTAATGACTTAGCAGCAGATGGCG
GCAGGAACCAGAGTACTATCATTGATAACTATGAGAATCAGAAGATTAATTTCACCAACCAGCTTAAGTCTATCCAACGTGGTGGTCAGATGC
AGATGCGTGAGTTTAAGAAGCCTTCTGCTATGAATACCTTGGTTAAAGGTATTCCAAGTCTGGCATCTGCCTATGTAACTGGTAGTAAGTCTG
GCAAGGCATTGGGTAAAGCCTTAACTGATTCTCGCACATATTCATCTGGAACAAGAGGTATTTAATGGCAATTGAGCGACAAGCAGTACAAG
GTCTGCCACAAGTGCAGGCCACTTCTCCTAATGTCATGACCTTTGCACCTCAACAAGTGGGAGGTGTGGAGGCTGGCGTGGCTTCTACCTCCG
GTAGTAGGTTTATCGAAGACCTTATTCGTGCAGCAAGCAGCGTGGCTGATGTTACCACTGGTATCCTTAATCAGAAGATTGAGGAAGATAAG
GTTGTTCAAATGGAACGGGCATATAACGGATTAATGCCTTCTGAGGATGCAACTCGTGGTGGCGCTCGTGCTAACATGCTTGTCAAAGCTCAA
CTGCTAGCTAATGATGAAGCAGCACGAATGAAAGACATGGCTACTCGTTTCCAAGGAACGGATGACGAATGGACACAACTTATGGTTGACTC
TCGTAATGAGATGCAGAATAAGCTGTTCCAGCAATACCCTGAGTTGCAAGGTGACAAAGATACTATGCGTATGGTCACTAATGTCTTCCAAGA
ACAGCAGCCTCAGATTTGGGCTACACGAACCCAGCATAAACTTGACCGTGAACAAGCAGACCGTGAGGATACCTTTGACGGGCGAGTGGCTT
CTACTTGGGATTCTAATATTGACCCTGAAGCCTCTGGCTATGCTTTACAGGAACGAATCCGCGAAGGTCTTACTCAAGGATTACTACCTGAACA
GATGTACAAGAAGTTAGTCCAGCGAGCAATTTCACTTGCACAAGGCGGTGATGTTAGCATGGCTGAAGCCCTGAAGTATGTGAAGGACGATA
AGGGTGTTTCTGTTTATGCTAAGAATCCACAGCTTATCACAGCCATCACTAGTGGTAATGCAGTTTGGGCTAGGAATAATGTAGCTGATGTAA
CTCGTATGTCTTTCGAAGTTAAAGAATCCTACCTTGCAGGTGATTTAACTGATGAAGAATTGTTGGAACGAGCACAGCACATTAATAATCTGA
CAGGTAACTCTGTCTTCTCTAATCCAGAACTAGAGGCACTGATGCGCCAACGGGCTAAGCAGAATGCAGAGCTAGGTGCAATGCAGGATATG
CGACGTGAGCTTTACTCCGACCGCCTGACTGGCTTCCAAGGTAAGACTGATAAAGAGAAGAAGGCTTACATTGATGTTATCAAACAGGATAG
CCAACTTTATGCAGACCAGCAAATCAAACAACGTGGCTTGGACCCTTACAGTCAAGAGGCTGAAGCTATTCGTGGTGCAGTGGAAGTGCAGC
GCCTGCAATTCATGAACTCCAAAGGCTTAGTGGATGATACCTTTGAGTCTCGTATCAAAGCCATGGAATCTATGCTATCGCCTGAGCACTTTGC
CAAGGGCGAACCACAGGAGTTGATGACTATTCGCCAGTTGTGGGAACAGTTACCAGAAGAGAGCCGAGGTGTCTTTGGTGACACGGTGAAT
GGCTACATGGATAACTACAACACTGCACTACAAATGGGAGAGACACCTTTGCAGGCTGCAAGGTTTGCGCGTAAAGCACAGCAGAAATTCTC
TCGTACTGAGAAGGAAACCAAGAAGTTCAACTCAGCTATTGGAGATGCACTGGATGAGGTATCTGGTGCTGGCTGGTTTGATGGTAAAACCG
AAGTGTCAGACTTAGGTAAAGCTATTGCGGAAGAAGAGTTACGAGCTAAGGCCAATATGTTGTGGTCTAGTGGTATGCGTAACATGGATTCC
ATCAAGAAGGCTTTAATTACTTGGGGCAATAAACGCTACACTCAATCAGAGGATGCAAAGACTTCCGGTGGCTATTTCATTAAAGGTGATTAC
ACTTCTGCATCTGATATGCTTATGTCAGTTGGGAAAGGCGTAAACCCTACCGATGTACCTCTGGCGCTTGGTAGGTATGTAGAAACACAGATG
CCAGAATTGAAGAAGGAGCTTCAAGAGGGGGAAACTAAAGATGATATATACATTGATTACAATGAACAGAAAGGTACTTTCGTGATTCGTGC
TGGTGCAGCAGGTCGCCCTCTTTCTGGAGTAATCCCTGTAACCTCTTTAGATACCACTTCACTACTAGATTCTGCCTATCAGAAGAAAGTAGAG
GAACGAGATAAAGGCGAGTATGTTCACCCGTATCGTACAGATATTGGTGCACAAGAGCCTATGCCAGCTAAACCAACTGCCAAAGATATTGG
TAAATTTGGACTAGCTAACTTCCTCATGTCTTCTGCTTTTGCTTCTGGTGAGAATCTGCCTTCTAACTTCGAGATTAACTATCGAGGTAATATGC
AACAATTCTATGACAAGCTAGCTATGGATGAGAATAAAGATAAAGTTGGCTTTAATAAGGCAACTGGAACCTTTACTCCATATAAAGACGCTC
ACGGTGAGTCTATCGGTTACGGTCATTTCTTAACGGAAGAAGAGAAGCGAAACGGGTATATTAAGATTGGCGATGAACTAGTTCCCTATCGA
GGGTCTATGTCTCAGCTTACAGAGAGCAAGGCTCGCGCTCTTATGGAGCAAGATGCTAAGAAGCATGTGCCTCCTACTCGTGACTGGAAGAT
TCCGTTTGACCAGATGCACCCTGCACAGCAACGTGGCTTGATGGATTTAAGCTACAATTTAGGTAAAGGTGGAATCCAGAACTCACCGCGTGC
TCTTGCTGCATTCAAAGCTGGTAAGCTTACGGAGGGCTTTATCGAAATGCTGGGCACTGCATCAAGTGAAGGTAAGCGTATTCCTGGCCTACT
GAAGCGACGCGCTGAGGCATACAATATGGCATCTGCTGGTGGTGTGCCTAAGATTACCGAAGTGGAGACTCGTGAAGATGGCTCCATGTGG
GTTAGGTTTGGTGGACCTATGCCAGCAGGTTCTGTCTCGGCATGGACTCATAAACGTATTGGCGCGGATGGTTGGTATCAGGTTTATGAGGC
TGCACCTACCAAGTTAGCTAAAGATTCTAAGGTAGGTAAAGTTAAGTTGTAGTACCTAACTCAAGGCTTGTCTCACATGTGAGACAGGTCTTT
ATGATAGGCACTATGGAGGAATTATGGAACAAGACATTAAGACTAATTGGGCTGGATATGTCCAGTCTACTCCTGAGCCGTTTTCTATTGAGG
CGGCTCCGGTATCGGCTCCTACGATACGCCAGCGTAATGAGTTACAAGAGCAAGTTCTTGAAGCTAAAGCTGACGCTGATATCTTAGGTGCT
GTAGGTGCTGCCTTCCAGAATGAGTGGTTGGCATTCGGAGGCAAGCGGTGGTATGACCGTGCCACTGCTGATTTCACACCTCAACCAGACTTT
GAGATACAACCTGAGCAACGTGAAGCACTACGTTTCAAATATGGTACGGATATGATGCAGACAATCACTGAGGGTGTTCGTTCTGAGGATGA
ATTGAACTTCCGTATTCAGAATGCGGATGAAGACCTTGAGCGCAATAAGCGCATTGCTCAGGCTGGCTGGGTTGGCTCTGTGGCGACGATTG
GCGCTGCTGTGCTTGACCCTGTGGGATGGGTTGCCTCTATTCCAACCGGTGGTGCCGCTAAAGTTGGACTCGTAGGCCGTGCTGTGCGTGGC
GCTATCGCCGCTGGCGTGAGTAATGCCGCTATTGAATCCGTATTGGTCCAAGGTGACATGACTCGTGATTTAGATGACATTATGGTAGCACTG
GGTTCCGGTATGGCTATGGGTGGCGTTATTGGCGCTGTAGCGCGTGGTAGGGCCACTAAGCTCAGTGAGCAAGGTGATGACAGGGCTGCTA
GCATTGTGCGCAGTGCAGACGCAGGGGACCGCTATGTTCGTGCTGTTGCCGATGACAGTATCGGTGCGATGCGTGTTAAGGGCGCAGAGGT
TCTCACTGAGGGTGTATTCGATATCTCCAGTAAGAGTGAAGACCTACTGAAAACCTTGCAACGAGAAGGTAATGCGATTGATATGACACCTCG
CCGTTGGGCTGGAACTATGTCTGCCCTCGGTACTGTCGTGCACTCATCTAAAGATGCAAGTATCCGAGGCCTTGGTGCTCGTCTGTTTGAATC
CCCACAAGGTCTAGGTATGCAGAAGGCATCTGCTAGTCTTATGCAGAATACTAACTTAAATCGCCTGAAATCTGCTGATATGAACCGCTTCAA
TGATGGGTTTGATTTGTGGCTTAAAGAGAATAATATCAATCCAGTAGCAGGGCATACCAACTCTCATTATGTACAGCAATACAATGAAAAGGT
```

Figure 5H

```
GTGGGAGGCAGTGCGTATTGGCATGGATGAGTCTACACCTAAATCTATCCGCATGGCTGCTGAGGGACAACAGGCTATGTACAGAGAGGCG
CTGGCTTTACGTCAACGTTCTGGTGAAGCGGGATTTGAAAAGGTAAAAGCCGACAACAAATATATGCCTGATATCTTTGATAGTATGAAAGCC
AGACGTCAATTCGATATGCACGATAAAGAAGACATCATCGAACTTTTCTCTCGTGCCTACCAGAATGGCGCTCGTAAGATTCCAAAGGAAGCA
GCAGATGAGATTGCACGAGCACAGGTAAATCGCGTTGCTGATGCTACCTTAACTGGAAAGCTTAGTTTTGAAAAGGCAATGTCAGGTCAGAC
TAAGGCAGAGTATGAAGCTATCATGCGTAAGGCAGGCTTCAGTGATGAAGAAATTGAAAAGATGATAGAAGCTCTGGATAACAAAGAAACC
AGAGATAACATCTCTAACCGAGCTAAAATGAGTTTAGGATTAGATGTTACTCAAGAATACAATGGCATTCGTATGCGTGACTTCATGAATACC
AACGTGGAAGAGCTAACAGATAACTATATGAAGGAAGCAGCAGGTGGCGCTGCATTGGCTCGCCAAGGCTTCTCTACCTATCAGGCTGCACT
TAATGCAATTGACCTTGTAGAGCGAAATGCACGAAACGCGGCTAAGGATAGCAAGGCTAGTTTGGCATTAGATGAAGAGATTCGTCAGATGC
GAGAAGGTCTTCGCCTGATTATGGGCAAGTCGATTGATGCAGACCCACAGGCTATATCTACTAAGATGATGCGTCGTGGTCGTGATATCACA
GGTGTGCTTCGCTTAGGTCAAATGGGCTTCGCACAGCTAGGTGAACTTGCCAACTTTATGGGTGAATTTGGTATTGCTGCAACTACTATGGCT
TTAGGTAAGCAATTCCGCTTCACCTCTAAGGCGTTGCGTAATGGCGATGGCTTCTTCCGAGATAAGAACTTAGCTGAGGTTGAGAGAATGGT
GGGGTACATTGGTGAGGATAACTGGCTAACAACTAAGGGTGCACGTCCTGATGAATTTGGTGATGTAACCACAGTAAGAGGGATGATGGCT
CACTTTGACCAATCCATGAACTCAATACGTCGTGCTCAAACCAACCTATCACTCTTCCGCATGGCACAGGGTTCTCTGGAGCGAATGACTAATA
GGCAAATAGCTTTGTCTTTCATTGACCACCTTGAAGGCAAGAAGATTATTCCTCAGAAGAAACTGGAGGAACTTGGTCTTACTCAGGAGTTCA
TGACTAACCTACAGAAGCACTATGATGCTAACTCTAAAGGTTCTGGCTTGCTTGGCTTTGATACAATGCCTTATGCCATGGGTGAAACTTTAGC
TAATGCTATTCGTCGTAAGTCAGGTCTAATCATCCAACGTAACTTCATTGGTGATGAAGGTATCTGGATGAACAAAGCACTAGGTAAGACATT
TGCACAGCTTAAGTCATTCTCTCTTGTATCTGGTGAGAAGCAATTTGGTCGAGGGATTCGCCACGATAAAATTGGTCTTGCTAAGAAGACAGC
TTACGGGTTTGCTTTGGGTTCAATAGTGTATGCGGCAAAAGCCTATGTGAACTCTATTGGGCGAGAAGACCAAGATGAATATTTGGAAGAGA
AGTTATCGCCTAAAGGGTTGGCCTTTGGTGCAATGGGTATGATGAGTACAACTGCTGTATTTAGTCTAGGTGGAGATTTCTTAGGTGGCCTAG
GTGTTCTACCTTCCGAACTCATTCAATCACGCTATGAAGCAGGTTTCCAAAGTAAGGGTCTGATTGACCAAATACCTCTGGTTGGCGTTGGTGC
AGATGCAGTAAATCTGGCTAACTCAATCAAGAAGTATGCAGAAGGTGACACAGAAGGTGTAGATATCGCTAAGCGAGCACTCCGTCTTGTGC
CACTTACCAATATAATAGGTGTCCAAAACGCATTGCGTTATGGCTTAGATGAACTGGAGGATTGATGAGTTATACTTTCACAGAACATACAGC
CAATGGTACGCAAGTCACCTATCCTTTTAGCTTTGCTGGTAGGGATAAAGGTTATCTTCGTGCCTCAGATGTGATAGTGGAGTCTCTTCAAGGT
AACACTTGGATTGAAGTTACATCTGGCTGGCAACTAACTGGCACGCACCAGATTACTTTTGATGTAGCACCAGTTGCAGGTTTGAAGTTCCGT
ATTCGAAGGGAAGTACAAAAAGAATATCCATACGCTGAGTTTGACCGTGGTGTTACCTTGGATATGAAGTCTTTAAATGGTTCTTTCATTCATA
TACTGGAGATTACACAGGAGTTACTTGACGGGTTTTATCCAGAAGGATACTTCATTAAACAGAATGTAAGCTGGGGCGGCAATAAGATTACT
GATTTGGCTGATGGCACAAATCCGGGAGATGCAGTAAATAAAGGGCAGCTTGATGCCATCGACAAGAAGCATACAGATTGGAACGCCAAAC
AGGACATTGAGATTGCTGGCCTTAAGGCTGGTATGACTTCTGGTATTGCGCACAGAACTGTTCCTTGGTACACGATAGCCCAAGGTGGTGAG
ATTTCCGTAAAACCACCTTATGAATTTCAAGATGCACTAGTTTTCCTTAATGGGGTATTGCAGCACCAAATTGTAGGCGCATACTCTATAAGCA
ACAACACTATCACTTTCGCAGAGCCGCTTGTGGCTGGTACAGAGGTGTATGTGCTGATTGGTAGTCGTGTGGCTACATCTGAACCTAATATTC
AGTTGGAGTTGAACTTTGACTTAGTAGAAGGCCAACAAGTAGTACAGATTGGCTCTGCATTTAAGTACATTGAGGTCTACCTTGATGGATTAT
TACAACCTAAACTTGCTTATCAGGTAGACGGTGACATTGTTACTTTCTCAGAAAGAGTACCAGAATGCCGGATGACTGCTAAGATTATCACAG
CATAAGGAGGTGGGATGATTAACTCCGAACTGGTAGATAGTGGTGTGAAGCTTGCGCCACCTGCACTCATATCAGGTGGGTACTTCCTCGGT
ATCAGTTGGGATAATTGGGTGTTAATAGCAACATTCATTTATACCGTGTTGCAAATTGGGGACTGGTTTTATAATAAGTTCAAGATTTGGAGG
GAGAAGCGTGAGCGTACACAATAAACATGCAGCTACAGAGGACGAGGTTGGCATTCTGCATGGTGCTATTACCAAAATCTTCAATAAGAAAG
CACAGGCAATACTGGACACTATAGAAGAAGACCCTGATGCAGCATTACATTTAGTGTCTGGTAAGGATATTGGTGCGATGTGTAAGTGGGTT
CTTGATAACGGCATTACCGCCACACCTGCTGCACAGCAGGAAGAGTCCAAGTTATCTAAGCGCCTCAAGGCTATCCGAGAGGCATCCAGTGG
TAAGATAATTCAATTCACTAAGGAGGATTGATGGCTAAGGCAAGAGAATCACAAGCGGAGGCTCTTGCCAGATGGGAGATGCTACAGGAGT
TACAGCAGACCTTTCCTTACACCGCGGAAGGTTTGCTTCTCTTTGCAGATACAGTTATTCATAACTTAATTGCAGGCAACCCTCATCTGATTCGT
ATGCAGGCGGATATCTTGAAGTTCCTATTTTACGGACACAAGTACCGCCTCATCGAAGCGCCTCGTGGTATCGCTAAGACAACACTATCAGCA
ATCTATACGGTATTCCGTATTATTCATGAACCGCATAAGCGTATCATGGTTGTGTCCCAAAACGCCAAGCGAGCAGAGGAAATCGCAGGTTG
GGTAGTTAAAATCTTCCGTGGCTTAGACTTTCTTGAGTTTATGCTGCCGGATATCTACGCTGGGGACCGTGCATCCGTTAAGGCGTTTGAGAT
TCATTACACCCTACGTGGTAGTGATAAGTCTCCTTCTGTATCCTGTTACTCAATCGAAGCAGGTATGCAGGGTGCTCGTGCTGATATTATTCTA
GCGGATGACGTAGAGTCGATGCAGAATGCTCGTACGGCAGCGGGCCGTGCCTTGCTTGAGGAGCTGACTAAGGAGTTTGAATCTATCAACC
AGTTTGGGGATATCATTTACCTTGGTACACCTCAGAACGTAAACTCTATCTACAACAACCTACCTGCTCGTGGTTACTCTGTTCGTATCTGGACT
GCGCGTTACCCTTCAGTAGAGCAAGAGCAATGTTATGGCGACTTCCTTGCACCTATGATTGTTCAAGATATGAAGGACAACCCAGCACTTCGC
TCAGGGTACGGGTTGGATGGTAATAGTGGTGCACCTTGTGCCCCTGAAATGTATGATGATGAAGTCCTGATTGAGAAGGAAATCTCTCAGGG
TGCTGCTAAGTTCCAGCTTCAGTTCATGCTTAACACTCGCATGATGGATGCTGACAGATACCCATTACGCCTGAACAATCTAATCTTCACCTCG
TTTGGTACAGAGGAAGTCCCTGTGATGCCTACGTGGAGTAATGATTCCATAAACATCATTGGTGATGCACCTAAGTATGGTAACAAGCCTACG
GATTTCATGTACAGACCTGTAGCTCGCCCATATGAATGGGGTGCTGTCTCCCGCAAGATTATGTATATTGACCCTGCGGGTGGTGGTAAGAAC
GGAGATGAGACGGGTGTAGCCATCGTATTCCTGCACGGCACATTCATTTATGTGTATCAGTGCTTTGGTGTACCTGGCGGATACCGAGAGTC
```

Figure 51

```
GTCCCTGAATCGCATTGTGCAGGCCGCAAAGCAGGCGGGTGTTAAAGAGGTATTCATTGAGAAGAACTTTGGTCATGGCGCGTTTGAGGCG
GTAATTAAGCCGTACTTTGAACGAGAGTGGCCTGTAACTCTGGAAGAGGATTACGCCACCGGACAGAAAGAGTTGCGTATCATTGAGACGCT
GGAGCCGCTCATGGCAGCCCATAGGCTTATCTTCAATGCAGAGATGGTGAAGTCAGACTTTGAGTCGGTACAGCACTATCCGCTTGAACTAC
GCATGTCCTACAGTCTTTTCAATCAAATGTCGAACATAACGATTGAGAAGAACAGCCTCCGGCACGATGACCGCCTAGACGCCCTGTATGGCG
CTATACGGCAATTAACTTCTCAGATAGACTATGACGAGGTTACACGGATTAATCGCCTCAGAGCGCAGGAGATGCGCGATTACATCCATGCTA
TGAACACACCTCATCTACGCAGGGCAATGCTATATGGAGATTACGGTACTGAGCGAAGAGTGACCAACACTTCCGTAGCGATGCAGCAGCGA
GTTTACGGGCAGAACTACCGAAATAAATCGGCAAGCAGAAATACACTTTCTGCAAGGATTTCAAGGACTTATTAATTACTGGACACTATAGAA
GGAAGGCCCAGATAATAAGAGAAAATAATAGGTAATATATATATAGGTTAACCTAGGTTATATAGGTATGCCTTAGTATGGGTGTACTCCTGT
ACACCCTATTCCTTACTACCTTACTATATTTACATAATAGGAGAGAGACAATGGCTAATGATTATAGTAGTCAACCATTAACAGGTAAGTCTAA
GAGAAAGCAGGTACAACCTGTAAGTGAAGAACTAATGCTTCCGGTGCTCAAAAAAGAGGAAGTTAGTAAGAAAAGCAATGTTATTAATGAT
GCCACCCAAATCAGGTAAACAGAAAGGGGCCATGGTGTGCCTTGAAGTGAAAGGTGGTGTATTGAAGATTGCTATCGCGGTTGATGGCAAAG
AAGATTCAGAGTGGAAGTTAGTAACAGTGGAACCAACTGTTAACCCAGTTTAAGATAAGGAGGAAGATTACATGGCTAAATATGGTACTACA
GGTTCTGTTACTGGTCAGGCTTTTCGAGTAAAAGCAGTACAAACTATTGCAACGGCAATCCCGATGCCTGTTGTTAAAGAAGAAGACCTTAAG
AGTAAAGACCACCCTATCAACATCAAACATTTATCAGGTAAACAGAAAGGTGCAATGGTTGCTCTTGAGAAAGGTGACACAACCTTACATATT
GCTGTTGCACGTGGTAGTGAACCCACAGACCCTTGGGATGTAACTGGTATGGAAAAGGACGCTGTTACTCCAGCAGGGGTATAATAATGCTT
AATAAATACTTCAAGCGTAAAGAGTTTGCTTGCCGTTGTGGGTGCGGTACATCCACTGTTGATGCTGAATTACTACAGGTAGTCACAGATGTG
CGTGAGCACTTTGGTTCTCCTGTAGTTATCACTTCGGGTCATCGCTGTGCTAAGCACAATGCCAATGTAGGTGGCGCTAAGAACTCCATGCAT
CTTACTGGTAAGGCTGCTGACATTAAAGTGTCTGGCATATTACCTTCTGAAGTGCATAAGTATCTTACTAGCAAATACCAAGGCAAGTATGGT
ATAGGTAAGTATAACTCCTTCACTCACATCGATGTACGGGATGGTTGTGCGCGATGGTAAGATGTGTTGAATGGTGTGAGCGTATGGTTGCC
CAAGCTGCCGAGGATGGCAACTATGATGACTGGAAGAACTACTCTGACTTGTTAGCTCAATGGAAAGGGAGATGCAATGAAAAAGCTGTTTA
AGTCTAAGAAGGTTGTAGGTGCACTGGTTGCACTTGTTATTGCTCTTGTTTCTGTAGGTCTTGGTGTAGACCTTGGCTCTGGCACGGAATCCTC
TGTGACAGATGTGGTCTGCCAAGTGATCACCTGTGAATAAGTTTCTAGAAGTTCTGGCAGGTCTTATTGGCCTGCTTGTCTCTGCTAAGAAGA
AACAAGAAGAGAAGGAGGCACAAAGTGAAGCGAATCATGTTAGTGACAACCCTTCTGATTGGTTCGCTGACCACTTCCGGGTGTCAGCAGG
CGTTACCAGAGAAAGCAATGGTGAAACCTCTGAGGCCGACGCTGACGGCAGTTTACGAGGTAGACGATAAGGTCTGCTTTAGTAAGCCTGAC
GCTACAAAACTTGGTTTGTACATTCTCTCGCTAGAACGCGGATACAATTAATACATAGCTTTATGTATCAGTGTCTTACGATTTACTGGACACT
ATAGAAGAGGTAAGATAGCGCCGTTCTTTTGAGCGGCCTATTACTAGCCAATCTTCATAGGGAGGGTTGGAAAGTAATAGGAGATAGCATG
GCTAAATTAACCAAACCTAATACTGAAGGAATCTTGCATAAAGGACAATCTTTGTATGAGTACCTTGATGCGAGAGTTTTAACATCAAAGCCG
TTTGGTGCTGCAGGTGACGCCACTACTGATGATACGGAGGTTATAGCTGCTTCATTAAACTCTCAGAAAGCTGTCACAGTCTCAGATGGTGTA
TTCTCTAGCTCTGGTATTAACAGTAATTACTGTAACTTAGACGGCAGGGGTAGTGGCGTGCTAAGTCACCGTTCAAGTACAGGTAACTACTTA
GTATTTAACAATCTACGTGCAGGTCGCTTAAGTAATATTACGGTAGAAAGTAATAAGGCGACTGATACAACTCAGGGACAGCAGGTATCCCTT
GCTGGTGGAAGTGATGTTACTGTAAGTGACGTTAACTTCTCAAACGTTAAAGGTACTGGTTTCAGTTTAATCGCATACCCTAATGATGCGCCA
CCTGATGGACTTATGATTAAAGGCATTCGAGGTAGCTATTCCGGCTATGCTACTAATAAGGCAGCCGGATGCGTACTTGCTGATTCCTCAGTT
AACTCCCTCATAGATAACGTCATTGCTAAGAACTACCCTCAGTTCGGAGCAGTAGAGTTGAAAGGTACAGCCAGTTACAACATAGTCAGTAAT
GTTATAGGGACAGATTGCCAGCATGTAACTTACAACGGCACTGAAGGGCCAATAGCTCCTTCTAATAACCTTATCAAGGGGGTGATGGCTAA
TAACCCTAAGTATGCAGCGGTTGTTGCAGGCAAAGGAAGTACGAACTTAATCTCAGACGTGCTCGTAGATTACTCAACTTCTGATGCTAGGCA
GGCTCATGGTGTTACAGTAGAGGGTTCTGATAACGTCATAAATAATGTGCTTATGTCAGGATGTGATGGTACTAACTCTTTAGGACAAGGGC
AGACTGCTACAATTGCACGCTTTATAGGTACAGCTAATAACAACTATGCGTCTGTATTTCCTAGCTACAGTGCTACAGGTGTTATTACTTTCGA
ATCCGGCTCTACCCGTAACTTCGTAGAGGTAAAGCACCCTGGCAGGAGAAACGACCTTCTCAGTTCTGCTAGTACTATTGACGGTGCAGCTAC
TATTGACGGCACTAGTAATAGTAACGTAGTGCACGCACCTGCCTTAGGGCAGTACATAGGTAGTATGTCAGGTAGGTTCGAATGGCGGATTA
AGTCCATGTCACTCCCTTCAGGCGTTCTTACTTCTGCTGATAAGTACAGAATGCTTGGAGATGGTGCTGTGTCATTAGCTGTAGGTGGGGCA
CTTCTTCTCAAGTTCGCCTATTTACTTCTGATGGTACTTCTCGGACAGTGTCCCTCACCAACGGTAACGTGCGTCTTTCTACCAGTAGCACAGGC
TTTTTGCAGTTAGGTGCTGATGCAATGACCCCAGACAGTACTGGTACATACGCATTAGGTTCCGCCAGCCGAGCATGGTCTGGCGGTTTTACT
CAAGCAGCATTCACTGTTACCTCAGATGCTCGGTGTAAAACAGAACCTCTTACTATCTCAGATGCCTTACTGGATGCTTGGTCTGAAGTTGACT
TTGTGCAGTTTCAGTATTTGGATCGTGTTGAGGAGAAGGGTGCAGACTCAGCTAGATGGCACTTCGGTATCATCGCTCAGCGAGCTAAGGAG
GCTTTCGAACGTCACGGTATAGATGCACATCGCTATGGCTTCTTGTGCTTCGACAGTTGGGATGATGTATACGAGGAAGATGCCAATGGCTCT
CGTAAACTGATTACACCAGCAGGTTCCCGCTACGGTATTCGTTACGAGGAAGTACTGATATTAGAGGCTGCGTTGATGCGGCGGACTATTAA
GCGTATGCAGGAAGCACTAGCTTCCCTGCCTAAGTAAGCAACAGGCAGTGCGTAAGCACTGCTTTTAGCGCAACTTTTCTTAAAGGTTATCAC
GGTGGTAGCCTTTCAGAAAAGGAGGTTACATGATTCAAAGACTAGGTTCTTCATTAGTTAAATTCAAGAGTAAAATAGCAGGTGCAATCTGG
CGTAACTTGGATGACAAGCTCACCGAGGTTGTATCGCTTAAAGATTTTGGAGCCAAAGGTGATGGTAAGACAAACGACCAAGATGCAGTAAA
TGCAGCGATGGCTTCAGGTAAGAGAATTGACGGTGCTGGTGCTACTTACAAAGTATCATCTTTACCTGATATGGAGCGATTCTATAACACCCG
CTTCGTATGGGAACGTTTAGCAGGTCAACCTCTTTACTATGTGAGTAAAGGTTTTATCAATGGTGAACTATATAAAATCACGGATAACCCTTAT
```

Figure 5J

```
TACAATGCTTGGCCTCAAGACAAAGCGTTTGTATATGAGAACGTGATATATGCACCTTACATGGGTAGTGACCGTCATGGTGTTAGTCGTCTG
CATGTATCATGGGTTAAGTCTGGTGACGATGGTCAAACATGGTCTACTCCAGAGTGGTTAACTGATCTGCATCCAGATTACCCTACAGTGAAC
TATCATTGTATGAGTATGGGTGTATGTCGCAACCGTCTGTTTGCCATGATTGAAACACGTACTTTAGCCAAGAACAAACTAACCAATTGTGCAT
TGTGGGATCGCCCTATGTCTCGTAGTCTGCATCTTACTGGTGGTATCACTAAGGCTGCAAATCAGCAATATGCAACAATACATGTACCAGATC
ACGGACTATTCGTGGGCGATTTTGTTAACTTCTCTAATTCTGCGGTAACAGGTGTATCAGGTGATATGACTGTTGCAACGGTAATAGATAAGG
ACAACTTCACGGTTCTTACACCTAACCAGCAGACTTCAGATTTGAATAACGCTGGAAAGAGTTGGCACATGGGTACTTCTTTCCATAAGTCTCC
ATGGCGTAAGACAGATCTTGGTCTAATCCCTAGTGTCACAGAGGTGCATAGCTTTGCTACTATTGATAACAATGGCTTTGTTATGGGCTATCAT
CAAGGTGATGTAGCTCCACGAGAAGTTGGTCTTTTCTACTTCCCTGATGCTTTCAATAGCCCATCTAATTATGTTCGTCGTCAGATACCATCTGA
GTATGAACCAGATGCGTCAGAGCCATGCATCAAGTACTATGACGGTGTATTATACCTTATCACTCGTGGCACTCTTGGTGACAGACTTGGAAG
CTCTTTGCATCGTAGTAGAGATATAGGTCAGACTTGGGAGTCACTGAGATTTCCACATAATGTTCATCATACTACCCTACCTTTTGCTAAAGTA
GGAGATGACCTTATTATGTTTGGTTCAGAACGTGCAGAAAATGAATGGGAAGCAGGTGCACCAGATGATCGTTACAAGGCATCTTATCCTCG
TACCTTCTATGCACGATTGAATGTAAACAATTGGAATGCAGATGATATTGAATGGGTTAACATCACAGACCAAATCTATCAAGGTGACATTGT
GAACTCTAGTGTAGGTGTAGGTTCGGTAGTAGTTAAAGACAGCTACATTTACTATATCTTTGGTGGCGAAAACCATTTCAACCCAATGACTTAT
GGTGACAACAAAGGTAAAGACCCATTTAAAGGTCATGGACACCCTACTGATATATACTGCTATAAGATGCAGATTGCAAATGACAATCGTGT
ATCTCGTAAGTTTACATATGGTGCAACTCCGGGTCAAGCTATACCTACTTTCATGGGTACTGATGGAATACGAAATATCCCTGCACCTTTGTAT
TTCTCAGATAACATTGTTACAGAGGATACTAAAGTTGGACACTTAACACTTAAAGCAAGCACAAGTTCCAATATACGATCTGAAGTGCAGATG
GAAGGTGAATATGGCTTTATTGGCAAGTCTGTTCCAAAGGACAACCCAACTGGTCAACGTTTGATTATTTGTGGTGGAGAAGAGACTTCGTCC
TCTTCAGGTGCACAGATAACTTTGCACGGCTCTAATTCAAGTAAGGCTAATCGTATCACTTATAACGGAAATGAGCACCTATTCCAAGGTGCA
CCAATCATGCCTGCTGTAGATAACCAGTTTGCTGCTGGTGGACCTAGTAACCGATTCACTACCATCTACCTAGGTAGTGACCCTGTTACAACTT
CAGATGCTGACCACAAGTACAGTATCTCTAGTATTAATACCAAGGTGTTAAAGGCTTGGAGCAGGGTTGGTTTTAAACAGTATGGTTTGAATA
GTGAAGCAGAGAGGGACCTTGATAGCATACACTTCGGTGTCTTGGCTCAGGATATTGTAGCTGCTTTTGAAGCTGAAGGGTTGGATGCCATT
AAGTATGGAATTGTGTCCTTCGAAGAAGGTAGGTACGGTGTGAGGTATAGTGAAGTTCTAATACTAGAGGCTGCTTATACTCGTTATCGTTTA
GACAAGTTAGAGGAGATGTATGCCACTAATAAAATCAGTTAAGCAAGCTGCTGTACTCCAGAACACAGAAGAGCTTATTCAATCAGGACGTG
ACCCTAAGCAGGCTTATGCCATTGCCAAGGATGTTCAACGTCGTGCCATGAAGAAACCTTCTGCATCTTCTGCGTAAGCAGGTTAATATCTTA
GTATAAACAAGGGCAGACTTAGGTTTGTCCTTAGTGTATTCCAAAGGAGGTAACATGCTGAAAGATGGTTGGGTTTCATATGACCCTACAGA
CCCTAAGAATTGGCTACAGGTTATCGCTATAGCTTGTGCAGGTAGCCTATTGGCTGCCCTGATGTATTCATTATGGATGTACACAAAGTAACC
AAAGTCAAAATTTTGATGTAGGCGTGTGTCAGCTCTCTCGCCCTCGCCCTCGCCGGGTTGTCCCCATAGGGTGGCCTGAGGGAATCCGTCTTC
GACGGGCAGGGCTGATGTACTCCTTGTCTAGTACAAGGGAGGCGGAGGGAACGCCTAGGGAGGCCTAGGAATGGCTTAGTGGTGGACAAG
GTGATTACCTTAGTGAAGCCTCTTAGTGCATTCCTGAGGCCATTCAGGGCGTTTATGAGGGATTGACAGGGTGTGAGGGCGTGGGCTA
```

Figure 8

```
Downstream cut site (sgRNA 89)
   D  D  Y  S  D  A  L  H  E  V  V
GATGATTACTCTGATGCACTACATAGGTTGTA  Sequence in K1-5 genome
|| || ||    || || || ||||||||||||
GACGACTATAGCGACGCCCTTCATGAGGTTGTA  Sequence in donor template
   D  D  Y  S  D  A  L  H  E  V  V Protospacer sequence
PAM sequence
▼ = Cas9 cut site
```

Figure 13

One hour infection of K1 *E. coli* maintained under ampicillin selection to prevent carryover of cells used for recombination (which express Nanoluc)

Used to re-infect for round 2

Individual plaques were obtained from these diluted lysates
- sgRNAs 86+89: 24/24 recombinant (100%)
- sgRNAs 1112+1122: 11/24 recombinant (45.8%)

Figure 14
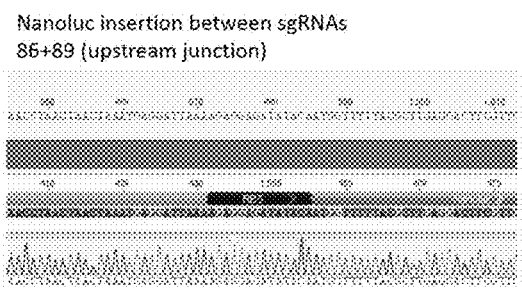 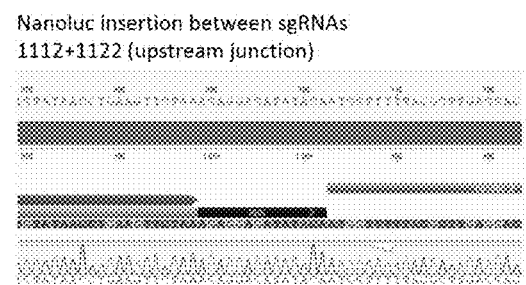

Figure 15

5' AACCTAACTAACTAAATGAGGATTAAAAGAGGAGATATACAATGGTTTTTACGCTTGAGGACTTCGTT 3' (SEQ ID NO: 10)

5' TGTATAACCTGAAGTTCTAAAGAGGAGATATACAATGGTTTTTACGCTTGAGGAC 3' (SEQ ID NO: 11)

Figure 17
sgRNA 86+89
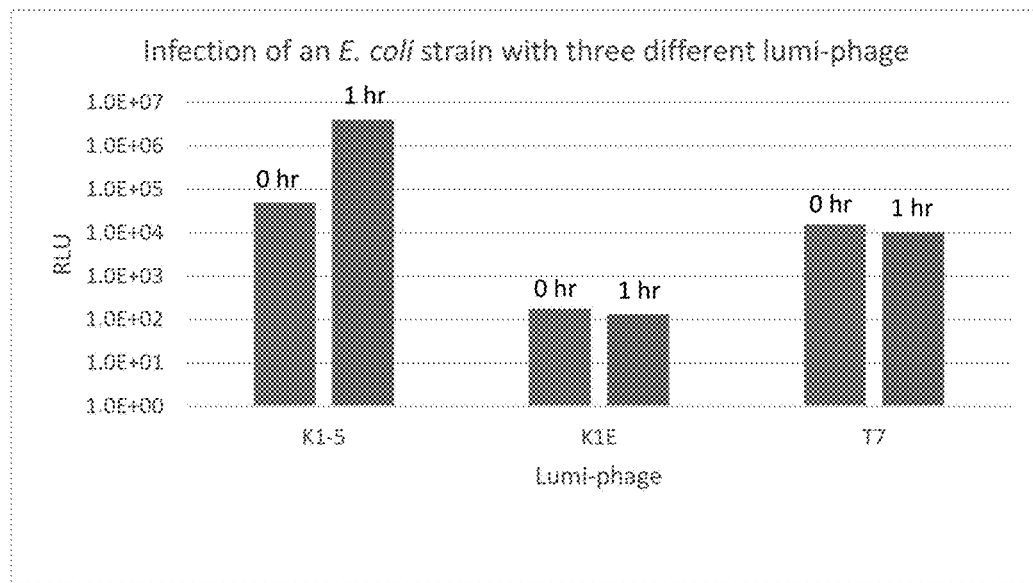
sgRNA 1112+1122
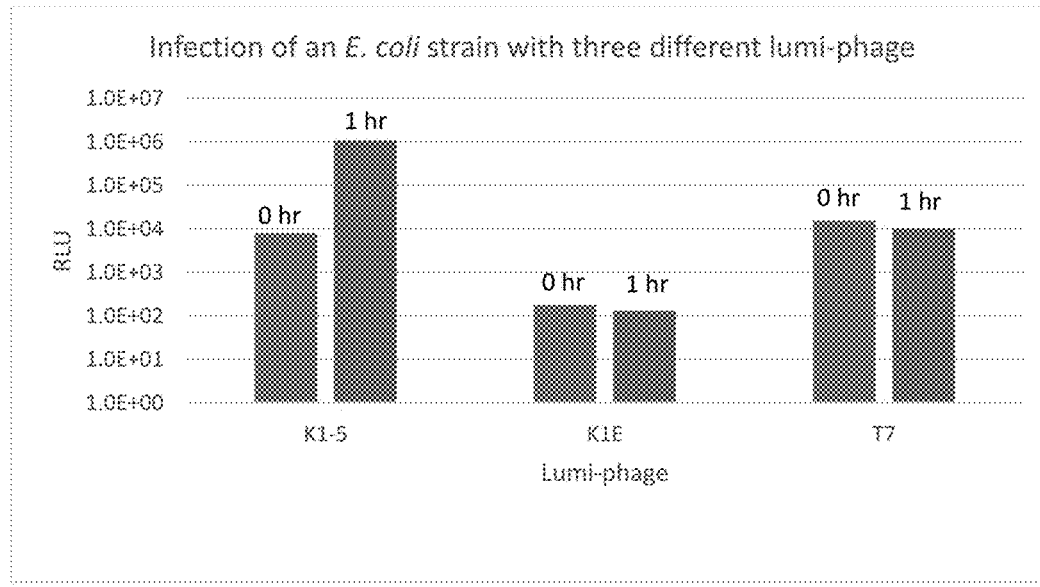

BACTERIOPHAGE RECOMBINATION FOLLOWED BY BLOCKAGE OF NON-RECOMBINANT BACTERIOPHAGE REPLICATION

CROSS-REFERENCE TO RELATED APPLICATIONS

This application claims the benefit of and priority to US Provisional Appl. No. 62/456,783, filed Feb. 9, 2017, and US Provisional Application No. 62/515,223, filed Jun. 5, 2017, the disclosures of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Feb. 21, 2018, is named 102590-0616_SL.txt and is 183,445 bytes in size.

TECHNICAL FIELD

The present technology relates generally to methods and kits for generating recombinant bacteriophage genomes. In particular, the present technology relates to methods of integrating a heterologous nucleic acid sequence into a bacteriophage DNA genome, and isolating recombinant bacteriophages that express the heterologous nucleic acid sequence.

BACKGROUND

The following description of the background of the present technology is provided simply as an aid in understanding the present technology and is not admitted to describe or constitute prior art to the present technology.

Model phages have been engineered using molecular biology techniques to deliver heterologous protein products to bacterial cells. E.g., US 2009/0155215; M. J. Loessner et. al., *Applied and Environmental Microbiology*, Vol. 62, No. 4, pp. 1133-40 (1996)). The natural host range of model phage engineered to date is limited. Methods for creating variations in phage genomes and engineering new phage genomes may lead to the identification of phages with varied properties (e.g., varied host ranges) that are useful for diagnostic and therapeutic purposes.

Engineering diverse phage is generally made more difficult by the properties of phage genomes. For example, phage genomes have relatively few restriction sites and are heavily modified, making use of traditional cloning techniques with phage challenging. Phages also have compact genomes with very little non-coding DNA, which can make it challenging to find sites within the genome that are compatible with traditional engineering. Many existing phage engineering technologies that rely on in vitro strategies are generally inefficient and challenging to scale up. Further, engineering phages within bacteria can be problematic due to toxicity of phages to bacteria as well as the difficulty in maintaining the stability of large engineered genomes.

SUMMARY OF THE PRESENT TECHNOLOGY

In one aspect, the present disclosure provides a method for making a recombinant bacteriophage DNA genome in a first bacterial host cell comprising (a) contacting a first bacteriophage DNA genome with a first sgRNA-CRISPR enzyme complex and a second sgRNA-CRISPR enzyme complex in vivo under conditions where (i) the first sgRNA-CRISPR enzyme complex cleaves a first protospacer sequence within the first bacteriophage DNA genome; and (ii) the second sgRNA-CRISPR enzyme complex cleaves a second protospacer sequence within the first bacteriophage DNA genome to produce a cleaved first bacteriophage DNA genome; and (b) recombining in vivo the cleaved first bacteriophage DNA genome with a heterologous nucleic acid sequence in the presence of a recombination system under conditions to produce the recombinant bacteriophage DNA genome, wherein the first bacterial host cell is infected with the first bacteriophage DNA genome, and wherein the heterologous nucleic acid sequence comprises an open reading frame that encodes a bioluminescent protein, a fluorescent protein, a chemiluminescent protein, or any combination thereof. The first bacteriophage DNA genome may be non-recombinant (e.g., wild-type) or may contain an alternate recombinant sequence. The first bacterial host cell may be a non-natural bacterial host cell or a natural bacterial host cell for the recombinant bacteriophage.

Examples of bioluminescent protein include, but are not limited to, Aequorin, firefly luciferase, *Renilla* luciferase, red luciferase, luxAB, and nanoluciferase. Examples of chemiluminescent protein include β-galactosidase, horseradish peroxidase (HRP), and alkaline phosphatase. Examples of fluorescent protein include, but are not limited to, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOK, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa.

Additionally or alternatively, in some embodiments of the methods, the first bacteriophage DNA genome corresponds to a bacteriophage family or order selected from the group consisting of Myoviridae, Siphoviridae, Podoviridae, Lipothrixviridae, Rudiviridae, Ampullaviridae, Bucaudaviridae, Clavaviridae, Corticoviridae, Cystoviridae, Fuselloviridae, Globuloviriade, Guttaviridae, Inoviridae, Leviviridae, Mircoviridae, Plasmaviridae, and Tectiviridae. In certain embodiments, the first bacteriophage DNA genome corresponds to T3, T7, M6, K11, F92, K1-5, or K1F.

Additionally or alternatively, in some embodiments of the methods disclosed herein, the cleaved first bacteriophage DNA genome comprises a first cleaved bacteriophage genomic fragment and a second cleaved bacteriophage genomic fragment. In certain embodiments of the methods disclosed herein, the heterologous nucleic acid sequence comprises a 5' flanking region that is homologous to the 3' end of the first cleaved bacteriophage genomic fragment, and a 3' flanking region that is homologous to the 5' end of the second cleaved bacteriophage genomic fragment.

Additionally or alternatively, in some embodiments of the methods disclosed herein, the recombination system is endogenous to the first bacterial host cell.

Additionally or alternatively, in some embodiments of the methods disclosed herein, the recombination system is a non-endogenous recombination system that is induced in the first bacterial host cell. The non-endogenous recombination system may comprise lambda Red proteins Gam, Exo, and Beta operably linked to an inducible promoter. Alternatively, the non-endogenous recombination system may comprise Exo, RecA, and Gam proteins operably linked to an inducible promoter. In some embodiments of the methods disclosed herein, the inducible promoter is araB and the non-endogenous recombination system is induced by the addition of arabinose.

Additionally or alternatively, in some embodiments of the methods disclosed herein, the first bacterial host cell comprises a first non-endogenous CRISPR expression vector comprising a nucleic acid sequence that encodes a first sgRNA, a second sgRNA, and a first CRISPR enzyme. In some embodiments, the first sgRNA and the second sgRNA are operably linked to a constitutive promoter. In certain embodiments, the first CRISPR enzyme is a Cas protein selected from the group consisting of Cas1, Cas1B, Cas2, Cas3, Cas4, Cas5, Cash, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. The first CRISPR enzyme may be operably linked to an inducible promoter, such as a tetracycline-inducible promoter. Additionally or alternatively, in some embodiments, the method further comprises propagating the recombinant bacteriophage DNA genome in the first bacterial host cell, wherein the first bacterial host cell comprises the first non-endogenous CRISPR expression vector.

In any of the above embodiments of the methods disclosed herein, the open reading frame of the heterologous nucleic acid is operably linked to an expression control sequence that is capable of directing expression of the bioluminescent protein, the fluorescent protein, the chemiluminescent protein, or any combination thereof. In some embodiments, the expression control sequence is an inducible promoter or a constitutive promoter. The heterologous nucleic acid can be about 100-500 base pairs in length, about 500-1000 base pairs in length, 1000-1500 base pairs in length, about 1500-2000 base pairs in length, 2000-2500 base pairs in length, about 2500-3000 base pairs in length, 3000-3500 base pairs in length, or about 3500-4000 base pairs in length.

In some embodiments of the methods disclosed herein, the first protospacer sequence is 5' ACTAAATGAGGAT-TAAATCA 3' (SEQ ID NO: 6) and the second protospacer sequence is 5' TTACTCTGATGCACTACATG 3' (SEQ ID NO: 7). In certain embodiments, the first sgRNA-CRISPR enzyme complex comprises Cas9 and a first sgRNA having the sequence of SEQ ID NO: 16, and the second sgRNA-CRISPR enzyme complex comprises Cas9 and a second sgRNA having the sequence of SEQ ID NO: 17.

In other embodiments of the methods disclosed herein, the first protospacer sequence is 5' TATATTATACCAGA-GAGGCG 3' (SEQ ID NO: 8) and the second protospacer sequence is 5' GAAGTTCTAAGGAGATAACA 3' (SEQ ID NO: 9). In certain embodiments, the first sgRNA-CRISPR enzyme complex comprises Cas9 and a first sgRNA having the sequence of SEQ ID NO: 18, and the second sgRNA-CRISPR enzyme complex comprises Cas9 and a second sgRNA having the sequence of SEQ ID NO: 19.

Additionally or alternatively, in some embodiments, the method further comprises enriching for the recombinant bacteriophage DNA genome by causing infected bacterial host cells to block the replication of the first bacteriophage DNA genome, while permitting replication of recombinant bacteriophage DNA genome.

In some embodiments, the method entails propagating the recombinant bacteriophage DNA genome in a second bacterial host cell. In some embodiments of the method, the second bacterial host cell comprises a second non-endogenous CRISPR expression vector comprising a nucleic acid sequence that encodes a second CRISPR enzyme, a third sgRNA, and a fourth sgRNA. In certain embodiments, the third sgRNA and the fourth sgRNA are operably linked to a constitutive promoter. Additionally or alternatively, in some embodiments, the second CRISPR enzyme is operably linked to an inducible promoter (e.g., tetracycline). In some embodiments, the third sgRNA binds to the second CRISPR enzyme to form a third sgRNA-CRISPR enzyme complex, and the fourth sgRNA binds to the second CRISPR enzyme to form a fourth sgRNA-CRISPR enzyme complex. Additionally or alternatively, in some embodiments, the second CRISPR enzyme is Cas9. In any of the above embodiments of the method, the third sgRNA-CRISPR enzyme complex and the fourth sgRNA-CRISPR enzyme complex (a) do not cleave the recombinant bacteriophage DNA genome and (b) cleave the first bacteriophage DNA genome. In certain embodiments, the sequence of the third sgRNA is identical to the sequence of the first sgRNA, and/or the sequence of the fourth sgRNA is identical to the sequence of the second sgRNA.

In some embodiments of the method, the second bacterial host cell comprises a non-endogenous Cascade complex expression vector comprising a nucleic acid sequence that encodes a casABCDE operon, and Cas3 nuclease. Cas3 is an HD-nuclease fused to DEAD-box helicase, and exhibits ssDNA endonuclease and exonuclease activity and helicase activity. In some embodiments, the casABCDE operon and Cas3 nuclease are operably linked to an inducible promoter (e.g., tetracycline) or a constitutive promoter (T7 promoter).

Additionally or alternatively, in some embodiments, the second bacterial host cell comprises a non-endogenous CRISPR RNA (crRNA) spacer array comprising one or more crRNA spacers that (a) induce cleavage in the first bacteriophage DNA genome and (b) do not induce cleavage in the recombinant bacteriophage DNA genome. In some embodiments, the crRNA spacer array is operably linked to a constitutive promoter (e.g., T7 promoter). Each crRNA spacer is complementary to a target sequence that is present within the first bacteriophage DNA genome, and is flanked by direct repeat sequences that serve as recognition/cleavage sites for CasE. The CasE-processed crRNA spacer serves as guide RNAs for Cas3 nuclease and specifies which genome sequence is targeted for endonucleolytic and/or exonucleolytic DNA cleavage by Cas3, thereby blocking the replication of the first bacteriophage DNA genome. The crRNAs do not induce cleavage in the recombinant bacteriophage DNA genome because these cleavage sites were restored in the recombinant bacteriophage DNA genome with codon reassigned equivalents. Codon-reassigned equivalents are sufficiently different so as to prevent them from being recognized by crRNAs.

Also disclosed herein are kits for integrating a heterologous nucleic acid sequence into a bacteriophage DNA genome.

BRIEF DESCRIPTION OF THE DRAWINGS

FIGS. 1A-1L show the complete genome sequence of non-recombinant K1-5 phage (GenBank Accession No.: AY370674.1; SEQ ID NO: 1).

FIG. 2 shows the heterologous nucleic acid sequence that was inserted into K1-5 phage genomic DNA that was cleaved after position 1,571 and after position 1,689 of SEQ ID NO: 1 using single guide RNAs (sgRNAs) sgRNA 86 and sgRNA 89 (SEQ ID NO: 2). The underlined sequences represent the homologous 5' and 3' flanking regions of the heterologous nucleic acid sequence.

FIG. 3 shows the heterologous nucleic acid sequence that was inserted into K1-5 phage genomic DNA that was cleaved after position 19,979 and after position 20,164 of SEQ ID NO: 1 using sgRNA 1112 and sgRNA 1122 (SEQ ID NO: 3).

FIGS. 4A-4J show the complete genome sequence of the recombinant NanoLuc® K1-5 phage that was cleaved with sgRNA 86 and sgRNA 89 (SEQ ID NO: 4).

FIGS. 5A-5J show the complete genome sequence of the recombinant NanoLuc® K1-5 phage that was cleaved with sgRNA 1112 and sgRNA 1122 (SEQ ID NO: 5).

FIG. 8 shows an example of codon reassignment to prevent Cas9 cleavage of the recombinant K1-5 phage. Alternate codons were used to encode the same amino acids where ever possible along the 20 bp protospacer sequence and NGG PAM sequence of a target site so as to create gaps in the alignment that would prevent sgRNA recognition in recombinant K1-5 phage sequences. There were amino acids to the right of the precise cleavage site that were deliberately not modified because it would have created an imperfect homology and potentially interfered with strand invasion during DNA repair. FIG. 8 discloses SEQ ID NOS 21, 20, 22 and 23, respectively, in order of appearance.

FIG. 13 shows the luminescence activity profile of the recombinant K1-5 phages of the present technology.

FIG. 14 shows the verification of the upstream junction between nanoluciferase and the intended insertion site of the phage genome via Sanger sequencing. FIG. 14 discloses the three sequences in the left-hand image as SEQ ID NO: 10 and the three sequences in the right-hand image as SEQ ID NO: 11.

FIG. 15 shows the upstream junction sequences of the nanoluciferase insertion in the recombinant K1-5 phage genome cleaved by sgRNAs 86 and 89 (SEQ ID NO: 10) and sgRNAs 1112 and 1122 (SEQ ID NO: 11).

FIG. 17 shows that the recombinant NanoLuc® K1-5 phages of the present technology successfully infected an *E. coli* clinical isolate that was incapable of being infected with a recombinant nanoluciferase expressing K1E phage or a recombinant nanoluciferase expressing T7 phage. An *E. coli* clinical isolate (designated as B3) was infected with the recombinant NanoLuc® K1-5 phages disclosed herein, a recombinant NanoLuc® K1E phage, and a recombinant NanoLuc® T7 phage for 1 hour.

DETAILED DESCRIPTION

Figures 6A, 6B:
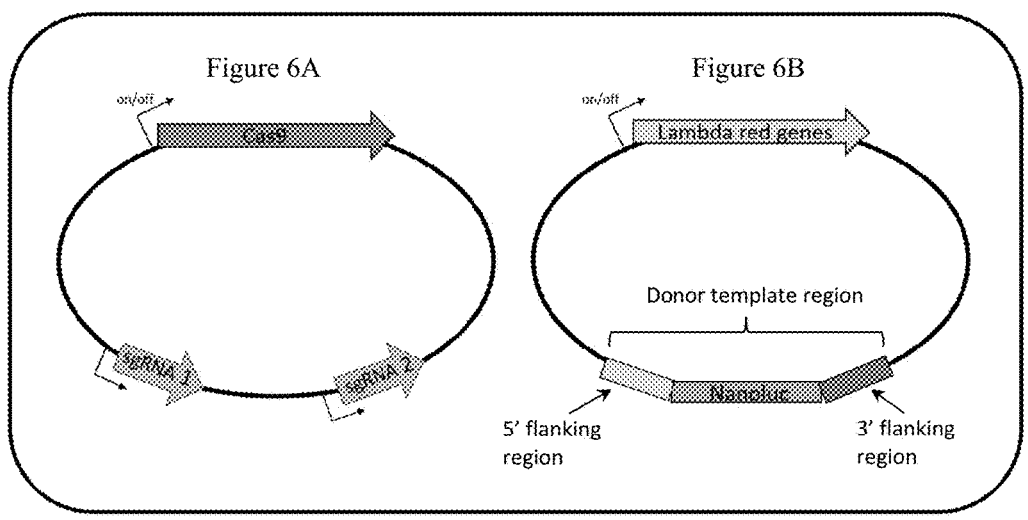
FIG. 6A shows a kanamycin-resistant CRISPR expression vector comprising the Cas9 gene operably linked to a tetracycline inducible promoter and two sgRNAs that are constitutively transcribed.
FIG. 6B shows a gentamicin-resistant recombination expression vector comprising the lambda red operon (Exo, Beta, Gam) operably linked to an arabinose-inducible promoter and a heterologous nucleic acid sequence comprising the nanoluciferase gene as well as 5' and 3' flanking regions that are homologous to a portion of the non-recombinant K1-5 phage genome.

It is to be appreciated that certain aspects, modes, embodiments, variations and features of the present methods are described below in various levels of detail in order to provide a substantial understanding of the present technology.

Manipulating phage genomes is more difficult compared to manipulating bacterial hosts. In vitro synthesis and assembly of phage genomes is inefficient and relies on the delivery of large DNA molecules across the cell membranes of a bacterial host. Some bacterial strains are recalcitrant to large DNA transformation across the membrane. Classic in vivo recombination strategies are also inefficient and are complicated by the fact that lytic phage genomes have a comparatively short residence time in a host before lysis.

One of the most commonly used and well-established methods for engineering phage genomes is homologous recombination in their bacterial hosts, which can occur between two homologous DNA sequences as short as 23 bp (Alberts B et al., MOLECULAR BIOLOGY OF THE CELL, 5th ed. Garland Science, New York, N.Y. (2007); Snyder L et al., MOLECULAR GENETICS OF BACTERIA, 4th ed. ASM Press, Washington, D.C. (2013)). Homologous recombination occurs between the plasmid and the phage genome, allowing the heterologous gene to be integrated into the phage genome and eventually packaged within the phage particle. However, homologous recombination only yields a small fraction of recombinant progeny phage. Reported recombination rates range from $10^{-10}$ to $10^{-4}$ (Loessner M. et al., *Appl Environ Microbiol* 62:1133-1140 (1996); Le S. et al., *PLoS One* 8:e68562 (2013); Mahichi F. et al., *FEMS Microbiol Lett* 295:211-217 (2009)). One of the major challenges of generating recombinant bacteriophages is that the recombinant processes used to create such bacteriophages are inefficient, and often result in a low yield of recombinant bacteriophage genomes. Transformation of large bacteriophage genomes (e.g., about or greater than 40-48 kb) is prohibitive in many bacterial strains and species, making it difficult to isolate viable bacteriophage particles post-transformation. See e.g., Chauthaiwale et al., *Microbiological Reviews* 56 (4): 577-592 (1992); see also Vaughan et al., *Nature Biotechnology* 14:309-314 (1996). Thus, finding the desired clone using conventional phage screening methods is labor-intensive and unpredictable.

The present disclosure provides methods for integrating a heterologous nucleic acid sequence into a bacteriophage DNA genome, and isolating recombinant bacteriophages that express the heterologous nucleic acid sequence. The methods disclosed herein permit higher recovery of recombinant bacteriophage genomes that express the phenotypic properties associated with the heterologous nucleic acid sequence relative to that observed with other phage engineering methods, such as bacteriophage recombineering of electroporated DNA (BRED) (Marinelli L J et al., *PLoS One* 3:e3957 (2008)).

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, "bacteriophage" or "phage" refers to a virus that infects bacteria. Bacteriophages are obligate intracellular parasites that multiply inside bacteria by co-opting some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid can be either DNA or RNA (but not both) and can exist in various forms.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, an "expression control sequence" refers to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences.

As used herein, "heterologous nucleic acid sequence" is any sequence placed at a location in the genome where it does not normally occur. A heterologous nucleic acid sequence may comprise a sequence that does not naturally occur in a bacteriophage, or it may comprise only sequences naturally found in the bacteriophage, but placed at a non-normally occurring location in the genome. In some embodiments, the heterologous nucleic acid sequence is not a natural phage sequence. In certain embodiments, the heterologous nucleic acid sequence is a natural phage sequence that is derived from a different phage. In other embodiments, the heterologous nucleic acid sequence is a sequence that occurs naturally in the genome of a wild-type phage but is then relocated to another site where it does not naturally occur, rendering it a heterologous sequence at that new site.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, a "host cell" is a bacterial cell that can be infected by a phage to yield progeny phage particles. A host cell can form phage particles from a particular type of phage genomic DNA. In some embodiments, the phage genomic DNA is introduced into the host cell by infecting the host cell with a phage. In some embodiments, the phage genomic DNA is introduced into the host cell using transformation, electroporation, or any other suitable technique. In some embodiments, the phage genomic DNA is substantially pure when introduced into the host cell. In some embodiments, the phage genomic DNA is present in a vector when introduced into the host cell. The definition of host cell can vary from one phage to another. For example, *E. coli* may be the natural host cell for a particular type of phage, but *Klebsiella pneumoniae* is not.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/or entities are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, "operably linked" means that expression control sequences are positioned relative to the nucleic acid of interest to initiate, regulate or otherwise control transcription of the nucleic acid of interest.

As used herein, a "phage genome" includes naturally occurring phage genomes and derivatives thereof. Generally, the derivatives possess the ability to propagate in the same hosts as the naturally occurring phage. In some embodiments, the only difference between a naturally occurring phage genome and a derivative phage genome is at least one of a deletion and an addition of nucleotides from at least one end of the phage genome (if the genome is linear) or at least one point in the genome (if the genome is circular).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous to the organism (originating from the same organism or progeny thereof) or exogenous (originating from a different organism or progeny thereof). By way of example, a promoter sequence can be substituted (e.g., by homologous recombination) for the native promoter of a gene in the genome of an organism, such that this gene has an altered expression pattern. This gene would be "recombinant" because it is separated from at least some of the sequences that naturally flank it. A nucleic acid is also considered "recombinant" if it contains any modifications that do not naturally occur in the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, a "recombinant bacteriophage genome" is a bacteriophage genome that has been genetically modified by the insertion of a heterologous nucleic acid sequence into the bacteriophage genome. A "recombinant bacteriophage"

means a bacteriophage that comprises a recombinant bacteriophage genome. In some embodiments, the bacteriophage genome is modified by recombinant DNA technology to introduce a heterologous nucleic acid sequence into the genome at a defined site. In some embodiments, the heterologous nucleic acid sequence is introduced with no corresponding loss of endogenous phage genomic nucleotides. In other words, if bases N1 and N2 are adjacent in the wild-type bacteriophage genome, the heterologous nucleic acid sequence is inserted between N1 and N2. Thus, in the resulting recombinant bacteriophage genome, the heterologous nucleic acid sequence is flanked by nucleotides N1 and N2. In some embodiments, endogenous phage nucleotides are removed or replaced during the insertion of the heterologous nucleic acid sequence. For example, in some embodiments, the heterologous nucleic acid sequence is inserted in place of some or all of the endogenous phage sequence which is removed. In some embodiments, endogenous phage sequences are removed from a position in the phage genome distant from the site(s) of insertion of the heterologous nucleic acid sequences.

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

Bacteriophage

Bacteriophage are obligate intracellular parasites that multiply inside bacteria by co-opting some or all of the host biosynthetic machinery. Phages contain nucleic acid and protein, and may be enveloped by a lipid membrane. Depending upon the phage, the nucleic acid genome can be either DNA or RNA but not both, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances no more than 500,000 bp. The number and amount of individual types of protein in phage particles will vary depending upon the phage. The proteins function in infection and to protect the nucleic acid genome from environmental nucleases.

Phage genomes come in a variety of sizes and shapes (e.g., linear or circular). Most phages range in size from 24-200 nm in diameter. The capsid is composed of many copies of one or more phage proteins, and acts as a protective envelope around the phage genome. Many phages have tails attached to the phage capsid. The tail is a hollow tube through which the phage nucleic acid passes during infection. The size of the tail can vary and some phages do not even have a tail structure. In the more complex phages, the tail is surrounded by a contractile sheath which contracts during infection of the bacterial host cell. At the end of the tail, phages have a base plate and one or more tail fibers attached to it. The base plate and tail fibers are involved in the binding of the phage to the host cell.

Lytic or virulent phages are phages which can only multiply in bacteria and lyse the bacterial host cell at the end of the life cycle of the phage. The lifecycle of a lytic phage begins with an eclipse period. During the eclipse phase, no infectious phage particles can be found either inside or outside the host cell. The phage nucleic acid takes over the host biosynthetic machinery and phage specific mRNAs and proteins are produced. Early phage mRNAs code for early proteins that are needed for phage DNA synthesis and for shutting off host DNA, RNA and protein biosynthesis. In some cases, the early proteins actually degrade the host chromosome. After phage DNA is made late mRNAs and late proteins are made. The late proteins are the structural proteins that comprise the phage as well as the proteins needed for lysis of the bacterial cell. In the next phase, the phage nucleic acid and structural proteins are assembled and infectious phage particles accumulate within the cell. The bacteria begin to lyse due to the accumulation of the phage lysis protein, leading to the release of intracellular phage particles. The number of particles released per infected cell can be as high as 1000 or more. Lytic phage may be enumerated by a plaque assay. The assay is performed at a low enough concentration of phage such that each plaque arises from a single infectious phage. The infectious particle that gives rise to a plaque is called a PFU (plaque forming unit).

Lysogenic phages are those that can either multiply via the lytic cycle or enter a quiescent state in the host cell. In the quiescent state, the phage genome exists as a prophage (i.e., it has the potential to produce phage). In most cases, the phage DNA actually integrates into the host chromosome and is replicated along with the host chromosome and passed on to the daughter cells. The host cell harboring a prophage is not adversely affected by the presence of the prophage and the lysogenic state may persist indefinitely. The lysogenic state can be terminated upon exposure to adverse conditions. Conditions which favor the termination of the lysogenic state include: desiccation, exposure to UV or ionizing radiation, exposure to mutagenic chemicals, etc. Adverse conditions lead to the production of proteases (rec A protein), the expression of the phage genes, reversal of the integration process, and lytic multiplication.

In some embodiments, a phage genome comprises at least 5 kilobases (kb), at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 95 kb, at least 100 kb, at least 105 kb, at least 110 kb, at least 115 kb, at least 120 kb, at least 125 kb, at least 130 kb, at least 135 kb, at least 140 kb, at least 145 kb, at least 150 kb, at least 175 kb, at least 200 kb, at least 225 kb, at least 250 kb, at least 275 kb, at least 300 kb, at least 325 kb, at least 350 kb, at least 375 kb, at least 400 kb, at least 425 kb, at least 450 kb, at least 475 kb, or at least 500 kb of nucleic acids.

Phage Engineering Methods of the Present Technology

In one aspect, the present disclosure provides sgRNAs that are useful for making the recombinant bacteriophages. In some embodiments, the sgRNA sequence is selected from the group consisting of SEQ ID NO: 16, SEQ ID NO: 17, SEQ ID NO: 18 and SEQ ID NO: 19.

In another aspect, the present disclosure provides a method for making a recombinant bacteriophage DNA genome in a first bacterial host cell. The first bacterial host cell may be a non-natural bacterial host cell or a natural bacterial host cell for the recombinant bacteriophage. The resulting phage lysate of the first bacterial host cell comprises the recombinant bacteriophage DNA genome.

In some embodiments, the method comprises (a) contacting a first bacteriophage DNA genome with a first sgRNA-CRISPR enzyme complex and a second sgRNA-CRISPR enzyme complex in vivo under conditions where (i) the first sgRNA-CRISPR enzyme complex cleaves a first protospacer sequence within the first bacteriophage DNA genome; and (ii) the second sgRNA-CRISPR enzyme complex cleaves a second protospacer sequence within the first bacteriophage DNA genome to produce a cleaved first bacteriophage DNA genome; and (b) recombining in vivo the cleaved first bacteriophage DNA genome with a heterologous nucleic acid sequence in the presence of a recombination system under conditions to produce the recombinant bacteriophage DNA genome, wherein the first bacterial host cell is infected with the first bacteriophage DNA genome, and wherein the heterologous nucleic acid sequence comprises an open reading frame that encodes a bioluminescent protein, a fluorescent protein, a chemiluminescent protein, or any combination thereof. The first bacteriophage DNA genome may be non-recombinant or may contain an alternate recombinant sequence. In any of the above embodiments, the recombination system may be endogenous or non-endogenous to the first bacterial host cell.

Figure 18:
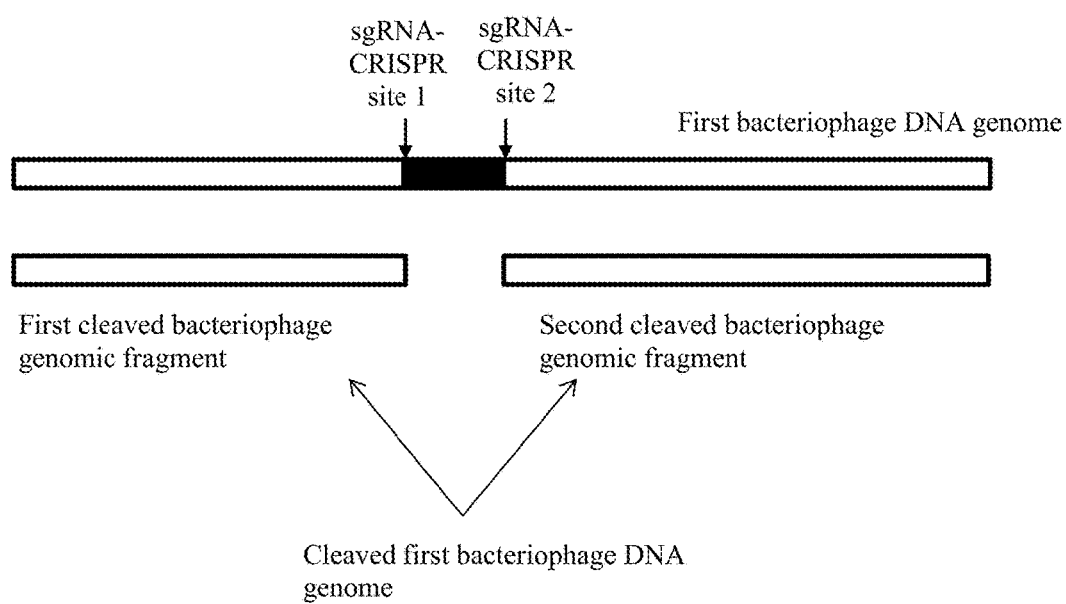
FIG. 18 shows a general schematic of a first bacteriophage DNA genome (i.e., an intact bacteriophage DNA genome) and a cleaved first bacteriophage DNA genome. The cleaved first bacteriophage DNA genome comprises a first cleaved bacteriophage genomic fragment and a second cleaved bacteriophage genomic fragment.

The cleaved first bacteriophage DNA genome comprises a first cleaved bacteriophage genomic fragment and a second cleaved bacteriophage genomic fragment (FIG. 18). In certain embodiments of the methods disclosed herein, the heterologous nucleic acid sequence comprises a 5' flanking region that is homologous to the 3' end of the first cleaved bacteriophage genomic fragment, and a 3' flanking region that is homologous to the 5' end of the second cleaved bacteriophage genomic fragment.

Additionally or alternatively, in some embodiments of the methods disclosed herein, the homologous 5' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the homologous 3' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the recombination system is a non-endogenous recombination system that is induced in the first bacterial host cell. The non-endogenous recombination system may include a recombination expression vector that comprises lambda Red proteins Gam, Exo, and Beta operably linked to an inducible promoter. In some embodiments of the methods disclosed herein, the inducible promoter is araB and the non-endogenous recombination system is induced by the addition of arabinose. In some embodiments, the recombination expression vector further comprises the heterologous nucleic acid sequence. In other embodiments, the expression vector comprising the heterologous nucleic acid sequence is separate and distinct from the recombination expression vector comprising lambda Red proteins.

In other embodiments of the methods disclosed herein, the recombination system is a non-endogenous recombination system that includes a recombination expression vector comprising RecET (RecE, RecT) operons operably linked to an inducible promoter, and optionally the heterologous nucleic acid sequence. In some embodiments, the inducible promoter is araB and the non-endogenous recombination system is induced by the addition of arabinose. In other embodiments, the expression vector comprising the heterologous nucleic acid sequence is separate and distinct from the recombination expression vector comprising RecET.

In another embodiment of the methods disclosed herein, the recombination system is a non-endogenous recombination system that includes a recombination expression vector comprising RecA recombinase or a RecA gain-of-function variant operably linked to an inducible promoter and optionally the heterologous nucleic acid sequence. In some embodiments, the recombination system comprises Exo, RecA, and Gam operably linked to an inducible promoter and optionally the heterologous nucleic acid sequence. In some embodiments, the inducible promoter is araB and the non-endogenous recombination system is induced by the addition of arabinose. In other embodiments, the expression vector comprising the heterologous nucleic acid sequence is separate and distinct from the recombination expression vector comprising RecA recombinase or the RecA gain-of-function variant.

Additionally or alternatively, in some embodiments of the methods disclosed herein, the first bacterial host cell comprises a first non-endogenous CRISPR expression vector comprising a nucleic acid sequence that encodes a first sgRNA, a second sgRNA, and a first CRISPR enzyme. In some embodiments, the first sgRNA and the second sgRNA are operably linked to a constitutive promoter. In some embodiments, the sequence of the first sgRNA and the second sgRNA is SEQ ID NO: 16 and SEQ ID NO: 17. In other embodiments, the sequence of the first sgRNA and the second sgRNA is SEQ ID NO: 18 and SEQ ID NO: 19. Additionally or alternatively, in some embodiments, the method further comprises propagating the recombinant bacteriophage DNA genome in the first bacterial host cell, wherein the first bacterial host cell comprises the first non-endogenous CRISPR expression vector. The first CRISPR enzyme may be operably linked to an inducible promoter, such as a tetracycline-inducible promoter.

A variety of CRISPR enzymes are available for use in conjunction with any of the methods of the present disclosure. In some embodiments, the CRISPR enzyme is a Type II or Type I CRISPR enzyme. In some embodiments, the CRISPR enzyme catalyzes DNA cleavage. In some embodiments, the CRISPR enzyme catalyzes RNA cleavage. In some embodiments, the CRISPR enzyme is any Cas9 protein, for instance any naturally-occurring bacterial Cas9 as well as any variants, homologs or orthologs thereof. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or variants thereof. In some embodiments, the CRISPR enzyme cleaves both strands of the target nucleic acid at the Protospacer Adjacent Motif (PAM) site.

In some embodiments of the methods disclosed herein, the first protospacer sequence is 5' ACTAAATGAGGAT-TAAATCA 3' (SEQ ID NO: 6) and the second protospacer sequence is 5' TTACTCTGATGCACTACATG 3' (SEQ ID NO: 7). Additionally or alternatively, in some embodiments, the first sgRNA-CRISPR enzyme complex comprises Cas9 and a first sgRNA having the sequence of SEQ ID NO: 16. Additionally or alternatively, in certain embodiments, the second sgRNA-CRISPR enzyme complex comprises Cas9 and a second sgRNA having the sequence of SEQ ID NO: 17.

In certain embodiments of the methods disclosed herein, the first protospacer sequence is 5' TATATTATACCAGA-GAGGCG 3' (SEQ ID NO: 8) and the second protospacer sequence is 5' GAAGTTCTAAGGAGATAACA 3' (SEQ ID NO: 9). Additionally or alternatively, in some embodiments, the first sgRNA-CRISPR enzyme complex comprises Cas9 and a first sgRNA having the sequence of SEQ ID NO: 18. Additionally or alternatively, in certain embodiments, the second sgRNA-CRISPR enzyme complex comprises Cas9 and a second sgRNA having the sequence of SEQ ID NO: 19.

Additionally or alternatively, in some embodiments of the methods disclosed herein, the first bacteriophage DNA genome corresponds to a family or an order selected from the group consisting of Myoviridae, Siphoviridae, Podoviridae, Lipothrixviridae, Rudiviridae, Ampullaviridae, Bucaudaviridae, Clavaviridae, Corticoviridae, Cystoviridae, Fuselloviridae, Globuloviriade, Guttaviridae, Inoviridae, Leviviridae, Mircoviridae, Plasmaviridae, and Tectiviridae. Additionally or alternatively, in some embodiments of the methods disclosed herein, the first bacteriophage DNA genome corresponds to T3, T7, M6, K11, F92, K1-5, or K1F. In some embodiments, the first bacteriophage DNA genome corresponds to K1-5 bacteriophage.

Additionally or alternatively, in some embodiments, the method further comprises enriching for the recombinant bacteriophage DNA genome by causing infected bacterial host cells to block the replication of the first bacteriophage DNA genome, while permitting replication of recombinant bacteriophage DNA genome.

In some embodiments, the method entails propagating the recombinant bacteriophage DNA genome in a second bacterial host cell. In some embodiments of the method, the second bacterial host cell comprises a second non-endogenous CRISPR expression vector comprising a nucleic acid sequence that encodes a second CRISPR enzyme, a third sgRNA, and a fourth sgRNA. In certain embodiments, the third sgRNA and the fourth sgRNA are operably linked to a constitutive promoter. Additionally or alternatively, in some embodiments, the second CRISPR enzyme is operably linked to an inducible promoter (e.g., tetracycline). In some embodiments, the third sgRNA binds to the second CRISPR enzyme to form a third sgRNA-CRISPR enzyme complex, and the fourth sgRNA binds to the second CRISPR enzyme to form a fourth sgRNA-CRISPR enzyme complex. Additionally or alternatively, in some embodiments, the second CRISPR enzyme is Cas9. In any of the above embodiments of the method, the third sgRNA-CRISPR enzyme complex and the fourth sgRNA-CRISPR enzyme complex (a) do not cleave the recombinant bacteriophage DNA genome and (b) cleave the first bacteriophage DNA genome. In certain embodiments, the sequence of the third sgRNA is identical to the sequence of the first sgRNA, and/or the sequence of the fourth sgRNA is identical to the sequence of the second sgRNA.

In some embodiments of the method, the second bacterial host cell comprises a non-endogenous Cascade complex expression vector comprising a nucleic acid sequence that encodes a casABCDE operon, and Cas3 nuclease. Cas3 is an HD-nuclease fused to DEAD-box helicase, and exhibits ssDNA endonuclease and exonuclease activity and helicase activity. In some embodiments, the casABCDE operon and Cas3 nuclease are operably linked to an inducible promoter (e.g., tetracycline) or a constitutive promoter (T7 promoter).

Additionally or alternatively, in some embodiments, the second bacterial host cell comprises a non-endogenous CRISPR RNA (crRNA) spacer array comprising one or more crRNA spacers that (a) induce cleavage in the first bacteriophage DNA genome and (b) do not induce cleavage in the recombinant bacteriophage DNA genome. In some embodiments, the crRNA spacer array is operably linked to a constitutive promoter (e.g., T7 promoter). Each crRNA spacer is complementary to a target sequence that is present within the first bacteriophage DNA genome, and is flanked by direct repeat sequences that serve as recognition/cleavage sites for CasE. The CasE-processed crRNA spacer serves as guide RNAs for Cas3 nuclease and specifies which genome sequence is targeted for endonucleolytic and/or exonucleolytic DNA cleavage by Cas3, thereby blocking the replication of the first bacteriophage DNA genome. The crRNAs do not induce cleavage in the recombinant bacteriophage DNA genome because these cleavage sites were restored in the recombinant bacteriophage DNA genome with codon reassigned equivalents. Codon-reassigned equivalents are sufficiently different so as to prevent them from being recognized by crRNAs.

Accurate identification of bacterial species within a biological sample informs the selection of suitable therapies for treating bacterial infections. Recombinant bacteriophage generated using the methods disclosed herein, may be used to identify bacteria present within a biological sample (e.g., whole blood, plasma, serum). Such methods entail contacting the biological sample with a recombinant bacteriophage generated using the methods disclosed herein, and detecting the presence of bacterial host cells infected by the recombinant phage, wherein the recombinant phage comprises a heterologous nucleic acid that encodes a detectable gene product, thereby leading to the identification of bacteria present within the biological sample.

Additionally or alternatively, recombinant bacteriophage generated using the methods disclosed herein, may be used in methods for profiling antibiotic susceptibility of bacteria present within a biological sample (e.g., whole blood, plasma, serum). These methods include (a) contacting the biological sample with an antibiotic and a recombinant bacteriophage generated using the methods disclosed herein, (b) detecting the presence of bacterial host cells infected by the recombinant phage, wherein the recombinant phage comprises a heterologous nucleic acid that encodes a detectable gene product, and (c) determining that the antibiotic is effective in inhibiting the bacteria present in the biological sample when the number of recombinant phage infected bacterial host cells is reduced relative to that observed in an untreated control sample.

Heterologous Nucleic Acids

In any of the above embodiments of the methods disclosed herein, the heterologous nucleic acid comprises an open reading frame that encodes a bioluminescent protein, a fluorescent protein, a chemiluminescent protein, or any combination thereof. In some embodiments, the encoded gene product(s) produces a detectable signal upon exposure to the appropriate stimuli, and the resulting signal permits detection of bacterial host cells infected by the recombinant phage. In certain embodiments, the open reading frame encodes a protein that serves as a marker that can be identified by screening bacterial host cells infected by a recombinant phage comprising a heterologous nucleic acid sequence comprising the open reading frame. Examples of such markers include by way of example and without limitation: a fluorescent label, a luminescent label, a chemiluminescence label, or an enzymatic label. In some embodiments, the heterologous nucleic acid sequence further comprises sequences naturally found in the bacteriophage, but placed at a non-normally occurring location in the genome.

In some embodiments of the methods disclosed herein, the length of the heterologous nucleic acid sequence is at least 100 bases, at least 200 bases, at least 300 bases, at least 400 bases, at least 500 bases, at least 600 bases, at least 700 bases, at least 800 bases, at least 900 bases, at least 1 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In certain embodiments, the heterologous nucleic acid sequence comprises a length that is less than or equal to a length selected from the group consisting of 1 kb, 2 kb, 3 kb, 4 kb, 5 kb, 6 kb, 7 kb, 8 kb, 9 kb, and 10 kb. In some embodiments, the heterologous nucleic acid sequence comprises a length that is less than or equal to the maximum length of heterologous nucleic acid sequence that can be packaged into a phage particle comprising the phage genome.

In some embodiments, the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments, the heterologous nucleic acid sequence is inserted into the phage genome with no loss of endogenous phage genomic sequence. In some embodiments, the heterologous nucleic acid sequence replaces an endogenous phage genomic sequence. In some embodiments, the heterologous nucleic acid sequence includes an endogenous phage genomic sequence that was previously excised from the phage genome.

In certain embodiments, the heterologous nucleic acid sequence replaces an endogenous phage genomic sequence that is less than the length of the heterologous nucleic acid sequence. Accordingly, in some embodiments, the length of the recombinant phage genome is longer than the length of the wild-type phage genome. In some embodiments, the heterologous nucleic acid sequence replaces an endogenous phage genomic sequence that is greater than the length of the heterologous nucleic acid sequence. Thus, in some embodiments, the length of the recombinant phage genome is shorter than the length of the wild-type phage genome. In certain embodiments, the heterologous nucleic acid sequence replaces an endogenous phage genomic sequence that is equal to the length of the heterologous nucleic acid sequence.

In certain embodiments, the open reading frame of the heterologous nucleic acid encodes a protein that confers a phenotype of interest on a host cell infected by a recombinant phage expressing the heterologous nucleic acid. In some embodiments, the phenotype of interest is the expression of the gene product encoded by the open reading frame of the heterologous nucleic acid.

In certain embodiments, the open reading frame of the heterologous nucleic acid is operably linked to an expression control sequence that is capable of directing expression of the open reading frame, wherein the open reading frame encodes a bioluminescent protein, a fluorescent protein, a chemiluminescent protein, or any combination thereof. In some embodiments, the expression control sequence is located within the heterologous nucleic acid sequence. In other embodiments, the expression control sequence is located in the endogenous phage genome sequence. For example, the open reading frame may be inserted into the phage genome downstream of or in the place of an endogenous phage open reading frame sequence. In some embodiments, the expression control sequence is an inducible promoter or a constitutive promoter (e.g., sarA promoter or lpp promoter). See e.g., Djordjevic & Klaenhammer, *Methods in Cell Science* 20(1):119-126 (1998). The inducible promoter or constitutive promoter may be an endogenous phage promoter sequence, a non-endogenous phage promoter sequence, or a bacterial host promoter sequence. Additionally or alternatively, in some embodiments, the inducible promoter is a pH-sensitive promoter, or a temperature sensitive promoter.

In some embodiments, the heterologous nucleic acid sequence comprises a first open reading frame and at least one supplemental open reading frame. In certain embodiments, the first and the at least one supplemental open reading frames are operably linked to the same expression control sequences. In some embodiments, the first and the at least one supplemental open reading frames are operably linked to different expression control sequences.

Fluorescent proteins include but are not limited to blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOK, mKO2, mOrange, and mOrange2), red fluorescent proteins (for example, mRaspberry, mCherry, dsRed, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatable fluorescent proteins (for example, PA-GFP, PAmCherry1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), fluorescein, rhodamine, and photoswitchable fluorescent proteins (for example, Dronpa).

Examples of bioluminescent proteins are aequorin (derived from the jellyfish *Aequorea victoria*) and luciferases (including luciferases derived from firefly and *Renilla*, nanoluciferase, red luciferase, luxAB, and the like). These proteins have also been genetically separated into two distinct functional domains that will generate light only when the protein domains are closely co-localized. A variety of emission spectrum-shifted mutant derivatives of both of these proteins have been generated over the past decade and have been used for multi-color imaging and co-localization within a living cell.

Examples of chemiluminescent protein include β-galactosidase, horseradish peroxidase (HRP), and alkaline phosphatase. Peroxidases generate peroxide that oxidizes luminol in a reaction that generates light, whereas alkaline phosphatases remove a phosphate from a substrate molecule, destabilizing it and initiating a cascade that results in the emission of light.

In some embodiments, the open reading frame of the heterologous nucleic acid comprises an epitope that can be detected with an antibody or other binding molecule. For example, an antibody that recognizes the epitope may be directly linked to a signal generating moiety (such as by covalent attachment of a chemiluminescent or fluorescent protein), or can be detected using at least one additional binding reagent such as a secondary antibody, directly linked to a signal generating moiety. In some embodiments, the epitope is absent in wild-type bacteriophage and the bacterial host cell. Accordingly, detection of the epitope in a sample demonstrates the presence of a bacterial host cell infected by a recombinant phage comprising a heterologous nucleic acid, wherein the open reading frame of the heterologous nucleic acid comprises the epitope. In other embodiments, the open reading frame of the heterologous nucleic acid comprises a polypeptide tag sequence, such that the expression product of the open reading frame comprises the tag fused to a polypeptide or protein encoded by the open reading frame (e.g., poly-histidine, FLAG, Glutathione S-transferase (GST) etc.).

In some embodiments, the open reading frame of the heterologous nucleic acid sequence comprises a biotin binding protein such as avidin, streptavidin, or neutrAvidin that can be detected with a biotin molecule conjugated to an enzyme (e.g., β-galactosidase, horseradish peroxidase (HRP), and alkaline phosphatase) or an antibody. In some embodiments, the antibody conjugated to a biotin molecule may be directly linked to a signal generating moiety (such as by covalent attachment of a chemiluminescent or fluorescent protein), or can be detected using at least one additional binding reagent such as a secondary antibody, directly linked to a signal generating moiety.

Kits

The present technology provides kits for integrating a heterologous nucleic acid sequence into a bacteriophage DNA genome.

In one aspect, the kits of the present technology comprise (a) one or more coded/labeled vials that contain a plurality of bacteriophage DNA genomes, and (b) at least one CRISPR expression vector. The kits may optionally comprise a non-endogenous recombination system, a non-endogenous Cascade complex expression vector, a non-endogenous crRNA spacer array, and/or a heterologous nucleic acid.

Additionally or alternatively, in some embodiments, the kits further comprise vials containing natural or non-natural bacterial host cells that can be, or are transformed with the CRISPR expression vector, the Cascade complex expression vector, the crRNA spacer array, the heterologous nucleic acid, and/or the non-endogenous recombination system disclosed herein. In some embodiments, the bacterial host cells are *E. coli*. In certain embodiments, the bacterial host cells are *E. coli* strain DH10β.

In some embodiments, each coded/labeled vial containing a plurality of bacteriophage DNA genomes corresponds to a different bacteriophage type. In other embodiments, each coded/labeled vial containing a plurality of bacteriophage DNA genomes corresponds to the same bacteriophage type. In some embodiments, each phage vial is assigned a unique code that identifies the bacteriophage in the phage vial, or the types of bacteria that the bacteriophage strain infects. The unique code can be encoded by a machine discernible pattern, such as a bar code, a QR code, an alphanumeric string, or any other pattern that can be discerned by a reader. Each unique code may be shown as, for example, a bar code sticker on a vial or container storing a corresponding phage sample. In some embodiments, the kit is stored under conditions that permit the preservation of the bacteriophage DNA genomes for extended periods, such as under bacteriophage-specific, controlled temperature, moisture, and pH conditions.

Additionally or alternatively, in some embodiments, the at least one CRISPR expression vector of the kits of the present technology comprises a nucleic acid sequence that encodes one or more sgRNAs, and a CRISPR enzyme. The CRISPR enzyme may be selected from the group consisting of Cas1, Cas1B, Cas2, Cas3, Cas4, Cas5, Cash, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4, and may be operably linked to an inducible promoter. In some embodiments, the at least one CRISPR expression vector of the kits of the present technology comprises a first sgRNA comprising the sequence of SEQ ID NO: 16 and a second sgRNA comprising the sequence of SEQ ID NO: 17. In other embodiments, the at least one CRISPR expression vector of the kits of the present technology comprises a first sgRNA comprising the sequence of SEQ ID NO: 18 and a second sgRNA comprising the sequence of SEQ ID NO: 19.

Additionally or alternatively, in some embodiments, the non-endogenous recombination system of the kits of the present technology may include a recombination expression vector that comprises (a) lambda Red proteins Gam, Exo, and Beta operably linked to an inducible promoter, and (b) optionally the heterologous nucleic acid sequence. In certain embodiments, the non-endogenous recombination system may include a recombination expression vector that comprises (a) RecA (e.g., Exo, RecA, and Gam) or a RecA gain-of-function variant operably linked to an inducible promoter, and (b) optionally the heterologous nucleic acid sequence. In other embodiments, the non-endogenous recombination system may include a recombination expression vector that comprises (a) RecET (RecE, RecT) operons operably linked to an inducible promoter, and (b) optionally the heterologous nucleic acid sequence. In any of the above embodiments of the non-endogenous recombination system, the inducible promoter is araB and the non-endogenous recombination system is induced by the addition of arabinose. Additionally or alternatively, in some embodiment, the expression vector comprising the heterologous nucleic acid sequence is separate and distinct from the recombination expression vector comprising lambda Red proteins, RecET, or RecA or a RecA gain-of-function variant.

Additionally or alternatively, in some embodiments, the non-endogenous Cascade complex expression vector of the kits disclosed herein comprises a nucleic acid sequence that encodes a casABCDE operon, and Cas3 nuclease. In some embodiments, the casABCDE operon and Cas3 nuclease are operably linked to an inducible promoter or a constitutive promoter.

Additionally or alternatively, in some embodiments, the non-endogenous crRNA spacer array of the kits disclosed herein comprise one or more spacers that (a) induce cleavage in the first bacteriophage DNA genome (e.g., wild-type bacteriophage genome) and (b) do not induce cleavage in the recombinant bacteriophage DNA genome. In some embodiments, the crRNA spacer array is operably linked to a constitutive promoter.

In some embodiments, the kits further comprise positive control heterologous nucleic acid sequences to correct for any variability in the recombination systems between experimental runs. The kits may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular detection technique for which the kit is intended. Protocols for using these buffers and reagents for performing different steps of the procedure may also be included in the kit. Further optional components of the kits may include expression media for gene products encoded by the heterologous nucleic acids disclosed herein, such as a medium containing nutrients and cofactors for bioluminescence, devices such as a lamp configured to illuminate at specific wavelengths of light to detect biofluorescence, and devices for measuring the extent of heterologous nucleic acid expression, such as a photometer or photodetector.

Additionally or alternatively, in some embodiments, the kits comprise one or more sgRNA sequences selected from the group consisting of SEQ ID NO: 16, SEQ ID NO: 17, SEQ ID NO: 18 and SEQ ID NO: 19.

EXAMPLES

Example 1: Generation of Recombinant K1-5 Bacteriophages Using the Methods of the Present Technology This Example demonstrates that the methods of the present technology are useful for making recombinant bacteriophages in a bacterial host cell.

Figure 7:
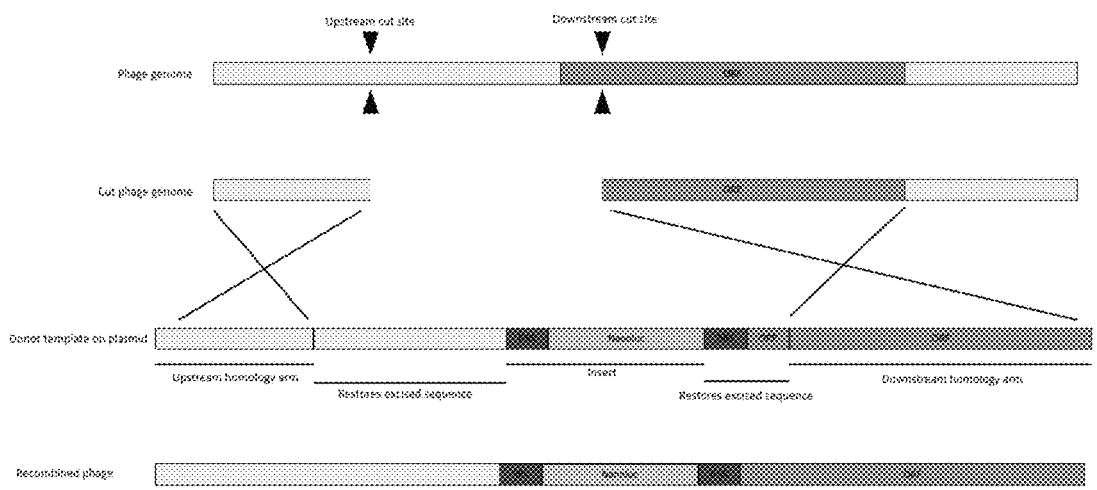
FIG. 7 shows a general schematic of the donor template design and recombination between a cleaved phage genome and the donor template. Two double-stranded breaks are generated by Cas9 at sites specified by the two sgRNAs. In some instances, Cas9 cleavage excises a phage DNA sequence that is important for phage viability. The donor template contains any exogenous reporter gene inserts like nanoluciferase, but must also restore the function of excised phage sequences. The 5' and 3' flanking regions of the donor template are homologous to the DNA sequences immediately adjacent to the two cleavage sites in the phage genome, and are necessary for repairing double-stranded breaks via homologous recombination.

Experimental Design. FIGS. 1A-1L show the complete genome sequence of non-recombinant K1-5 phage (GenBank Accession No.: AY370674.1; SEQ ID NO: 1). FIG. 6A shows a kanamycin-resistant CRISPR expression vector comprising the Cas9 gene operably linked to a tetracycline inducible promoter and two sgRNAs that are constitutively transcribed. FIG. 6B shows a gentamicin-resistant recombination expression vector comprising the lambda red operon (Exo, Beta, Gam) operably linked to an arabinose-inducible promoter and a heterologous nucleic acid sequence. Exo is a 5' DNA exonuclease, Beta is a single-stranded binding protein and recombinase, and Gam inhibits the activity of host cell RecBCD. The heterologous nucleic acid sequence comprises the nanoluciferase gene with an upstream ribosome binding site as well as 5' and 3' flanking regions that are homologous to a portion of the non-recombinant K1-5 phage genome (collectively, referred to as the donor template region). The donor template region also contains sequences that restore the function of any K1-5 phage DNA that was excised by the sgRNA-CRISPR enzyme complexes. The 5' and 3' flanking regions (about several hundred base pairs in length) are homologous to the DNA sequences immediately adjacent to the two cleavage sites in the phage genome (FIG. 7), and are necessary for repairing double-stranded breaks via homologous recombination.

When designing the donor template, it was necessary to eliminate the protospacer sites via codon reassignment to prevent Cas9 cleavage of recombinant K1-5 phage. Codon reassignment was used in the donor template to obviate sgRNA recognition, but still encode the same protein (FIG. 8). The K1-5 protospacer sequences along with their adjacent PAM sites (PAM site underlined) are provided below:

```
sgRNA 86     ACTAAATGAGGATTAAATCATGG (SEQ ID NO: 12)

sgRNA 89     TTACTCTGATGCACTACATGAGG (SEQ ID NO: 13)

sgRNA 1112   TATATTATACCAGAGAGGCGAGG (SEQ ID NO: 14)

sgRNA 1122   GAAGTTCTAAGGAGATAACATGG (SEQ ID NO: 15)
```

The complete sequences of sgRNA 86, sgRNA 89, sgRNA 1112 and sgRNA 1122 are provided below:

```
sgRNA 86 sequence:
                                       (SEQ ID NO: 16)
ACUAAAUGAGGAUUAAAUCAGUUUUAGAGCUAGAAAUAGCAAGUUAAAA

UAAGGCUAGUCCGUUAUCAACUUGAAAAAGUGGCACCGAGUCGGUGCUU

UUUUU sgRNA 89 sequence:
                                       (SEQ ID NO: 17)
UUACUCUGAUGCACUACAUGGUUUUAGAGCUAGAAAUAGCAAGUUAAAA

UAAGGCUAGUCCGUUAUCAACUUGAAAAAGUGGCACCGAGUCGGUGCUU

UUUUU sgRNA 1112 sequence:
                                       (SEQ ID NO: 18)
UAUAUUAUACCAGAGGCGGUUUUAGAGCUAGAAAUAGCAAGUUAAAAUA

AGGCUAGUCCGUUAUCAACUUGAAAAAGUGGCACCGAGUCGGUGCUUUU

UUU sgRNA 1122 sequence:
                                       (SEQ ID NO: 19)
GAAGUUCUAAGGAGAUAACAGUUUUAGAGCUAGAAAUAGCAAGUUAAAA

UAAGGCUAGUCCGUUAUCAACUUGAAAAAGUGGCACCGAGUCGGUGCUU

UUUUU
```

To ensure that the 5' and 3' flanking regions of the donor template were in fact perfectly homologous to the regions adjacent to the cleavage sites, codon reassignment was only done on sequences located to the right of the upstream cut site or to the left of the downstream cut site.

FIG. 2 shows the donor template sequence for K1-5 phage genomic DNA that was cleaved with sgRNA 86 and sgRNA 89 (SEQ ID NO: 2). FIG. 3 shows the donor template sequence for K1-5 phage genomic DNA that was cleaved with sgRNA 1112 and sgRNA 1122 (SEQ ID NO: 3).

The CRISPR expression vector and recombination expression vector were designed to cleave a non-recombinant phage genome at two locations after the bacterial host cell containing both these expression vectors had been infected with a non-recombinant K1-5 bacteriophage. Once cleaved, the ends were acted upon by recombination proteins that facilitated recombination between the phage genome and the donor template region present on the recombination plasmid. This process repaired the double strand breaks, while simultaneously inserting the nanoluciferase gene into the K1-5 phage genome. The recombinant K1-5 phage was not susceptible to Cas9 cleavage. FIGS. 4A-4J show the complete genome sequence of the recombinant NanoLuc® K1-5 phage that was cleaved with sgRNA 86 and sgRNA 89 (SEQ ID NO: 4). FIGS. 5A-5J shows the complete genome sequence of the recombinant NanoLuc® K1-5 phage that was cleaved with sgRNA 1112 and sgRNA 1122 (SEQ ID NO: 5).

Experimental Conditions. K1 *E. coli* strains were generated for cleaving and recombining at locations specified by either sgRNAs 86+89 or sgRNAs 1112+1122. Cells were maintained with 50 µg/mL kanamycin (for the CRISPR expression vector) and 10 pg/mL gentamicin (for the recombination expression vector). Cells were grown while shaking at 37° C. to $OD_{600}$~0.6 and were then subjected to various induction treatments. Cultures were either (1) not induced, (2) induced with 100 ng/mL anhydrotetracycline (aTc) to activate Cas9 expression, (3) induced with 0.2% arabinose to activate lambda red operon expression, or (4) induced with both 100 ng/mL anhydrotetracycline and 0.2% arabinose to activate expression of Cas9 and lambda red genes. Induction was carried out for 2 hours while shaking at 37° C.

K1-5 lysate was then used to infect 200 µL cultures of each bacterial strain/induction condition at $10^6$, $10^4$, and $10^2$ PFU. This infection was given 10 minutes for the phage to adsorb before being added to 3 mL of 0.65% LB top agar. The appropriate inducer was spiked into each top agar tube to maintain induction. The top agar was then spread over an LB agar plate containing the appropriate antibiotics to maintain the CRISPR and recombination expression vectors. The agar plates were incubated in an airtight container for approximately 16 hours at 37° C. Plates with top agar containing phage were washed in LB broth to collect the phage. These plate lysates were used as templates for PCR reactions that assayed for a recombinant junction (spanning from an internal site within the nanoluciferase insertion to a site in the phage genome) and a flanking product (primed from 2 sites flanking the insertion site).

Genotypic Analysis. Without wishing to be bound by theory, it is believed that continual replication of recombinant K1-5 phage through a bacterial strain that only contained an inducible CRISPR expression vector (but no recombination expression vector) would enrich for the recombinant K1-5 phage because recombinant K1-5 phage would have used the donor template for repairing double-stranded breaks (the donor template utilized altered protospacers that do not exactly match the sgRNAs used for cleaving non-recombinant K1-5 phage genomic DNA) and is thus not susceptible to Cas9 cleavage, whereas wild-type phage would be targeted by the sgRNAs without a means to repair the double-stranded breaks.

A lysate containing a mixed population of recombinant and wild-type K1-5 bacteriophage was collected following the BAR (Break and Recombine) experiment described above, which was not 100% efficient.

A 5 mL culture of strain K1 *E. coli* containing the inducible Cas9 endonuclease and constitutively expressed sgRNAs (86+89) or sgRNAs (1112+1122) were grown under kanamycin selection (50 µg/mL) to $OD_{600}$~0.6. The culture was then induced with 100 ng/mL anhydrotetracycline for 1 hour at 37° C. while shaking to induce Cas9 expression. Next, 50 µL of the previously collected mixed-population lysates (i.e., Cas9 induced, lambda red induced, or Cas9+lambda red induced plate lysates) were used to infect the pre-induced cutting strain for three hours. During the infection step, the Cas9-sgRNA complexes were expected to cleave the locations specified by sgRNAs 86+89 or sgRNAs 1112+1122 that are present in wild-type phage, but are not present in recombinants. A lysate from this culture was then clarified and used as a template for junctional and flanking PCR. The phage population after this enrichment step was assessed by PCR. The relative abundance of recombinant phage increased after this treatment.

Figure 9:
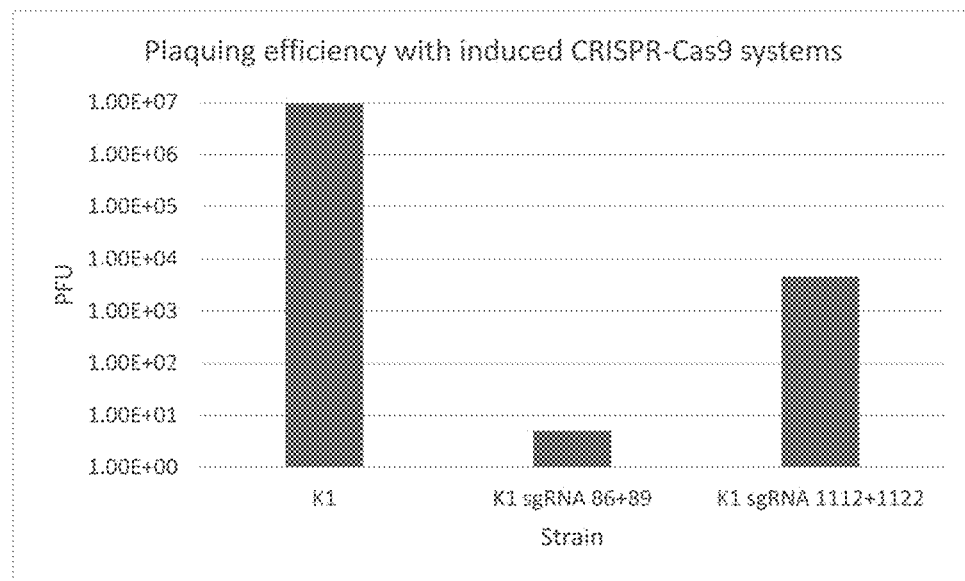
FIG. 9 shows that the plaquing efficiency was reduced when K1-5 phage was plated on a bacterial strain comprising an inducible CRISPR-Cas9 system that targeted the K1-5 phage genome.

Results. FIG. 9 shows that the bacterial strains expressing sgRNAs 86+89 and sgRNAs 1112+1122 exhibited a high reduction in plaquing efficiency (~$1.9 \times 10^6$-fold and 2105-fold reduction, respectively) in the absence of homology for repair.

Figure 11:
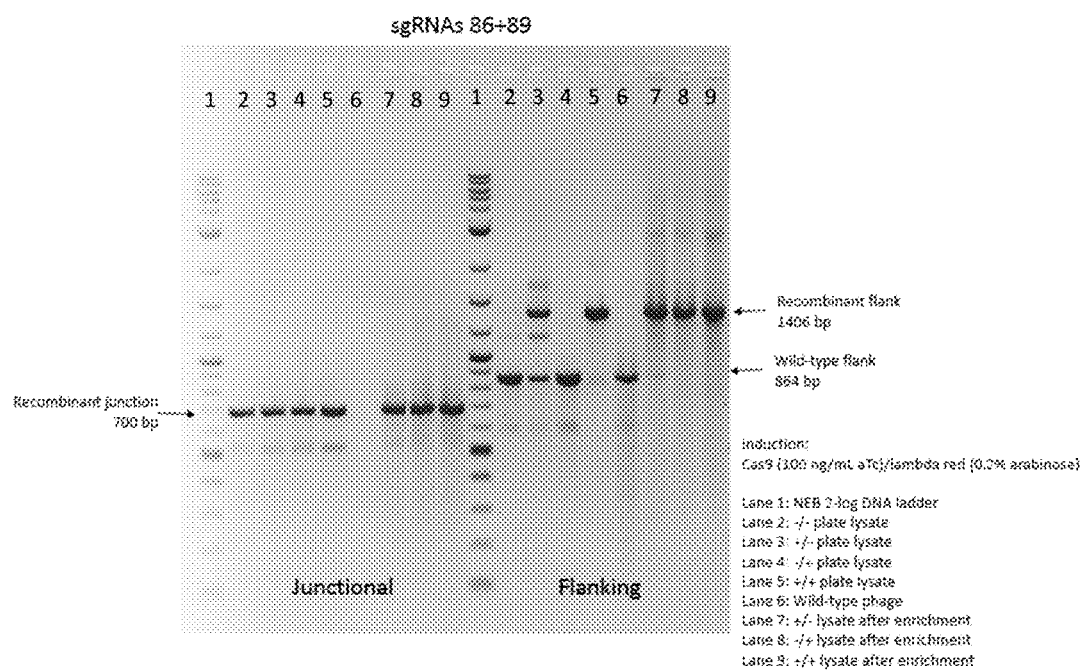
FIG. 11 shows the junctional and flanking PCR assays that tested for the presence of recombinant K1-5 bacteriophage in sgRNAs 86+89 bacterial strain under different induction conditions.

As shown in FIG. 11, all induction conditions within the sgRNAs 86+89 strain produced a detectable quantity of recombinant junctions (700 bp amplicon) that were absent in wild-type K1-5 phage. See junctional PCR lanes 3-5 and 7-9 vs. lane 6 of FIG. 11. The flanking PCR assay provided an estimate of the relative abundance of wild-type and recombinant K1-5 phage. As shown in FIG. 11, induction of lambda red expression alone in the sgRNAs 86+89 strain did not produce a substantial quantity of recombinant flank amplicons, but yielded 864 bp wild-type flank amplicons comparable to that observed in the non-induced sgRNAs 86+89 strain. See flanking PCR lanes 2 and 4 of FIG. 11. In contrast, induction of Cas9 alone in the sgRNAs 86+89 strain produced an approximately equal mixture of 1406 bp recombinant flank amplicons and 864 bp wild-type flank amplicons. See flanking PCR lane 3 of FIG. 11. Induction of both Cas9 and lambda red expression in the sgRNAs 86+89 strain yielded mostly recombinant flank amplicons. See flanking PCR lane 5 of FIG. 11. Enrichment for three hours drastically increased the relative abundance of recombinant K1-5 phage from each starting lysate, particularly in the plate lysate from the strain that was induced for lambda red expression only. Initially, the recombinant K1-5 phage was undetectable by flanking PCR, but after the three hour enrichment step, the recombinant K1-5 phage vastly outnumbered the wild-type non-recombinant phage. See flanking PCR lanes 7-9 of FIG. 11.

Figure 12:
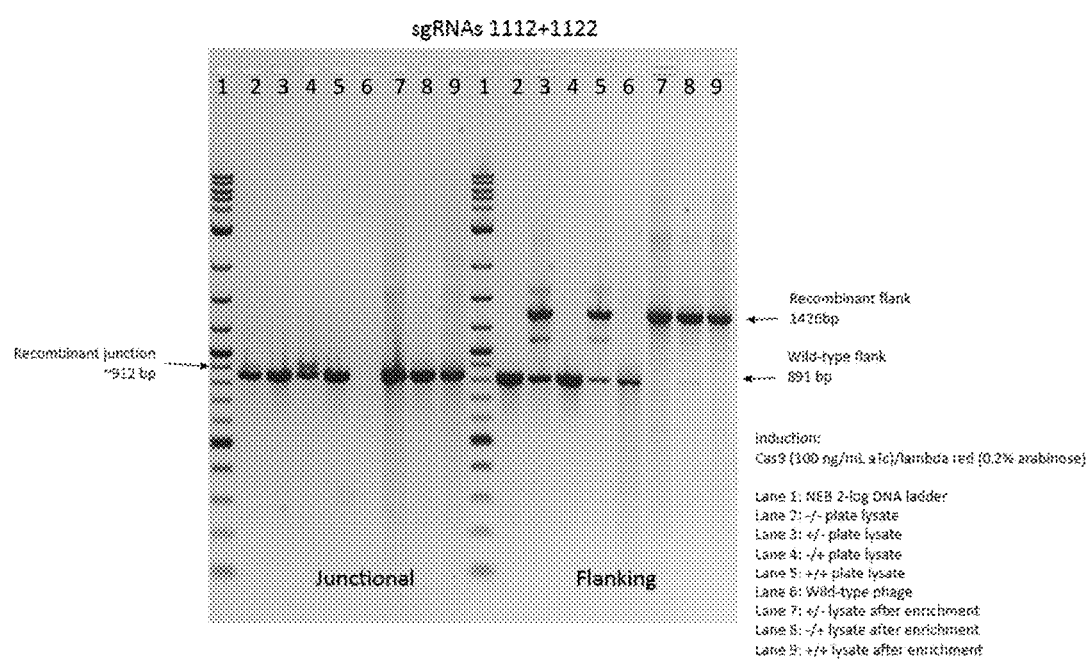
FIG. 12 shows the junctional and flanking PCR assays that tested for the presence of recombinant K1-5 bacteriophage in sgRNAs 1112+1122 bacterial strain under different induction conditions.

As shown in FIG. 12, all induction conditions within the sgRNAs 1112+1122 strain produced a detectable quantity of recombinant junctions (912 bp amplicon) that were absent in wild-type K1-5 phage. See junctional PCR lanes 3-5 and 7-9 vs. lane 6 of FIG. 12. The flanking PCR assay provided an estimate of the relative abundance of wild-type and recombinant K1-5 phage. As shown in FIG. 12, induction of lambda red expression alone in the sgRNAs 1112+1122 strain did not produce a substantial quantity of recombinant flank amplicons, but yielded 891 bp wild-type flank amplicons comparable to that observed in the non-induced sgRNAs 1112+1122 strain. See flanking PCR lanes 2 and 4 of FIG. 12. In contrast, induction of Cas9 alone in the sgRNAs 1112+1122 strain produced a mixture of 1426 bp recombinant flank amplicons and 891 bp wild-type flank amplicons. See flanking PCR lane 3 of FIG. 12. Induction of both Cas9 and lambda red expression in the sgRNAs 1112+1122 strain yielded mostly recombinant flank amplicons. See flanking PCR lane 5 of FIG. 12. However, even a low abundance of recombinant K1-phages could be enriched with a three hour infection in the Cas9 strain that selected against wild-type phage. See flanking PCR lanes 7-9 of FIG. 12.

After passage through an ampicillin-resistant K1 *E. coli* culture, a lysate for both the recombinant NanoLuc® K1-5 phage modified at sgRNA sites 86+89 and recombinant NanoLuc® K1-5 phage modified at sgRNA sites 1112+1122 was used to infect wild-type K1 *E. coli* which was plated in a bacterial overlay on LB. Single plaques were isolated and a region spanning the recombination site was amplified via PCR and submitted for Sanger sequencing. FIG. 14 and FIG. 15 show the upstream junction sequences of the nanoluciferase insertion in the recombinant K1-5 phage modified at sgRNA sites 86+89 (SEQ ID NO: 10) and sgRNA sites 1112+1122 (SEQ ID NO: 11).

These results demonstrate that the methods of the present technology are useful for making the recombinant bacteriophages disclosed herein in a bacterial host cell. Accordingly, the methods disclosed herein are useful for generating recombinant bacteriophages that can be used in the identification and/or antibiotic susceptibility profiling of specific bacterial strains/species present in a sample.

Example 2: Generation of Recombinant K1-5 Bacteriophages Using the Methods of the Present Technology Variants of the in vivo phage engineering methodology described in Example 1 was evaluated by attempting to insert the NanoLuc® luciferase gene into a non-recombinant K1-5 phage genome at the insertion sites specified by sgRNAs 86 and 89 using different recombination proteins. The exact same CRISPR expression vector and donor template region described in Example 1 were used in this variant systems.

The CRISPR expression vector comprised a *S. pyogenes* Cas9 endonuclease operably linked to an anhydrotetracycline-inducible promoter, and two sgRNAs (sgRNA86 and sgRNA 89) operably linked to the constitutive J23119 promoter. The recombination expression vectors included a donor template region comprising the NanoLuc® luciferase gene along with 5' and 3' homologous flanking regions of approximately 300 bp.

The recombination expression vectors contained (1) an arabinose-inducible lambda red operon (Exo, Beta, Gam), (2) an arabinose-inducible Exo, RecA, Gam operon, or (3) no exogenous recombination protein sequences. Bacterial strains containing both the CRISPR expression vector and one of the three recombination expression vectors were grown in 5 mL cultures with 10 mM $MgSO_4$ under antibiotic selection to $OD_{600}$ of ~0.4. These cultures were then split into 1 mL cultures which were induced with 100 ng/mL anhydrotetracycline (aTc), 0.2% arabinose, both, or neither. All cultures were then infected with ~$10^5$ PFU of non-recombinant K1-5 phage overnight at 37° C. while shaking. The following day, cells and debris were removed by centrifugation to obtain 1 µL of phage lysate that could be assayed via flanking PCR. The relative abundance of wild-type and recombinant K1-5 phage could be determined by assessing the differences in the amplicon size: 864 bp for wild-type K1-5 phage and 1406 bp for recombinant K1-5 phage.

Figure 10:
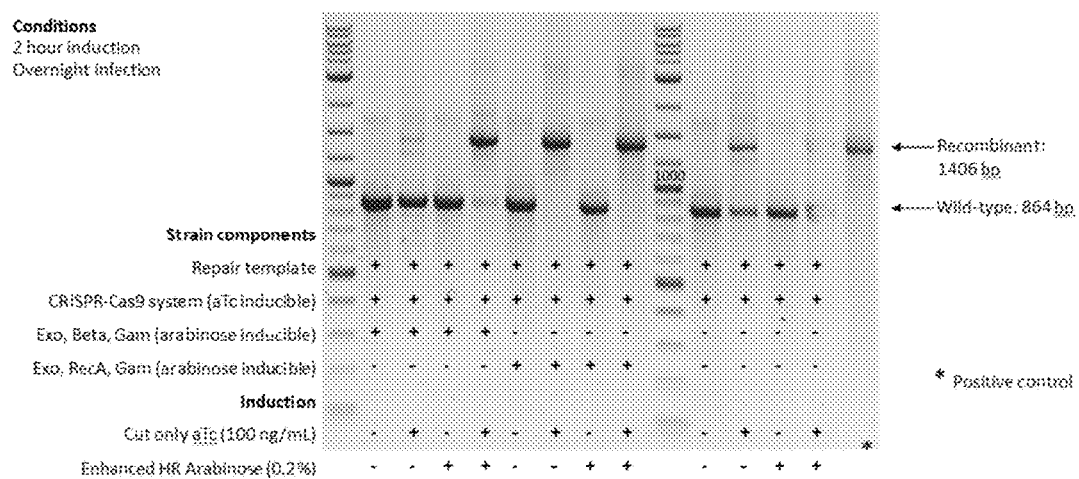
FIG. 10 shows that induction of Cas9 expression in sgRNAs 86+89 bacterial strains was sufficient to produce detectable levels of recombinant NanoLuc® K1-5 phage.

FIG. 10 shows that induction of Cas9 expression alone in all sgRNAs 86+89 bacterial strains was sufficient to produce detectable levels of recombinant NanoLuc® K1-5 phage. Moreover, FIG. 10 also demonstrates that induction of both Cas9 and the recombination protein operons (Exo, Beta, Gam; or Exo, RecA, Gam) in the sgRNAs 86+89 bacterial strains yielded higher levels of NanoLuc® K1-5 phage.

These results demonstrate that the methods of the present technology are useful for making the recombinant bacteriophages disclosed herein in a bacterial host cell. Accordingly, the methods disclosed herein are useful for generating recombinant bacteriophages that can be used in the identification and/or antibiotic susceptibility profiling of specific bacterial strains/species present in a sample.

Example 3: Functional Activity of the Recombinant Bacteriophages

To ensure that the genotypically recombinant K1-5 phage described herein are capable of expressing nanoluciferase during active infection, plate lysates were used infect 5 mL cultures of K1 *E. coli* housing the ampicillin-resistant pUC19 plasmid. The kanamycin and gentamicin resistant strains harboring the CRISPR expression vector and recombination expression vectors would therefore be killed off, or at least strongly selected against, such that any background nanoluciferase expression attributable to the donor template would be minimized. After three hours of infection under ampicillin selection, the lysate was subjected to limiting dilutions to ensure that any residual NanoLuc® protein or NanoLue-expressing cells were diluted out, and that any luminescence detected during a subsequent infection was due to active infection by the recombinant K1-5 phages of the present technology.

Briefly, a tenfold dilution series of lysates were used to infect K1 *E. coli* maintained under ampicillin selection for one hour. In round one, the cutoff for recombinant K1-5 phage being present was observed at 1.0 E-8. See FIG. 13. At dilutions ranging from 1.0 E-3 through 1.0 E-8, a large increase in luminescence was observed in phage infected *E. coli* samples compared to phage samples containing LB medium only (background NanoLuc® protein or NanoLue-expressing cells). The increased luminescence was therefore attributable to active phage infection. The infection from the lowest phage containing dilution (1.0 E-8) was subjected to a second round of limiting dilutions. As shown in FIG. 13, the luminescence activity increased in a cell-dependent manner.

Figure 16:
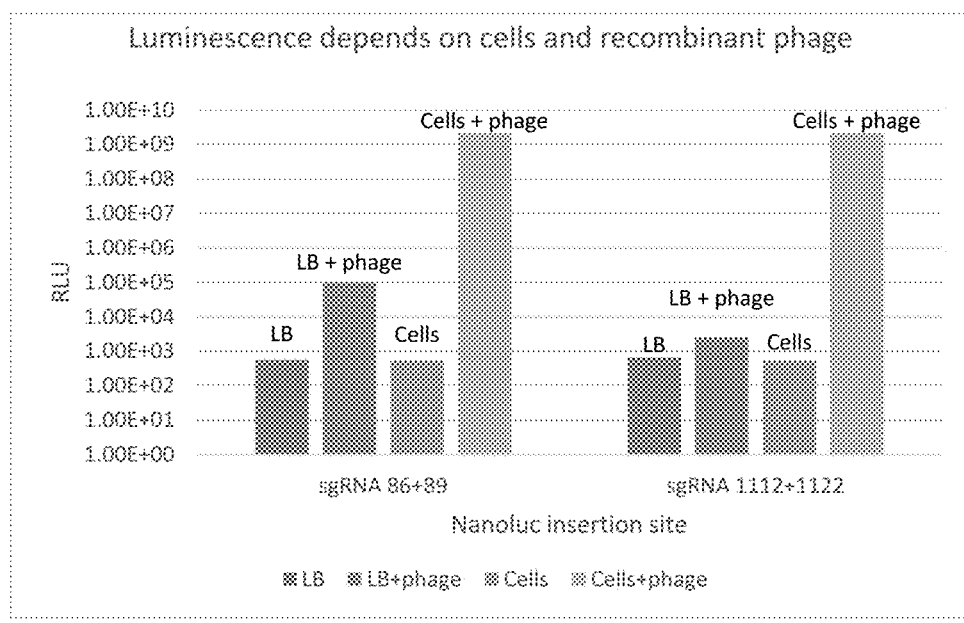
FIG. 16 shows the luminescence activity profile of a recombinant K1-5 phage of the present technology. 100 µL samples of either LB alone, LB+1 µL phage, K1 *E. coli* cells, or K1 *E. coli* cells+1 µL phage were incubated for one hour. The high background luminescence of the LB+phage sample can be attributed to the residual nanoluciferase in the unpurified phage lysate. However, active infection of K1 *E. coli* cells with the recombinant K1-5 phage greatly increased the luminescent signal.

Plaques containing the recombinant K1-5 bacteriophages disclosed herein were used to infect a host population of K1 *E. coli* for one-hour. The infected bacterial host cells exhibited luminescence that was at least four-five orders of magnitude above the background level. See FIG. 16.

As shown in FIG. 17, the recombinant NanoLuc® K1-5 phages of the present technology successfully infected an *E. coli* clinical isolate that was incapable of being infected with a recombinant nanoluciferase expressing K1E phage or a recombinant nanoluciferase expressing T7 phage. Only *E. coli* cells infected with the recombinant NanoLuc® K1-5 phages of the present technology exhibited an increase in relative luminescence units (RLU) during active infection. The high luminescent signal observed in the *E. coli* cells contacted with the recombinant nanoluciferase expressing T7 phage represents background NanoLuc® that was already present in the unpurified lysate. No increase in RLU was observed during active infection (compare T7 infection at 0 hr vs. 1 hr; FIG. 17).

Example 4: Enrichment of Recombinant Bacteriophages Using Cas3/Cascade Complex

Figure 19:
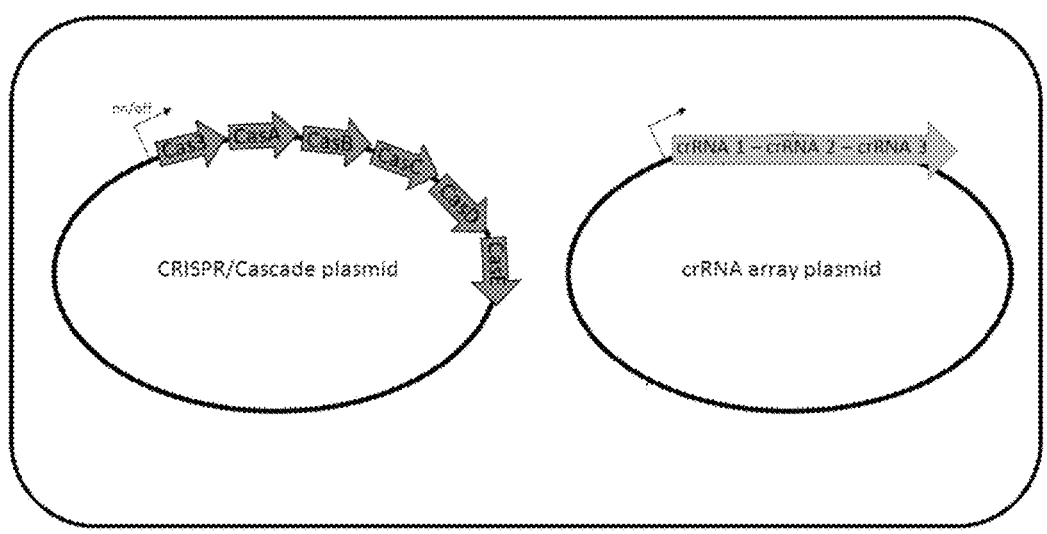
FIG. 19 shows the plasmid containing the CRISPR-Cascade proteins ('Cascade complex') and a plasmid containing site-specific crRNA-spacer elements ('targeting plasmid').

This Example provides a counter-selection process to enrich for recombinant K1-5 bacteriophage, and utilizes a CRISPR Type I-E counter-selection system. This counter-selection process requires a K1 *E. coli* strain containing a plasmid containing the CRISPR-Cascade proteins ('Cascade complex') and a plasmid containing site-specific crRNA-spacer elements ('targeting plasmid'). See FIG. 19. The 'Cascade complex' comprises the following genes from the Type I-E CRISPR system found in the *E. coli* strain MG1655: casA, casB, casC, casD, casE (also known as cse1, cse2, cas7, cas5e, and cas6e, respectively), and cas3. All genes are included as they exist in *E. coli* MG1655 without any heterologous transcriptional control. The 'Cascade complex' plasmid contains a gentamicin resistance marker. The 'targeting plasmid' contains the CRISPR RNA (crRNA) locus from *E. coli* MG1655, which consists of the crRNA leader sequence and a repeat-spacer array, in which the spacer sequences are altered to be complementary to sequences present in the wild-type K1-5 phage genome but not present in the recombinant K1-5 genome. The crRNA leader sequence includes a promoter sequence, thus dispensing the need for additional transcriptional elements. The targeting plasmid contains a kanamycin resistance marker.

It is anticipated that the methods of the present technology will enrich for recombinant bacteriophage. These results demonstrate that the methods of the present technology are useful for making the recombinant bacteriophages disclosed herein in a bacterial host cell.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for making a recombinant bacteriophage DNA genome in a first bacterial host cell comprising
   (a) contacting a first bacteriophage DNA genome with a first sgRNA-CRISPR enzyme complex and a second sgRNA-CRISPR enzyme complex in vivo under conditions where
      (i) the first sgRNA-CRISPR enzyme complex cleaves a first protospacer sequence within the first bacteriophage DNA genome; and
      (ii) the second sgRNA-CRISPR enzyme complex cleaves a second protospacer sequence within the first bacteriophage DNA genome to produce a cleaved first bacteriophage DNA genome; and
   (b) recombining in vivo the cleaved first bacteriophage DNA genome with a heterologous nucleic acid sequence under conditions to produce the recombinant bacteriophage DNA genome,
   wherein the first bacterial host cell is infected with the first bacteriophage DNA genome,
   wherein the heterologous nucleic acid sequence comprises an open reading frame that encodes a bioluminescent protein, a fluorescent protein, a chemiluminescent protein, or any combination thereof,
   wherein the first bacterial host cell comprises
      a first non-endogenous expression vector comprising a nucleic acid sequence that encodes a first sgRNA, a second sgRNA, and a first CRISPR enzyme, and
      a second non-endogenous expression vector comprising:
         lambda Red proteins Gam, Exo, and Beta operably linked to an inducible promoter; or
         Exo, RecA, and Gam proteins operably linked to an inducible promoter.

2. The method of claim 1, wherein the first bacterial host cell may be a non-natural bacterial host cell or a natural bacterial host cell for the recombinant bacteriophage DNA genome.

3. The method of claim 1, wherein the first bacteriophage DNA genome corresponds to a bacteriophage family or order selected from the group consisting of Myoviridae, Siphoviridae, Podoviridae, Lipothrixviridae, Rudiviridae, Ampullaviridae, Bucaudaviridae, Clavaviridae, Corticoviridae, Cystoviridae, Fuselloviridae, Globuloviriade, Guttaviridae, Inoviridae, Leviviridae, Mircoviridae, Plasmaviridae, and Tectiviridae.

4. The method of claim 1, wherein the first bacteriophage DNA genome corresponds to T3, T7, M6, K11, F92, K1-5, or K1F.

5. The method of claim 1, wherein the cleaved first bacteriophage DNA genome comprises a first cleaved bacteriophage genomic fragment and a second cleaved bacteriophage genomic fragment.

6. The method of claim 5, wherein the heterologous nucleic acid sequence comprises a 5' flanking region that is homologous to the 3' end of the first cleaved bacteriophage genomic fragment, and a 3' flanking region that is homologous to the 5' end of the second cleaved bacteriophage genomic fragment.

7. The method of claim 1, wherein the first sgRNA and the second sgRNA are operably linked to a constitutive promoter.

8. The method of claim 1, wherein the first CRISPR enzyme is a Cas protein selected from the group consisting of Cas1, Cas1B, Cas2, Cas3, Cas4, Cas5, Cash, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4, and optionally wherein the first CRISPR enzyme is operably linked to an inducible promoter.

9. The method of claim 1, wherein the bioluminescent protein is Aequorin, firefly luciferase, *Renilla* luciferase, red luciferase, luxAB, or nanoluciferase.

10. The method of claim 1, wherein the chemiluminescent protein is β-galactosidase, horseradish peroxidase (HRP), or alkaline phosphatase.

11. The method of claim 1, wherein the fluorescent protein is TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOK, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa.

12. The method of claim 1, wherein the open reading frame of the heterologous nucleic acid is operably linked to an expression control sequence that is capable of directing expression of the bioluminescent protein, the fluorescent protein, the chemiluminescent protein, or any combination thereof.

13. The method of claim 12, wherein the expression control sequence is an inducible promoter or a constitutive promoter.

14. The method of claim 1, wherein the heterologous nucleic acid is about 100-500 base pairs in length or about 500-1500 base pairs in length.

15. The method of claim 1, further comprising propagating the recombinant bacteriophage DNA genome in the first bacterial host cell.

16. The method of claim 1, further comprising propagating the recombinant bacteriophage DNA genome in a second bacterial host cell.

17. A method for making a recombinant bacteriophage DNA genome in bacterial host cells comprising
   (a) contacting a first bacteriophage DNA genome with a first sgRNA-CRISPR enzyme complex and a second sgRNA-CRISPR enzyme complex in vivo under conditions where (i) the first sgRNA-CRISPR enzyme complex cleaves a first protospacer sequence within the first bacteriophage DNA genome; and
(ii) the second sgRNA-CRISPR enzyme complex cleaves a second protospacer sequence within the first bacteriophage DNA genome to produce a cleaved first bacteriophage DNA genome, wherein a first bacterial host cell is infected with the first bacteriophage DNA genome; and
(b) recombining in vivo the cleaved first bacteriophage DNA genome with a heterologous nucleic acid sequence under conditions to produce the recombinant bacteriophage DNA genome,
wherein the heterologous nucleic acid sequence comprises an open reading frame that encodes a bioluminescent protein, a fluorescent protein, a chemiluminescent protein, or any combination thereof
wherein the first bacterial host cell comprises
a first non-endogenous expression vector comprising a nucleic acid sequence that encodes a first sgRNA, a second sgRNA, and a first CRISPR enzyme, and
a second non-endogenous expression vector comprising:
lambda Red proteins Gam, Exo, and Beta operably linked to an inducible promoter; or
Exo, RecA, and Gam proteins operably linked to an inducible promoter; and
(c) propagating the recombinant bacteriophage DNA genome in a second bacterial host cell, wherein the second bacterial host cell comprises a third non-endogenous expression vector comprising a nucleic acid sequence that encodes a second CRISPR enzyme, a third sgRNA, and a fourth sgRNA, wherein the third sgRNA and the fourth sgRNA are operably linked to a constitutive promoter, wherein the second CRISPR enzyme is operably linked to an inducible promoter, and wherein expression of the second CRISPR enzyme is induced prior to propagating the recombinant bacteriophage DNA genome in the second bacterial host cell.

18. The method of claim 17, wherein the third sgRNA binds to the second CRISPR enzyme to form a third sgRNA-CRISPR enzyme complex, and the fourth sgRNA binds to the second CRISPR enzyme to form a fourth sgRNA-CRISPR enzyme complex.

19. The method of claim 18, wherein the third sgRNA-CRISPR enzyme complex and the fourth sgRNA-CRISPR enzyme complex (a) do not cleave the recombinant bacteriophage DNA genome and (b) cleave the first bacteriophage DNA genome.

20. The method of claim 17, wherein the second CRISPR enzyme is Cas9.

21. A method for making a recombinant bacteriophage DNA genome in bacterial host cells comprising
(a) contacting a first bacteriophage DNA genome with a first sgRNA-CRISPR enzyme complex and a second sgRNA-CRISPR enzyme complex in vivo under conditions where
(i) the first sgRNA-CRISPR enzyme complex cleaves a first protospacer sequence within the first bacteriophage DNA genome; and
(ii) the second sgRNA-CRISPR enzyme complex cleaves a second protospacer sequence within the first bacteriophage DNA genome to produce a cleaved first bacteriophage DNA genome, wherein a first bacterial host cell is infected with the first bacteriophage DNA genome; and
(b) recombining in vivo the cleaved first bacteriophage DNA genome with a heterologous nucleic acid sequence under conditions to produce the recombinant bacteriophage DNA genome,
wherein the heterologous nucleic acid sequence comprises an open reading frame that encodes a bioluminescent protein, a fluorescent protein, a chemiluminescent protein, or any combination thereof
wherein the first bacterial host cell comprises
a first non-endogenous expression vector comprising a nucleic acid sequence that encodes a first sgRNA, a second sgRNA, and a first CRISPR enzyme, and
a second non-endogenous expression vector comprising:
lambda Red proteins Gam, Exo, and Beta operably linked to an inducible promoter; or
Exo, RecA, and Gam proteins operably linked to an inducible promoter; and
(c) propagating the recombinant bacteriophage DNA genome in a second bacterial host cell, wherein the second bacterial host cell comprises a non-endogenous Cascade complex expression vector comprising a nucleic acid sequence that encodes a casABCDE operon, and Cas3 nuclease.

22. The method of claim 21, wherein the casABCDE operon and Cas3 nuclease are operably linked to an inducible promoter or a constitutive promoter.

23. The method of claim 21, wherein the second bacterial host cell comprises a non-endogenous CRISPR RNA (crRNA) spacer array comprising one or more spacers that (a) induce cleavage in the first bacteriophage DNA genome and (b) do not induce cleavage in the recombinant bacteriophage DNA genome.

* * * * *

SEQUENCE LISTING

```
<160> NUMBER OF SEQ ID NOS: 23

<210> SEQ ID NO 1
<211> LENGTH: 44385
<212> TYPE: DNA
<213> ORGANISM: Escherichia virus K1-5

<400> SEQUENCE: 1
tcgccctcgc cctcgccggg ttgtccccat agggtggcct gagggaatcc gtcttcgacg      60
ggcagggctg atgtactcct tgtctagtac aagggaggcg gagggaacgc ctagggaggc     120
ctaggaatgg cttagtggtg gacaaggtga ttaccttagt gaagcctctt agtgcattcc     180
tgaggccatt cagggcgttt atgagggatt gacagggtgt gagggcgtgg gctatctgtt     240
cctttgctcc tcacttcgtt cgtcgctgcg gtagcctgat gtgtaccttg ggttattcct     300
tgatggatag cttaggttag ccttagtgga ttaccttagt taaagcctta gtgcttcact     360
tagtatcagc ttagtagtgt accttagtaa gtcttagtgt cttctcttag tgattgcaca     420
tgcaagcatg taagatgcta ataggtcgcg gtcggcagac cgctaaagaa agagaatggt     480
```

```
aataagatgc agtaggagga acaccagaag cctagccaac ctaagctatc ctagctctat    540
atctattgct tttccttagt ctaacacgtt agacaaccta tcttattctt agtgatggta    600
acttagtgtt gacaagataa tcttagtgta atactatgca tcacgtaggc ggtgctgagg    660
cacctagtag ccagctagta aggcatacga agagactagc gcttacattg ctctttaaca    720
atttgcttag tgtaacctat gtatgccgtg gttaactact tattgaatga ggtattaact    780 atgcacattaa ataaccgtga actgtccgtt ctcttcactc tgttgtgcta catgattcgt    840
aacaacgaat tacttacaga tgatgagtta gccttgtatc accgctttct taacgaaggt    900
tggaccgata cagttaatca ataccgtaac atgatagatg agttgaggga gggtaaataa    960
tgtatcaaca tgaggtattc tttgaatcag ctagcgaagc tattcgcttc cgtgatgata   1020
tgatgcaagc tggtgtaggc gttgatgtgt atcactattt gatagattac gacactgaat   1080
atcaccgagt taccttagta tctgagtatg acaaccaagt cattactgag tatctaggca   1140
gtgaagatta cgattacgat gaagtaatca cgacaaatct ctaaattaac tgttgacagc   1200
cacggcatac aaggttacat taagcatcaa gacggcgacg tctttaaaca tcccgctctt   1260
taacaatacg gtttgtgtct tgataggcta actaactaac taaggtaatt atcatgaaag   1320
ggttaatttg tgtagaacgt atggtcaatg gtaaacttga aatattacca ctggaaaacc   1380
aatctagctt caaagagtgg tatggctgtt tctcactgat ttaaggtaaa ggctggcact   1440
agtcagccta tcaaggcgca aaccaagctc tttaacaatt tggatggtag cttcttagtc   1500
tggataggtt aaacctagga gattctcttg agtctcctat aatgtaacct aactaactaa   1560
atgaggatta aatcatggaa cgcaatgcta acgcttacta caaccttctg gctgcaactg   1620
ttgaagcatt caacgagcgt attcagtttg atgagattcg cgaaggtgat gattactctg   1680
atgcactaca tgaggttgta gacagcaatg ttccagttta ttacagcgaa atctttacag   1740
tgatggctgc tgatggtatt gatgttgatt ttgaggatgc tggtttgatt cctgacacga   1800
aggatgtaac caagattcta caagctcgca tctatgaagc tctttataat gatgtaccaa   1860
atgacagcga tgtagtttgg tgtgaaggcg aagaagagga agaataagga tggaaaagca   1920
atataacttt atcttttcag acggtgtaac cctgaagtgt tccctacgat tcgcacaaat   1980
tcgtgaggaa gtactaggca ctacatacaa actatttagc tgacactata agagaaggct   2040
taacaaggcg ttactaaggt agcgcctgat taaactttca cttactagga gttgagatta   2100
tgaaaacctt gattggatgc ttcttgttgg cttctcttgc tctggcattt accgctaaag   2160
ctggttatga cgcttataaa gtagaacaag cccagcaaga ctgggccaaa aaaaagttca   2220
acttgtgcag caagagcaac acctacgagt actgcaacaa aacactaaga cacttatgga   2280
aagagtaact agcctatagc ccacctgagt gggctatgtg atatttactt aacactatat   2340
aaggtgatta ctatgactac tgaaaacacc ctcgtgtctg tccgtgaagc tgcaaccgct   2400
gaaatcaagc aacatttaga caatatcggc acttcttaca tcaaagtagg gcttgtctg    2460 aatgagttac gcggagactt tgaaggtcaa aaagagtttt tagcctatgt tgaagcagag   2520
tttgccatta agaaggcaca atgttacaag ctgatgagtg tagcccgtgt ctttgaaggc   2580
gatgatcgct ttaaaggcgt ggcgatgcgt gtaatgctgg cgcttgttcc tttcgctgat   2640
gaaaatataa tcatggagaa ggccgcagaa ctcgccgcaa atggcaagct ggacactaat   2700
gccgtaaacg ccctgattga acctaagaaa gagtcaaagg ccgaaacggt acaatctaag   2760
gctgagacag taaaaccgca ggagaacgcg actgagtccg cagaatcaca tgaaatgcaa   2820
gcgccgcagg tagtgccacc cgcgagcgag caggagtccg acgaatcagc ccttgggaa    2880
```

```
gaggaaagca aaccggaagc gccaaaggca gctccgatgg ataacacggc taatactgag   2940
aatgccgcta ttgctggtct gctggcacaa attaaagcac tgactgagca attacaggca   3000
gccaatgacc gcatcgcctc cttaagtagc gcacgcgaaa gcaagaaggc atccgcacct   3060
atgctgccgc agttcaaatc ttcctgcttc tacgctcgct taggcttgag cgcggaggag   3120
gcaacgaaga aaacagcagt taacaaggca cgccgcgaac tggttaagct gggatacggt   3180
gaaggccatg aggcatggcc cttaatctct gaggcagtag aagagttgac taagtaacct   3240
tatcggtggc atcttcttag gtgtcaccta ttaaggtttc tttcactagg agtaaacaag   3300
atgcaaggcc tacacgctat tcaacttcaa cttgaagaag aaatgtttaa cggcggtatc   3360
cgtcgctttg aagcggacca acaacgccag attgcatccg gtaatgaatc agacacggca   3420
tggaatcgcc gcttattgtc cgagttaatc gcgccaatgg ctgaaggtat tcaggcatac   3480
aaggaagagt atgaaggtaa aagaggccgt gcaccgcgtg cattagcttt cattaactgc   3540
gtagaaaacg aagtggcagc atatatcacg atgaaaatcg ttatggatat gctgaacacg   3600
gatgtaacct tgcaggctat agccatgaat gtagctgacc gcattgagga ccaagtacgt   3660
tttagcaagc tggaaggtca cgccgccaaa tactttgaaa aagttaagaa gtcacttaag   3720
gcaagtaaga ctaaatcata tcgccatgcg cacaacgtag cggtagtggc tgagaagtca   3780
gtagctgacc gtgacgctga tttctcccgc tgggaggcat ggcctaaaga caccttgctg   3840
caaattggga tgaccttgct tgaaatctta gagaatagcg tattcttcaa cgggcaacct   3900
gtcttcctcc gcaccttgcg cactaatggc ggcaaacatg gtgtttacta cctacagact   3960
agtgaacacg taggtgagtg gataactgca ttcaaagagc acgtagcgca actgagtcct   4020
gcctatgctc cttgcgtcat ccctccgcgt ccgtgggtat caccttttaa cggcggtttc   4080
cacactgaga aagtagcaag ccgtattcgt ctggtaaaag gaaaccgcga acacgtccgc   4140
aagctgacca aaaagcaaat gccagaggtt tacaaggctg ttaacgcgtt gcaggcgact   4200
aaatggcagg ttaacaagga agttttacag gttgtggaag acgtcatccg tctagaccta   4260
ggttatggtg taccttcctt taaaccactc attgaccgcg agaacaagcc agctaatcca   4320
gtgccgctag aatttcagca cctacggggc cgtgaactga agaaaatgct tacgccggaa   4380
caatggcaag cctttatcaa ctggaaaggt gaatgtacta agctgtacac cgctgaaact   4440
aagcgcggaa gcaaatcggc ggcaaccgtt cgcatggttg gtcaggcccg taaatatagc   4500
cagttcgacg caatctactt cgtgtatgca ctggacagcc gcagccgcgt ctacgcgcaa   4560
tctagcacac tctcaccgca atcaaatgac ttgggcaagg ccttgctccg tttttaccgaa   4620 gggcagcgtc ttgatagcgc tgaggcgctt aagtggtttt tggtgaacgg ggctaataac   4680 tgggggttggg ataagaaaac ttttgacgtg cgcaccgcta acgtgctgga tagtgaatt   4740 caagacatgt gccgcgacat tgcagcggat ccgctgacct tcactcaatg ggtaaatgcc   4800
gactcccctt acggcttcct tgcatggtgc tttgaatatg cgcgttatct ggatgcactg   4860
gatgaaggca cgcaagacca attcatgacg cacctcccag tccatcaaga tggtagttgt   4920
tctggtatcc agcactacag tgctatgcta cgcgatgcag taggtgcgaa agcagtaaac   4980
cttaagccct ctgactctcc tcaagatatt tatggtgccg ttgcgcaggt agtaattcag   5040
aagaattatg catacatgaa tgcagaggat gcggaaacct tcacttctgg cagcgtgact   5100
ttaacaggtg cggagctgcg tagtatggct agtgcgtggg atatgatagg aatcactcgc   5160
ggcctgacca aaaagcccgt aatgacacta ccttatggca gcacacgtct aacctgccgt   5220
```

```
gagtcagtga ttgattatat cgttgattta gaagaaaaag aggcccaacg ggctattgcg    5280
gaagggcgta ccgccaatcc tgtacaccct tttgataatg accgtaaaga cagcctgaca    5340
cctagcgcag cttataacta tatgacagct ttaatctggc cttctatttc ggaagtggtt    5400
aaagccccta tagtggcaat gaaaatgatt cgtcagcttg cccgtttcgc agctaaaagg    5460
aatgaaggct tagagtatac cctgcctact ggcttcatct tgcaacaaaa gattatggct    5520
actgatatgc tccgcgtatc tacttgcttg atgggagaaa tcaagatgag tctacagatt    5580
gaaacagacg tagtggatga acggcaatg atgggcgctg ctgctcctaa ctttgtgcat     5640
ggtcatgatg ccagccacct tatcttaaca gtctgcgacc ttgttgataa agggattaca    5700
tctatcgcag ttattcatga ctcttttggc actcatgcag gccgtacagc cgaccttcgt    5760
gatagcttaa gggcagaaat ggtgaagatg tatcaaggcc gtaatgcact gcaaagcctg    5820
ctagatgagc acgaagaacg ctggttagtt gataccggaa tacaagtacc agagcaaggg    5880
gagtttgacc ttaacgaaat cttagtttca gactattgct tcgcataata ttaataggcc    5940
attccttcgg gagtggcctt tcttttacct actacctgta acatttcatt aacataaaag    6000
tgtctcacat gtgagactta tttaccggac actataggat agccgtcgga gacgggaaag    6060
aaagggaaga taaggatat aaaggaagta ataggtatta aaggttatat aggttatcta     6120
ggaataccta ttccttctt ccttcctctt attaccactc agaggaaggg cagacctagg      6180
ttgtctcaca tgtgagactt cgtatttacc ggacagtata gataagatta actcactttg    6240
gagatttaac catgcgcaac tttgagaaga tggcccgtaa agctaaccgt tttgacatgg    6300 aagagggggca gaagaaaggc aagaagctga ataagcctgt ccgtgaccgt gcatctaaac    6360
gcgctgcgtg ggagttctaa gttatggcta ttattcagaa tgtaccgtgt cctgcctgtc    6420
aaaagaatgg acatgatatt actggcaacc atctcatgat atttgatgat ggtgccggct    6480
actgtaatcg tggacacttt catgataatg gtagacctta ctatcacaag ccggaaggtg    6540
gcatcgagat aaccgagtta tctattactg gcaatatcaa atatacacct tctcaattca    6600
aagaaatgga gaaggaaggg aagataagcg accctaaatt acgtgccatc gcacttggtg    6660
gtatgcgtat gaaagaccgt tgggaggtca tgaatgaaca agaaagggca gagcaagaag    6720
cagagtggaa acttgatgtt gaatggttcc tcacgcttaa gcgtaagaac cttgtttcca    6780
ggcacattcg cggcgacatt tgcgcattgt atgatgtacg tgttgggcac gatgaagagg    6840
gtagagtctc acggcattac tatccgcgct tcgaaaaagg tgagctagta ggcgctaagt    6900
gtcgcacatt acctaaagat tttaagtttg gtcatttagg taaactcttt ggtatgcaag    6960 atctttttcgg tatgaatact ttgtctcacg tgttagacaa gggaagacga aaggattgct    7020
tgctcattgt cggcggcgaa ctggatgcac tagcagcgca gcagatgctc cttgattctg    7080
ccaagggtac taagtgggaa ggccagccat accatgtatg gtctgtcaac aaaggcgagt    7140
cttgccttga agagatagtg cagaaccgtg agcatatcgc ccaattcaag aagattatat    7200
ggggttttga tggagatgag gtagggcaga agcagaatca gcaagcggct cgcctgtttc    7260
ctggtaaatc ctatatcctt gaataccccct ctggttgcaa agatgctaac aaggcattga    7320
tggctggcaa ggctaaagaa tttgtagatg catggtttaa tgccaagtca tctgatgaag    7380
tctttggtag ccagattaaa tctatcgcat ctcaaaggga taagctcaag gctgcacgtc    7440
cagagcaagg actgtcatgg ccttggccta agctgaacaa ggtaacgcta ggtattcgta    7500
agaaccagct tatcattgta ggtgcagggt ctggtgtagg taagactgag ttccttcgtg    7560
aagtagttaa gcacctcatt gaagaacacg gtgaatctgt aggcatcatt tctacagaag    7620
```

```
acccgatggt caaggtgtcc cgtgctttta tcggcaagtg gattgataag cgtattgagt   7680
tacctccaac caacgacccg aaagaagacg gataccgtga ggtgttcgac tataccgagg   7740
aagaagctaa cgccgccatt gattatgtag ctgatacagg taagctgttt gtagctgacc   7800
tagagggtga ctattcgatg gaaaaggtag agcaaacttg cctagagttt gaggctatgg   7860
gtatttctaa tatcatcatt gataacttaa cggggattaa attagatgag cgtgcttttg   7920
gtgggaaggt tggtgcactt gatgaatgcg tcaagcggat tggtactatc aaagaccgac   7980
acccggttac tatattcctt gtatcacacc ttacacgtcc tccggcaaac cgtacccaac   8040
acgaagaagg tggcgaagtt atcctttctg acttccgagg ctcaggcgct atcggattct   8100
gggcatctta cgccttgggg attgagcgta atacaagagc tgaaacgctt gacgaaagga   8160
ctaccacgta catctcatgt gtcaaagacc gcgaccaagg tatctacact ggaaccaagg   8220
tcatgcttaa gggtgacatt caaaccggac gtttaatgga accacaagcc cgtactaagt   8280
catttgatac aggtgaagca aggcaacaag aagtaccaga tttaccggat actatagaag   8340
agactacctt cgatgaagaa agtgagttct gattagtgta tttatcaggc ttgtctcaca   8400
tgtgagacag gctcttatta agtacattaa ataactggag attgattatg tataacttag   8460
tgttgaatgt aggtgacttt gtacgcaaca tcaagaaaga ttcaagtcgc tatctttgcc   8520
gtggtgttgt aacctttgta ggtgagaacc tgtattatgt agaatatcgc agtggtgtta   8580
agcaatatta ccacaagaag acagcacata atatcttga aaagattgta gagataaaca   8640
atcaatgtaa gtgcatacat gatgaggttt gcgataaatg tgctcgccag atgcttaaga   8700
atttcctagc tcctctttat tatggtgctg gtcctcaaac actagcagag tgcatggcag   8760
aaaagaaaac cacactcaag aaagagcgtc gcaatgtaat cactggtaag actcaaagtg   8820
agatgattaa gcaatgtggc actgcattag gtgttacaca gtttaatact cgtgcattgg   8880
gtaaatccac aggacaagct atggtaaaga ttggagaagc catgatgcat ccaaatgtac   8940
ctgtgcgaat catggatgtt gaccatgcaa tcacagaaca aggtacgcaa cgacgtgtaa   9000
ttaataagca ttttgccgac actatagaag gcattattcg taagcaaggg ttgaaaggtc   9060
ttcacatctt aaatggtgaa gaattactgt acctacctat cgttactgaa gaaacatacg   9120
tgaatatcta aggagttaat catgactaag gtattaattt atatgcgtgg acctcataaa   9180
tgctatgcag ttgtagcacc aaatggtgtt aagccttatc gtacttcaaa aagattggca   9240
ttaataggtg ctagtagtag tgcaagtttc caaatggaac ttttttggtca ttggactgaa   9300 aggcaattcc gtgaggattt taaagtcatt ggcagcttca tggtgaaata tgcagaataa   9360
acatagtctt agaatgttcg atggtcatga aaacctgcaa gccaagatta ctaaccaagc   9420
cttcctgttc gcacagttaa ctatggctga ggctaagaag aatagtctca ctcgtgaaca   9480
ggttatcaag gaggccactt gggaaccaca ccaaggtaaa tatatgggcc acaaattaac   9540
tgtaacacgc agtcgataag tcaagggttg tccaacgtgt tggacagcct ttcatcatat   9600
tgattgggag gtattaaatg actaagttta ctatgcaaga cctcattaaa ttacgtgatg   9660
aaatagaatc accggaagtt aatacagagt ttcactacat tgatccacga gataaacgag   9720
agattcctga ttatcagatt gagacggagt taatgtatga agattattga ttggaagaag   9780
gaagcagaag gccgtatcct agtgatggat gcggaggcta aaggcctgct gggtgctatc   9840
cgctacggtc atcgtgaaga tgtacacatt atttgctgca tggacttgct caccactgag   9900
gagttcctct tcttcgaccc atatgagatg cgtgaccctg aagcaaggga acacttgaaa   9960
```

```
gagtgggaag gccatcaaga tgggaccttg gttgatggtg ttaacttcct aaagcactgt    10020
gaagccatcg tctcacagaa cttcctaggc tatgacgggc ttctctttga gaaagccttc    10080
cctgacatct ggaagggatt taactacacc gagaggcgcg gcaagggcag actacgtgct    10140
gacttgtgtc cggtacgcgt catggatacg ctggtcatga gtcgcctgtt aaacccagat    10200
agacgccttc ctccgcaagc atatgccaaa ggtatgggta acgttgcccc tcactcaatt    10260
gaggcgcacg gcattcgtat aggccgttat aagccgagga acgaggattg gtctaaacta    10320
actgaccaca tggtacatcg tgtacgcgag gacgtggcga taggccgtga cctattcctc    10380
tggctattta acgagaatg gacggagcac aaacgccgtg gcgtgaataa acgcactggc    10440
ctaggtattg agacagcctt ccacatggag tccattgtga cgctggagat gagccgtcag    10500
gccgagcgtg gattccgtct ggatatagat aaagcattag cacgatgcga ggaattggac    10560
gctaagattg atgagacagt cgcagcgttc cgtccgcaca tgcctatgcg tatcaagtct    10620 aaaccttta accggaaga aaagaatgaa gtatgccaac gcgcaaatga gtatggagct    10680
agcaacaata tacctactgt ccttgacccc tctcactttc ttcacgcaga gagacgagga    10740
gatcgcaaga cagtatggag tgtcactact aagtctggtg attggtcggc tagcgtcaag    10800
aaagactttc ctcaccttag aggaaaccgt aatgacacgc caagtgtcaa gtggattggc    10860
gcttactcgc ctgttacttt cgaagagatt cccttgggta acaggggatac agttaagcaa    10920 gtgctctatg attatggatg gaaaggtgtt gaatttaacg ataccgagca agcgcatctc    10980
gatgagcatg gcgtattacc caagccttgg agtgggaaga taaatgaaaa gtccttact    11040 ttatggcaag agagagccgc acgtgaaggt aaaacagtcc ctgattggtg cttgggtatc    11100
gctgcatggt acatactcgt atcccgtcgt ggtcagatcc tcaaccgtgg tgacgttgaa    11160
gccttcgacc agaagggggt gtggccttcg caagctggta tacgaaagtg tcgcggcctt    11220
gtacctgtag catttaacaa ggagttagga atcaatgcgc agcaatacta cgaaaggtac    11280
ggatgctggc ctacgtcaga caaggatgac ggagaatggc gtgtgccagc tattgctatt    11340
agtattggaa cttctacgtt ccgtatgcgt catcgtaacg tggttaatat tcctgcccgt    11400
ggcttgtatc ctttacgtga tttattcata gcagggaaag gcaagctaat ccttggttgt    11460
gacggtgcag gtcttgaact gcgtgtcctg tctcacttca tgaatgaccc tgagtaccaa    11520
gagattgtac tgcacggtga tattcatacg cataaccaga tgaaggctgg tcttcctaag    11580
cgtgatatgg cgaagacatt tatatatgcc ttcctatatg ggtctggtat agctaacctt    11640
gcagcagtat gtggtgttac tgaggaagaa atggaggaag ttgtggcaag atttgaggtt    11700
gaactaccat ctcttgcacg tcttcgtgag aatgttatcg cacaaggtaa caagtttggc    11760
tacctacaag cacctgatgg tcattggggt cgcatccgta tgtctggtgg tgaacttaaa    11820
gaacacacta tgcttaacgt actactccag atgactggtt ctctgtgtat gaaatacgca    11880
ttggtcagag cgtttgcagt gatgcgcaag gaaggtgtgg ccttagatag catgggaaac    11940
ccttgcggta tagctaacgt gcacgatgaa atccagatgg aagtccctga agatgaggtc    12000
ttgtatctca actacgactt gcctttcacc ttagaagggt tcgaaacaga gaaggctgct    12060
gtgaaagcag tgttcgatgc agaggagaaa cgtgttcatg tggattctga aggacgtatg    12120
tggtctgctg caaatctcgt tagtgttgat gctggtgtac ttcattgcca gcgtcgttat    12180
caccgtgcag gcatatcat tgccgacgca atgacctggg cgggtcagta cctgaagatg    12240
cgttgtccga tggcaggtga gtataagatt ggtgcaagtt ggaaggaaac acactgatgg    12300
acaggtttga tattgtttgc ctattctcta ccttcttct tatattcctt atgcttgctt    12360
```

```
gctatggaag tatgcgatta gatatacctg atgaagagga gggttacgat tgatgcaggc    12420
atcttttatt attcttggag tcatattatt tatggtagta ttctgggctt tctctggcat    12480
tgacccagat tgtgatggta actacgactg agttatactc aaggtcactt acgagtggcc    12540
tttatgaata acttattcct acttattttg tctaacatga tttactggac actatagaag    12600
gaaagcatag gtaatctagg tttataaggt agtataggta attaagtaaa tataggagat    12660
ataaatatgt ctatggtaac tactctggta ttcgtggctc aatactttcg tggtcttgct    12720
aataagttca agtccaaggc tatcaaagct attgaggctc gcatcgaagc agtacaggca    12780
gagcaagtta aagttgaaga acatcgtagt tctcaaatga ttgactgtca taaccgctac    12840
tatgcatctc gtgatgaact aaatgcacgt caagtcaaag aggtagaaga tatgctggca    12900
cgtcaccagc aagagcgtga cagcctgaaa gctgaatttg aagagaacaa ggcatcaatt    12960
gctcttgtac atcaagctgc atctgacagt ctgaagaaag agattgttat gctggaaatc    13020
gaactggata acctgaccaa ataagggggg gttatgatgg aagaagtaat tcaagctaaa    13080
catgtaggta ttatctttcg cgatctagag cagcgtaaag ttgcaggtca tactcgtctg    13140
gctaaagagg aagacaccgc aatcactact gtagaacaag cagatgccta tcgtggacca    13200
gagttcactc aaggtgaaac ttgtcaccaa ttgagcctat caatttgtga cactatggct    13260
attgtaaatg tgcaagaagt cgaagagggt gagtgtgtca gttacatcta ccctttagat    13320
actattgcac gcattaaggt aatccataag taattactag acactataga acaataggtc    13380
ggcttagttc ggcctatgat tgtaaagtgt tgttgatgtt gaaccattgt gcatcttgca    13440
caacccgata ccgtataggg cttctagtg agtacatgct tgtgctcagt acaaagctaa    13500
ctgacaatag gagactaaat aaatggcacg tggtgatttt gattttggtg ctcaggttac    13560
taaatctgaa ggtaaagtct ttaagaatcc agaagtaggt gatcatgaag cagtaatctc    13620
tggcatcatt catgttggtt ccttccaaga catctttaag aaaggtaata ccactgaagt    13680
taagaagcca gcaaactttg ttctggttaa gattgtcctg atgggtgacg atgacaagaa    13740
cgaagatggt tctcgcatgg aacaatggat ggctgtgcct ctgaagtctg gtgataaggc    13800
aacactgact aagttcctga atgcagttga ccctaaagag ttgctgggtg gcttcgatga    13860
tttcattggt gaatgcctga ctgcaacgat ggtcggttct ggtgataaga atgacgatgg    13920
ctcattcaag tatgttaact ggaagggatt tggtggtatg ccggacaagc tgaagaaact    13980
ggtcattgct caggttgaag aggaaggtct gtctatgaca ggtcacatta ccttcgacaa    14040
gctgaccaaa gaaatccttg atgacatccc agccaacttg gtgcgtcaat acttcctgaa    14100
cgagacgcct cgtggtaaga acctgtctgt tgctggttct cacgtagaag caatcattaa    14160
agctgctcgt gaagaagacc cagaatggaa gaaggctaag aagaaagacg aggaagatgc    14220
taccccagct aatcgtaaat ctctggatac tggtgagtct gttccacagg aagtacctga    14280
agcagagaat actcctgcac cggagatgga tgaggacgcg gaatattaag gagaaaggat    14340
gaaagtacaa atcgtaaccc tgcactgcaa gaaaggaatt acaactcttg gcggcaacac    14400
ttttcactcc ttctctgaag gggacacata tgccgacctg cactacatct ggcgcgacgg    14460
acagcacgtg gtgaactaca gcgacccagc tacggggaaa cgccacggcg tatcgcttcc    14520
ggcgcatgac attgctcagg tgaacacagt tttataaagt ctcacgtgtg agacaaatcg    14580
gtgtccggta tttactggac actatagaag agaagaattt taatcggcga taatgccata    14640
accaacaaaa ggagaattta atatgttcaa gattgaaact atcgtaaacc gtgttgttaa    14700
```

-continued

```
aggtgctgct ctggtatccg ttgagtcttt cattatcgtc gatgaaactg atcaactggt   14760
agctggtact aaggcttacg atacccgtga agaagctcag gctaagattg acagcatggg   14820
taacttcgct gctggtctgg agttcgctcg tgcttgcttc cctgagcagg ctgacaaagc   14880
tcagattggt aaggctaata tcgtagctga atatctggat tggggttgctg ctggtaaacc   14940
```
(line 14940: `tcagattggt aaggctaata tcgtagctga atatctggat tgggttgctg ctggtaaacc`)
```
agtgaaagaa gttaaggctg ctgaagaagc tgaagctcca gcagaagaag tagctgcacc   15000
ggaaactccg gtaagtgaag aggaagaatt ttgataatag caggtgttgc ctctgttagt   15060
cctagctgac tatcacgctc acctcatcta atgccctgtc tgccttagtg taggcagggt   15120
cttttgcgta atagttattg gagaatgaat tatgccgact attgaatctc gaattgaact   15180
ggacattagc tacaatgcaa tcaccagaca gtatattggg gttgcctatg attacaaaac   15240
tggtgagaag ctagtggagg tgagacaatg ggatgactat tggttaagac agaacctcca   15300
tgatgcggtg tcctccttcc tgaaggagtg gcctacatgc gaccaaactt cgacttcgga   15360
gctacagtat cggaagacaa taacctgttg ctgtggccaa ctgaaggtaa tcgaatcgct   15420
ttaatagatg ctgatatgtt accttacatc atagggtata caatcagtga tatgacttat   15480
gtacgagcca caactcgtgt taagtcaggg caagtcccct caatcaaaga tacacctgag   15540
tgtaagcaag cgtgtgaccg tgtgaactcc ttgcttaact cttgggtgta tgcagcgaaa   15600
tgtgatgcag ctaagttgtt catgacgaaa tcagaagcta acttccgtgt ccgcctagca   15660
ttcaccaagc cttataaagg tcaacgtaag accgagaagc ctccattctt ctatgaattg   15720
cgagagcatc tcttagaggt tcacggtgca atcttggcag atggagagga agcagatgac   15780
ctcatgagta tcgcacaatg ggacagccac cgccgcttcc agcaagatac aggtaacgag   15840
ttccctatcg gtagtccaga gcataaagca ttctctgata cttgcatcgt ttccttggat   15900
aaggatttga tgattgttcc cggttggcat ctacagccgg tcaagagaa gaaatgggta   15960
```
(line 15960: `aaggatttga tgattgttcc cggttggcat ctacagccgg tcaagagaaa gaaatgggta`)
```
gagcctatgg gttggcttga gctacgccgt aaggctaatg ggcaagtcaa agatctaaaa   16020
ggtgctggcc tcatgttcca ctatgcacag atgattatcg gtgatgatat tgataactat   16080
gctggcatac caggtcgtgg tgctaaatat gcctatgatc ttctcaaaga ttgtaagaca   16140
gagaaagagt tgtacatggc agtgctgggt gcttacaagg ctaagttcgg gcatggacaa   16200
gttaaaatta agaattaccg aggtggttat cgtatcggca aagcctttga cctaatgctt   16260
gagtgtggtc gcttatctca catggcaaga ttcaagggtg atatatggcg agccgataag   16320
aacccaatct tgtggggaga tgatgcggaa tggttagcaa attaaaatca tcggaggtgg   16380
cagcttataa gaaggaattg ctagataagc aaggatggaa atgccctctg tgtggcggca   16440
gtctcaaagc tgtcacacct gtaaaccgtg tacttgacca tgaccatgag acaggattct   16500
gccgcgctgt tgtatgccga ggctgcaatg gtgcggaagg gaagattaag ggtgttatct   16560
ctggttatgg taaggctggt aacaaccgtt acttccagct tcaatggtta gagcgactat   16620
atgaatactg gaagttacat agtacgcctc agacagataa gttatatcac aaacatcaaa   16680
cggaggcaga gaagcgcgag gctaagaacc gtaaggcacg ccttgcttat gcaagaaaga   16740
aggaggttaa agttgggtaa gctgcgcagc ttgtacaaag actccgaggt acttgatgca   16800
atcgagcaag ctaccgacga gaaaggtaat gttaactaca atgagatggc acgtgtatta   16860
tcgtgtcata ctgtgggtaa aagattaccc cgccagttgg ctcgatactg gcatggtcaa   16920
ttcaagaaga ccaagaagaa tggtgattac taccagaccc ttctgcaaga agataagcgt   16980
atcaaagaag agcgtaagct caggactcct gaccgctacg aggatttggc tattgtgcca   17040
ttgcctgact cgcctcatcg aagtgtactg gtgatccctg atactcatgc accttatgag   17100
```

```
cacccagata ccctagagtt ccttgcagcc gtggcagcac gttaccgtcc agacacagtg   17160
gtacacctag gagatgaggc agacaaacat gccctgtcat tccacgattc ggacccaaat   17220
ctggatagtg ctggcatgga gttagagaag gctcgtatct tcatgcacaa attgcacaag   17280
atgttccctg tgatgcgcct gtgtcactct aaccacggct ctatgcactt ccgtaaggca   17340
agcgccaaag gcatccctgt gcaatacctg cgcacctatc gtgaagtctt cttcccgcag   17400
ggaggtggcg accagtggga ttggcaacat acgcacgtcc ttgagttgcc gaatggtgaa   17460
caagtggcat tcaagcatca acctgctggc tctgtcctag cagatgcagc gcatgagcgt   17520
atgaaccttg tgtgtggtca cttgcacggt aagatgtctg tggagtacgc acgtaataca   17580
catgaacagt attgggctgt gcaaggtggc tgcttaattg atgagtcatc ccgtgcattt   17640
gcctatggtc gtgagtctaa atacaagcca gcattaggtt gtgtggtcat tctggagggt   17700
gtgcctcaca ttgtcccgat gcaaaccaat agcgacaacc gttggattgg caagatttag   17760
ttgacactat agaacaaagg gctaggtaag actttatcgg ctggcgtatc caaatgatat   17820
tgcactagcc cttgattgta tagtgaatgg aggattcaat atgtcacact atgaatgtaa   17880
gaagtgtcat aagcgttatg attactgtac ttgtggtcaa gagaaaacat cttttaaagt   17940
tggagacaag gtatttcgta atgaaaaaga ttcgattcct tggaatcaat actgcaaaga   18000
agctggtatt gaccctgata gccctgtaac catgagatga ttgatggca ttaacttgtg   18060 cttcgtgag gtgaggggta caggttggga ttccaaaaaa ttcaaacttg catctgataa   18120
gttagacaac aatatggtaa ttaagcctaa gcactacgag ttctttgatg gcgtagaggc   18180
aatcactatc attgcccgca gtatgaccga gaagcaattc gctggctatt gcatgggtaa   18240
tgctttgaag taccgtctac gtgcaggtaa gaagttcaac actgaagaag acctgaagaa   18300
agcagattac tacaaagagt tattccagaa gcatcgtcac gaatgtattg atgaggatat   18360
ttgatatgaa tatctttgag ttcctaggtc ttccagaaga ccaccgcaat cacccattca   18420
tgctggtgaa gcatcgcggt gaagttcctg agaagaaatt aactttttcca tgttatgcac   18480 aggtgaaacg agatggtatc ttttctgctg ttgttgttcg cactgatggt gtcgttggca   18540
tttttggtcg cactggtaag aaattggcaa acactgaagg actcgaacaa gcctttgcta   18600
cctttccggt tggcatttat cttggtgagc ttcagtctat ggccattgat atctaccttg   18660
aggcaatctc tgggggttgtg aaccccaatc gcactgagcc acttgatttc ataggccagc   18720
agattaaaga caacctgtat atcgacttct tcgatatgtt aactattaag gcattccatg   18780
atggattcac tgatgtttct tatctcaaac gttacgatgc tttacatcgt cgtatcggcg   18840
ctcatcttag cgggtgcaac gctatccttc ctatcactcc ttgccataat gagcgagaag   18900
ttgaagcgtt tgcgcaagag caaatagatg caggacgtga gggtgctgta ttcaaactgg   18960
actgcgatta tgaagcagga cacaaaggtt atcgtcagac taaagaagtc cgtaaggtaa   19020
cctatgacct tacttgtatt ggctttgaag aaggtaaagg caaatacaaa ggtaaggtag   19080
ctaacctcat tttcaaatgg aaaggaggca agacaatcaa agctatgtta ggtaagggt   19140 ggactcatgc agatgcagag cagatgttcc acgacattaa acatggtgga cgattgaatg   19200
tcattggtaa aatctttgaa gtcaaaggtc ttcaggattc aagcaagggc aacattcgtc   19260
tgcccaaagc gggagaatta agacatgaca aagatgaacc agatttcttt tgatagcatg   19320
aaggcaactc gtgcagttga ggtagcagaa gctatcttcg aaactttatc ctgtggcatg   19380
gaagtgccat atactttact tgctgatgca gaagaacttg gtctttctgt agaagctatc   19440
```

```
caagagaagg ttgacgaatt atatggtaca gacgaagaag aaaccgacga tttcatttga    19500
aggaatggag atgcttgaga tgattctcaa gccttcttct cctaaggtga ctaagactca    19560
tgaagagtta atcgttgatg aagttaagcg ttacatcatg gattgtgtca gagcacaact    19620
ggtggtccaa tgatacgtcc agcctccttc ctagatattc ctgagattat aaaccttggg    19680
aataaatatg tggaagagga agtcaaggtt gtagcccacc actcagcctc atggaatgca    19740
gaacaaagtg ccataacctt tgtgcatctc ttaatagaga cccaccactc agcctcatgg    19800
aatgcagaac aaagtgcaca taacctttgt gcatctctta gtagagaaga tttatcccta    19860
tgggttgctg tagatgaagg gcagattgta gggttcctgt gggctggcta tcacgagttg    19920
gccccttgga cacctgtaag agttgcctct gacattctct tttatattat accagagagg    19980
cgaggaacac tacttggtat gcgtctcatc aaagccctaa agcaatgggc tagtgataat    20040
gaatgctctg aggttcgcct gtctatcgcc tctggtatta atgaagaacg tgtcggacgt    20100
atgtataagc gacttggctt tgaaccgttt ggcactgtgt ataacctgaa gttctaagga    20160
gataacatgg gtgttgtaaa gaaagcattt aaggctatcg gtcttgctca agatgcacca    20220
cgtattgaag ccaaagtccc agcacagcag cttgagcgta agcctgagac tgaagctgaa    20280
gatattcaaa ttggtgcagg ggatgatgct actgcatctg caaaaggtaa gcgtggcctt    20340
gtccgtccgg tagcttctag cttgaaggtg taatatgaaa cagagcatag atttggagta    20400
tggaggtaag cggtctaaga tacctaagct atgggagaag ttctccaata aacgtagctc    20460
tttccttgat agggcgaagc attactccaa attaaccttg ccctatctga tgaatgacaa    20520
aggtgataac gagacttcgc agaatggatg caaggtgta ggtgctcagg caaccaacca    20580
tctagccaac aagctagcgc aagtactatt ccctgcacag cgttccttct tccgtgtaga    20640
cttaactgca caaggtgaga aggttcttaa tcagcgtggc ctgaagaaga cagagctagc    20700
taccatcttc gctcaagtgg aaacacgggc aatgaaagag ttagagcaac gtcaattccg    20760
gcctgctgta gtagaagcat taagcatctc tattgttgct ggcagctgta tgctatacaa    20820
gccgagcaaa ggtgcaatca gtgctatccc aatgcatcac tacgtagtta accgtgatac    20880
caatggcgac ctgttagaca ttatcttgct acaagagaaa gccttacgta cctttgaccc    20940
agctacacgt gcggtagtag aggttggcct gaaaggtaag aagtgcaagg aagatgacag    21000
cgttaagctg tacacacatg ctaagtatct tggtgatgga ttttgggaac tcaagcaatc    21060
tgctgatgat atccctgtgg gtaaggtgag taaaatcaaa tcagaaaagc taccttttcat    21120
cccattaact tggaagcgaa gctatggtga ggattgggt cgacctcttg cagaggatta    21180
ctccggtgat ttattcgtta ccaattctt atctgaagcg gttgccgtg tgctgcgct    21240
gatggcagat atcaagtacc tgattcgtcc tggtgctcaa actgatgttg accactttgt    21300
taactctggc actggtgagg ttgtcactgg tgtagaagaa gacatccata ttgtacagtt    21360
aggtaagtac gcagacctca cacctattag cgcggttcta gaggtataca ctcgccgtat    21420
cggtgttgtc ttcatgatgg agacaatgac acgccgtgac gccgaacgtg ttactgctgt    21480
agaaatccag cgagatgcgt tagagattga gcagaacatg ggtggtgtat actccctctt    21540
tgctactact atgcaatcgc cagtagcgat gtggggtctg ctggaggcag gggagtcctt    21600
cactagtgac ttagtggacc ctgtgattat cacaggtatt gaagctttag gacgcatggc    21660
tgagttggat aaactggcta actttgctca gtatatgtca ctgccattac aatggcctga    21720
gcctgtccta gctgctgtga atggcctga ctatatggat tgggtgcgtg gtcaaatctc    21780
tgctgaactg ccgttcctta aatcggctga agagatggca caagaacagg aagcacagat    21840
```

```
gcaagcacag caagcacaga tgcttgaaga aggtgtggct aaggccgtgc cgggtgtaat    21900
tcaacaagaa cttaaggagg cgtaatgtct ttctcattta ctgaaccgtc aaccactcac    21960
cctactgctg aagagggtcc ggtagaaacc aaggaggtaa caactgatgc tgctactact    22020
gatgctcctg ctgacgctgg cacttctgta caagatgaca atgctggtgc acaacctact    22080
gaagacaccg gaggagaagc ttctggacag ccttcagaaa aaggagacaa tggcggagag    22140
aatggtgaac ctaagccaga tgataccgcg accgacactg aggaagtgca atacttcttc    22200
ggagaacatg aagtaacagt agacatccca caggatgtaa ctgacagcct taaagagaaa    22260
ggcattgatg ccaagcaggt tgccaaggaa ctctattcca aggtggcaa gtttgaactg    22320
tcagatgcaa ccaagcagaa attgtatgat gcttttggca gtttgcggt agatgcttac    22380
ctatcaggtc taaaggctca aaatgaagcc ttcttcctga aagaagccaa cgcagctaaa    22440
gagttggaag cagctaacac ccaacgcttc tctgatgttt ctaaggaaat tggtggcgaa    22500
gaaggttggt cccgtcttga ggagtgggca cttgaagcgc tgtctgatga cgaactaatg    22560
gcattcaatg cggtgatgga atctggcaac cagtacctgc aacaatatgc tgttcgtgaa    22620
ctggagggtc gtcgtaagca ggcacagggg gatgataagc catccctgat tgagccatca    22680
gcacctgcta aggctaatga agagaatggc ccactgacgc gagatcagta cgttcaagca    22740
atcgcaactc ttagccagaa gtacggcaat gaccgtaaag ctatggcaga agctcaggct    22800
aaactggacg cccgtcgccg tgctggcatg gctcgcggta tctaattcag tatttactgg    22860
acactataga agggagaaaa gttctcccta gttatcaatt tgatttataa ggagattata    22920
atacatgtct acaccgaata ctctgactaa cgttgctgta tctgcgtccg gtgaggttga    22980
cagccttctc attgagaagt ttaatggtaa ggtcaatgag cagtacctga aggtgagaa    23040
cattctgtcc tactttgatg tacaaactgt tactggcact aacacagtga gcaacaaata    23100
tttgggcgaa actgagttgc aggtgctagc accgggtcag tcccctaatg ccaccccctac   23160
tcaggcggat aaaaaccagt tggtaattga taccactgtc attgctcgta acactgtggc    23220
tcacatccac gatgtacaag gtgacatcga tagcctgaaa ccaaaactgg ctatgaacca    23280
agccaagcaa ctgaaacgtc tggaagacca gatggcaatt cagcagatgc tgttaggcgg    23340
tattgctaac accaaggccg aacgtaacaa gccgcgtgtt aaagggcatg gcttctctat    23400
caacgttaac gtaactgaga gtgaagcact ggctaaccct cagtatgtta tggctgcggt    23460
agagtatgct ctggagcaac agcttgagca ggaagtggac atctctgatg tagctatcat    23520
gatgccgtgg aagttcttca atgctttgcg tgatgcagac cgaattgtag ataagactta    23580
cactatcagc cagtctggtg caaccattaa tggcttcgtt ctctcttctt ataactgccc    23640
tgtgatcccg tctaaccgat tccctacctt cgctcaggat caggctcacc acctgttgtc    23700
taatgaagat aacggctatc gttatgaccc tatcgcagag atgaatggtg cagttgctgt    23760
tctgttcact tccgacgcac tgctggtggg tcgtaccatt gaagtgactg gtgacatctt    23820
ctatgagaag aaagagaaga cttattacat tgacaccttc atggctgagg gtgcaatccc    23880
tgaccgttgg gaagcagtgt ctgtagttac cactaaacgt gatgcaacta ctggtgatgc    23940
tggaggtcct ggtgatgatc acgcaaccgt actggctcgt gcacagcgta aggctgtata    24000
tgtcaaaacc gaaggtgctg cggctgcatt ctctgctgcc ccagcaggta tccaagcgga    24060
agaccttgta gcggcggtac gtgctgtaat ggcaaatgac attaagccga ctgcaatgaa    24120
acctactgag taacacctat gccctatcta ccttgcgtag gtagggttct ttttgttagg    24180
```

```
aggattcatg cctgtaatta gacaaaccag taaattagga catatgatgg aagatgtggc    24240
cttccagatt attgatagta agctggaagc ggtaaacttg tgtatgcgag ctattggtcg    24300
tgagggtgtg gattccctcg actcagggga cttggacgca gaagatgcaa gcaaaatgat    24360
cgacatcgta tcccagcggt tccagtacaa caaaggaggg ggctggtggt tcaatcgtga    24420
accaaactgg caacttgcac cagacactaa cggtgaagtt aatttaccta caaactgcct    24480
agcagtattg cagtgttatg ctttaggtga aaagaaagta cctatgacta tgcgagcagg    24540
taagctctac tctacttgga gtcacacctt tgatatgcgt aagcatgtta atgctaatgg    24600
tatgattcgt cttaccttac tcaccttact accctacgag catctaccta caagtgtaat    24660
gcaggctatt gcctatcaag ctgctgtaga gtttattgtg tctaaggatg cagatcagac    24720
taagctagcc actgcgcagc agatagccac tcagcttctt atggatgtac aatctgagca    24780
aatgtcacag aagcgattaa acatgctggt acataaccct actcagcgtc agtttggtat    24840
catggctggt ggctctcaga atgtacctgc ttactctcat tcaccttatg agagttgggc    24900
gctccgtccg tgggaggatc gttaatggaa gtacaaggtt cattaggtag acaaatccaa    24960
gggattagcc agcagccgcc agcggtacgc ttggatggtc agtgcacagc tatggttaat    25020
atgatacctg atgtagtgaa tggtactcaa tcacgcatgg gtacaactca tattgcaaag    25080
atacttgatg cggggactga tgacatggct actcatcatt atcgcagagg tgatggtgat    25140
gaagagtatt tcttcacgtt gaagaaagga caagttcctg agatatttga taagtatggg    25200
cgcaaatgta atgtgacttc acaagatgca cctatgacct acctctctga ggttgttaat    25260
ccaagggaag atgtgcaatt catgacgata gctgatgtta cttcatgct taatcgtagg    25320 aaagtagtta aagctagtag caggaagtca cctaaagttg gaaacaaagc cattgtgttt    25380
tgtgcgtatg gtcaatatgg tacatcttat tccattgtaa ttaatggggc caacgctgct    25440
agttttaaaa caccggatgg tggaagtgca gaccatgttg aacaaattcg aactgaacgt    25500
atcacttctg aattgtactc taagttgcag caatggagcg gtgtgagtga ctatgaaata    25560
caaagagacg gtactagtat atttatcgag agacgggatg gtgctagctt tacaataaca    25620
accaccgatg gtgcaaaagg taaggactta gtggctatca agaataaagt tagctctact    25680
gacctactcc cttctcgtgc gcctgctggt tataaagtac aagtgtggcc tactggcagc    25740
aaacctgagt ctcgttactg gctgcaagct gagcctaaag agggaaacct tgtgtcttgg    25800
aaagaaacaa tagctgctga tgtattactt gggtttgata aaggcacaat gccttacatt    25860
attgaacgta cagatatcat caacggcata gctcaattca agataagaca aggtgattgg    25920
gaagatcgta agtagggga tgacttgact aaccctatgc cctcttttat tgatgaggaa    25980
gtaccccaga caataggtgg aatgttcatg gtgcagaacc gcctatgctt tacagcaggt    26040
gaagcggtta ttgcttctcg tacatcatac ttcttcgatt tctttcgtta tacggttatc    26100
tctgcattgg caactgaccc ctttgatatt ttctcagatg ctagtgaagt ctaccagcta    26160
aaacatgcag tgaccttaga tggcgctacc gtgttgttct ctgataagtc acaattcata    26220
ctgccaggcg ataagcccttt agagaagtca aatgcactgc ttaagcctgt tacaacattt    26280
gaagtgaaca ataaagtgaa gccagtagta actggtgaat cggtaatgtt tgccactaat    26340
gatggttctt actctggtgt acgagagttc tatacagact cttatagtga cactaagaag    26400
gcacaagcaa tcacaagtca tgtgaataaa ctcatcgaag gtaacattac caacatggca    26460
gcaagcacca atgtcaacag gttacttgtc actaccgata agtatcgtaa cataatctac    26520
tgctacgatt ggttatggca aggaacagac cgtgtacaat cagcatggca tgtatggaag    26580
```

-continued

```
tggcctatag gtacaaaggt gcgaggtatg ttttattctg gtgaattact ttacctgctc    26640
cttgagcgag gagatggcgt gtatctggag aagatggaca tgggtgatgc actaacctac    26700
ggtttgaatg accgcatcag aatggatagg caagcagagt tagtcttcaa gcatttcaaa    26760
gcagaagatg aatgggtatc tgagccgctc ccttgggttc ctactaaccc agaactttta    26820
gattgcatct taatcgaggg ttgggattca tatattggcg gctctttctt attcaagtac    26880
aaccctagtg acaatacttt gtctacaacc tttgatatgt atgatgacag ccatgtaaaa    26940
gcgaaggtta ttgttggtca gatttaccct caagagtttg aacctacgcc tgtggttatc    27000
agagacaatc aagaccgtgt atcctacatt gatgtaccag ttgtaggatt ggttcacctt    27060
aatcttgaca tgtaccccga tttctccgta gaagttaaga atgtgaagag tggtaaagta    27120
cgtagagtat tagcgtcaaa ccgtataggt ggtgctctca ataatacagt aggctatgtt    27180
gaaccgagag aaggtgtctt cagatttcca ctgagagcta agagcacgga tgttgtttat    27240
cgtattattg tagagtcacc tcacacattc cagcttcgtg atattgagtg ggaagggagc    27300
tacaatccaa ccaaaaggag ggtctaatgg ctataggttc agccgttatg gctggtatgt    27360
cttctattgg tagcatgttt gcaggcagtg gtgcagcagc cgctgctgga ggtgctgccg    27420
caggtggcgg aggtttgcta ggttcactag gtggattcct aagtggctct actgctggtt    27480
tctctaatgc tggccttctt ggtgctggcc ttcaagggtt aggcttgatt ggtgatctat    27540
ttggtggaag tgatgaagcc aaggcgatga agaaagcaca agaagagcaa tggcggcagc    27600
agcttattgc tacacaagag gcgtacaaga cagtggcaga cgcagaacgt tctgctgcta    27660
aacaatatca tgcagatgca atcagtaatc aggcttcact gctacagcag cgagcacagg    27720
ttgcattact tgctggggct actggtactg gtggtaattc tgtgtcctct atgcttaatg    27780
acttagcagc agatggcggc aggaaccaga gtactatcat tgataactat gagaatcaga    27840
agattaattt caccaaccag cttaagtcta tccaacgtgg tggtcagatg cagatgcgtg    27900
agtttaagaa gccttctgct atgaatacct tggttaaagg tattccaagt ctggcatctg    27960
cctatgtaac tggtagtaag tctggcaagg cattgggtaa agccttaact gattctcgca    28020
catattcatc tggaacaaga ggtatttaat ggcaattgag cgacaagcag tacaaggtct    28080
gccacaagtg caggccactt ctcctaatgt catgaccttt gcacctcaac aagtgggagg    28140
tgtggaggct ggcgtggctt ctacctccgg tagtaggttt atcgaagacc ttattcgtgc    28200
agcaagcagc gtggctgatg ttaccactgg tatccttaat cagaagattg aggaagataa    28260
ggttgttcaa atggaacggg catataacgg attaatgcct tctgaggatg caactcgtgg    28320
tggcgctcgt gctaacatgc ttgtcaaagc tcaactgcta gctaatgatg aagcagcacg    28380
aatgaaagac atggctactc gtttccaagg aacggatgac gaatggacac aacttatggt    28440
tgactctcgt aatgagatgc agaataagct gttccagcaa taccctgagt tgcaaggtga    28500
caaagatact atgcgtatgg tcactaatgt cttccaagaa cagcagcctc agatttgggc    28560
tacacgaacc cagcataaac ttgaccgtga acaagcagac cgtgaggata cctttgacgg    28620
gcgagtggct tctacttggg attctaatat tgaccctgaa gcctctggct atgctttaca    28680
ggaacgaatc cgcgaaggtc ttactcaagg attactacct gaacagatgt acaagaagtt    28740
agtccagcga gcaatttcac ttgcacaagg cggtgatgtt agcatggctg aagcccctga    28800
gtatgtgaag gacgataagg gtgtttctgt ttatgctaag aatccacagc ttatcacagc    28860
catcactagt ggtaatgcag tttgggctag gaataatgta gctgatgtaa ctcgtatgtc    28920
```

```
tttcgaagtt aaagaatcct accttgcagg tgatttaact gatgaagaat tgttggaacg   28980
agcacagcac attaataatc tgacaggtaa ctctgtcttc tctaatccag aactagaggc   29040
actgatgcgc aacgggcta agcagaatgc agagctaggt gcaatgcagg atatgcgacg    29100
tgagctttac tccgaccgcc tgactggctt ccaaggtaag actgataaag agaagaaggc   29160
ttacattgat gttatcaaac aggatagcca actttatgca gaccagcaaa tcaaacaacg   29220
tggcttggac ccttacagtc aagaggctga agctattcgt ggtgcagtgg aagtgcagcg   29280
cctgcaattc atgaactcca aaggcttagt ggatgatacc tttgagtctc gtatcaaagc   29340
catgaatcct atgctatcgc ctgagcactt tgccaagggc gaaccacagg agttgatgac   29400
tattcgccag ttgtgggaac agttaccaga agagagccga ggtgtctttg gtgacacggt   29460
gaatggctac atggataact acaacactgc actacaaatg ggagagacac ctttgcaggc   29520
tgcaaggttt gcgcgtaaag cacagcagaa attctctcgt actgagaagg aaaccaagaa   29580
gttcaactca gctattggag atgcactgga tgaggtatct ggtgctggct ggtttgatgg   29640
taaaaccgaa gtgtcagact aggtaaagc tattgcggaa gaagagttac gagctaaggc    29700
caatatgttg tggtctagtg gtatgcgtaa catggattcc atcaagaagg ctttaattac   29760
ttggggcaat aaacgctaca ctcaatcaga ggatgcaaag acttccggtg ctatttcat    29820 taaaggtgat tacacttctg catctgatat gcttatgtca gttgggaaag gcgtaaaccc   29880
taccgatgta cctctggcgc ttggtaggta tgtagaaaca cagatgccag aattgaagaa   29940
ggagcttcaa gagggggaaa ctaaagatga tatatacatt gattacaatg aacagaaagg   30000
tactttcgtg attcgtgctg gtgcagcagg tcgccctctt tctggagtaa tccctgtaac   30060
ctctttagat accacttcac tactagattc tgcctatcag aagaaagtag aggaacgaga   30120
taaaggcgag tatgttcacc cgtatcgtac agatattggt gcacaagagc ctatgccagc   30180
taaaccaact gccaaagata ttggtaaatt tggactagct aacttcctca tgtcttctgc   30240
ttttgcttct ggtgagaatc tgccttctaa cttcgagatt aactatcgag gtaatatgca   30300
acaattctat gacaagctag ctatggatga gaataaagat aaagttggct taataaggc    30360 aactggaacc tttactccat ataaagacgc tcacggtgag tctatcggtt acggtcattt   30420
cttaacggaa gaagagaagc gaaacgggta tattaagatt ggcgatgaac tagttcccta   30480
tcgagggtct atgtctcagc ttacagagag caaggctcgc gctcttatgg agcaagatgc   30540
taagaagcat gtgcctccta ctcgtgactg gaagattccg tttgaccaga tgcaccctgc   30600
acagcaacgt ggcttgatgg atttaagcta caatttaggt aaaggtggaa tccagaactc   30660
accgcgtgct cttgctgcat tcaaagctgg taagcttacg gagggctta tcgaaatgct    30720 gggcactgca tcaagtgaag gtaagcgtat tcctggccta ctgaagcgac gcgctgaggc   30780
atacaatatg gcatctgctg gtggtgtgcc taagattacc gaagtggaga ctcgtgaaga   30840
tggctccatg tgggtaggt ttggtggacc tatgccagca ggttctgtct cggcatggac    30900
tcataaacgt attggcgcgg atggttggta tcaggtttat gaggctgcac taccaagtt    30960 agctaaagat tctaaggtag gtaaagttaa gttgtagtac ctaactcaag gcttgtctca   31020
catgtgagac aggtctttat gataggcact atggaggaat tatggaacaa gacattaaga   31080
ctaattgggc tggatatgtc cagtctactc ctgagccgtt ttctattgag gcggctccgg   31140
tatcggctcc tacgatacgc cagcgtaatg agttacaaga gcaagttctt gaagctaaag   31200
ctgacgctga tatcttaggt gctgtaggtg ctgccttcca gaatgagtgg ttggcattcg   31260
gaggcaagcg gtggtatgac cgtgccactg ctgatttcac acctcaacca gactttgaga   31320
```

```
tacaacctga gcaacgtgaa gcactacgtt tcaaatatgg tacgatatg atgcagacaa    31380 tcactgaggg tgttcgttct gaggatgaat tgaacttccg tattcagaat gcggatgaag    31440
accttgagcg caataagcgc attgctcagg ctggctgggt tggctctgtg gcgacgattg    31500
gcgctgctgt gcttgacoct gtgggatggg ttgcctctat tccaaccggt ggtgccgcta    31560
aagttggact cgtaggccgt gctgtgcgtg gcgctatcgc cgctggcgtg agtaatgccg    31620
ctattgaatc cgtattggtc caaggtgaca tgactcgtga tttagatgac attatgatag    31680
cactgggttc cggtatggct atgggtggcg ttattggcgc tgtagcgcgt ggtagggcca    31740
ctaagctcag tgagcaaggt gatgacaggg ctgctagcat tgtgcgcagt gcagacgcag    31800
gggaccgcta tgttcgtgct gttgccgatg acagtatcgg tgcgatgcgt gttaagggcg    31860
cagaggttct cactgagggt gtattcgata tctccagtaa gagtgaagac ctactgaaaa    31920
ccttgcaacg agaaggtaat gcgattgata tgacacctcg ccgttgggct ggaactatgt    31980
ctgccctcgg tactgtcgtg cactcatcta aagatgcaag tatccgaggc cttggtgctc    32040
gtctgtttga atccccacaa ggtctaggta tgcagaaggc atctgctagt cttatgcaga    32100
atactaactt aaatcgcctg aaatctgctg atatgaaccg cttcaatgat gggtttgatt    32160
tgtggcttaa agagaataat atcaatccag tagcagggca taccaactct cattatgtac    32220
agcaatacaa tgaaaaggtg tgggaggcag tgcgtattgg catggatgag tctacaccta    32280
aatctatccg catggctgct gagggacaac aggctatgta cagagaggcg ctggctttac    32340
gtcaacgttc tggtgaagcg ggatttgaaa aggtaaaagc cgacaacaaa tatatgcctg    32400
atatctttga tagtatgaaa gccagacgtc aattcgatat gcacgataaa gaagacatca    32460
tcgaactttt ctctcgtgcc taccagaatg gcgctcgtaa gattccaaag gaagcagcag    32520
atgagattgc acgagcacag gtaaatcgcg ttgctgatgc taccttaact ggaaagctta    32580
gttttgaaaa ggcaatgtca ggtcagacta aggcagagta tgaagctatc atgcgtaagg    32640
caggcttcag tgatgaagaa attgaaaaga tgatagaagc tctggataac aaagaaacca    32700
gagataacat ctctaaccga gctaaaatga gtttaggatt agatgttact caagaataca    32760
atggcattcg tatgcgtgac ttcatgaata ccaacgtgga agagctaaca gataactata    32820
tgaaggaagc agcaggtggc gctgcattgg ctcgccaagg cttctctacc tatcaggctg    32880
cacttaatgc aattgacctt gtagagcgaa atgcacgaaa cgcggctaag gatagcaagg    32940
ctagtttggc attagatgaa gagattcgtc agatgcgaga aggtcttcgc ctgattatgg    33000
gcaagtcgat tgatgcagac ccacaggcta tatctactaa gatgatgcgt cgtggtcgtg    33060
atatcacagg tgtgcttcgc ttaggtcaaa tgggcttcgc acagctaggt gaacttgcca    33120
actttatggg tgaatttggt attgctgcaa ctactatggc tttaggtaag caattccgct    33180
tcacctctaa ggcgttgcgt aatggcgatg gcttcttccg agataagaac ttagctgagg    33240
ttgagagaat ggtggggtac attggtgagg ataactggct aacaactaag ggtgcacgtc    33300
ctgatgaatt tggtgatgta accacagtaa gagggatgat ggctcacttt gaccaatcca    33360
tgaactcaat acgtcgtgct caaaccaacc tatcactctt ccgcatggca cagggttctc    33420
tggagcgaat gactaatagg caaatagctt tgtctttcat tgaccacctt gaaggcaaga    33480
agattattcc tcagaagaaa ctggaggaac ttggtcttac tcaggagttc atgactaacc    33540
tacagaagca ctatgatgct aactctaaag gttctggctt gcttggcttt gatacaatgc    33600
cttatgccat gggtgaaact ttagctaatg ctattcgtcg taagtcaggt ctaatcatcc    33660
```

```
aacgtaactt cattggtgat gaaggtatct ggatgaacaa agcactaggt aagacatttg    33720
cacagcttaa gtcattctct cttgtatctg gtgagaagca atttggtcga gggattcgcc    33780
acgataaaat tggtcttgct aagaagacag cttacgggtt tgctttgggt tcaatagtgt    33840
atgcggcaaa agcctatgtg aactctattg ggcgagaaga ccaagatgaa tatttggaag    33900
agaagttatc gcctaaaggg ttggcctttg gtgcaatggg tatgatgagt acaactgctg    33960
tatttagtct aggtggagat ttcttaggtg gcctaggtgt tctaccttcc gaactcattc    34020
aatcacgcta tgaagcaggt ttccaaagta agggtctgat tgaccaaata cctctggttg    34080
gcgttggtgc agatgcagta aatctggcta actcaatcaa gaagtatgca gaaggtgaca    34140
cagaaggtgt agatatcgct aagcgagcac tccgtcttgt gccacttacc aatataatag    34200
gtgtccaaaa cgcattgcgt tatggcttag atgaactgga ggattgatga gttatacttt    34260
cacagaacat acagccaatg gtacgcaagt cacctatcct tttagctttg ctggtaggga    34320
taaaggttat cttcgtgcct cagatgtgat agtggagtct cttcaaggta acacttggat    34380
tgaagttaca tctggctggc aactaactgg cacgcaccag attacttttg atgtagcacc    34440
agttgcaggt ttgaagttcc gtattcgaag ggaagtacaa aaagaatatc catacgctga    34500
gtttgaccgt ggtgttacct tggatatgaa gtctttaaat ggttctttca ttcatatact    34560
ggagattaca caggagttac ttgacgggtt ttatccagaa ggatacttca ttaaacagaa    34620
tgtaagctgg ggcggcaata agattactga tttggctgat ggcacaaatc cgggagatgc    34680
agtaaataaa gggcagcttg atgccatcga caagaagcat acagattgga acgccaaaca    34740
ggacattgag attgctggcc ttaaggctgg tatgacttct ggtattgcgc acagaactgt    34800
tccttggtac acgatagccc aaggtggtga gatttccgta aaaccaccct tatgaatttca    34860 agatgcacta gttttcctta atggggtatt gcagcaccaa attgtaggcg catactctat    34920
aagcaacaac actatcactt tcgcagagcc gcttgtggct ggtacagagg tgtatgtgct    34980
gattggtagt cgtgtggcta catctgaacc taatattcag ttggagttga actttgactt    35040
agtagaaggc caacaagtag tacagattgg ctctgcattt aagtacattg aggtctacct    35100
tgatggatta ttacaaccta acttgctta tcaggtagac ggtgacattg ttactttctc    35160
agaaagagta ccagaatgcc ggatgactgc taagattatc acagcataag gaggtgggat    35220
gattaactcc gaactggtag atagtggtgt gaagcttgcg ccacctgcac tcatatcagg    35280
tgggtacttc ctcggtatca gttgggataa ttgggtgtta atagcaacat tcatttatac    35340
cgtgttgcaa attggggact ggttttataa taagttcaag atttggaggg agaagcgtga    35400
gcgtacacaa taaacatgca gctacagagg acgaggttgg cattctgcat ggtgctatta    35460
ccaaaatctt caataagaaa gcacaggcaa tactggacac tatagaagaa gaccctgatg    35520
cagcattaca tttagtgtct ggtaaggata ttggtgcgat gtgtaagtgg gttcttgata    35580
acggcattac cgccacacct gctgcacagc aggaagagtc caagttatct aagcgcctca    35640
aggctatccg agaggcatcc agtggtaaga taattcaatt cactaaggag gattgatggc    35700
taaggcaaga gaatcacaag cggaggctct tgccagatgg gagatgctac aggagttaca    35760
gcagaccttt ccttacaccg cggaaggttt gcttctcttt gcagatacag ttattcataa    35820
cttaattgca ggcaacctc atctgattcg tatgcaggcg gatatcttga gttcctatt    35880 ttacggacac aagtaccgcc tcatcgaagc gcctcgtggt atcgctaaga caacactatc    35940
agcaatctat acggtattcc gtattattca tgaaccgcat aagcgtatca tggttgtgtc    36000
ccaaaacgcc aagcgagcag aggaaatcgc aggttgggta gttaaaatct ccgtggctt    36060
```

```
agactttctt gagtttatgc tgccggatat ctacgctggg gaccgtgcat ccgttaaggc   36120
gtttgagatt cattacaccc tacgtggtag tgataagtct ccttctgtat cctgttactc   36180
aatcgaagca ggtatgcagg gtgctcgtgc tgatattatt ctagcggatg acgtagagtc   36240
gatgcagaat gctcgtacgg cagcgggccg tgccttgctt gaggagctga ctaaggagtt   36300
tgaatctatc aaccagtttg gggatatcat ttaccttggt acacctcaga acgtaaactc   36360
tatctacaac aacctacctg ctcgtggtta ctctgttcgt atctggactg cgcgttaccc   36420
ttcagtagag caagagcaat gttatggcga cttccttgca cctatgattg ttcaagatat   36480
gaaggacaac ccagcacttc gctcagggta cgggttggat ggtaatagtg gtgcaccttg   36540
tgcccctgaa atgtatgatg atgaagtcct gattgagaag gaaatctctc agggtgctgc   36600
taagttccag cttcagttca tgcttaacac tcgcatgatg gatgctgaca gataccccatt   36660 acgcctgaac aatctaatct tcacctcgtt tggtacagag gaagtccctg tgatgcctac   36720
gtggagtaat gattccataa acatcattgg tgatgcacct aagtatggta acaagcctac   36780
ggatttcatg tacagacctg tagctcgccc atatgaatgg ggtgctgtct cccgcaagat   36840
tatgtatatt gaccctgcgg gtggtggtaa aacggagtg gagacgggtg tagccatcgt   36900
attcctgcac ggcacattca tttatgtgta tcagtgcttt ggtgtacctg gcggataccg   36960
agagtcgtcc ctgaatcgca ttgtgcaggc cgcaaagcag gcgggtgtta agaggtatt   37020 cattgagaag aactttggtc atggcgcgtt tgaggcggta attaagccgt actttgaacg   37080
agagtggcct gtaactctgg aagaggatta cgccaccgga cagaaagagt tgcgtatcat   37140
tgagacgctg gagccgctca tggcagccca taggcttatc ttcaatgcag agatggtgaa   37200
gtcagacttt gagtcggtac agcactatcc gcttgaacta cgcatgtcct acagtctttt   37260
caatcaaatg tcgaacataa cgattgagaa gaacagcctc cggcacgatg accgcctaga   37320
cgccctgtat ggcgctatac ggcaattaac ttctcagata gactatgacg aggttacacg   37380
gattaatcgc ctcagagcgc aggagatgcg cgattacatc catgctatga acacacctca   37440
tctacgcagg gcaatgctat atggagatta cggtactgag cgaagagtga ccaacacttc   37500
cgtagcgatg cagcagcgag tttacgggca gaactaccga aataaatcgg caagcagaaa   37560
tacactttct gcaaggattt caaggactta ttaattactg gacactatag aaggaaggcc   37620
cagataataa gagaaaataa taggtaatat atatataggt taacctaggt tataaggta   37680 tgccttagta tgggtgtact cctgtacacc ctattcctta ctaccttact atatttacat   37740
aataggagag agacaatggc taatgattat agtagtcaac cattaacagg taagtctaag   37800
agaaagcagg tacaacctgt aagtgaagaa ctaatgcttc cggtgctcaa aaaagaggaa   37860
gttagtaaga aaagcaatgt tattaatgat gccaccaaat caggtaaaca gaaagggggc   37920
atggtgtgcc ttgaagtgaa aggtggtgta ttgaagattg ctatcgcggt tgatggcaaa   37980
gaagattcag agtggaagtt agtaacagtg gaaccaactg ttaacccagt ttaagataag   38040
gaggaagatt acatggctaa atatggtact acaggttctg ttactggtca ggcttttcga   38100
gtaaaagcag tacaaactat tgcaacggca atcccgatgc tgttgttaa agaagaagac   38160 cttaagagta aagaccaccc tatcaacatc aaacattat caggtaaaca gaaaggtgca   38220
atggttgctc ttgagaaagg tgacacaacc ttacatattg ctgttgcacg tggtagtgaa   38280
cccacagacc cttgggatgt aactggtatg gaaaaggacg ctgttactcc agcagggta   38340 taataatgct taataaatac ttcaagcgta aagagtttgc ttgccgttgt gggtgcggta   38400
```

```
catccactgt tgatgctgaa ttactacagg tagtcacaga tgtgcgtgag cactttggtt   38460
ctcctgtagt tatcacttcg ggtcatcgct gtgctaagca caatgccaat gtaggtggcg   38520
ctaagaactc catgcatctt actggtaagg ctgctgacat taaagtgtct ggcatattac   38580
cttctgaagt gcataagtat cttactagca aataccaagg caagtatggt ataggtaagt   38640
ataactcctt cactcacatc gatgtacggg atggttgtgc gcgatggtaa gatgtgttga   38700
atggtgtgag cgtatggttg cccaagctgc cgaggatggc aactatgatg actgaagaa    38760
ctactctgac ttgttagctc aatggaaagg gagatgcaat gaaaaagctg tttaagtcta   38820
agaaggttgt aggtgcactg gttgcacttg ttattgctct tgtttctgta ggtcttggtg   38880
tagaccttgg ctctggcacg gaatcctctg tgacagatgt ggtctgccaa gtgatcacct   38940
gtgaataagt ttctagaagt tctggcaggt cttattggcc tgcttgtctc tgctaagaag   39000
aaacaagaag agaaggaggc acaaagtgaa gcgaatcatg ttagtgacaa cccttctgat   39060
tggttcgctg accacttccg ggtgtcagca ggcgttacca gagaaagcaa tggtgaaacc   39120
tctgaggccg acgctgacgg cagtttacga ggtagacgat aaggtctgct ttagtaagcc   39180
tgacgctaca aaacttggtt tgtacattct ctcgctagaa cgcggataca attaatacat   39240
agctttatgt atcagtgtct tacgatttac tggacactat agaagaggta agatagcgcc   39300
gttcttttga gcggcctatt actagccaat cttcataggg agggttggaa agtaatagga   39360
gatagcatgg ctaaattaac caaacctaat actgaaggaa tcttgcataa aggacaatct   39420
ttgtatgagt accttgatgc gagagtttta acatcaaagc cgtttggtgc tgcaggtgac   39480
gccactactg atgatacgga ggttatagct gcttcattaa actctcagaa agctgtcaca   39540
gtctcagatg gtgtattctc tagctctggt attaacagta attactgtaa cttagacggc   39600
aggggtagtg gcgtgctaag tcaccgttca agtacaggta actacttagt atttaacaat   39660
ctacgtgcag gtcgcttaag taatattacg gtagaaagta ataaggcgac tgatacaact   39720
cagggacagc aggtatccct tgctggtgga agtgatgtta ctgtaagtga cgttaacttc   39780
tcaaacgtta aaggtactgg tttcagttta atcgcatacc ctaatgatgc gccacctgat   39840
ggacttatga ttaaaggcat tcgaggtagc tattccggct atgctactaa taaggcagcc   39900
ggatgcgtac ttgctgattc ctcagttaac tccctcatag ataacgtcat tgctaagaac   39960
tacccctcagt tcggagcagt agagttgaaa ggtacagcca gttacaacat agtcagtaat   40020
gttataggga cagattgcca gcatgtaact tacaacggca ctgaagggcc aatagctcct   40080
tctaataacc ttatcaaggg ggtgatggct aataacccta gtatgcagc ggttgttgca    40140
ggcaaaggaa gtacgaactt aatctcagac gtgctcgtag attactcaac ttctgatgct   40200
aggcaggctc atggtgttac agtagagggt tctgataacg tcataaataa tgtgcttatg   40260
tcaggatgtg atggtactaa ctcttttagga caagggcaga ctgctacaat tgcacgcttt   40320
ataggtacag ctaataacaa ctatgcgtct gtatttccta gctacagtgc tacaggtgtt   40380
attactttcg aatccggctc tacccgtaac ttcgtagagg taaagcaccc tggcaggaga   40440
aacgaccttc tcagttctgc tagtactatt gacggtgcag ctactattga cggcactagt   40500
aatagtaacg tagtgcacgc acctgcctta gggcagtaca taggtagtat gtcaggtagg   40560
ttcgaatggc ggattaagtc catgtcactc ccttcaggcg ttcttacttc tgctgataag   40620
tacagaatgc ttggagatgg tgctgtgtca ttagctgtag gtggggcac ttcttctcaa    40680
gttcgcctat ttacttctga tggtacttct cggacagtgt ccctcaccaa cggtaacgtg   40740
cgtcttttcta ccagtagcac aggcttttttg cagttaggtg ctgatgcaat gaccccagac   40800
```

```
agtactggta catacgcatt aggttccgcc agccgagcat ggtctggcgg ttttactcaa   40860
gcagcattca ctgttacctc agatgctcgg tgtaaaacag aacctcttac tatctcagat   40920
gccttactgg atgcttggtc tgaagttgac tttgtgcagt ttcagtattt ggatcgtgtt   40980
gaggagaagg gtgcagactc agctagatgg cacttcggta tcatcgctca gcgagctaag   41040
gaggctttcg aacgtcacgg tatagatgca catcgctatg gcttcttgtg cttcgacagt   41100
tgggatgatg tatacgagga agatgccaat ggctctcgta aactgattac accagcaggt   41160
tcccgctacg gtattcgtta cgaggaagta ctgatattag aggctgcgtt gatgcggcgg   41220
actattaagc gtatgcagga agcactagct tccctgccta gtaagcaac aggcagtgcg    41280 taagcactgc ttttagcgca acttttctta aaggttatca cggtggtagc ctttcagaaa   41340
aggaggttac atgattcaaa gactaggttc ttcattagtt aaattcaaga gtaaaatagc   41400
aggtgcaatc tggcgtaact tggatgacaa gctcaccgag gttgtatcgc ttaaagattt   41460
tggagccaaa ggtgatggta agacaaacga ccaagatgca gtaaatgcag cgatggcttc   41520
aggtaagaga attgacggtg ctggtgctac ttacaaagta tcatctttac ctgatatgga   41580
gcgattctat aacacccgct tcgtatggga acgtttagca ggtcaacctc tttactatgt   41640
gagtaaaggt tttatcaatg gtgaactata aaaatcacg gataaccctt attacaatgc    41700
ttggcctcaa gacaaagcgt ttgtatatga gaacgtgata tatgcacctt acatgggtag   41760
tgaccgtcat ggtgttagtc gtctgcatgt atcatgggtt aagtctggtg acgatggtca   41820
aacatggtct actccagagt ggttaactga tctgcatcca gattacccta cagtgaacta   41880
tcattgtatg agtatgggtg tatgtcgcaa ccgtctgttt gccatgattg aaacacgtac   41940
tttagccaag aacaaactaa ccaattgtgc attgtgggat cgccctatgt ctcgtagtct   42000
gcatcttact ggtggtatca ctaaggctgc aaatcagcaa tatgcaacaa tacatgtacc   42060
agatcacgga ctattcgtgg gcgattttgt taacttctct aattctgcgg taacaggtgt   42120
atcaggtgat atgactgttg caacggtaat agataaggac aacttcacgg ttcttacacc   42180
taaccagcag acttcagatt tgaataacgc tggaaagagt tggcacatgg gtacttcttt   42240
ccataagtct ccatggcgta agacagatct tggtctaatc cctagtgtca cagaggtgca   42300
tagctttgct actattgata caatggctt tgttatgggc tatcatcaag gtgatgtagc    42360
tccacgagaa gttggtcttt tctacttccc tgatgctttc aatagcccat ctaattatgt   42420
tcgtcgtcag ataccatctg agtatgaacc agatgcgtca gagccatgca tcaagtacta   42480
tgacggtgta ttataccta tcactcgtgg cactcttggt gacagacttg gaagctcttt    42540
gcatcgtagt agagatatag gtcagacttg ggagtcactg agatttccac ataatgttca   42600
tcatactacc ctacctttg ctaaagtagg agatgacctt attatgtttg gttcagaacg    42660
tgcagaaaat gaatgggaag caggtgcacc agatgatcgt acaaggcat cttatcctcg    42720 taccttctat gcacgattga atgtaaacaa ttggaatgca gatgatattg aatgggtaa    42780 catcacagac caaatctatc aaggtgacat tgtgaactct agtgtaggtg taggttcggt   42840
agtagttaaa gacagctaca tttactatat ctttggtggc gaaaaccatt tcaacccaat   42900
gacttatggt gacaacaaag gtaaagaccc atttaaaggt catggacacc ctactgatat   42960
atactgctat aagatgcaga ttgcaaatga caatcgtgta tctcgtaagt ttacatatgg   43020
tgcaactccg ggtcaagcta tacctacttt catgggtact gatggaatac gaaatatccc   43080
tgcacctttg tatttctcag ataacattgt tacagaggat actaaagttg gacacttaac   43140
```

| | | | | | |
|---|---|---|---|---|---|
| acttaaagca | agcacaagtt | ccaatatacg | atctgaagtg | cagatggaag | gtgaatatgg | 43200 |
| ctttattggc | aagtctgttc | caaaggacaa | cccaactggt | caacgtttga | ttatttgtgg | 43260 |
| tggagaagag | acttcgtcct | cttcaggtgc | acagataact | ttgcacggct | ctaattcaag | 43320 |
| taaggctaat | cgtatcactt | ataacggaaa | tgagcaccta | ttccaaggtg | caccaatcat | 43380 |
| gcctgctgta | gataaccagt | ttgctgctgg | tggacctagt | aaccgattca | ctaccatcta | 43440 |
| cctaggtagt | gaccctgtta | caacttcaga | tgctgaccac | aagtacagta | tctctagtat | 43500 |
| taataccaag | gtgttaaagg | cttggagcag | ggttggtttt | aaacagtatg | gtttgaatag | 43560 |
| tgaagcagag | agggaccttg | atagcataca | cttcggtgtc | ttggctcagg | atattgtagc | 43620 |
| tgcttttgaa | gctgaagggt | tggatgccat | taagtatgga | attgtgtcct | tcgaagaagg | 43680 |
| taggtacggt | gtgaggtata | gtgaagttct | aatactagag | gctgcttata | ctcgttatcg | 43740 |
| tttagacaag | ttagaggaga | tgtatgccac | taataaaatc | agttaagcaa | gctgctgtac | 43800 |
| tccagaacac | agaagagctt | attcaatcag | gacgtgaccc | taagcaggct | tatgccattg | 43860 |
| ccaaggatgt | tcaacgtcgt | gccatgaaga | aaccttctgc | atcttctgcg | taagcaggtt | 43920 |
| aatatcttag | tataaacaag | ggcagactta | ggtttgtcct | tagtgtattc | caaggaggt | 43980 |
| aacatgctga | aagatggttg | ggtttcatat | gacccctacag | accctaagaa | ttggctacag | 44040 |
| gttatcgcta | tagcttgtgc | aggtagccta | ttggctgccc | tgatgtattc | attatggatg | 44100 |
| tacacaaagt | aaccaaagtc | aaaatttga | tgtaggcgtg | tgtcagctct | ctcgccctcg | 44160 |
| ccctcgccgg | gttgtcccca | tagggtggcc | tgagggaatc | cgtcttcgac | gggcagggct | 44220 |
| gatgtactcc | ttgtctagta | caaggaggc | ggagggaacg | cctagggagg | cctaggaatg | 44280 |
| gcttagtggt | ggacaaggtg | attaccttag | tgaagcctct | tagtgcattc | ctgaggccat | 44340 |
| tcagggcgtt | tatgagggat | tgacagggtg | tgagggcgtg | ggcta | | 44385 |

<210> SEQ ID NO 2
<211> LENGTH: 1309
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

| | | | | | |
|---|---|---|---|---|---|
| tgacagccac | ggcatacaag | gttacattaa | gcatcaagac | ggcgacgtct | ttaaacatcc | 60 |
| cgctctttaa | caatacggtt | tgtgtcttga | taggctaact | aactaactaa | ggtaattatc | 120 |
| atgaaagggt | taatttgtgt | agaacgtatg | gtcaatggta | aacttgaaat | attaccactg | 180 |
| gaaaaccaat | ctagcttcaa | agagtggtat | ggctgtttct | cactgattta | aggtaaaggc | 240 |
| tggcactagt | cagcctatca | aggcgcaaac | caagctcttt | aacaatttgg | atggtagctt | 300 |
| cttagtctgg | ataggttaaa | cctaggagat | tctcttgagt | ctcctataat | gtaacctaac | 360 |
| taactaaatg | aggattaaaa | gaggagatat | acaatggttt | ttacgcttga | ggacttcgtt | 420 |
| ggtgactggc | gtcaaaccgc | ggggtataat | cttgatcagg | tcctggagca | gggcggagtt | 480 |
| tcgtccttat | tccagaactt | aggggtaagt | gttacgccga | ttcagcgcat | cgtgctgagt | 540 |
| ggagagaatg | gattgaaaat | tgacattcac | gttatcattc | cgtatgaggg | tttgagtgga | 600 |
| gaccagatgg | gacagattga | aaagattttc | aaagtggtgt | atcccgtcga | tgaccatcac | 660 |
| tttaaagtaa | ttctgcacta | tgggacccctt | gtgatcgacg | gtgtaacgcc | aaacatgatt | 720 |
| gactatttcg | gtcgccctta | cgaaggtatc | gccgtcttcg | acggaaaaaa | aatcactgtc | 780 |

| acgggaacat tatggaacgg aaataaaatt atcgacgaac gtctgatcaa tcctgatgga | 840 |
| agcctgttat ttcgcgttac gatcaatgga gtgaccggat ggcgtttatg cgaacgtatt | 900 |
| ttggcttaaa gaggagatat acaatggaac gcaacgcaaa tgcatattat aatttattag | 960 |
| cagctacggt tgaagccttt aatgaacgca tccaattcga cgaaatccgt gagggcgacg | 1020 |
| actatagcga cgcccttcat gaggttgtag acagcaatgt tccagtttat tacagcgaaa | 1080 |
| tctttacagt gatggctgct gatggtattg atgttgattt tgaggatgct ggtttgattc | 1140 |
| ctgacacgaa ggatgtaacc aagattctac aagctcgcat ctatgaagct ctttataatg | 1200 |
| atgtaccaaa tgacagcgat gtagtttggt gtgaaggcga agaagaggaa gaataaggat | 1260 |
| ggaaaagcaa tataacttta tcttttcaga cggtgtaacc ctgaagtgt | 1309 |

<210> SEQ ID NO 3
<211> LENGTH: 1408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| acgtccagcc tccttcctag atattcctga gattataaac cttgggaata aatatgtgga | 60 |
| agaggaagtc aaggttgtag cccaccactc agcctcatgg aatgcagaac aaagtgccat | 120 |
| aacctttgtg catctcttaa tagagaccca ccactcagcc tcatggaatg cagaacaaag | 180 |
| tgcacataac ctttgtgcat ctcttagtag agaagattta tccctatggg ttgctgtaga | 240 |
| tgaagggcag attgtagggt tcctgtgggc tggctatcac gagttggccc cttggacacc | 300 |
| tgtaagagtt gcctctgaca ttctcttttta tattatacca gagagaaggg gaacactact | 360 |
| tggtatgcgc ttaattaagg cattgaaaca gtgggcatca gataatgaat gctctgaagt | 420 |
| gcgtttaagt attgcaagtg gcatcaacga ggagcgcgta gggcgcatgt acaaacggct | 480 |
| cggctttgaa ccgtttggca ctgtgtataa cctgaagttc taaagaggag atatacaatg | 540 |
| gtttttacgc ttgaggactt cgttggtgac tggcgtcaaa ccgcggggta taatcttgat | 600 |
| caggtcctgg agcagggcgg agtttcgtcc ttattccaga acttaggggt aagtgttacg | 660 |
| ccgattcagc gcatcgtgct gagtggagag aatggattga aaattgacat tcacgttatc | 720 |
| attccgtatg agggttttgag tggagaccag atggacaga ttgaaaagat ttcaaagtg | 780 |
| gtgtatcccg tcgatgacca tcactttaaa gtaattctgc actatgggac ccttgtgatc | 840 |
| gacggtgtaa cgccaaacat gattgactat ttcggtcgcc cttacgaagg tatcgccgtc | 900 |
| ttcgacggaa aaaaaatcac tgtcacggga acattatgga acggaaataa aattatcgac | 960 |
| gaacgtctga tcaatcctga tggaagcctg ttatttcgcg ttacgatcaa tggagtgacc | 1020 |
| ggatggcgtt tatgcgaacg tattttggct taaagaggag atatacaatg ggtgttgtaa | 1080 |
| agaaagcatt taaggctatc ggtcttgctc aagatgcacc acgtattgaa gccaaagtcc | 1140 |
| cagcacagca gcttgagcgt aagcctgaga ctgaagctga agatattcaa attggtgcag | 1200 |
| gggatgatgc tactgcatct gcaaaaggta agcgtggcct tgtccgtccg gtagcttcta | 1260 |
| gcttgaaggt gtaatatgaa acagagcata gatttggagt atggaggtaa gcggtctaag | 1320 |
| atacctaagc tatgggagaa gttctccaat aaacgtagct cttttccttga tagggcgaag | 1380 |
| cattactcca aattaacctt gccctatc | 1408 |

<210> SEQ ID NO 4

<211> LENGTH: 44927
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
tcgccctcgc cctcgccggg ttgtccccat agggtggcct gagggaatcc gtcttcgacg      60
ggcagggctg atgtactcct tgtctagtac aagggaggcg gagggaacgc ctagggaggc     120
ctaggaatgg cttagtggtg acaaggtgat taccttagt gaagcctctt agtgcattcc      180
tgaggccatt cagggcgttt atgagggatt gacagggtgt gagggcgtgg gctatctgtt     240
cctttgctcc tcacttcgtt cgtcgctgcg gtagcctgat gtgtacctta ggttattcct     300
tgatggatag cttaggttag ccttagtgga ttaccttagt taaagcctta gtgcttcact     360
tagtatcagc ttagtagtgt accttagtaa gtcttagtgt cttctcttag tgattgcaca     420
tgcaagcatg taagatgcta ataggtcgcg gtcggcagac cgctaaagaa agagaatggt     480
aataagatgc agtaggagga acaccagaag cctagccaac ctaagctatc ctagctctat     540
atctattgct tttccttagt ctaacacgtt agacaaccta tcttattctt agtgatggta     600
acttagtgtt gacaagataa tcttagtgta atactatgca tcacgtaggc ggtgctgagg     660
cacctagtag ccagctagta aggcatacga agagactagc gcttacattg ctctttaaca     720
atttgcttag tgtaacctat gtatgccgtg gttaactact tattgaatga ggtattaact     780
atgacattaa ataaccgtga actgtccgtt ctcttcactc tgttgtgcta catgattcgt     840
aacaacgaat tacttacaga tgatgagtta gccttgtatc accgctttct taacgaaggt     900
tggaccgata cagttaatca ataccgtaac atgatagatg agttgaggga gggtaaataa     960
tgtatcaaca tgaggtattc tttgaatcag ctagcgaagc tattcgcttc cgtgatgata    1020
tgatgcaagc tggtgtaggc gttgatgtgt atcactattt gatagattac gacactgaat    1080
atcaccgagt taccttagta tctgagtatg acaaccaagt cattactgag tatctaggca    1140
gtgaagatta cgattacgat gaagtaatca cgacaaatct ctaaattaac tgttgacagc    1200
cacggcatac aaggttacat taagcatcaa gacggcgacg tctttaaaca tcccgctctt    1260
taacaatacg gtttgtgtct tgataggcta actaactaac taaggtaatt atcatgaaag    1320
ggttaatttg tgtagaacgt atggtcaatg gtaaacttga aatattacca ctggaaaacc    1380
aatctagctt caaagagtgg tatggctgtt tctcactgat ttaaggtaaa ggctggcact    1440
agtcagccta tcaaggcgca aaccaagctc tttaacaatt tggatggtag cttcttagtc    1500
tggataggtt aaacctagga gattctcttg agtctcctat aatgtaacct aactaactaa    1560
atgaggatta aagaggagat atacaatgg tttttacgct tgaggacttc gttggtgact     1620
ggcgtcaaac cgcggggtat aatcttgatc aggtcctgga gcagggcgga gtttcgtcct    1680
tattccagaa cttaggggta agtgttacgc cgattcagcg catcgtgctg agtggagaga    1740
atggattgaa aattgacatt cacgttatca ttccgtatga gggtttgagt ggagaccaga    1800
tgggacagat tgaaaagatt ttcaaagtgg tgtatcccgt cgatgaccat cactttaaag    1860
taattctgca ctatgggacc cttgtgatcg acggtgtaac gccaaacatg attgactatt    1920
tcggtcgccc ttacgaaggt atcgccgtct tcgacggaaa aaaaatcact gtcacgggaa    1980
cattatggaa cggaaataaa attatcgacg aacgtctgat caatcctgat ggaagcctgt    2040
tatttcgcgt tacgatcaat ggagtgaccg gatggcgttt atgcgaacgt attttggctt    2100
```

```
aaagaggaga tatacaatgg aacgcaacgc aaatgcatat tataatttat tagcagctac    2160
ggttgaagcc tttaatgaac gcatccaatt cgacgaaatc cgtgagggcg acgactatag    2220
cgacgcccct catgaggttg tagacagcaa tgttccagtt tattacagcg aaatctttac    2280
agtgatggct gctgatggta ttgatgttga ttttgaggat gctggtttga ttcctgacac    2340
gaaggatgta accaagattc tacaagctcg catctatgaa gctctttata atgatgtacc    2400
aaatgacagc gatgtagttt ggtgtgaagg cgaagaagag gaagaataag gatggaaaag    2460
caatataact ttatcttttc agacggtgta accctgaagt gttccctacg attcgcacaa    2520
attcgtgagg aagtactagg cactacatac aaactattta gctgacacta taagagaagg    2580
cttaacaagg cgttactaag gtagcgcctg attaaacttt cacttactag gagttgagat    2640
tatgaaaacc ttgattggat gcttcttgtt ggcttctctt gctctggcat ttaccgctaa    2700
agctggttat gacgcttata agtagaaaca agcccagcaa gactgggcca aaaaaaagtt    2760
caacttgtgc agcaagagca acacctacga gtactgcaac aaaacactaa gacacttatg    2820
gaaagagtaa ctagcctata gcccacctga gtgggctatg tgatatttac ttaacactat    2880
ataaggtgat tactatgact actgaaaaca ccctcgtgtc tgtccgtgaa gctgcaaccg    2940
ctgaaatcaa gcaacattta gacaaatatcg gcacttctta catcaaagta ggggcttgtc    3000
tgaatgagtt acgcggagac tttgaaggtc aaaaagagtt tttagcctat gttgaagcag    3060
agtttgccat taagaaggca caatgttaca agctgatgag tgtagcccgt gtctttgaag    3120
gcgatgatcg ctttaaaggc gtggcgatgc gtgtaatgct ggcgcttgtt cctttcgctg    3180
atgaaaatat aatcatggag aaggccgcag aactcgccgc aaatggcaag ctggacacta    3240
atgccgtaaa cgccctgatt gaacctaaga aagagtcaaa ggccgaaacg gtacaatcta    3300
aggctgagac agtaaaaccg caggagaacg cgactgagtc cgcagaatca catgaaatgc    3360
aagcgccgca ggtagtgcca cccgcgagcg agcaggagtc cgacgaatca gcaccttggg    3420
aagaggaaag caaaccggaa gcgccaaagg cagctccgat ggataacacg gctaatactg    3480
agaatgccgc tattgctggt ctgctggcac aaattaaagc actgactgag caattacagg    3540
cagccaatga ccgcatcgcc tccttaagta gcgcacgcga aagcaagaag gcatccgcac    3600
ctatgctgcc gcagttcaaa tcttcctgct tctacgctcg cttaggcttg agcgcggagg    3660
aggcaacgaa gaaacagca gttaacaagg cacgccgcga actggttaag ctgggatacg    3720
gtgaaggcca tgaggcatgg cccttaatct ctgaggcagt agaagagttg actaagtaac    3780
cttatcggtg gcatcttctt aggtgtcacc tattaaggtt tctttcacta ggagtaaaca    3840
agatgcaagg cctacacgct attcaacttc aacttgaaga gaaatgttt aacggcggta    3900 tccgtcgctt tgaagcggac caacaacgcc agattgcatc cggtaatgaa tcagacacgg    3960
catggaatcg ccgcttattg tccgagttaa tcgcgccaat ggctgaaggt attcaggcat    4020
acaaggaaga gtatgaaggt aaaagaggcc gtgcaccgcg tgcattagct ttcattaact    4080
gcgtagaaaa cgaagtggca gcatatatca cgatgaaaat cgttatggat atgctgaaca    4140
cggatgtaac cttgcaggct atagccatga atgtagctga ccgcattgag gaccaagtac    4200
gttttagcaa gctggaaggt cacgccgcca aatactttga aaaagttaag aagtcactta    4260
aggcaagtaa gactaaatca tatcgccatg cgcacaacgt agcggtagtg gctgagaagt    4320
cagtagctga ccgtgacgct gatttctccc gctgggaggc atggcctaaa gacacccttgc    4380 tgcaaattgg gatgaccttg cttgaaatct tagagaatag cgtattcttc aacgggcaac    4440
ctgtcttcct ccgcaccttg cgcactaatg gcggcaaaca tggtgtttac tacctacaga    4500
```

```
ctagtgaaca cgtaggtgag tggataactg cattcaaaga gcacgtagcg caactgagtc    4560
ctgcctatgc tccttgcgtc atccctccgc gtccgtgggt atcacctttt aacggcggtt    4620
tccacactga gaaagtagca agccgtattc gtctggtaaa aggaaaccgc gaacacgtcc    4680
gcaagctgac caaaaagcaa atgccagagg tttacaaggc tgttaacgcg ttgcaggcga    4740
ctaaatggca ggttaacaag gaagttttac aggttgtgga agacgtcatc cgtctagacc    4800
taggttatgg tgtaccttcc tttaaaccac tcattgaccg cgagaacaag ccagctaatc    4860
cagtgccgct agaatttcag cacctacggg gccgtgaact gaaagaaatg cttacgccgg    4920
aacaatggca agcctttatc aactggaaag gtgaatgtac taagctgtac accgctgaaa    4980
ctaagcgcgg aagcaaatcg gcggcaaccg ttcgcatggt tggtcaggcc cgtaaatata    5040
gccagttcga cgcaatctac ttcgtgtatg cactggacag ccgcagccgc gtctacgcgc    5100
aatctagcac actctcaccg caatcaaatg acttgggcaa ggccttgctc cgttttaccg    5160
aagggcagct tcttgatagc gctgaggcgc ttaagtggtt tttggtgaac ggggctaata    5220
actggggttg ggataagaaa acttttgacg tgcgcaccgc taacgtgctg gatagtgaat    5280
ttcaagacat gtgccgcgac attgcagcgg atccgctgac cttcactcaa tgggtaaatg    5340
ccgactcccc ttacggcttc cttgcatggt gctttgaata tgcgcgttat ctggatgcac    5400
tggatgaagg cacgcaagac caattcatga cgcacctccc agtccatcaa gatggtagtt    5460
gttctggtat ccagcactac agtgctatgc tacgcgatgc agtaggtgcg aaagcagtaa    5520
accttaagcc ctctgactct cctcaagata tttatggtgc cgttgcgcag gtagtaattc    5580
agaagaatta tgcatacatg aatgcagagg atgcggaaac cttcacttct ggcagcgtga    5640
ctttaacagg tgcggagctg cgtagtatgg ctagtgcgtg ggatatgata ggaatcactc    5700
gcggcctgac caaaaagccc gtaatgacac taccttatgg cagcacacgt ctaacctgcc    5760
gtgagtcagt gattgattat atcgttgatt tagaagaaaa agaggcccaa cgggctattg    5820
cggaagggcg taccgccaat cctgtacacc cttttgataa tgaccgtaaa gacagcctga    5880
cacctagcgc agcttataac tatatgacag ctttaatctg gccttctatt tcggaagtgg    5940
ttaaagcccc tatagtggca atgaaaatga ttcgtcagct tgcccgtttc gcagctaaaa    6000
ggaatgaagg cttagagtat accctgccta ctggcttcat cttgcaacaa aagattatgg    6060
ctactgatat gctccgcgta tctacttgct tgatgggaga aatcaagatg agtctacaga    6120
ttgaaacaga cgtagtggat gaaacggcaa tgatgggcgc tgctgctcct aactttgtgc    6180
atggtcatga tgccagccac cttatcttaa cagtctgcga ccttgttgat aaagggatta    6240
catctatcgc agttattcat gactcttttg gcactcatgc aggccgtaca gccgaccttc    6300
gtgatagctt aagggcagaa atggtgaaga tgtatcaagg ccgtaatgca ctgcaaagcc    6360
tgctagatga gcacgaagaa cgctggttag ttgataccgg aatacaagta ccagagcaag    6420
gggagtttga ccttaacgaa atcttagttt cagactattg cttcgcataa tattaatagg    6480
ccattccttc gggagtggcc tttcttttac ctactacctg taacatttca ttaacataaa    6540
agtgtctcac atgtgagact tatttaccgg acactatagg atagccgtcg gagacgggaa    6600
agaaagggaa gataaaggat ataaaggaag taataggtat taaaggttat ataggttatc    6660
taggaatacc tattccttc ttccttcctc ttattaccac tcagaggaag ggcagaccta    6720
ggttgtctca catgtgagac ttcgtattta ccggacagta tagataagat taactcactt    6780
tggagattta accatgcgca actttgagaa gatggcccgt aaagctaacc gttttgacat    6840
```

```
ggaagagggg cagaagaaag gcaagaagct gaataagcct gtccgtgacc gtgcatctaa    6900
acgcgctgcg tgggagttct aagttatggc tattattcag aatgtaccgt gtcctgcctg    6960
tcaaaagaat ggacatgata ttactggcaa ccatctcatg atatttgatg atggtgccgg    7020
ctactgtaat cgtggacact tcatgataa tggtagacct tactatcaca agccggaagg     7080
tggcatcgag ataaccgagt tatctattac tggcaatatc aaatatacac cttctcaatt    7140
caaagaaatg gagaaggaag ggaagataag cgaccctaaa ttacgtgcca tcgcacttgg    7200
tggtatgcgt atgaaagacc gttgggaggt catgaatgaa caagaaggg cagagcaaga     7260 agcagagtgg aaacttgatg ttgaatggtt cctcacgctt aagcgtaaga accttgtttc    7320
caggcacatt cgcggcgaca tttgcgcatt gtatgatgta cgtgttgggc acgatgaaga    7380
gggtagagtc tcacggcatt actatccgcg cttcgaaaaa ggtgagctag taggcgctaa    7440
gtgtcgcaca ttacctaaag attttaagtt tggtcattta ggtaaactct ttggtatgca    7500
agatcttttc ggtatgaata ctttgtctca cgtgttagac aagggaagac gaaaggattg    7560
cttgctcatt gtcggcggcg aactggatgc actagcagcg cagcagatgc tccttgattc    7620
tgccaagggt actaagtggg aaggccagcc ataccatgta tggtctgtca acaaaggcga    7680
gtcttgcctt gaagagatag tgcagaaccg tgagcatatc gcccaattca agaagattat    7740
atggggtttt gatggagatg aggtagggca gaagcagaat cagcaagcgg ctcgcctgtt    7800
tcctggtaaa tcctatatcc ttgaataccc ctctggttgc aaagatgcta acaaggcatt    7860
gatggctggc aaggctaaag aatttgtaga tgccatggttt aatgccaagt catctgatga    7920
agtctttggt agccagatta aatctatcgc atctcaaagg gataagctca aggctgcacg    7980
tccagagcaa ggactgtcat ggccttggcc taagctgaac aaggtaacgc taggtattcg    8040
taagaaccag cttatcattg taggtgcagg gtctggtgta ggtaagactg agttccttcg    8100
tgaagtagtt aagcacctca ttgaagaaca cggtgaatct gtaggcatca tttctacaga    8160
agacccgatg tcaaggtgt cccgtgctt tatcggcaag tggattgata agcgtattga      8220
gttacctcca accaacgacc cgaaagaaga cggataccgt gaggtgttcg actataccga    8280
ggaagaagct aacgccgcca ttgattatgt agctgataca ggtaagctgt ttgtagctga    8340
cctagagggt gactattcga tggaaaaggt agagcaaact tgcctagagt ttgaggctat    8400
gggtatttct aatatcatca ttgataactt aacggggatt aaattagatg agcgtgcttt    8460
tggtgggaag gttggtgcac ttgatgaatg cgtcaagcgg attggtacta tcaaagaccg    8520
acacccggtt actatattcc ttgtatcaca ccttacacgt cctccggcaa accgtaccca    8580
acacgaagaa ggtggcgaag ttatcctttc tgacttccga ggctcaggcg ctatcggatt    8640
ctgggcatct tacgccttgg ggattgagcg taatacaaga gctgaaacgc ttgacgaaag    8700
gactaccacg tacatctcat gtgtcaaaga ccgcgaccaa ggtatctaca ctggaaccaa    8760
ggtcatgctt aagggtgaca ttcaaaccgg acgtttaatg gaaccacaag cccgtactaa    8820
gtcatttgat acaggtgaag caaggcaaca agaagtacca gatttaccgg atactataga    8880
agagactacc ttcgatgaag aaagtgagtt ctgattagtg tatttatcag gcttgtctca    8940
catgtgagac aggctcttat taagtacatt aaataactgg agattgatta tgtataactt    9000
agtgttgaat gtaggtgact tgtacgcaa catcaagaaa gattcaagtc gctatctttg     9060
ccgtggtgtt gtaacctttg taggtgagaa cctgtattat gtagaatatc gcagtggtgt    9120
taagcaatat taccacaaga agacagcaca taaatatctt gaaaagattg tagagataaa    9180
caatcaatgt aagtgcatac atgatgaggt ttgcgataaa tgtgctcgcc agatgcttaa    9240
```

```
gaatttccta gctcctcttt attatggtgc tggtcctcaa acactagcag agtgcatggc    9300
agaaaagaaa accacactca agaaagagcg tcgcaatgta atcactggta agactcaaag    9360
tgagatgatt aagcaatgtg gcactgcatt aggtgttaca cagtttaata ctcgtgcatt    9420
gggtaaatcc acaggacaag ctatggtaaa gattggagaa gccatgatgc atccaaatgt    9480
acctgtgcga atcatggatg ttgaccatgc aatcacagaa caaggtacgc aacgacgtgt    9540
aattaataag cattttgccg acactataga aggcattatt cgtaagcaag ggttgaaagg    9600
tcttcacatc ttaaatggtg aagaattact gtacctacct atcgttactg aagaaacata    9660
cgtgaatatc taaggagtta atcatgacta aggtattaat ttatatgcgt ggacctcata    9720
aatgctatgc agttgtagca ccaaatggtg ttaagcctta tcgtacttca aaaagattgg    9780
cattaatagg tgctagtagt agtgcaagtt ccaaatggaa acttttttggt cattggactg    9840 aaaggcaatt ccgtgaggat tttaaagtca ttggcagctt catggtgaaa tatgcagaat    9900
aaacatagtc ttagaatgtt cgatggtcat gaaaacctgc aagccaagat tactaaccaa    9960
gccttcctgt tcgcacagtt aactatggct gaggctaaga agaatagtct cactcgtgaa    10020
caggttatca aggaggccac ttgggaacca caccaaggta aatatatggg ccacaaatta    10080
actgtaacac gcagtcgata agtcaagggt tgtccaacgt gttggacagc ctttcatcat    10140
attgattggg aggtattaaa tgactaagtt tactatgcaa gacctcatta aattacgtga    10200
tgaaatagaa tcaccggaag ttaatacaga gtttcactac attgatccac gagataaacg    10260
agagattcct gattatcaga ttgagacgga gttaatgtat gaagattatt gattggaaga    10320
aggaagcaga aggccgtatc ctagtgatgg atgcggaggc taaaggcctg ctgggtgcta    10380
tccgctacgg tcatcgtgaa gatgtacaca ttatttgctg catggacttg ctcaccactg    10440
aggagttcct cttcttcgac ccatatgaga tgcgtgaccc tgaagcaagg gaacacttga    10500
aagagtggga aggccatcaa gatgggacct tggttgatgg tgttaacttc ctaaagcact    10560
gtgaagccat cgtctcacag aacttcctag gctatgacgg gcttctcttt gagaaagcct    10620
tccctgacat ctggaaggga tttaactaca ccgagaggcg cggcaagggc agactacgtg    10680
ctgacttgtg tccggtacgc gtcatggata cgctggtcat gagtcgcctg ttaaacccag    10740
atagacgcct tcctccgcaa gcatatgcca aaggtatggg taacgttgcc cctcactcaa    10800
ttgaggcgca cggcattcgt ataggccgtt ataagccgga gaacgaggat tggtctaaac    10860
taactgacca catggtacat cgtgtacgcg aggacgtggc gataggccgt gacctattcc    10920
tctggctatt taacggagaa tggacggagc acaaacgccg tggcgtgaat aaacgcactg    10980
gcctaggtat tgagacagcc ttccacatgg agtccattgt gacgctggag atgagccgtc    11040
aggccgagcg tggattccgt ctggatatag ataaagcatt agcacgatgc gaggaattgg    11100
acgctaagat tgatgagaca gtcgcagcgt tccgtccgca catgcctatg cgtatcaagt    11160
ctaaaccttt taaaccggaa gaaaagaatg aagtatgcca acgcgcaaat gagtatggag    11220
ctagcaacaa tatacctact gtccttgacc cctctcactt tcttcacgca gagagacgag    11280
gagatcgcaa gacagtatgg agtgtcacta ctaagtctgg tgattggtcg gctagcgtca    11340
agaaagactt tcctcacctt agaggaaacc gtaatgacac gccaagtgtc aagtggattg    11400
gcgcttactc gcctgttact ttcgaagaga ttcccttggg taacagggat acagttaagc    11460
aagtgctcta tgattatgga tggaaggtg ttgaatttaa cgataccgag caagcgcatc    11520
tcgatgagca tggcgtatta cccaagccct ggagtgggaa gataaatgaa aagtccctta    11580
```

```
ctttatggca agagagagcc gcacgtgaag gtaaaacagt ccctgattgg tgcttgggta   11640
tcgctgcatg gtacatactc gtatcccgtc gtggtcagat cctcaaccgt ggtgacgttg   11700
aagccttcga ccagaagggg gtgtggcctt cgcaagctgg tatacgaaag tgtcgcggcc   11760
ttgtacctgt agcatttaac aaggagttag gaatcaatgc gcagcaatac tacgaaaggt   11820
acggatgctg gcctacgtca gacaaggatg acggagaatg gcgtgtgcca gctattgcta   11880
ttagtattgg aacttctacg ttccgtatgc gtcatcgtaa cgtggttaat attcctgccc   11940
gtggcttgta tcctttacgt gatttattca tagcagggaa aggcaagcta atccttggtt   12000
gtgacggtgc aggtcttgaa ctgcgtgtcc tgtctcactt catgaatgac cctgagtacc   12060
aagagattgt actgcacggt gatattcata cgcataacca gatgaaggct ggtcttccta   12120
agcgtgatat ggcgaagaca tttatatatg ccttcctata tgggtctggt atagctaacc   12180
ttgcagcagt atgtggtgtt actgaggaag aaatggagga agttgtggca agatttgagg   12240
ttgaactacc atctcttgca cgtcttcgtg agaatgttat cgcacaaggt aacaagtttg   12300
gctacctaca agcacctgat ggtcattggg gtcgcatccg tatgtctggt ggtgaactta   12360
aagaacacac tatgcttaac gtactactcc agatgactgg ttctctgtgt atgaaatacg   12420
cattggtcag agcgtttgca gtgatgcgca aggaaggtgt ggccttagat agcatgggaa   12480
acccttgcgg tatagctaac gtgcacgatg aaatccagat ggaagtccct gaagatgagg   12540
tcttgtatct caactacgac ttgccttttca ccttagaagg gttcgaaaca gagaaggctg   12600
ctgtgaaagc agtgttcgat gcagaggaga acgtgttcca tgtggattct gaaggacgta   12660
tgtggtctgt gcaaatctc gttagtgttg atgctggtgt acttcattgc cagcgtcgtt   12720
atcaccgtgc agggcatatc attgccgacg caatgacctg gcgggtcag tacctgaaga   12780 tgcgttgtcc gatggcaggt gagtataaga ttggtgcaag ttggaaggaa acacactgat   12840
ggacaggttt gatattgttt gcctattctc taccttcttt cttatattcc ttatgcttgc   12900
ttgctatgga agtatgcgat tagatatacc tgatgaagag gagggttacg attgatgcag   12960
gcatctttta ttattcttgg agtcatatta tttatggtag tattctgggc tttctctggc   13020
attgacccag attgtgatgg taactacgac tgagttatac tcaaggtcac ttacgagtgg   13080
cctttatgaa taacttattc ctacttattt tgtctaacat gatttactgg acactataga   13140
aggaaagcat aggtaatcta ggtttataag gtagtatagg taattaagta aatataggag   13200
atataaatat gtctatggta actactctgg tattcgtggc tcaatacttt cgtggtcttg   13260
ctaataagtt caagtccaag gctatcaaag ctattgaggc tcgcatcgaa gcagtacagg   13320
cagagcaagt taaagttgaa gaacatcgta gttctcaaat gattgactgt cataaccgct   13380
actatgcatc tcgtgatgaa ctaaatgcac gtcaagtcaa agaggtagaa gatatgctgg   13440
cacgtcacca gcaagagcgt gacagcctga aagctgaatt tgaagagaac aaggcatcaa   13500
ttgctcttgt acatcaagct gcatctgaca gtctgaagaa agagattgtt atgctggaaa   13560
tcgaactgga taacctgacc aaataagggg gggttatgat ggaagaagta attcaagcta   13620
aacatgtagg tattatcttt cgcgatctag agcagcgtaa agttgcaggt catactcgtc   13680
tggctaaaga ggaagacacc gcaatcacta ctgtagaaca agcagatgcc tatcgtggac   13740
cagagttcac tcaaggtgaa acttgtcacc aattgagcct atcaatttgt gacactatgg   13800
ctattgtaaa tgtgcaagaa gtcgaagagg tgagtgtgt cagttacatc tacccttag   13860 atactattgc acgcattaag gtaatccata agtaattact agacactata gaacaatagg   13920
tcggcttagt tcggcctatg attgtaaagt gttgttgatg ttgaaccatt gtgcatcttg   13980
```

```
cacaacccga taccgtatag ggctttctag tgagtacatg cttgtgctca gtacaaagct   14040
aactgacaat aggagactaa ataaatggca cgtggtgatt ttgattttgg tgctcaggtt   14100
actaaatctg aaggtaaagt ctttaagaat ccagaagtag gtgatcatga agcagtaatc   14160
tctggcatca ttcatgttgg ttccttccaa gacatcttta agaaaggtaa taccactgaa   14220
gttaagaagc cagcaaactt tgttctggtt aagattgtcc tgatgggtga cgatgacaag   14280
aacgaagatg gttctcgcat ggaacaatgg atggctgtgc ctctgaagtc tggtgataag   14340
gcaacactga ctaagttcct gaatgcagtt gaccctaaag agttgctggg tggcttcgat   14400
gatttcattg gtgaatgcct gactgcaacg atggtcggtt ctggtgataa gaatgacgat   14460
ggctcattca gtatgttaa ctggaaggga tttggtggta tgccggacaa gctgaagaaa   14520
ctggtcattg ctcaggttga agaggaaggt ctgtctatga caggtcacat taccttcgac   14580
aagctgacca agaaatcct tgatgacatc ccagccaact tggtgcgtca atacttcctg   14640
aacgagacgc ctcgtggtaa gaacctgtct gttgctggtt ctcacgtaga agcaatcatt   14700
aaagctgctc gtgaagaaga cccagaatgg aagaaggcta agaagaaaga cgaggaagat   14760
gctaccccag ctaatcgtaa atctctggat actggtgagt ctgttccaca ggaagtacct   14820
gaagcagaag atactcctgc accggagatg gatgaggacg cggaatatta aggagaaagg   14880
atgaaagtac aaatcgtaac cctgcactgc aagaaaggaa ttacaactct tggcggcaac   14940
acttttcact ccttctctga aggggacaca tatgccgacc tgcactacat ctggcgcgac   15000
ggacagcacg tggtgaacta cagcgaccca gctacgggga aacgccacgg cgtatcgctt   15060
ccggcgcatg acattgctca ggtgaacaca gtttttataaa gtctcacgtg tgagacaaat   15120
cggtgtccgg tatttactgg acactataga agagaagaat tttaatcggc gataatgcca   15180
taaccaacaa aaggagaatt taatatgttc aagattgaaa ctatcgtaaa ccgtgttgtt   15240
aaaggtgctg ctctggtatc cgttgagtct ttcattatcg tcgatgaaac tgatcaactg   15300
gtagctggta ctaaggctta cgatacccgt gaagaagctc aggctaagat tgacagcatg   15360
ggtaacttcg ctgctggtct ggagttcgct cgtgcttgct tccctgagca ggctgacaaa   15420
gctcagattg gtaaggctaa tatcgtagct gaatatctgg attgggttgc tgctggtaaa   15480
ccagtgaaag aagttaaggc tgctgaagaa gctgaagctc cagcagaaga agtagctgca   15540
ccggaaactc cggtaagtga agaggaagaa ttttgataat agcaggtgtt gcctctgtta   15600
gtcctagctg actatcacgc tcacctcatc taatgccctg tctgccttag tgtaggcagg   15660
gtcttttgcg taatagttat tggagaatga attatgccga ctattgaatc tcgaattgaa   15720
ctggacatta gctacaatgc aatcaccaga cagtatattg gggttgccta tgattacaaa   15780
actggtgaga agctagtgga ggtgagacaa tgggatgact attggttaag acagaacctc   15840
catgatgcgg tgtcctcctt cctgaaggag tggcctacat gcgaccaaac ttcgacttcg   15900
gagctacagt atcggaagac aataacctgt tgctgtggcc aactgaaggt aatcgaatcg   15960
ctttaataga tgctgatatg ttaccttaca tcataggta tacaatcagt gatatgactt   16020
atgtacgagc cacaactcgt gttaagtcag ggcaagtccc ctcaatcaaa gatacacctg   16080
agtgtaagca agcgtgtgac cgtgtgaact ccttgcttaa ctcttgggtg tatgcagcag   16140
aatgtgatgc agctaagttg ttcatgacga aatcagaagc taacttccgt gtccgcctag   16200
cattcaccaa gccttataaa ggtcaacgta agaccgagaa gcctccattc ttctatgaat   16260
tgcgagagca tctcttagag gttcacggtg caatcttggc agatggagag gaagcagatg   16320
```

```
acctcatgag tatcgcacaa tgggacagcc accgccgctt ccagcaagat acaggtaacg   16380
agttccctat cggtagtcca gagcataaag cattctctga tacttgcatc gtttccttgg   16440
ataaggattt gatgattgtt cccggttggc atctacagcc gggtcaagag aagaaatggg   16500
tagagcctat gggttggctt gagctacgcc gtaaggctaa tgggcaagtc aaagatctaa   16560
aaggtgctgg cctcatgttc cactatgcac agatgattat cggtgatgat attgataact   16620
atgctggcat accaggtcgt ggtgctaaat atgcctatga tcttctcaaa gattgtaaga   16680
cagagaaaga gttgtacatg gcagtgctgg gtgcttacaa ggctaagttc gggcatggac   16740
aagttaaaat taagaattac cgaggtggtt atcgtatcgg caaagccttt gacctaatgc   16800
ttgagtgtgg tcgcttatct cacatggcaa gattcaaggg tgatatatgg cgagccgata   16860
agaacccaat cttgtgggga gatgatgcgc aatggttagc aaattaaaat catcggaggt   16920
ggcagcttat aagaaggaat tgctagataa gcaaggatgg aaatgccctc tgtgtggcgg   16980
cagtctcaaa gctgtcacac ctgtaaaccg tgtacttgac catgaccatg agacaggatt   17040
ctgccgcgct gttgtatgcc gaggctgcaa tggtgcggaa gggaagatta agggtgttat   17100
ctctggttat ggtaaggctg gtaacaaccg ttacttccag cttcaatggt tagagcgact   17160
atatgaatac tggaagttac atagtacgcc tcagacagat aagttatatc acaaacatca   17220
aacggaggca gagaagcgcg aggctaagaa ccgtaaggca cgccttgctt atgcaagaaa   17280
gaaggaggtt aaagttgggt aagctgcgca gcttgtacaa agactccgag gtacttgatg   17340
caatcgagca agctaccgac gagaaaggta atgttaacta caatgagatg gcacgtgtat   17400
tatcgtgtca tactgtgggt aagaagatta cccgccagtt ggctcgatac tggcatggtc   17460
aattcaagaa gaccaagaag aatggtgatt actaccagac ccttctgcaa gaagataagc   17520
gtatcaaaga agagcgtaag ctcaggactc ctgaccgcta cgaggatttg gctattgtgc   17580
cattgcctga ctcgcctcat cgaagtgtac tggtgatccc tgatactcat gcaccttatg   17640
agcacccaga tacctagag ttccttgcag ccgtggcagc acgttaccgt ccagacacag   17700
tggtacacct aggagatgag gcagacaaac atgccctgtc attccacgat tcggacccaa   17760
atctggatag tgctggcatg gagttagaga aggctcgtat cttcatgcac aaattgcaca   17820
agatgttccc tgtgatgcgc ctgtgtcact ctaaccacgg ctctatgcac ttccgtaagg   17880
caagcgccaa aggcatccct gtgcaatacc tgcgcaccta tcgtgaagtc ttcttcccgc   17940
agggaggtgg cgaccagtgg gattggcaac atacgcacgt ccttgagttg ccgaatggtg   18000
aacaagtggc attcaagcat caacctgctg gctctgtcct agcagatgca gcgcatgagc   18060
gtatgaacct tgtgtgtggt cacttgcacg gtaagatgtc tgtggagtac gcacgtaata   18120
cacatgaaca gtattgggct gtgcaaggtg gctgcttaat tgatgagtca tcccgtgcat   18180
ttgcctatgg tcgtgagtct aaatacaagc cagcattagg ttgtgtggtc attctggagg   18240
gtgtgcctca cattgtcccg atgcaaacca atagcgacaa ccgttggatt ggcaagattt   18300
agttgacact atagaacaaa gggctaggta agactttatc ggctggcgta tccaaatgat   18360
attgcactag cccttgattg tatagtgaat ggaggattca atatgtcaca ctatgaatgt   18420
aagaagtgtc ataagcgtta tgattactgt acttgtggtc aagagaaaac atcttttaaa   18480
gttggagaca aggtatttcg taatgaaaaa gattcgattc cttggaatca atactgcaaa   18540
gaagctggta ttgaccctga tagccctgta accatagatg atattgatgg cattaacttg   18600
tgctttcgtg aggtgagggg tacagcttgg gattccaaaa aattcaaact tgcatctgat   18660 aagtttagaca acaatatggt aattaagcct aagcactacg agttctttga tggcgtagag   18720
```

```
gcaatcacta tcattgcccg cagtatgacc gagaagcaat tcgctggcta ttgcatgggt   18780
aatgctttga agtaccgtct acgtgcaggt aagaagttca acactgaaga agacctgaag   18840
aaagcagatt actacaaaga gttattccag aagcatcgtc acgaatgtat tgatgaggat   18900
atttgatatg aatatctttg agttcctagg tcttccagaa gaccaccgca atcacccatt   18960
catgctggtg aagcatcgcg gtgaagttcc tgagaagaaa ttaactttc catgttatgc    19020 acaggtgaaa cgagatggta tcttttctgc tgttgttgtt cgcactgatg gtgtcgttgg   19080 cattttggt cgcactggta agaaattggc aaacactgaa ggactcgaac aagcctttgc     19140
tacctttccg gttggcattt atcttggtga gcttcagtct atggccattg atatctacct   19200
tgaggcaatc tctggggttg tgaaccccaa tcgcactgag ccacttgatt tcataggcca   19260
gcagattaaa gacaacctgt atatcgactt cttcgatatg ttaactatta aggcattcca   19320
tgatggattc actgatgttt cttatctcaa acgttacgat gctttacatc gtcgtatcgg   19380
cgctcatctt agcgggtgca acgctatcct tcctatcact ccttgccata atgagcgaga   19440
agttgaagcg tttgcgcaag agcaaataga tgcaggacgt gagggtgctg tattcaaact   19500
ggactgcgat tatgaagcag acacaaagg ttatcgtcag actaaagaag tccgtaaggt    19560
aacctatgac cttacttgta ttggctttga agaaggtaaa ggcaaataca aggtaaggt    19620 agctaacctc attttcaaat ggaaaggagg caagacaatc aaagctatgt taggtaaggg    19680
gtggactcat gcagatgcag agcagatgtt ccacgacatt aaacatggtg gacgattgaa   19740
tgtcattggt aaaatctttg aagtcaaagg tcttcaggat tcaagcaagg gcaacattcg   19800
tctgcccaaa gcgggagaat taagacatga caaagatgaa ccagatttct tttgatagca    19860
tgaaggcaac tcgtgcagtt gaggtagcag aagctatctt cgaaacttta tcctgtggca   19920
tggaagtgcc atatacttta cttgctgatg cagaagaact tggtctttct gtagaagcta   19980
tccaagagaa ggttgacgaa ttatatggta cagacgaaga agaaaccgac gatttcattt   20040
gaaggaatgg agatgcttga tgattctc aagccttctt ctcctaaggt gactaagact     20100
catgaagagt taatcgttga tgaagttaag cgttacatca tggattgtgt cagagcacaa   20160
ctggtggtcc aatgatacgt ccagcctcct tcctagatat tcctgagatt ataaaccttg   20220
ggaataaata tgtggaagag gaagtcaagg ttgtagccca ccactcagcc tcatggaatg   20280
cagaacaaag tgccataacc tttgtgcatc tcttaataga gacccaccac tcagcctcat   20340
ggaatgcaga acaaagtgca cataacctt gtgcatctct tagtagagaa gatttatccc    20400
tatgggttgc tgtagatgaa gggcagattg tagggttcct gtgggctggc tatcacgagt   20460
tggccccttg acacctgta agagttgcct ctgacattct cttttatatt ataccagaga    20520
ggcgaggaac actacttggt atgcgtctca tcaaagccct aaagcaatgg ctagtgata    20580 atgaatgctc tgaggttcgc ctgtctatcg cctctggtat taatgaagaa cgtgtcggac    20640
gtatgtataa gcgacttggc tttgaaccgt tggcactgt gtataacctg aagttctaag    20700
gagataacat gggtgttgta aagaaagcat ttaaggctat cggtcttgct caagatgcac   20760
cacgtattga agccaaagtc ccagcacagc agcttgagcg taagcctgag actgaagctg   20820
aagatattca aattggtgca ggggatgatg ctactgcatc tgcaaaaggt aagcgtggcc   20880
ttgtccgtcc ggtagcttct agcttgaagg tgtaatatga aacagagcat agatttggag   20940
tatggaggta agcggtctaa gatacctaag ctatgggaga agttctccaa taaacgtagc   21000
tcttttcttg ataggggcgaa gcattactcc aaattaacct tgccctatct gatgaatgac    21060
```

```
aaaggtgata acgagacttc gcagaatgga tggcaaggtg taggtgctca ggcaaccaac   21120
catctagcca acaagctagc gcaagtacta ttccctgcac agcgttcctt cttccgtgta   21180
gacttaactg cacaaggtga aaggttctt aatcagcgtg gcctgaagaa gacagagcta    21240
gctaccatct tcgctcaagt ggaaacacgg gcaatgaaag agttagagca acgtcaattc   21300
cggcctgctg tagtagaagc atttaagcat cttattgttg ctggcagctg tatgctatac   21360
aagccgagca aaggtgcaat cagtgctatc ccaatgcatc actacgtagt taaccgtgat   21420
accaatggcg acctgttaga cattatcttg ctacaagaga aagccttacg taccttttgac  21480 ccagctacac gtgcggtagt agaggttggc ctgaaaggta agaagtgcaa ggaagatgac   21540
agcgttaagc tgtacacaca tgctaagtat cttggtgatg attttggga actcaagcaa   21600 tctgctgatg atatccctgt gggtaaggtg agtaaaatca atcagaaaa gctacctttc    21660 atcccattaa cttggaagcg aagctatggt gaggattggg gtcgacctct tgcagaggat   21720
tactccggtg atttattcgt tatccaattc ttatctgaag cggttgcccg tggtgctgcg   21780
ctgatggcag atatcaagta cctgattcgt cctggtgctc aaactgatgt tgaccacttt   21840
gttaactctg gcactggtga ggttgtcact ggtgtagaag aagacatcca tattgtacag   21900
ttaggtaagt acgcagacct cacacctatt agcgcggttc tagaggtata cactcgccgt   21960
atcggtgttg tcttcatgat ggagacaatg acacgccgtg acgccgaacg tgttactgct   22020
gtagaaatcc agcgagatgc gttagagatt gagcagaaca tgggtggtgt atactccctc   22080
tttgctacta ctatgcaatc gccagtagcg atgtggggtc tgctggaggc aggggagtcc   22140
ttcactagta acttagtgga ccctgtgatt atcacaggta ttgaagcttt aggacgcatg   22200
gctgagttgg ataaactggc taactttgct cagtatatgt cactgccatt acaatggcct   22260
gagcctgtcc tagctgctgt gaaatggcct gactatatgg attgggtgcg tggtcaaatc   22320
tctgctgaac tgccgttcct taaatcggct gaagagatgg cacaagaaca ggaagcacag   22380
atgcaagcac agcaagcaca gatgcttgaa gaaggtgtgg ctaaggccgt gccgggtgta   22440
attcaacaag aacttaagga ggcgtaatgt cttcctcatt tactgaaccg tcaaccactc   22500
accctactgc tgaagagggt ccggtagaaa ccaaggaggg aacaactgat gctgctacta   22560
ctgatgctcc tgctgacgct ggcacttctg tacaagatga caatgctggt gcacaaccta   22620
ctgaagacac cggaggagaa gcttctggac agccttcaga aaaaggagac aatgcggag    22680 agaatggtga acctaagcca gatgatacc g cgaccgacac tgaggaagtg caatacttct   22740
tcggagaaca tgaagtaaca gtagacatcc cacaggatgt aactgacagc cttaaagaga   22800
aaggcattga tgccaagcag gttgccaagg aactctattc caaaggtggc aagtttgaac   22860
tgtcagatgc aaccaagcag aaattgtatg atgcttttgg caagtttcgc gtagatgctt   22920
acctatcagg tctaaaggct caaaatgaag ccttcttcct gaaagaagcc aacgcagcta   22980
aagagttgga agcagctaac acccaacgct tctctgatgt ttctaaggaa attggtggcg   23040
aagaaggttg gtcccgtctt gaggagtggg cacttgaagc gctgtctgat gacgaactaa   23100
tggcattcaa tgcggtgatg gaatctggca accagtacct gcaacaatat gctgttcgtg   23160
aactggaggt tcgtcgtaag caggcacagg gggatgataa gccatccctg attgagccat   23220
cagcacctgc taaggctaat gaagagaatg gcccactgac gcgagatcag tacgttcaag   23280
caatcgcaac tcttagccag aagtacggca atgaccgtaa agctatggca gaagctcagg   23340
ctaaactgga cgcccgtcgc cgtgctggca tggctcgcgg tatctaattc agtatttact   23400
ggacactata gaagggagaa aagttctccc tagttatcaa tttgatttat aaggagatta   23460
```

```
taatacatgt ctacaccgaa tactctgact aacgttgctg tatctgcgtc cggtgaggtt    23520
gacagccttc tcattgagaa gtttaatggt aaggtcaatg agcagtacct gaaaggtgag    23580
aacattctgt cctactttga tgtacaaact gttactggca ctaacacagt gagcaacaaa    23640
tatttgggcg aaactgagtt gcaggtgcta gcaccgggtc agtcccctaa tgccacccct    23700
actcaggcgg ataaaaacca gttggtaatt gataccactg tcattgctcg taacactgtg    23760
gctcacatcc acgatgtaca aggtgacatc gatagcctga aaccaaaact ggctatgaac    23820
caagccaagc aactgaaacg tctggaagac cagatggcaa ttcagcagat gctgttaggc    23880
ggtattgcta acaccaaggc cgaacgtaac aagccgcgtg ttaaagggca tggcttctct    23940
atcaacgtta acgtaactga gagtgaagca ctggctaacc ctcagtatgt tatggctgcg    24000
gtagagtatg ctctggagca acagcttgag caggaagtgg acatctctga tgtagctatc    24060
atgatgccgt ggaagttctt caatgctttg cgtgatgcag accgaattgt agataagact    24120
tacactatca gccagtctgg tgcaaccatt aatggcttcg ttctctcttc ttataactgc    24180
cctgtgatcc cgtctaaccg attccctacc ttcgctcagg atcaggctca ccacctgttg    24240
tctaatgaag ataacggcta tcgttatgac cctatcgcag agatgaatgg tgcagttgct    24300
gttctgttca cttccgacgc actgctggtg ggtcgtacca ttgaagtgac tggtgacatc    24360
ttctatgaga agaaagagaa gacttattac attgacacct tcatggctga gggtgcaatc    24420
cctgaccgtt gggaagcagt gtctgtagtt accactaaac gtgatgcaac tactggtgat    24480
gctggaggtc ctggtgatga tcacgcaacc gtactggctc gtgcacagcg taaggctgta    24540
tatgtcaaaa ccgaaggtgc tgcggctgca ttctctgctg ccccagcagg tatccaagcg    24600
gaagaccttg tagcggcggt acgtgctgta atggcaaatg acattaagcc gactgcaatg    24660
aaacctactg agtaacacct atgccctatc taccttgcgt aggtagggtt cttttttgtta    24720 ggaggattca tgcctgtaat tagacaaacc agtaaattag acatatgat ggaagatgtg    24780 gccttccaga ttattgatag taagctggaa gcggtaaact tgtgtatgcg agctattggt    24840
cgtgagggtg tggattccct cgactcaggg gacttggacg cagaagatgc aagcaaaatg    24900
atcgacatcg tatcccagcg gttccagtac aacaaaggag gtggctggtg gttcaatcgt    24960
gaaccaaact ggcaacttgc accagacact aacggtgaag ttaatttacc taacaactgc    25020
ctagcagtat tgcagtgtta tgcttttaggt gaaaagaaag tacctatgac tatgcgagca    25080
ggtaagctct actctacttg gagtcacacc tttgatatgc gtaagcatgt taatgctaat    25140 ggtatgatte gtcttacctt actcaccttα ctaccctacg agcatctacc tacaagtgta    25200
atgcaggcta ttgcctatca agctgctgta gagtttattg tgtctaagga tgcagatcag    25260
actaagctag ccactgcgca gcagatagcc actcagcttc ttatggatgt acaatctgag    25320
caaatgtcac agaagcgatt aaacatgctg gtacataacc ctactcagcg tcagtttgqt    25380 atcatgcgtg tggctctcca gaatgtacct gcttactctc attcaccttα tgagagttgg    25440 gcgctccgtc cgtgggagga tcgttaatgg aagtacaagg ttcattaggt agacaaatcc    25500
aagggattag ccagcagccg ccagcggtac gcttggatgg tcagtgcaca gctatggtta    25560
atatgatacc tgatgtagtg aatggtactc aatcacgcat gggtacaact catattgcaa    25620
agatacttga tgcggggact gatgacatgg ctactcatca ttatcgcaga ggtgatggtg    25680
atgaagagta tttcttcacg ttgaagaaag gacaagttcc tgagatattt gataagtatg    25740
ggcgcaaatg taatgtgact tcacaagatg cacctatgac ctacctctct gaggttgtta    25800
```

| | |
|---|---|
| atccaaggga agatgtgcaa ttcatgacga tagctgatgt tactttcatg cttaatcgta | 25860 |
| ggaaagtagt taaagctagt agcaggaagt cacctaaagt tggaaacaaa gccattgtgt | 25920 |
| tttgtgcgta tggtcaatat ggtacatctt attccattgt aattaatggg gccaacgctg | 25980 |
| ctagttttaa acaccggat ggtggaagtg cagaccatgt tgaacaaatt cgaactgaac | 26040 |
| gtatcacttc tgaattgtac tctaagttgc agcaatggag cggtgtgagt gactatgaaa | 26100 |
| tacaaagaga cggtactagt atatttatcg agagacggga tggtgctagc tttacaataa | 26160 |
| caaccaccga tggtgcaaaa ggtaaggact tagtggctat caagaataaa gttagctcta | 26220 |
| ctgacctact cccttctcgt gcgcctgctg gttataaagt acaagtgtgg cctactggca | 26280 |
| gcaaacctga gtctcgttac tggctgcaag ctgagcctaa agagggaaac cttgtgtctt | 26340 |
| ggaaagaaac aatagctgct gatgtattac ttgggtttga taaaggcaca atgccttaca | 26400 |
| ttattgaacg tacagatatc atcaacggca tagctcaatt caagataaga caaggtgatt | 26460 |
| gggaagatcg taaagtaggg gatgacttga ctaaccctat gccctctttt attgatgagg | 26520 |
| aagtaccca gacaataggt ggaatgttca tggtgcagaa ccgccatgc tttacagcag | 26580 |
| gtgaagcggt tattgcttct cgtacatcat acttcttcga tttctttcgt tatacggtta | 26640 |
| tctctgcatt ggcaactgac ccctttgata ttttctcaga tgctagtgaa gtctaccagc | 26700 |
| taaaacatgc agtgaccta gatggcgcta ccgtgttgtt ctctgataag tcacaattca | 26760 |
| tactgccagg cgataagcct ttagagaagt caaatgcact gcttaagcct gttacaacat | 26820 |
| ttgaagtgaa caataaagtg aagccagtag taactggtga atcggtaatg tttgccacta | 26880 |
| atgatggttc ttactctggt gtacgagagt tctatacaga ctcttatagt gacactaaga | 26940 |
| aggcacaagc aatcacaagt catgtgaata aactcatcga aggtaacatt accaacatgg | 27000 |
| cagcaagcac caatgtcaac aggttacttg tcactaccga taagtatcgt aacataatct | 27060 |
| actgctacga ttggttatgg caaggaacag accgtgtaca atcagcatgg catgtatgga | 27120 |
| agtggcctat aggtacaaag gtgcgaggta tgttttattc tggtgaatta ctttacctgc | 27180 |
| tccttgagcg aggagatggc gtgtatctgg agaagatgga catgggtgat gcactaacct | 27240 |
| acggtttgaa tgaccgcatc agaatggata ggcaagcaga gttagtcttc aagcatttca | 27300 |
| aagcagaaga tgaatgggta tctgagccgc tcccttgggt tcctactaac ccagaacttt | 27360 |
| tagattgcat cttaatcgag ggttgggatt catatattgg cggctctttc ttattcaagt | 27420 |
| acaaccctag tgacaatact ttgtctacaa cctttgatat gtatgatgac agccatgtaa | 27480 |
| aagcgaaggt tattgttggt cagatttacc ctcaagagtt tgaacctacg cctgtggtta | 27540 |
| tcagagacaa tcaagaccgt gtatcctaca ttgatgtacc agttgtagga ttggttcacc | 27600 |
| ttaatcttga catgtacccc gatttctccg tagaagttaa gaatgtgaag agtggtaaag | 27660 |
| tacgtagagt attagcgtca aaccgtatag gtggtgctct caataataca gtaggctatg | 27720 |
| ttgaaccgag agaaggtgtc ttcagatttc cactgagagc taagagcacg gatgttgttt | 27780 |
| atcgtattat tgtagagtca cctcacacat tccagcttcg tgatattgag tgggaaggga | 27840 |
| gctacaatcc aaccaaaagg agggtctaat ggctataggt tcagccgtta tggctggtat | 27900 |
| gtcttctatt ggtagcatgt ttgcaggcag tggtgcagca gccgctgctg gaggtgctgc | 27960 |
| cgcaggtggc ggaggtttgc taggttcact aggtggattc ctaagtggct ctactgctgg | 28020 |
| tttctctaat gctggccttc ttggtgctgg ccttcaaggg ttaggcttga ttggtgatct | 28080 |
| atttggtgga agtgatgaag ccaaggcgat gaagaaagca caagaagagc aatgcgcca | 28140 |
| gcagcttatt gctacacaag aggcgtacaa gacagtggca gacgcagaac gttctgctgc | 28200 |

```
taaacaatat catgcagatg caatcagtaa tcaggcttca ctgctacagc agcgagcaca   28260
ggttgcatta cttgctgggg ctactggtac tggtggtaat tctgtgtcct ctatgcttaa   28320
tgacttagca gcagatggcg gcaggaacca gagtactatc attgataact atgagaatca   28380
gaagattaat ttcaccaacc agcttaagtc tatccaacgt ggtggtcaga tgcagatgcg   28440
tgagtttaag aagccttctg ctatgaatac cttggttaaa ggtattccaa gtctggcatc   28500
tgcctatgta actggtagta agtctggcaa ggcattgggt aaagccttaa ctgattctcg   28560
cacatattca tctggaacaa gaggtattta atggcaattg agcgacaagc agtacaaggt   28620
ctgccacaag tgcaggccac ttctcctaat gtcatgacct ttgcacctca acaagtggga   28680
ggtgtggagg ctggcgtggc ttctacctcc ggtagtaggt ttatcgaaga ccttattcgt   28740
gcagcaagca gcgtggctga tgttaccact ggtatcctta atcagaagat tgaggaagat   28800
aaggttgttc aaatggaacg ggcatataac ggattaatgc cttctgagga tgcaactcgt   28860
ggtggcgctc gtgctaacat gcttgtcaaa gctcaactgc tagctaatga tgaagcagca   28920
cgaatgaaag acatggctac tcgtttccaa ggaacggatg acgaatggac acaacttatg   28980
gttgactctc gtaatgagat gcagaataag ctgttccagc aatacccctga gttgcaaggt   29040 gacaaagata ctatgcgtat ggtcactaat gtcttccaag aacagcagcc tcagatttgg   29100
gctacacgaa cccagcataa acttgaccgt gaacaagcag accgtgagga tacctttgac   29160
gggcgagtgg cttctacttg ggattctaat attgaccctg aagcctctgg ctatgcttta   29220
caggaacgaa tccgcgaagg tcttactcaa ggattactac ctgaacagat gtacaagaag   29280
ttagtccagc gagcaatttc acttgcacaa ggcggtgatg ttagcatggc tgaagccctg   29340
aagtatgtga aggacgataa gggtgtttct gtttatgcta agaatccaca gcttatcaca   29400
gccatcacta gtggtaatgc agtttgggct aggaataatg tagctgatgt aactcgtatg   29460
tctttcgaag ttaaagaatc ctaccttgca ggtgatttaa ctgatgaaga attgttggaa   29520
cgagcacagc acattaataa tctgacaggt aactctgtct tctctaatcc agaactagag   29580
gcactgatgc gccaacgggc taagcagaat gcagagctag gtgcaatgca ggatatgcga   29640
cgtgagcttt actccgaccg cctgactggc ttccaaggta agactgataa agagaagaag   29700
gcttacattg atgttatcaa acaggatagc caactttatg cagaccagca aatcaaacaa   29760
cgtggcttgg accttacaga tcaagaggct gaagctattc gtggtgcagt ggaagtgcag   29820
cgcctgcaat tcatgaactc caaaggctta gtggatgata cctttgagtc tcgtatcaaa   29880
gccatggaat ctatgctatc gcctgagcac tttgccaagg cgaaccaca ggagttgatg   29940 actattcgcc agttgtggga acagttacca gaagagagcc gaggtgtctt tggtgacacg   30000
gtgaatggct acatggataa ctacaacact gcactacaaa tgggagagac accttttgcag  30060 gctgcaaggt ttgcgcgtaa agcacagcag aaattctctc gtactgagaa ggaaaccaag   30120
aagttcaact cagctattgg agatgcactg gatgaggtat ctggtgctgg ctggtttgat   30180
ggtaaaaccg aagtgtcaga cttaggtaaa gctattgcgg aagaagagtt acgagctaag   30240
gccaatatgt tgtggtctag tggtatgcgt aacatggatt ccatcaagaa ggctttaatt   30300
acttggggca ataaacgcta cactcaatca gaggatgcaa agacttccgg tggctatttc   30360
attaaaggtg attacacttc tgcatctgat atgcttatgt cagttgggaa aggcgtaaac   30420
cctaccgatg tacctctggc gcttggtagg tatgtgaaaa cacagatgcc agaattgaag   30480
aaggagcttc aagaggggga aactaaagat gatatataca ttgattacaa tgaacagaaa   30540
```

```
ggtactttcg tgattcgtgc tggtgcagca ggtcgccctc tttctggagt aatccctgta    30600
acctctttag ataccacttc actactagat tctgcctatc agaagaaagt agaggaacga    30660
gataaaggcg agtatgttca cccgtatcgt acagatattg gtgcacaaga gcctatgcca    30720
gctaaaccaa ctgccaaaga tattggtaaa tttggactag ctaacttcct catgtcttct    30780
gcttttgctt ctggtgagaa tctgccttct aacttcgaga ttaactatcg aggtaatatg    30840
caacaattct atgacaagct agctatggat gagaataaag ataaagttgg ctttaataag    30900
gcaactggaa cctttactcc atataaagac gctcacggtg agtctatcgg ttacggtcat    30960
ttcttaacgg aagaagagaa gcgaaacggg tatattaaga ttggcgatga actagttccc    31020
tatcgagggt ctatgtctca gcttacagag agcaaggctc gcgctcttat ggagcaagat    31080
gctaagaagc atgtgcctcc tactcgtgac tggaagattc cgtttgacca gatgcaccct    31140
gcacagcaac gtggcttgat ggatttaagc tacaatttag gtaaaggtgg aatccagaac    31200
tcaccgcgtg ctcttgctgc attcaaagct ggtaagctta cggagggctt tatcgaaatg    31260
ctgggcactg catcaagtga aggtaagcgt attcctggcc tactgaagcg acgcgctgag    31320
gcatacaata tggcatctgc tggtggtgtg cctaagatta ccgaagtgga gactcgtgaa    31380
gatggctcca tgtgggttag gtttggtgga cctatgccag caggttctgt ctcggcatgg    31440
actcataaac gtattggcgc ggatggttgg tatcaggttt atgaggctgc acctaccaag    31500
ttagctaaag attctaaggt aggtaaagtt aagttgtagt acctaactca aggcttgtct    31560
cacatgtgag acaggtcttt atgataggca ctatggagga attatggaac aagacattaa    31620
gactaattgg gctggatatg tccagtctac tcctgagccg ttttctattg aggcggctcc    31680
ggtatcggct cctacgatac gccagcgtaa tgagttacaa gagcaagttc ttgaagctaa    31740
agctgacgct gatatcttag gtgctgtagg tgctgccttc cagaatgagt ggttggcatt    31800
cggaggcaag cggtggtatg accgtgccac tgctgatttc acacctcaac cagactttga    31860
gatacaacct gagcaacgtg aagcactacg tttcaaatat ggtacggata tgatgcagac    31920
aatcactgag ggtgttcgtt ctgaggatga attgaacttc cgtattcaga atgcggatga    31980
agaccttgag cgcaataagc gcattgctca ggctggctgg gttggctctg tggcgacgat    32040
tggcgctgct gtgcttgacc ctgtgggatg ggttgcctct attccaaccg gtggtgccgc    32100
taaagttgga ctcgtaggcc gtgctgtgcg tggcgctatc gccgctggcg tgagtaatgc    32160
cgctattgaa tccgtattgg tccaaggtga catgactcgt gatttagatg acattatggt    32220
agcactgggt tccggtatgg ctatgggtgg cgttattggc gctgtagcgc gtggtagggc    32280
cactaagctc agtgagcaag gtgatgacag ggctgctagc attgtgcgca gtgcagacgc    32340
aggggaccgc tatgttcgtg ctgttgccga tgacagtatc ggtgcgatgc gtgttaaggg    32400
cgcagaggtt ctcactgagg gtgtattcga tatctccagt aagagtgaag acctactgaa    32460
aaccttgcaa cgagaaggta atgcgattga tatgacacct cgccgttggg ctggaactat    32520
gtctgccctc ggtactgtcg tgcactcatc taaagatgca agtatccgag gccttggtgc    32580
tcgtctgttt gaatccccac aaggtctagg tatgcagaag gcatctgcta gtcttatgca    32640
gaatactaac ttaaatcgcc tgaaatctgc tgatatgaac cgcttcaatg atgggtttga    32700
tttgtggctt aaagagaata atatcaatcc agtagcaggg cataccaact ctcattatgt    32760
acagcaatac aatgaaaagg tgtgggaggc agtgcgtatt ggcatggatg agtctacacc    32820
taaatctatc cgcatggctg ctgagggaca acaggctatg tacagagagg cgctggcttt    32880
acgtcaacgt tctggtgaag cgggatttga aaaggtaaaa gccgacaaca atatatgcc    32940
```

```
tgatatcttt gatagtatga aagccagacg tcaattcgat atgcacgata aagaagacat   33000
catcgaactt ttctctcgtg cctaccagaa tggcgctcgt aagattccaa aggaagcagc   33060
agatgagatt gcacgagcac aggtaaatcg cgttgctgat gctaccttaa ctggaaagct   33120
tagttttgaa aaggcaatgt caggtcagac taaggcagag tatgaagcta tcatgcgtaa   33180
ggcaggcttc agtgatgaag aaattgaaaa gatgatagaa gctctggata caaagaaac    33240 cagagataac atctctaacc gagctaaaat gagtttagga ttagatgtta ctcaagaata   33300
caatggcatt cgtatgcgtg acttcatgaa taccaacgtg gaagagctaa cagataacta   33360
tatgaaggaa gcagcaggtg gcgctgcatt ggctcgccaa ggcttctcta cctatcaggc   33420
tgcacttaat gcaattgacc ttgtagagcg aaatgcacga aacgcggcta aggatagcaa   33480
ggctagtttg gcattagatg aagagattcg tcagatgcga gaaggtcttc gcctgattat   33540
gggcaagtcg attgatgcag acccacaggc tatatctact aagatgatgc gtcgtggtcg   33600
tgatatcaca ggtgtgcttc gcttaggtca aatgggcttc gcacagctag gtgaacttgc   33660
caactttatg ggtgaatttg gtattgctgc aactactatg gctttaggta agcaattccg   33720
cttcacctct aaggcgttgc gtaatggcga tggcttcttc cgagataaga acttagctga   33780
ggttgagaga atggtggggt acattggtga ggataactgg ctaacaacta agggtgcacg   33840
tcctgatgaa tttggtgatg taaccacagt aagagggatg atggctcact ttgaccaatc   33900
catgaactca atacgtcgtg ctcaaaccaa cctatcactc ttccgcatgg cacagggttc   33960
tctggagcga atgactaata ggcaaatagc tttgtctttc attgaccacc ttgaaggcaa   34020
gaagattatt cctcagaaga aactggagga acttggtctt actcaggagt tcatgactaa   34080
cctacagaag cactatgatg ctaactctaa aggttctggc ttgcttggct ttgatacaat   34140
gccttatgcc atgggtgaaa cttagctaa tgctattcgt cgtaagtcag gtctaatcat   34200
ccaacgtaac ttcattggtg atgaaggtat ctggatgaac aaagcactag gtaagacatt   34260
tgcacagctt aagtcattct ctcttgtatc tggtgagaag caatttggtc gagggattcg   34320
ccacgataaa attggtcttg ctaagaagac agcttacggg tttgctttgg gttcaatagt   34380
gtatgcggca aaagcctatg tgaactctat tgggcgagaa gaccaagatg aatatttgga   34440
agagaagtta tcgcctaaag ggttggcctt tggtgcaatg ggtatgatga gtacaactgc   34500
tgtatttagt ctaggtggag atttcttagg tggcctaggt gttctacctt ccgaactcat   34560
tcaatcacgc tatgaagcag gttttccaaag taagggtctg attgaccaaa tacctctggt   34620
tggcgttggt gcagatgcag taaatctggc taactcaatc aagaagtatg cagaaggtga   34680
cacagaaggt gtagatatcg ctaagcgagc actccgtctt gtgccactta ccaatataat   34740
aggtgtccaa aacgcattgc gttatggctt agatgaactg gaggattgat gagttatact   34800
ttcacagaac atacagccaa tggtacgcaa gtcacctatc cttttagctt tgctggtagg   34860
gataaaggtt atcttcgtgc ctcagatgtg atagtggagt ctcttcaagg taacacttgg   34920
attgaagtta catctggctg gcaactaact ggcacgcacc agattacttt tgatgtagca   34980
ccagttgcag gtttgaagtt ccgtattcga agggaagtac aaaaagaata tccatacgct   35040
gagtttgacc gtggtgttac cttggatatg aagtctttaa atggttcttt cattcatata   35100
ctggagatta cacaggagtt acttgacggg ttttatccag aaggatactt cattaaacag   35160
aatgtaagct ggggcggcaa taagattact gatttggctg atggcacaaa tccgggagat   35220
gcagtaaata aagggcagct tgatgccatc gacaagaagc atacagattg gaacgccaaa   35280
```

```
caggacattg agattgctgg ccttaaggct ggtatgactt ctggtattgc gcacagaact    35340
gttccttggt acacgatagc ccaaggtggt gagatttccg taaaaccacc ttatgaattt    35400
caagatgcac tagttttcct taatggggta ttgcagcacc aaattgtagg cgcatactct    35460
ataagcaaca acactatcac tttcgcagag ccgcttgtgg ctggtacaga ggtgtatgtg    35520
ctgattggta gtcgtgtggc tacatctgaa cctaatattc agttggagtt gaactttgac    35580
ttagtagaag gccaacaagt agtacagatt ggctctgcat ttaagtacat tgaggtctac    35640
cttgatggat tattacaacc taaacttgct tatcaggtag acggtgacat tgttactttc    35700
tcagaaagag taccagaatg ccggatgact gctaagatta tcacagcata aggaggtggg    35760
atgattaact ccgaactggt agatagtggt gtgaagcttg cgccacctgc actcatatca    35820
ggtgggtact tcctcggtat cagttgggat aattgggtgt taatagcaac attcatttat    35880
accgtgttgc aaattgggga ctggttttat aataagttca agatttggag ggagaagcgt    35940
gagcgtacac aataaacatg cagctacaga ggacgaggtt ggcattctgc atggtgctat    36000
taccaaaatc ttcaataaga aagcacaggc aatactggac actatagaag aagaccctga    36060
tgcagcatta catttagtgt ctggtaagga tattggtgcg atgtgtaagt gggttcttga    36120
taacggcatt accgccacac ctgctgcaca gcaggaagag tccaagttat ctaagcgcct    36180
caaggctatc cgagaggcat ccagtggtaa gataattcaa ttcactaagg aggattgatg    36240
gctaaggcaa gagaatcaca agcggaggct cttgccagat gggagatgct acaggagtta    36300
cagcagacct ttccttacac cgcggaaggt ttgcttctct ttgcagatac agttattcat    36360
aacttaattg caggcaaccc tcatctgatt cgtatgcagg cggatatctt gaagttccta    36420
ttttacggac acaagtaccg cctcatcgaa gcgcctcgtg gtatcgctaa gacaacacta    36480
tcagcaatct atacggtatt ccgtattatt catgaaccgc ataagcgtat catggttgtg    36540
tcccaaaacg ccaagcgagc agaggaaatc gcaggttggg tagttaaaat cttccgtggc    36600
ttagactttc ttgagtttat gctgccggat atctacgctg ggaccgtgc atccgttaag    36660 gcgtttgaga ttcattacac cctacgtggt agtgataagt ctccttctgt atcctgttac    36720
tcaatcgaag caggtatgca gggtgctcgt gctgatatta ttctagcgga tgacgtagag    36780
tcgatgcaga atgctcgtac ggcagcgggc cgtgccttgc ttgaggagct gactaaggag    36840
tttgaatcta tcaaccagtt tggggatatc atttaccttg gtacacctca gaacgtaaac    36900
tctatctaca acaacctacc tgctcgtggt tactctgttc gtatctggac tgcgcgttac    36960
ccttcagtag agcaagagca atgttatggc gacttccttg cacctatgat tgttcaagat    37020
atgaaggaca acccagcact cgctcaggg tacgggttgg atggtaatag tggtgcacct    37080
tgtgcccctg aaatgtatga tgatgaagtc ctgattgaga aggaaatctc tcagggtgct    37140
gctaagttcc agcttcagtt catgcttaac actcgcatga tggatgctga cagatcccca    37200
ttacgcctga caatctaat cttcacctcg tttggtacag aggaagtccc tgtgatgcct    37260
acgtggagta atgattccat aaacatcatt ggtgatgcac ctaagtatgg taacaagcct    37320
acggatttca tgtacagacc tgtagctcgc ccatatgaat ggggtgctgt ctcccgcaag    37380
attatgtata ttgaccctgc gggtggtggt aagaacggag atgagacggg tgtagccatc    37440
gtattcctgc acggcacatt catttatgtg tatcagtgct tggtgtacc tggcggatac    37500 cgagagtcgt ccctgaatcg cattgtgcag gccgcaaagc aggcgggtgt taaagaggta    37560
ttcattgaga agaactttgg tcatggcgcg tttgaggcgg taattaagcc gtactttgaa    37620
cgagagtggc ctgtaactct ggaagaggat tacgccaccg gacagaaaga gttgcgtatc    37680
```

```
attgagacgc tggagccgct catggcagcc cataggctta tcttcaatgc agagatggtg   37740
aagtcagact ttgagtcggt acagcactat ccgcttgaac tacgcatgtc ctacagtctt   37800
ttcaatcaaa tgtcgaacat aacgattgag aagaacagcc tccggcacga tgaccgccta   37860
gacgccctgt atggcgctat acggcaatta acttctcaga tagactatga cgaggttaca   37920
cggattaatc gcctcagagc gcaggagatg cgcgattaca tccatgctat gaacacacct   37980
catctacgca gggcaatgct atatggagat tacggtactg agcgaagagt gaccaacact   38040
tccgtagcga tgcagcagcg agtttacggg cagaactacc gaaataaatc ggcaagcaga   38100
aatacacttt ctgcaaggat ttcaaggact tattaattac tggacactat agaaggaagg   38160
cccagataat aagagaaaat aataggtaat atatatatag gttaacctag gttatatagg   38220
tatgccttag tatgggtgta ctcctgtaca ccctattcct tactacctta ctatatttac   38280
ataataggag agagacaatg gctaatgatt atagtagtca accattaaca ggtaagtcta   38340
agagaaagca ggtacaacct gtaagtgaag aactaatgct tccggtgctc aaaaaagagg   38400
aagttagtaa gaaaagcaat gttattaatg atgccaccaa atcaggtaaa cagaaagggg   38460
ccatggtgtg ccttgaagtg aaaggtggtg tattgaagat tgctatcgcg gttgatggca   38520
aagaagattc agagtggaag ttagtaacag tggaaccaac tgttaaccca gtttaagata   38580
aggaggaaga ttacatggct aaatatggta ctacaggttc tgttactggt caggcttttc   38640
gagtaaaagc agtacaaact attgcaacgg caatcccgat gcctgttgtt aaagaagaag   38700
accttaagag taaagaccac cctatcaaca tcaaacattt atcaggtaaa cagaaaggtg   38760
caatggttgc tcttgagaaa ggtgacacaa ccttacatat tgctgttgca cgtggtagtg   38820
aacccacaga cccttgggat gtaactggta tggaaaagga cgctgttact ccagcagggg   38880
tataataatg cttaataaat acttcaagcg taaagagttt gcttgccgtt gtgggtgcgg   38940
tacatccact gttgatgctg aattactaca ggtagtcaca gatgtgcgtg agcactttgg   39000
ttctcctgta gttatcactt cgggtcatcg ctgtgctaag cacaatgcca atgtaggtgg   39060
cgctaagaac tccatgcatc ttactggtaa ggctgctgac attaaagtgt ctggcatatt   39120
accttctgaa gtgcataagt atcttactag caaataccaa ggcaagtatg gtataggtaa   39180
gtataactcc ttcactcaca tcgatgtacg ggatggttgt gcgcgatggt aagatgtgtt   39240
gaatggtgtg agcgtatggt tgcccaagct gccgaggatg gcaactatga tgactggaag   39300
aactactctg acttgttagc tcaatggaaa gggagatgca atgaaaaagc tgtttaagtc   39360
taagaaggtt gtaggtgcac tggttgcact tgttattgct cttgtttctg taggtcttgg   39420
tgtagacctt ggctctggca cggaatcctc tgtgacagat gtggtctgcc aagtgatcac   39480
ctgtgaataa gtttctagaa gttctggcag gtcttattgg cctgcttgtc tctgctaaga   39540
agaaacaaga agagaaggag gcacaaagtg aagcgaatca tgttagtgac aacccttctg   39600
attggttcgc tgaccacttc cgggtgtcag caggcgttac cagagaaagc aatggtgaaa   39660
cctctgaggc cgacgctgac ggcagtttac gaggtagacg ataaggtctg ctttagtaag   39720
cctgacgcta caaaacttgg tttgtacatt ctctcgctag aacgcggata caattaatac   39780
atagctttat gtatcagtgt cttacgattt actggacact atagaagagg taagatagcg   39840
ccgttctttt gagcggccta ttactagcca atcttcatag ggagggttgg aaagtaatag   39900
gagatagcat ggctaaatta accaaaccta atactgaagg aatcttgcat aaaggacaat   39960
ctttgtatga gtaccttgat gcgagagttt taacatcaaa gccgtttggt gctgcaggtg   40020
```

```
acgccactac tgatgatacg gaggttatag ctgcttcatt aaactctcag aaagctgtca    40080
cagtctcaga tggtgtattc tctagctctg gtattaacag taattactgt aacttagacg    40140 gcagggtag tggcgtgcta agtcaccgtt caagtacagg taactactta gtatttaaca    40200
atctacgtgc aggtcgctta agtaatatta cggtagaaag taataaggcg actgatacaa    40260
ctcagggaca gcaggtatcc cttgctggtg gaagtgatgt tactgtaagt gacgttaact    40320
tctcaaacgt taaaggtact ggtttcagtt taatcgcata ccctaatgat gcgccacctg    40380
atggacttat gattaaaggc attcgaggta gctattccgg ctatgctact aataaggcag    40440
ccggatgcgt acttgctgat tcctcagtta actccctcat agataacgtc attgctaaga    40500
actaccctca gttcggagca gtagagttga aaggtacagc cagttacaac atagtcagta    40560
atgttatagg gacagattgc cagcatgtaa cttacaacgg cactgaaggg ccaatagctc    40620
cttctaataa ccttatcaag ggggtgatgg ctaataaccc taagtatgca gcggttgttg    40680
caggcaaagg aagtacgaac ttaatctcag acgtgctcgt agattactca acttctgatg    40740
ctaggcaggc tcatggtgtt acagtagagg gttctgataa cgtcataaat aatgtgctta    40800
tgtcaggatg tgatggtact aactcttttag gacaagggca gactgctaca attgcacgct    40860
ttataggtac agctaataac aactatgcgt ctgtatttcc tagctacagt gctacaggtg    40920
ttattacttt cgaatccggc tctacccgta acttcgtaga ggtaaagcac cctggcagga    40980
gaaacgacct tctcagttct gctagtacta ttgacggtgc agctactatt gacggcacta    41040
gtaatagtaa cgtagtgcac gcacctgcct tagggcagta cataggtagt atgtcaggta    41100
ggttcgaatg gcggattaag tccatgtcac tcccttcagg cgttcttact tctgctgata    41160
agtacagaat gcttggagat ggtgctgtgt cattagctgt aggtgggggc acttcttctc    41220
aagttcgcct atttacttct gatggtgtact ctcggacagt gtccctcacc aacggtaacg    41280
tgcgtctttc taccagtagc acaggctttt tgcagttagg tgctgatgca atgacccag    41340 acagtactgg tacatacgca ttaggttccg ccagccgagc atggtctggc ggttttactc    41400
aagcagcatt cactgttacc tcagatgctc ggtgtaaaac agaacctctt actatctcag    41460
atgccttact ggatgcttgg tctgaagttg acttttgtgca gtttcagtat ttggatcgtg    41520
ttgaggagaa gggtgcagac tcagctagat ggcacttcgg tatcatcgct cagcgagcta    41580
aggaggcttt cgaacgtcac ggtatagatg cacatcgcta tggcttcttg tgcttcgaca    41640
gttgggatga tgtatacgag gaagatgcca atggctctcg taaactgatt acaccagcag    41700
gttcccgcta cggtattcgt tacgaggaag tactgatatt agaggctgcg ttgatgcggc    41760
ggactattaa gcgtatgcag gaagcactag cttccctgcc taagtaagca acaggcagtg    41820
cgtaagcact gcttttagcg caacttttct taaaggttat cacggtggta gcctttcaga    41880
aaaggaggtt acatgattca aagactaggt tcttcattag ttaaattcaa gagtaaaata    41940
gcaggtgcaa tctggcgtaa cttggatgac aagctcaccg aggttgtatc gcttaaagat    42000
tttggagcca aaggtgatgg taagacaaac gaccaagatg cagtaaatgc agcgatggct    42060
tcaggtaaga gaattgacgg tgctggtgct acttacaaag tatcatcttt acctgatatg    42120
gagcgattct ataacacccg cttcgtatgg gaacgtttag caggtcaacc tctttactat    42180
gtgagtaaag gttttatcaa tggtgaacta tataaaatca cggataaccc ttattacaat    42240
gcttggcctc aagacaaagc gtttgtatat gagaacgtga tatatgcacc ttacatgggt    42300
agtgaccgtc atggtgttag tcgtctgcat gtatcatggg ttaagtctgg tgacgatggt    42360
caaacatggt ctactccaga gtggttaact gatctgcatc cagattaccc tacagtgaac    42420
```

```
tatcattgta tgagtatggg tgtatgtcgc aaccgtctgt ttgccatgat tgaaacacgt   42480
actttagcca agaacaaact aaccaattgt gcattgtggg atcgccctat gtctcgtagt   42540
ctgcatctta ctggtggtat cactaaggct gcaaatcagc aatatgcaac aatacatgta   42600
ccagatcacg gactattcgt gggcgatttt gttaacttct ctaattctgc ggtaacaggt   42660
gtatcaggtg atatgactgt tgcaacggta atagataagg acaacttcac ggttcttaca   42720
cctaaccagc agacttcaga tttgaataac gctggaaaga gttggcacat gggtacttct   42780
ttccataagt ctccatggcg taagacagat cttggtctaa tccctagtgt cacagaggtg   42840
catagctttg ctactattga taacaatggc tttgttatgg gctatcatca aggtgatgta   42900
gctccacgag aagttggtct tttctacttc cctgatgctt tcaatagccc atctaattat   42960
gttcgtcgtc agataccatc tgagtatgaa ccagatgcgt cagagccatg catcaagtac   43020
tatgacggtg tattatacct tatcactcgt ggcactcttg gtgacagact tggaagctct   43080
ttgcatcgta gtagagatat aggtcagact tgggagtcac tgagatttcc acataatgtt   43140
catcatacta ccctaccttt tgctaaagta ggagatgacc ttattatgtt tggttcagaa   43200
cgtgcagaaa atgaatggga agcaggtgca ccagatgatc gttacaaggc atcttatcct   43260
cgtaccttct atgcacgatt gaatgtaaac aattggaatg cagatgatat tgaatgggtt   43320
aacatcacag accaaatcta tcaaggtgac attgtgaact ctagtgtagg tgtaggttcg   43380
gtagtagtta aagacagcta catttactat atctttggtg gcgaaaacca tttcaaccca   43440
atgacttatg gtgacaacaa aggtaaagac ccatttaaag gtcatggaca ccctactgat   43500
atatactgct ataagatgca gattgcaaat gacaatcgtg tatctcgtaa gtttacatat   43560
ggtgcaactc cgggtcaagc tatacctact ttcatgggta ctgatggaat acgaaatatc   43620
cctgcacctt tgtatttctc agataacatt gttacagagg atactaaagt tggacactta   43680
acacttaaag caagcacaag ttccaatata cgatctgaag tgcagatgga aggtaaatat   43740
ggctttattg gcaagtctgt tccaaaggac aacccaactg gtcaacgttt gattatttgt   43800
ggtggagaag agacttcgtc ctcttcaggt gcacagataa cttttgcacgg ctctaattca   43860 agtaaggcta atcgtatcac ttataacgga aatgagcacc tattccaagg tgcaccaatc   43920
atgcctgctg tagataacca gtttgctgct ggtggaccta gtaaccgatt cactaccatc   43980
tacctaggta gtgaccctgt tacaacttca gatgctgacc acaagtacag tatctctagt   44040
attaatacca aggtgttaaa ggcttggagc agggttggtt ttaaacagta tggtttgaat   44100
agtgaagcag agagggacct tgatagcata cacttcggtg tcttggctca ggatattgta   44160
gctgcttttg aagctgaagg gttggatgcc attaagtatg gaattgtgtc cttcgaagaa   44220
ggtaggtacg gtgtgaggta tagtgaagtt ctaatactag aggctgctta tactcgttat   44280
cgtttagaca agttagagga gatgtatgcc actaataaaa tcagttaagc aagctgctgt   44340
actccagaac acagaagagc ttattcaatc aggacgtgac cctaagcagg cttatgccat   44400
tgccaaggat gttcaacgtc gtgccatgaa gaaaccttct gcatcttctg cgtaagcagg   44460
ttaatatctt agtataaaca agggcagact taggtttgtc cttagtgtat tccaaaggag   44520
gtaacatgct gaaagatggt tgggtttcat atgaccctac agaccctaag aattggctac   44580
aggttatcgc tatagcttgt gcaggtagcc tattggctgc cctgatgtat tcattatgga   44640
tgtacacaaa gtaaccaaag tcaaaatttt gatgtaggcg tgtgtcagct ctctcgccct   44700
cgccctcgcc gggttgtccc catagggtgg cctgagggaa tccgtcttcg acgggcaggg   44760
```

-continued

```
ctgatgtact ccttgtctag tacaagggag gcggagggaa cgcctaggga ggcctaggaa    44820
tggcttagtg gtggacaagg tgattacctt agtgaagcct cttagtgcat tcctgaggcc    44880
attcagggcg tttatgaggg attgacaggg tgtgagggcg tgggcta                 44927
```

<210> SEQ ID NO 5
<211> LENGTH: 44920
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
tcgccctcgc cctcgccggg ttgtccccat agggtggcct gagggaatcc gtcttcgacg      60
ggcagggctg atgtactcct tgtctagtac aagggaggcg gagggaacgc ctagggaggc     120
ctaggaatgg cttagtggtg gacaaggtga ttaccttagt gaagcctctt agtgcattcc     180
tgaggccatt cagggcgttt atgagggatt gacagggtgt gagggcgtgg gctatctgtt     240
cctttgctcc tcacttcgtt cgtcgctgcg gtagcctgat gtgtacctta ggttattcct     300
tgatggatag cttaggttag ccttagtgga ttaccttagt aaagccttag tgcttcact     360 tagtatcagc ttagtagtgt accttagtaa gtcttagtgt cttctcttag tgattgcaca     420
tgcaagcatg taagatgcta ataggtcgcg gtcggcagac cgctaaagaa agagaatggt     480
aataagatgc agtaggagga acaccagaag cctagccaac ctaagctatc ctagctctat     540
atctattgct tttccttagt ctaacacgtt agacaaccta tcttattctt agtgatggta     600
acttagtgtt gacaagataa tcttagtgta atactatgca tcacgtaggc ggtgctgagg     660
cacctagtag ccagctagta aggcatacga agagactagc gcttacattg ctctttaaca     720
atttgcttag tgtaacctat gtatgccgtg gttaactact tattgaatga ggtattaact     780
atgacattaa ataaccgtga actgtccgtt ctcttcactc tgttgtgcta catgattcgt     840
aacaacgaat tacttacaga tgatgagtta gccttgtatc accgctttct taacgaaggt     900
tggaccgata cagttaatca ataccgtaac atgatagatg agttgaggga gggtaaataa     960
tgtatcaaca tgaggtattc tttgaatcag ctagcgaagc tattcgcttc cgtgatgata    1020
tgatgcaagc tggtgtaggc gttgatgtgt atcactattt gatagattac gacactgaat    1080
atcaccgagt taccttagta tctgagtatg acaaccaagt cattactgag tatctaggca    1140
gtgaagatta cgattacgat gaagtaatca cgacaaatct ctaaattaac tgttgacagc    1200
cacggcatac aaggttacat taagcatcaa gacggcgacg tctttaaaca tcccgctctt    1260
taacaatacg gtttgtgtct tgataggcta actaactaac taaggtaatt atcatgaaag    1320
ggttaatttg tgtagaacgt atggtcaatg gtaaacttga atattaccca ctggaaaacc    1380
aatctagctt caaagagtgg tatggctgtt tctcactgat ttaaggtaaa ggctggcact    1440
agtcagccta tcaaggcgca aaccaagctc tttaacaatt tggatggtag cttcttagtc    1500
tggataggtt aaacctagga gattctcttg agtctcctat aatgtaacct aactaactaa    1560
atgaggatta aatcatggaa cgcaatgcta acgcttacta caaccttctg gctgcaactg    1620
ttgaagcatt caacgagcgt attcagtttg atgagattcg cgaaggtgat gattactctg    1680
atgcactaca tgaggttgta gacagcaatg ttccagttta ttacagcgaa atctttacag    1740
tgatggctgc tgatggtatt gatgttgatt ttgaggatgc tggtttgatt cctgacacga    1800
aggatgtaac caagattcta caagctcgca tctatgaagc tctttataat gatgtaccaa    1860
```

```
atgacagcga tgtagtttgg tgtgaaggcg aagaagagga agaataagga tggaaaagca   1920
atataacttt atcttttcag acggtgtaac cctgaagtgt tccctacgat tcgcacaaat   1980
tcgtgaggaa gtactaggca ctacatacaa actatttagc tgacactata agagaaggct   2040
taacaaggcg ttactaaggt agcgcctgat taaactttca cttactagga gttgagatta   2100
tgaaaacctt gattggatgc ttcttgttgg cttctcttgc tctggcattt accgctaaag   2160
ctggttatga cgcttataaa gtagaacaag cccagcaaga ctgggccaaa aaaaagttca   2220
acttgtgcag caagagcaac acctacgagt actgcaacaa aacactaaga cacttatgga   2280
aagagtaact agcctatagc ccacctgagt gggctatgtg atatttactt aacactatat   2340
aaggtgatta ctatgactac tgaaaacacc ctcgtgtctg tccgtgaagc tgcaaccgct   2400
gaaatcaagc aacatttaga caatatcggc acttcttaca tcaaagtagg gcttgtctg    2460
aatgagttac gcggagactt tgaaggtcaa aaagagtttt tagcctatgt tgaagcagag   2520
tttgccatta agaaggcaca atgttacaag ctgatgagtg tagcccgtgt ctttgaaggc   2580
gatgatcgct ttaaaggcgt ggcgatgcgt gtaatgctgg cgcttgttcc tttcgctgat   2640
gaaaatataa tcatggagaa ggccgcagaa ctcgccgcaa atggcaagct ggacactaat   2700
gccgtaaacg ccctgattga acctaagaaa gagtcaaagg ccgaaacggt acaatctaag   2760
gctgagacag taaaaccgca ggagaacgcg actgagtccg cagaatcaca tgaaatgcaa   2820
gcgccgcagg tagtgccacc cgcgagcgag caggagtccg acgaatcagc accttgggaa   2880
gaggaaagca aaccggaagc gccaaaggca gctccgatgg ataacacggc taatactgag   2940
aatgccgcta ttgctggtct gctggcacaa attaaagcac tgactgagca attacaggca   3000
gccaatgacc gcatcgcctc cttaagtagc gcacgcgaaa gcaagaaggc atccgcacct   3060
atgctgccgc agttcaaatc ttcctgcttc tacgctcgct taggcttgag cgcggaggag   3120
gcaacgaaga aaacagcagt taacaaggca cgccgcgaac tggttaagct gggatacggt   3180
gaaggccatg aggcatggcc cttaatctct gaggcagtag aagagttgac taagtaacct   3240
tatcggtggc atcttcttag gtgtcaccta ttaaggtttc tttcactagg agtaaacaag   3300
atgcaaggcc tacacgctat tcaacttcaa cttgaagaag aaatgtttaa cggcggtatc   3360
cgtcgctttg aagcggacca acaacgccag attgcatccg gtaatgaatc agacacggca   3420
tggaatcgcc gcttattgtc cgagttaatc gcgccaatgg ctgaaggtat tcaggcatac   3480
aaggaagagt atgaaggtaa aagaggccgt gcaccgcgtg cattagcttt cattaactgc   3540
gtagaaaacg aagtggcagc atatatcacg atgaaaatcg ttatggatat gctgaacacg   3600
gatgtaacct tgcaggctat agccatgaat gtagctgacc gcattgagga ccaagtacgt   3660
tttagcaagc tggaaggtca cgccgccaaa tactttgaaa agttaagaa gtcacttaag   3720
gcaagtaaga ctaaatcata tcgccatgcg cacaacgtag cggtagtggc tgagaagtca   3780
gtagctgacc gtgacgctga tttctcccgc tgggaggcat ggcctaaaga caccttgctg   3840
caaattggga tgaccttgct tgaaatctta gagaatagcg tattcttcaa cgggcaacct   3900
gtcttcctcc gcaccttgcg cactaatggc ggcaaacatg gtgtttacta cctacagact   3960
agtgaacacg taggtgagtg gataactgca ttcaaagagc acgtagcgca actgagtcct   4020
gcctatgctc cttgcgtcat ccctccgcgt ccgtgggtat cacctttaa cggcggtttc    4080
cacactgaga aagtagcaag ccgtattcgt ctggtaaaag gaaaccgcga acacgtccgc   4140
aagctgacca aaaagcaaat gccagaggtt tacaaggctg ttaacgcgtt gcaggcgact   4200
aaatggcagg ttaacaagga agttttacag gttgtggaag acgtcatccg tctagaccta   4260
```

```
ggttatggtg taccttcctt taaaccactc attgaccgcg agaacaagcc agctaatcca   4320
gtgccgctag aatttcagca cctacggggc cgtgaactga agaaatgct tacgccggaa    4380 caatggcaag cctttatcaa ctggaaaggt gaatgtacta agctgtacac cgctgaaact   4440
aagcgcggaa gcaaatcggc ggcaaccgtt cgcatggttg gtcaggcccg taaatatagc   4500
cagttcgacg caatctactt cgtgtatgca ctggacagcc gcagccgcgt ctacgcgcaa   4560
tctagcacac tctcaccgca atcaaatgac ttgggcaagg ccttgctccg ttttaccgaa   4620
gggcagcgtc ttgatagcgc tgaggcgctt aagtggtttt tggtgaacgg ggctaataac   4680
tggggttggg ataagaaaac ttttgacgtg cgcaccgcta acgtgctgga tagtgaattt   4740
caagacatgt gccgcgacat tgcagcggat ccgctgacct tcactcaatg ggtaaatgcc   4800 gactccccctt acggcttcct tgcatggtgc tttgaatatg cgcgttatct ggatgcactg   4860
gatgaaggca cgcaagacca attcatgacg cacctcccag tccatcaaga tggtagttgt   4920
tctggtatcc agcactacag tgctatgcta cgcgatgcag taggtgcgaa agcagtaaac   4980
cttaagccct ctgactctcc tcaagatatt tatggtgccg ttgcgcaggt agtaattcag   5040
aagaattatg catacatgaa tgcagaggat gcggaaacct tcacttctgg cagcgtgact   5100
ttaacaggtg cggagctgcg tagtatggct agtgcgtggg atatgatagg aatcactcgc   5160
ggcctgacca aaaagcccgt aatgacacta ccttatggca gcacacgtct aacctgccgt   5220
gagtcagtga ttgattatat cgttgattta aagaaaaag aggcccaacg ggctattgcg    5280
gaagggcgta ccgccaatcc tgtacaccct tttgataatg accgtaaaga cagcctgaca   5340
cctagcgcag cttataacta tatgacagct ttaatctggc cttctatttc ggaagtggtt   5400
aaagccccta tagtggcaat gaaaatgatt cgtcagcttg cccgtttcgc agctaaaagg   5460
aatgaaggct tagagtatac cctgcctact ggcttcatct tgcaacaaaa gattatggct   5520
actgatatgc tccgcgtatc tacttgcttg atgggagaaa tcaagatgag tctacagatt   5580
gaaacagacg tagtggatga acggcaatg atgggcgctg ctgctcctaa cttttgtgcat   5640 ggtcatgatg ccagccacct tatcttaaca gtctgcgacc ttgttgataa agggattaca   5700
tctatcgcag ttattcatga ctctttttggc actcatgcag gccgtacagc cgaccttcgt   5760
gatagcttaa gggcagaaat ggtgaagatg tatcaaggcc gtaatgcact gcaaagcctg   5820
ctagatgagc acgaagaacg ctggttagtt gataccggaa tacaagtacc agagcaaggg   5880
gagtttgacc ttaacgaaat cttagtttca gactattgct tcgcataata ttaataggcc   5940
attccttcgg gagtggcctt tcttttacct actacctgta acatttcatt aacataaaag   6000
tgtctcacat gtgagactta tttaccggac actataggat agccgtcgga gacgggaaag   6060
aaagggaaga taaaggatat aaaggaagta ataggtatta aaggttatat aggttatcta   6120
ggaataccta ttaccttctt ccttcctctt attaccactc agaggaaggg cagacctagg   6180
ttgtctcaca tgtgagactt cgtatttacc ggacagtata gataagatta actcactttg   6240
gagatttaac catgcgcaac tttgagaaga tggcccgtaa agctaaccgt tttgacatgg   6300
aagaggggca gaagaaaggc aagaagctga ataagcctgt ccgtgaccgt gcatctaaac   6360
gcgctgcgtg ggagttctaa gttatggcta ttattcagaa tgtaccgtgt cctgcctgtc   6420
aaaagaatgg acatgatatt actggcaacc atctcatgat atttgatgat ggtgccggct   6480
actgtaatcg tggacacttt catgataatg gtagaccttta ctatcacaag ccggaaggtg   6540
gcatcgagat aaccgagtta tctattactg gcaatatcaa atatacacct tctcaattca   6600
```

```
aagaaatgga gaaggaaggg aagataagcg accctaaatt acgtgccatc gcacttggtg    6660
gtatgcgtat gaaagaccgt tgggaggtca tgaatgaaca agaaagggca gagcaagaag    6720
cagagtggaa acttgatgtt gaatggttcc tcacgcttaa gcgtaagaac cttgtttcca    6780
ggcacattcg cggcgacatt tgcgcattgt atgatgtacg tgttgggcac gatgaagagg    6840
gtagagtctc acggcattac tatccgcgct tcgaaaaagg tgagctagta ggcgctaagt    6900
gtcgcacatt acctaaagat tttaagtttg gtcatttagg taaactcttt ggtatgcaag    6960
atcttttcgg tatgaatact ttgtctcacg tgttagacaa gggaagacga aaggattgct    7020
tgctcattgt cggcggcgaa ctggatgcac tagcagcgca gcagatgctc cttgattctg    7080
ccaagggtac taagtgggaa ggccagccat accatgtatg gtctgtcaac aaaggcgagt    7140
cttgccttga agagatagtg cagaaccgtg agcatatcgc ccaattcaag aagattatat    7200
ggggttttga tggagatgag gtagggcaga agcagaatca gcaagcggct cgcctgtttc    7260
ctggtaaatc ctatatcctt gaatacccct ctggttgcaa agatgctaac aaggcattga    7320
tggctggcaa ggctaaagaa tttgtagatg catggtttaa tgccaagtca tctgatgaag    7380
tctttggtag ccagattaaa tctatcgcat ctcaaaggga taagctcaag gctgcacgtc    7440
cagagcaagg actgtcatgg ccttggccta agctgaacaa ggtaacgcta ggtattcgta    7500
agaaccagct tatcattgta ggtgcagggt ctggtgtagg taagactgag ttccttcgtg    7560
aagtagttaa gcacctcatt gaagaacacg gtgaatctgt aggcatcatt tctacagaag    7620
acccgatggt caaggtgtcc cgtgctttta tcggcaagtg gattgataag cgtattgagt    7680
tacctccaac caacgacccg aaagaagacg gataccgtga ggtgttcgac tataccgagg    7740
aagaagctaa cgccgccatt gattatgtag ctgatacagg taagctgttt gtagctgacc    7800
tagagggtga ctattcgatg gaaaaggtag agcaaacttg cctagagttt gaggctatgg    7860
gtatttctaa tatcatcatt gataacttaa cggggattaa attagatgag cgtgctttg    7920 gtgggaaggt tggtgcactt gatgaatgcg tcaagcggat tggtactatc aaagaccgac    7980
acccggttac tatattcctt gtatcacacc ttacacgtcc tccggcaaac cgtacccaac    8040
acgaagaagg tggcgaagtt atcctttctg acttccgagg ctcaggcgct atcggattct    8100
gggcatctta cgccttgggg attgagcgta atacaagagc tgaaacgctt gacgaaagga    8160
ctaccacgta catctcatgt gtcaaagacc gcgaccaagg tatctacact ggaaccaagg    8220
tcatgcttaa gggtgacatt caaaccggac gtttaatgga accacaagcc cgtactaagt    8280
catttgatac aggtgaagca aggcaacaag aagtaccaga tttaccggat actatagaag    8340
agactacctt cgatgaagaa agtgagttct gattagtgta tttatcaggc ttgtctcaca    8400
tgtgagacag gctcttatta agtacattaa ataactggag attgattatg tataacttag    8460
tgttgaatgt aggtgacttt gtacgcaaca tcaagaaaga ttcaagtcgc tatctttgcc    8520
gtggtgttgt aaccttttgta ggtgagaacc tgtattatgt agaatatcgc agtggtgtta    8580
agcaatatta ccacaagaag acagcacata aatatcttga aaagattgta gagataaaca    8640
atcaatgtaa gtgcatacat gatgaggttt gcgataaatg tgctcgccag atgcttaaga    8700
atttcctagc tcctctttat tatggtgctg gtcctcaaac actagcagag tgcatggcag    8760
aaaagaaaac cacactcaag aaagagcgtc gcaatgtaat cactggtaag actcaaagtg    8820
agatgattaa gcaatgtggc actgcattag gtgttacaca gtttaatact cgtgcattgg    8880
gtaaatccac aggacaagct atggtaaaga ttggagaagc catgatgcat ccaaatgtac    8940
ctgtgcgaat catggatgtt gaccatgcaa tcacagaaca aggtacgcaa cgacgtgtaa    9000
```

```
ttaataagca ttttgccgac actatagaag gcattattcg taagcaaggg ttgaaaggtc    9060
ttcacatctt aaatggtgaa gaattactgt acctacctat cgttactgaa gaaacatacg    9120
tgaatatcta aggagttaat catgactaag gtattaattt atatgcgtgg acctcataaa    9180
tgctatgcag ttgtagcacc aaatggtgtt aagccttatc gtacttcaaa agattggca    9240 ttaataggtg ctagtagtag tgcaagtttc caaatggaac tttttggtca ttggactgaa    9300
aggcaattcc gtgaggattt taaagtcatt ggcagcttca tggtgaaata tgcagaataa    9360
acatagtctt agaatgttcg atggtcatga aaacctgcaa gccaagatta ctaaccaagc    9420
cttcctgttc gcacagttaa ctatggctga ggctaagaag aatagtctca ctcgtgaaca    9480
ggttatcaag gaggccactt gggaaccaca ccaaggtaaa tatatgggcc acaaattaac    9540
tgtaacacgc agtcgataag tcaagggttg tccaacgtgt tggacagcct ttcatcatat    9600
tgattgggag gtattaaatg actaagttta ctatgcaaga cctcattaaa ttacgtgatg    9660
aaatagaatc accggaagtt aatacagagt ttcactacat tgatccacga gataaacgag    9720
agattcctga ttatcagatt gagacggagt taatgtatga agattattga ttggaagaag    9780
gaagcagaag gccgtatcct agtgatggat gcggaggcta aaggcctgct gggtgctatc    9840
cgctacggtc atcgtgaaga tgtacacatt atttgctgca tggacttgct caccactgag    9900
gagttcctct tcttcgaccc atatgagatg cgtgaccctg aagcaaggga acacttgaaa    9960
gagtgggaag gccatcaaga tgggaccttg gttgatggtg ttaacttcct aaagcactgt   10020
gaagccatcg tctcacagaa cttcctaggc tatgacgggc ttctctttga aaagccttc   10080 cctgacatct ggaagggatt taactacacc gagaggcgcg gcaagggcag actacgtgct   10140
gacttgtgtc cggtacgcgt catggatacg ctggtcatga gtcgcctgtt aaacccagat   10200
agacgccttc ctccgcaagc atatgccaaa ggtatgggta acgttgcccc tcactcaatt   10260
gaggcgcacg gcattcgtat aggccgttat aagccggaga acgaggattg gtctaaacta   10320
actgaccaca tggtacatcg tgtacgcgag gacgtggcga taggccgtga cctattcctc   10380 tggctatttta acgagaatg gacgagcac aaacgccgtg gcgtaataa acgcactggc   10440 ctaggtattg agacagcctt ccacatggag tccattgtga cgctggagat gagccgtcag   10500
gccgagcgtg gattccgtct ggatatagat aaagcattag cacgatgcga ggaattggac   10560
gctaagattg atgagacagt cgcagcgttc cgtccgcaca tgcctatgcg tatcaagtct   10620
aaacctttta aaccggaaga aaagaatgaa gtatgccaac gcgcaaatga gtatggagct   10680
agcaacaata tacctactgt ccttgacccc tctcactttc ttcacgcaga gagcgagga   10740 gatcgcaaga cagtatggag tgtcactact aagtctggtg attggtcggc tagcgtcaag   10800
aaaagacttc ctcaccttag aggaaaccgt aatgacacgc caagtgtcaa gtggattggc   10860
gcttactcgc ctgttacttt cgaagagatt cccttgggta acagggatac agttaagcaa   10920
gtgctctatg attatggatg gaaagtgtt gaatttaacg ataccgagca agcgcatctc   10980
gatgagcatg gcgtattacc caagccttgg agtgggaaga taaatgaaaa gtcccttact   11040
ttatggcaag agagagccgc acgtgaaggt aaaacagtcc ctgattggtg cttgggtatc   11100
gctgcatggt acatactcgt atcccgtcgt ggtcagatcc tcaaccgtgg tgacgttgaa   11160
gccttcgacc agaagggggt gtggccttcg caagctggta tacgaaagtg tcgcggcctt   11220
gtacctgtag catttaacaa ggagttagga atcaatgcgc agcaatacta cgaaaggtac   11280
ggatgctggc ctacgtcaga caaggatgac ggagaatggc gtgtgccagc tattgctatt   11340
```

```
agtattggaa cttctacgtt ccgtatgcgt catcgtaacg tggttaatat tcctgcccgt   11400
ggcttgtatc ctttacgtga tttattcata gcagggaaag gcaagctaat ccttggttgt   11460
gacggtgcag gtcttgaact gcgtgtcctg tctcacttca tgaatgaccc tgagtaccaa   11520
gagattgtac tgcacggtga tattcatacg cataaccaga tgaaggctgg tcttcctaag   11580
cgtgatatgg cgaagacatt tatatatgcc ttcctatatg ggtctggtat agctaacctt   11640
gcagcagtat gtggtgttac tgaggaagaa atggaggaag ttgtggcaag atttgaggtt   11700
gaactaccat ctcttgcacg tcttcgtgag aatgttatcg cacaaggtaa caagtttggc   11760
tacctacaag cacctgatgg tcattggggt cgcatccgta tgtctggtgg tgaacttaaa   11820
gaacacacta tgcttaacgt actactccag atgactggtt ctctgtgtat gaaatacgca   11880
ttggtcagag cgtttgcagt gatgcgcaag gaaggtgtgg ccttagatag catgggaaac   11940
ccttgcggta tagctaacgt gcacgatgaa atccagatgg aagtccctga agatgaggtc   12000
ttgtatctca actacgactt gccttcacc ttagaagggt tcgaaacaga gaaggctgct   12060
gtgaaagcag tgttcgatgc agaggagaaa cgtgttcatg tggattctga aggacgtatg   12120
tggtctgctg caaatctcgt tagtgttgat gctggtgtac ttcattgcca gcgtcgttat   12180
caccgtgcag ggcatatcat tgccgacgca atgacctggg cgggtcagta cctgaagatg   12240
cgttgtccga tggcaggtga gtataagatt ggtgcaagtt ggaaggaaac acactgatgg   12300
acaggtttga tattgtttgc ctattctcta ccttctttct tatattcctt atgcttgctt   12360
gctatggaag tatgcgatta gatatacctg atgaagagga gggttacgat tgatgcaggc   12420
atctttattt attcttggag tcatattatt tatggtagta ttctgggctt tctctggcat   12480
tgacccagat tgtgatggta actacgactg agttatactc aaggtcactt acgagtggcc   12540
tttatgaata acttattcct acttattttg tctaacatga tttactggac actatagaag   12600
gaaagcatag gtaatctagg tttataaggt agtataggta attaagtaaa tataggagat   12660
ataaatatgt ctatggtaac tactctggta ttcgtggctc aatactttcg tggtcttgct   12720
aataagttca agtccaaggc tatcaaagct attgaggctc gcatcgaagc agtacaggca   12780
gagcaagtta agttgaaga acatcgtagt tctcaaatga ttgactgtca taaccgctac   12840
tatgcatctc gtgatgaact aaatgcacgt caagtcaaag aggtagaaga tatgctggca   12900
cgtcaccagc aagagcgtga cagcctgaaa gctgaatttg aagagaacaa ggcatcaatt   12960
gctcttgtac atcaagctgc atctgacagt ctgaagaaag agattgttat gctggaaatc   13020
gaactggata acctgaccaa ataagggggg gttatgatgg aagaagtaat tcaagctaaa   13080
catgtaggta ttatctttcg cgatctagag cagcgtaaag ttgcaggtca tactcgtctg   13140
gctaaagagg aagacaccgc aatcactact gtagaacaag cagatgccta tcgtggacca   13200
gagttcactc aaggtgaaac ttgtcaccaa ttgagcctat caatttgtga cactatggct   13260
attgtaaatg tgcaagaagt cgaagagggt gagtgtgtca gttacatcta ccctttagat   13320
actattgcac gcattaaggt aatccataag taattactag acactataga acaataggtc   13380
ggcttagttc ggcctatgat tgtaaagtgt tgttgatgtt gaaccattgt gcatcttgca   13440
caacccgata ccgtataggg cttttctagt agtacatgct tgtgctcagt acaaagctaa   13500
ctgacaatag gagactaaat aaatggcacg tggtgatttt gattttggtg ctcaggttac   13560
taaatctgaa ggtaaagtct ttaagaatcc agaagtaggt gatcatgaag cagtaatctc   13620
tggcatcatt catgttggtt ccttccaaga catctttaag aaaggtaata ccactgaagt   13680
taagaagcca gcaaactttg ttctggttaa gattgtcctg atgggtgacg atgacaagaa   13740
```

```
cgaagatggt tctcgcatgg aacaatggat ggctgtgcct ctgaagtctg gtgataaggc    13800
aacactgact aagttcctga atgcagttga ccctaaagag ttgctgggtg gcttcgatga    13860
tttcattggt gaatgcctga ctgcaacgat ggtcggttct ggtgataaga atgacgatgg    13920
ctcattcaag tatgttaact ggaagggatt tggtggtatg ccggacaagc tgaagaaact    13980
ggtcattgct caggttgaag aggaaggtct gtctatgaca ggtcacatta ccttcgacaa    14040
gctgaccaaa gaaatccttg atgacatccc agccaacttg gtgcgtcaat acttcctgaa    14100
cgagacgcct cgtggtaaga acctgtctgt tgctggttct cacgtagaag caatcattaa    14160
agctgctcgt gaagaagacc cagaatggaa gaaggctaag aagaaagacg aggaagatgc    14220
taccccagct aatcgtaaat ctctggatac tggtgagtct gttccacagg aagtacctga    14280
agcagaagat actcctgcac cggagatgga tgaggacgcg gaatattaag gagaaaggat    14340
gaaagtacaa atcgtaaccc tgcactgcaa gaaaggaatt acaactcttg gcggcaacac    14400
ttttcactcc ttctctgaag gggacacata tgccgacctg cactacatct ggcgcgacgg    14460
acagcacgtg gtgaactaca gcgacccagc tacggggaaa cgccacggcg tatcgcttcc    14520
ggcgcatgac attgctcagg tgaacacagt tttataaagt ctcacgtgtg agacaaatcg    14580
gtgtccggta tttactggac actatagaag agaagaattt taatcggcga taatgccata    14640
accaacaaaa ggagaattta atatgttcaa gattgaaact atcgtaaacc gtgttgttaa    14700
aggtgctgct ctggtatccg ttgagtcttt cattatcgtc gatgaaactg atcaactggt    14760
agctggtact aaggcttacg ataccgtga agaagctcag gctaagattg acagcatggg    14820
taacttcgct gctggtctgg agttcgctcg tgcttgcttc cctgagcagg ctgacaaagc    14880
tcagattggt aaggctaata tcgtagctga atatctggat tgggttgctg ctggtaaacc    14940
agtgaaagaa gttaaggctg ctgaagaagc tgaagctcca gcagaagaag tagctgcacc    15000
ggaaactccg gtaagtgaag aggaagaatt ttgataatag caggtgttgc ctctgttagt    15060
cctagctgac tatcacgctc acctcatcta atgccctgtc tgccttagtg taggcagggt    15120
cttttgcgta atagttattg gagaatgaat tatgccgact attgaatctc gaattgaact    15180
ggacattagc tacaatgcaa tcaccagaca gtatattggg gttgcctatg attacaaaac    15240
tggtgagaag ctagtggagg tgagacaatg ggatgactat tggttaagac agaacctcca    15300
tgatgcggtg tcctccttcc tgaaggagtg gcctacatgc gaccaaactt cgacttcgga    15360
gctacagtat cggaagacaa taacctgttg ctgtggccaa ctgaaggtaa tcgaatcgct    15420
ttaatagatg ctgatatgtt accttacatc atagggtata caatcagtga tatgacttat    15480
gtacgagcca caactcgtgt taagtcaggg caagtccct caatcaaaga tacacctgag    15540
tgtaagcaag cgtgtgaccg tgtgaactcc ttgcttaact cttgggtgta tgcagcagaa    15600
tgtgatgcag ctaagttgtt catgacgaaa tcagaagcta acttccgtgt ccgcctagca    15660
ttcaccaagc cttataaagg tcaacgtaag accgagaagc ctccattctt ctatgaattg    15720
cgagagcatc tcttagaggt tcacggtgca atcttggcag atggagagga agcagatgac    15780
ctcatgagta tcgcacaatg ggacagccac cgccgcttcc agcaagatac aggtaacgag    15840
ttccctatcg gtagtccaga gcataaagca ttctctgata cttgcatcgt ttccttggat    15900
aaggatttga tgattgttcc cggttggcat ctacagccgg tcaagagaa gaaatgggta    15960 gagcctatgg gttggcttga gctacgccgt aaggctaatg gcaagtcaa agatctaaaa    16020 ggtgctggcc tcatgttcca ctatgcacag atgattatcg gtgatgatat tgataactat    16080
```

```
gctggcatac caggtcgtgg tgctaaatat gcctatgatc ttctcaaaga ttgtaagaca    16140
gagaaagagt tgtacatggc agtgctgggt gcttacaagg ctaagttcgg catggacaa    16200 gttaaaatta agaattaccg aggtggttat cgtatcggca aagcctttga cctaatgctt    16260
gagtgtggtc gcttatctca catggcaaga ttcaagggtg atatatggcg agccgataag    16320
aacccaatct tgtggggaga tgatgcggaa tggttagcaa attaaaatca tcggaggtgg    16380
cagcttataa gaaggaattg ctagataagc aaggatggaa atgccctctg tgtggcggca    16440
gtctcaaagc tgtcacacct gtaaaccgtg tacttgacca tgaccatgag acaggattct    16500
gccgcgctgt tgtatgccga ggctgcaatg gtgcggaagg gaagattaag ggtgttatct    16560
ctggttatgg taaggctggt aacaaccgtt acttccagct tcaatggtta gagcgactat    16620
atgaatactg gaagttacat agtacgcctc agacagataa gttatatcac aaacatcaaa    16680
cggaggcaga gaagcgcgag gctaagaacc gtaaggcacg ccttgcttat gcaagaaaga    16740
aggaggttaa agttgggtaa gctgcgcagc ttgtacaaag actccgaggt acttgatgca    16800
atcgagcaag ctaccgacga gaaaggtaat gttaactaca atgagatggc acgtgtatta    16860
tcgtgtcata ctgtgggtaa gaagattacc cgccagttgg ctcgatactg gcatggtcaa    16920
ttcaagaaga ccaagaagaa tggtgattac taccagaccc ttctgcaaga agataagcgt    16980
atcaaagaag agcgtaagct caggactcct gaccgctacg aggatttggc tattgtgcca    17040
ttgcctgact cgcctcatcg aagtgtactg gtgatccctg atactcatgc accttatgag    17100
cacccagata ccctagagtt ccttgcagcc gtggcagcac gttaccgtcc agacacagtg    17160
gtacacctag gagatgaggc agacaaacat gccctgtcat ccacgattc ggacccaaat    17220 ctggatagtg ctggcatgga gttagagaag gctcgtatct tcatgcacaa attgcacaag    17280
atgttccctg tgatgcgcct gtgtcactct aaccacggct ctatgcactt ccgtaaggca    17340
agcgccaaag gcatccctgt gcaatacctg cgcacctatc gtgaagtctt cttcccgcag    17400
ggaggtggcg accagtggga ttggcaacat acgcacgtcc ttgagttgcc gaatggtgaa    17460
caagtggcat tcaagcatca acctgctggc tctgtcctag cagatgcagc gcatgagcgt    17520
atgaaccttg tgtgtggtca cttgcacggt aagatgtctg tggagtacgc acgtaataca    17580
catgaacagt attgggctgt gcaaggtggc tgcttaattg atgagtcatc ccgtgcattt    17640
gcctatggtc gtgagtctaa atacaagcca gcattaggtt gtgtggtcat tctgaggggt    17700
gtgcctcaca ttgtcccgat gcaaaccaat agcgacaacc gttggattgg caagatttag    17760
ttgacactat agaacaaagg gctaggtaag actttatcgg ctggcgtatc caaatgatat    17820
tgcactagcc cttgattgta tagtgaatgg aggattcaat atgtcacact atgaatgtaa    17880
gaagtgtcat aagcgttatg attactgtac ttgtggtcaa gagaaaacat cttttaaagt    17940
tggagacaag gtatttcgta tgaaaaaga ttcgattcct tggaatcaat actgcaaaga    18000
agctggtatt gaccctgata gccctgtaac catgatgat attgatggca ttaacttgtg    18060
ctttcgtgag gtgagggggta caggttggga ttccaaaaaa ttcaaacttg catctgataa    18120
gttagacaac aatatggtaa ttaagcctaa gcactacgag ttctttgatg gcgtagaggc    18180
aatcactatc attgcccgca gtatgaccga gaagcaattc gctggctatt gcatgggtaa    18240
tgctttgaag taccgtctac gtgcaggtaa gaagttcaac actgaagaag acctgaagaa    18300
agcagattac tacaaagagt tattccagaa gcatcgtcac gaatgtattg atgaggatat    18360
ttgatatgaa tatctttgag ttcctaggtc ttccagaaga ccaccgcaat cacccattca    18420
tgctggtgaa gcatcgcggt gaagttcctg agaagaaatt aactttttcca tgttatgcac    18480
```

```
aggtgaaacg agatggtatc ttttctgctg ttgttgttcg cactgatggt gtcgttggca   18540
tttttggtcg cactggtaag aaattggcaa acactgaagg actcgaacaa gcctttgcta   18600
cctttccggt tggcatttat cttggtgagc ttcagtctat ggccattgat atctaccttg   18660
aggcaatctc tggggttgtg aaccccaatc gcactgagcc acttgatttc ataggccagc   18720
agattaaaga caacctgtat atcgacttct tcgatatgtt aactattaag gcattccatg   18780
atggattcac tgatgtttct tatctcaaac gttacgatgc tttacatcgt cgtatcggcg   18840
ctcatcttag cgggtgcaac gctatccttc ctatcactcc ttgccataat gagcgagaag   18900
ttgaagcgtt tgcgcaagag caaatagatg caggacgtga gggtgctgta ttcaaactgg   18960
actgcgatta tgaagcagga cacaaaggtt atcgtcagac taaagaagtc cgtaaggtaa   19020
cctatgacct tacttgtatt ggctttgaag aaggtaaagg caaatacaaa ggtaaggtag   19080
ctaacctcat tttcaaatgg aaaggaggca agacaatcaa agctatgtta ggtaaggggt   19140
ggactcatgc agatgcagag cagatgttcc acgacattaa acatggtgga cgattgaatg   19200
tcattggtaa aatctttgaa gtcaaaggtc ttcaggattc aagcaagggc aacattcgtc   19260
tgcccaaagc gggagaatta agacatgaca aagatgaacc agatttcttt tgatagcatg   19320
aaggcaactc gtgcagttga ggtagcagaa gctatcttcg aaactttatc ctgtggcatg   19380
gaagtgccat atactttact tgctgatgca gaagaacttg gtctttctgt agaagctatc   19440
caagagaagg ttgacgaatt atatggtaca gacgaagaag aaaccgacga tttcatttga   19500
aggaatggag atgcttgaga tgattctcaa gccttcttct cctaaggtga ctaagactca   19560
tgaagagtta atcgttgatg aagttaagcg ttacatcatg gattgtgtca gagcacaact   19620
ggtggtccaa tgatacgtcc agcctccttc ctagatattc ctgagattat aaaccttggg   19680
aataaatatg tggaagagga agtcaaggtt gtagcccacc actcagcctc atggaatgca   19740
gaacaaagtg ccataacctt tgtgcatctc ttaatagaga cccaccactc agcctcatgg   19800
aatgcagaac aaagtgcaca taaccttttgt gcatctctta gtagagaaga tttatcccta   19860
tgggttgctg tagatgaagg gcagattgta gggttcctgt gggctggcta tcacgagttg   19920
gccccttgga cacctgtaag agttgcctct gacattctct tttatattat accagagaga   19980
agggaacac tacttggtat gcgcttaatt aaggcattga acagtgggc atcagataat   20040
gaatgctctg aagtgcgttt aagtattgca agtggcatca acgaggagcg cgtagggcgc   20100
atgtacaaac ggctcggctt tgaaccgttt ggcactgtgt ataacctgaa gttctaaaga   20160
ggagatatac aatggttttt acgcttgagg acttcgttgg tgactggcgt caaccgcgg   20220
ggtataatct tgatcaggtc ctggagcagg gcggagtttc gtccttattc cagaacttag   20280
gggtaagtgt tacgccgatt cagcgcatcg tgctgagtgg agagaatgga ttgaaaattg   20340
acattcacgt tatcattccg tatgagggtt tgagtggaga ccagatggga cagattgaaa   20400
agattttcaa agtggtgtat cccgtcgatg accatcactt taaagtaatt ctgcactatg   20460
ggacccttgt gatcgacggt gtaacgccaa acatgattga ctatttcggt cgcccttacg   20520
aaggtatcgc cgtcttcgac ggaaaaaaaa tcactgtcac gggaacatta tggaacggaa   20580
ataaaattat cgacgaacgt ctgatcaatc ctgatgaag cctgttattt cgcgttacga   20640
tcaatggagt gaccggatgg cgtttatgcg aacgtatttt ggcttaaaga ggagatatac   20700
aatgggtgtt gtaaagaaag catttaaggc tatcggtctt gctcaagatg caccacgtat   20760
tgaagccaaa gtcccagcac agcagcttga gcgtaagcct gagactgaag ctgaagatat   20820
```

```
tcaaattggt gcaggggatg atgctactgc atctgcaaaa ggtaagcgtg gccttgtccg   20880
tccggtagct tctagcttga aggtgtaata tgaaacagag catagatttg gagtatggag   20940
gtaagcggtc taagatacct aagctatggg agaagttctc caataaacgt agctctttcc   21000
ttgatagggc gaagcattac tccaaattaa ccttgcccta tctgatgaat gacaaaggtg   21060
ataacgagac ttcgcagaat ggatggcaag gtgtaggtgc tcaggcaacc aaccatctag   21120
ccaacaagct agcgcaagta ctattccctg cacagcgttc cttcttccgt gtagacttaa   21180
ctgcacaagg tgagaaggtt cttaatcagc gtggcctgaa gaagacagag ctagctacca   21240
tcttcgctca agtggaaaca cgggcaatga aagagttaga gcaacgtcaa ttccggcctg   21300
ctgtagtaga agcatttaag catcttattg ttgctggcag ctgtatgcta tacaagccga   21360
gcaaaggtgc aatcagtgct atcccaatgc atcactacgt agttaaccgt gataccaatg   21420
gcgacctgtt agacattatc ttgctacaag agaaagcctt acgtaccttt gacccagcta   21480
cacgtgcggt agtagaggtt ggcctgaaag gtaagaagtg caaggaagat gacagcgtta   21540
agctgtacac acatgctaag tatcttggtg atggattttg ggaactcaag caatctgctg   21600
atgatatccc tgtgggtaag gtgagtaaaa tcaaatcaga aaagctacct ttcatcccat   21660
taacttggaa gcgaagctat ggtgaggatt ggggtcgacc tcttgcagag gattactccg   21720
gtgatttatt cgttatccaa ttcttatctg aagcggttgc ccgtggtgct gcgctgatgg   21780
cagatatcaa gtacctgatt cgtcctggtg ctcaaactga tgttgaccac tttgttaact   21840
ctggcactgg tgaggttgtc actggtgtag aagaagacat ccatattgta cagttaggta   21900
agtacgcaga cctcacacct attagcgcgg ttctagaggt atacactcgc cgtatcggtg   21960
ttgtcttcat gatggagaca atgacacgcc gtgacgccga acgtgttact gctgtagaaa   22020
tccagcgaga tgcgttagag attgagcaga acatgggtgg tgtatactcc ctctttgcta   22080
ctactatgca atcgccagta gcgatgtggg gtctgctgga ggcaggggag tccttcacta   22140
gtgacttagt ggaccctgtg attatcacag gtattgaagc tttaggacgc atggctgagt   22200
tggataaact ggctaacttt gctcagtata tgtcactgcc attacaatgg cctgagcctg   22260
tcctagctgc tgtgaaatgg cctgactata tggattgggt gcgtggtcaa atctctgctg   22320
aactgccgtt ccttaaatcg gctgaagaga tggcacaaga acaggaagca cagatgcaag   22380
cacagcaagc acagatgctt gaagaaggtg tggctaaggc cgtgccgggt gtaattcaac   22440
aagaacttaa ggaggcgtaa tgtctttctc atttactgaa ccgtcaacca ctcaccctac   22500
tgctgaagag ggtccggtag aaaccaagga ggtaacaact gatgctgcta ctactgatgc   22560
tcctgctgac gctggcactt ctgtacaaga tgacaatgct ggtgcacaac tactgaaga   22620
caccggagga gaagcttctg gacagccttc agaaaaagga gacaatggcg gagagaatgg   22680
tgaacctaag ccagatgata ccgcgaccga cactgaggaa gtgcaatact tcttcggaga   22740
acatgaagta acagtagaca tcccacagga tgtaactgac agccttaaag agaaaggcat   22800
tgatgccaag caggttgcca aggaactcta ttccaaaggt ggcaagtttg aactgtcaga   22860
tgcaaccaag cagaaattgt atgatgcttt tggcaagttt cggtagatg cttacctatc   22920
aggtctaaag gctcaaaatg aagccttctt cctgaaagaa gccaacgcag ctaaagagtt   22980
ggaagcagct aacacccaac gcttctctga tgtttctaag gaaattggtg cgaagaagg   23040
ttggtcccgt cttgaggagt gggcacttga agcgctgtct gatgacgaac taatggcatt   23100
caatgcggta atggaatctg caaccagta cctgcaacaa tatgctgttc gtgaactgga   23160
gggtcgtcgt aagcaggcac aggggatga taagccatcc ctgattgagc catcagcacc   23220
```

```
tgctaaggct aatgaagaga atggcccact gacgcgagat cagtacgttc aagcaatcgc   23280
aactcttagc cagaagtacg gcaatgaccg taaagctatg gcagaagctc aggctaaact   23340
ggacgcccgt cgccgtgctg gcatggctcg cggtatctaa ttcagtattt actggacact   23400
atagaaggga gaaaagttct ccctagttat caatttgatt tataaggaga ttataataca   23460
tgtctacacc gaatactctg actaacgttg ctgtatctgc gtccggtgag gttgacagcc   23520
ttctcattga gaagtttaat ggtaaggtca atgagcagta cctgaaaggt gagaacattc   23580
tgtcctactt tgatgtacaa actgttactg gcactaacac agtgagcaac aaatatttgg   23640
gcgaaactga gttgcaggtg ctagcaccgg gtcagtcccc taatgccacc cctactcagg   23700
cggataaaaa ccagttggta attgatacca ctgtcattgc tcgtaacact gtggctcaca   23760
tccacgatgt acaaggtgac atcgatagcc tgaaaccaaa actggctatg aaccaagcca   23820
agcaactgaa acgtctggaa gaccagatgg caattcagca gatgctgtta ggcggtatthg   23880
```

```
acctgatgta gtgaatggta ctcaatcacg catgggtaca actcatattg caaagatact  25620
tgatgcgggg actgatgaca tggctactca tcattatcgc agaggtgatg gtgatgaaga  25680
gtatttcttc acgttgaaga aaggacaagt tcctgagata tttgataagt atgggcgcaa  25740
atgtaatgtg acttcacaag atgcacctat gacctacctc tctgaggttg ttaatccaag  25800
ggaagatgtg caattcatga cgatagctga tgttactttc atgcttaatc gtaggaaagt  25860
agttaaagct agtagcagga agtcacctaa agttggaaac aaagccattg tgttttgtgc  25920
gtatggtcaa tatggtacat cttattccat tgtaattaat ggggccaacg ctgctagttt  25980
taaaacaccg gatggtggaa gtgcagacca tgttgaacaa attcgaactg aacgtatcac  26040
ttctgaattg tactctaagt tgcagcaatg gagcggtgtg agtgactatg aaatacaaag  26100
agacggtact agtatattta tcgagagacg ggatggtgct agctttacaa taacaaccac  26160
cgatggtgca aaaggtaagg acttagtggc tatcaagaat aaagttagct ctactgacct  26220
actcccttct cgtgcgcctg ctggttataa agtacaagtg tggcctactg gcagcaaacc  26280
tgagtctcgt tactggctgc aagctgagcc taaagaggga aaccttgtgt cttggaaaga  26340
aacaatagct gctgatgtat tacttgggtt tgataaaggc acaatgcctt acattattga  26400
acgtacagat atcatcaacg gcatagctca attcaagata agacaaggtg attgggaaga  26460
tcgtaaagta ggggatgact tgactaaccc tatgccctct tttattgatg aggaagtacc  26520
ccagacaata ggtggaatgt tcatggtgca gaaccgccta tgcttacag caggtgaagc  26580
ggttattgct tctcgtacat catacttctt cgatttcttt cgttatacgg ttatctctgc  26640
attggcaact gaccccttg atattttctc agatgctagt gaagtctacc agctaaaaca  26700
tgcagtgacc ttagatggcg ctaccgtgtt gttctctgat aagtcacaat tcatactgcc  26760
aggcgataag cctttagaga agtcaaatgc actgcttaag cctgttacaa catttgaagt  26820
gaacaataaa gtgaagccag tagtaactgg tgaatcggta atgtttgcca ctaatgatgg  26880
ttcttactct ggtgtacgag agttctatac agactcttat agtgacacta gaaggcaca  26940
agcaatcaca agtcatgtga ataaactcat cgaaggtaac attaccaaca tggcagcaag  27000
caccaatgtc aacaggttac ttgtcactac cgataagtat cgtaacataa tctactgcta  27060
cgattggtta tggcaaggaa cagaccgtgt acaatcagca tggcatgtat ggaagtggcc  27120
tataggtaca aaggtgcgag gtatgttta ttctggtgaa ttactttacc tgctccttga  27180
gcgaggagat ggcgtgtatc tggagaagat ggacatgggt gatgcactaa cctacggttt  27240
gaatgaccgc atcagaatgg ataggcaagc agagttagtc ttcaagcatt caaagcaga  27300
agatgaatgg gtatctgagc cgctcccttg gattcctact aacccagaac ttttagattg  27360
catcttaatc gagggttggg attcatatat tggcggctct ttcttattca agtacaaccc  27420
tagtgacaat actttgtcta caacctttga tatgtatgat gacagccatg taaaagcgaa  27480
ggttattgtt ggtcagattt accctcaaga gtttgaacct acgcctgtgg ttatcagaga  27540
caatcaagac cgtgtatcct acattgatgt accagttgta ggattggttc accttaatct  27600
tgacatgtac cccgattct ccgtagaagt taagaatgtg aagagtggta aagtacgtag  27660
agtattagcg tcaaaccgta taggtggtgc tctcaataat acagtaggct atgttgaacc  27720
gagagaaggt gtcttcagat ttccactgag agctaagagc acggatgttg tttatcgtat  27780
tattgtagag tcacctcaca cattccagct tcgtgatatt gagtgggaag ggagctacaa  27840
tccaaccaaa aggagggtct aatggctata ggttcagccg ttatggctgg tatgtcttct  27900
attggtagca tgtttgcagg cagtggtgca gcagccgctg ctggaggtgc tgccgcaggt  27960
```

```
ggcggaggtt tgctaggttc actaggtgga ttcctaagtg gctctactgc tggtttctct   28020
aatgctggcc ttcttggtgc tggccttcaa gggttaggct tgattggtga tctatttggt   28080
ggaagtgatg aagccaaggc gatgaagaaa gcacaagaag agcaatggcg gcagcagctt   28140
attgctacac aagaggcgta caagacagtg gcagacgcag aacgttctgc tgctaaacaa   28200
tatcatgcag atgcaatcag taatcaggct tcactgctac agcagcgagc acaggttgca   28260
ttacttgctg gggctactgg tactggtggt aattctgtgt cctctatgct taatgactta   28320
gcagcagatg gcggcaggaa ccagagtact atcattgata actatgagaa tcagaagatt   28380
aatttcacca accagcttaa gtctatccaa cgtggtggtc agatgcagat gcgtgagttt   28440
aagaagcctt ctgctatgaa taccttggtt aaaggtattc caagtctggc atctgcctat   28500
gtaactggta gtaagtctgg caaggcattg ggtaaagcct taactgattc tgcacatat    28560 tcatctggaa caagaggtat ttaatggcaa ttgagcgaca agcagtacaa ggtctgccac   28620
aagtgcaggc cacttctcct aatgtcatga cctttgcacc tcaacaagtg ggaggtgtgg   28680
aggctggcgt ggcttctacc tccggtagta ggtttatcga agaccttatt cgtgcagcaa   28740
gcagcgtggc tgatgttacc actggtatcc ttaatcagaa gattgaggaa gataaggttg   28800
ttcaaatgga acgggcatat aacggattaa tgccttctga ggatgcaact cgtggtggcg   28860
ctcgtgctaa catgcttgtc aaagctcaac tgctagctaa tgatgaagca gcacgaatga   28920
aagacatggc tactcgtttc caaggaacgg atgacgaatg gacacaactt atggttgact   28980
ctcgtaatga gatgcagaat aagctgttcc agcaataccc tgagttgcaa ggtgacaaag   29040
atactatgcg tatggtcact aatgtcttcc aagaacagca gcctcagatt tgggctacac   29100
gaacccagca taaacttgac cgtgaacaag cagaccgtga ggatacctt  gacgggcgag   29160 tggcttctac ttgggattct aatattgacc ctgaagcctc tggctatgct ttacaggaac   29220
gaatccgcga aggtcttact caaggattac tacctgaaca gatgtacaag aagttagtcc   29280
agcgagcaat ttcacttgca caaggcggtg atgttagcat ggctgaagcc ctgaagtatg   29340
tgaaggacga taagggtgtt tctgtttatg ctaagaatcc acagcttatc acagccatca   29400
ctagtggtaa tgcagtttgg gctaggaata atgtagctga tgtaactcgt atgtctttcg   29460
aagttaaaga atcctacctt gcaggtgatt taactgatga agaattgttg gaacgagcac   29520
agcacattaa taatctgaca ggtaactctg tcttctctaa tccagaacta gaggcactga   29580
tgcgccaacg ggctaagcag aatgcagagc taggtgcaat gcaggatatg cgacgtgagc   29640
tttactccga ccgcctgact ggcttccaag gtaagactga taaagagaag aaggcttaca   29700
ttgatgttat caaacaggat agccaacttt atgcagacca gcaaatcaaa caacgtggct   29760 tggacccttat cagtcaagag gctgaagcta ttcgtggtgc agtggaagtg cagcgcctgc   29820
aattcatgaa ctccaaaggc ttagtggatg ataccttga  gtctcgtatc aaagccatgg   29880
aatctatgct atcgcctgag cacttttgcca agggcgaacc acaggagttg atgactattc   29940
gccagttgtg ggaacagtta ccagaagaga gccgaggtgt ctttggtgac acggtgaatg   30000
gctacatgga taactacaac actgcactac aaatgggaga gacacctttg caggctgcaa   30060
ggtttgcgcg taaagcacag cagaaattct ctcgtactga gaaggaaacc aagaagttca   30120
actcagctat tggagatgca ctggatgagg tatctggtgc tggctggttt gatggtaaaa   30180
ccgaagtgtc agacttaggt aaagctattg cggaagaaga gttacgagct aaggccaata   30240
tgttgtggtc tagtggtatg cgtaacatgg attccatcaa gaaggctta  attacttggg   30300
```

```
gcaataaacg ctacactcaa tcagaggatg caaagacttc cggtggctat ttcattaaag   30360
gtgattacac ttctgcatct gatatgctta tgtcagttgg gaaaggcgta aaccctaccg   30420
atgtacctct ggcgcttggt aggtatgtag aaacacagat gccagaattg aagaaggagc   30480
ttcaagaggg ggaaactaaa gatgatatat acattgatta caatgaacag aaaggtactt   30540
tcgtgattcg tgctggtgca gcaggtcgcc ctctttctgg agtaatccct gtaacctctt   30600
tagataccac ttcactacta gattctgcct atcagaagaa agtagaggaa cgagataaag   30660
gcgagtatgt tcacccgtat cgtacagata ttggtgcaca agagcctatg ccagctaaac   30720
caactgccaa agatattggt aaatttggac tagctaactt cctcatgtct tctgcttttg   30780
cttctggtga aatctgcct tctaacttcg agattaacta tcgaggtaat atgcaacaat   30840
tctatgacaa gctagctatg gatgagaata agataaagt tggctttaat aaggcaactg   30900
gaacctttac tccatataaa gacgctcacg gtgagtctat cggttacggt catttcttaa   30960
cggaagaaga gaagcgaaac gggtatatta agattggcga tgaactagtt ccctatcgag   31020
ggtctatgtc tcagcttaca gagagcaagg ctcgcgctct tatggagcaa gatgctaaga   31080
agcatgtgcc tcctactcgt gactggaaga ttccgtttga ccagatgcac cctgcacagc   31140
aacgtggctt gatggattta agctacaatt taggtaaagg tggaatccag aactcaccgc   31200
gtgctcttgc tgcattcaaa gctggtaagc ttacggaggg ctttatcgaa atgctgggca   31260
ctgcatcaag tgaaggtaag cgtattcctg gcctactgaa gcgacgcgct gaggcataca   31320
atatggcatc tgctggtggt gtgcctaaga ttaccgaagt ggagactcgt gaagatggct   31380
ccatgtgggt taggtttggt ggacctatgc cagcaggttc tgtctcggca tggactcata   31440
aacgtattgg cgcggatggt tggtatcagg tttatgaggc tgcacctacc aagttagcta   31500
aagattctaa ggtaggtaaa gttaagttgt agtacctaac tcaaggcttg tctcacatgt   31560
gagacaggtc tttatgatag gcactatgga ggaattatgg aacaagacat taagactaat   31620
tgggctggat atgtccagtc tactcctgag ccgttttcta ttgaggcggc tccggtatcg   31680
gctcctacga tacgccagcg taatgagtta caagagcaag ttcttgaagc taaagctgac   31740
gctgatatct taggtgctgt aggtgctgcc ttccagaatg agtggttggc attcggaggc   31800
aagcggtggt atgaccgtgc cactgctgat ttcacacctc aaccagactt tgagatacaa   31860
cctgagcaac gtgaagcact acgtttcaaa tatggtacgg atatgatgca gacaatcact   31920
gagggtgttc gttctgagga tgaattgaac ttccgtattc agaatgcgga tgaagacctt   31980
gagcgcaata agcgcattgc tcaggctggc tgggttggct ctgtggcgac gattggcgct   32040
gctgtgcttg accctgtggg atgggttgcc tctattccaa ccggtggtgc cgctaaagtt   32100
ggactcgtag gccgtgctgt gcgtggcgct atcgccgctg gcgtgagtaa tgccgctatt   32160
gaatccgtat tggtccaagg tgacatgact cgtgatttag atgacattat ggtagcactg   32220
ggttccggta tggctatggg tggcgttatt ggcgctgtag cgcgtggtag ggccactaag   32280
ctcagtgagc aaggtgatga cagggctgct agcattgtgc gcagtgcaga cgcaggggac   32340
cgctatgttc gtgctgttgc cgatgacagt atcggtgcga tgcgtgttaa gggcgcagag   32400
gttctcactg agggtgtatt cgatatctcc agtaagagtg aagacctact gaaaaccttg   32460
caacgagaag gtaatgcgat tgatatgaca cctcgccgtt gggctggaac tatgtctgcc   32520
ctcggtactg tcgtgcactc atctaaagat gcaagtatcc gaggccttgg tgctcgtctg   32580
tttgaatccc cacaaggtct aggtatgcag aaggcatctg ctagtcttat gcagaatact   32640
aacttaaatc gcctgaaatc tgctgatatg aaccgcttca atgatgggtt tgatttgtgg   32700
```

```
cttaaagaga ataatatcaa tccagtagca gggcatacca actctcatta tgtacagcaa   32760
tacaatgaaa aggtgtggga ggcagtgcgt attggcatgg atgagtctac acctaaatct   32820
atccgcatgg ctgctgaggg acaacaggct atgtacagag aggcgctggc tttacgtcaa   32880
cgttctggtg aagcgggatt tgaaaaggta aaagccgaca acaaatatat gcctgatatc   32940
tttgatagta tgaaagccag acgtcaattc gatatgcacg ataaagaaga catcatcgaa   33000
cttttctctc gtgcctacca gaatggcgct cgtaagattc aaaggaagc agcagatgag    33060 attgcacgag cacaggtaaa tcgcgttgct gatgctacct taactggaaa gcttagtttt   33120
gaaaaggcaa tgtcaggtca gactaaggca gagtatgaag ctatcatgcg taaggcaggc   33180
ttcagtgatg aagaaattga aaagatgata gaagctctgg ataacaaaga aaccagagat   33240
aacatctcta accgagctaa aatgagttta ggattagatg ttactcaaga atacaatggc   33300
attcgtatgc gtgacttcat gaataccaac gtggaagagc taacagataa ctatatgaag   33360
gaagcagcag gtgcgctgc attggctcgc caaggcttct ctacctatca ggctgcactt    33420
aatgcaattg accttgtaga gcgaaatgca cgaaacgcgg ctaaggatag caaggctagt   33480
ttggcattag atgaagagat tcgtcagatg cgagaaggtc ttcgcctgat tatgggcaag   33540
tcgattgatg cagacccaca ggctatatct actaagatga tgcgtcgtgg tcgtgatatc   33600
acaggtgtgc ttcgcttagg tcaaatgggc ttcgcacagc taggtgaact tgccaacttt   33660
atgggtgaat ttggtattgc tgcaactact atggctttag gtaagcaatt ccgcttcacc   33720
tctaaggcgt tgcgtaatgg cgatggcttc ttccgagata gaacttagc tgaggttgag    33780 agaatggtgg ggtacattgg tgaggataac tggctaacaa ctaagggtgc acgtcctgat   33840
gaatttggtg atgtaaccac agtaagaggg atgatggctc actttgacca atccatgaac   33900
tcaatacgtc gtgctcaaac caacctatca ctcttccgca tggcacaggg ttctctggag   33960
cgaatgacta ataggcaaat agcttttgtct ttcattgacc accttgaagg caagaagatt   34020
attcctcaga agaaactgga ggaacttggt cttactcagg agttcatgac taacctacag   34080
aagcactatg atgctaactc taaaggttct ggcttgcttg gctttgatac aatgccttat   34140
gccatgggtg aaactttagc taatgctatt cgtcgtaagt caggtctaat catccaacgt   34200
aacttcattg gtgatgaagg tatctggatg aacaaagcac taggtaagac atttgcacag   34260
cttaagtcat tctctcttgt atctggtgag aagcaatttg gtcgagggat tcgccacgat   34320
aaaattggtc ttgctaagaa gacagcttac gggtttgctt tgggttcaat agtgtatgcg   34380
gcaaaagcct atgtgaactc tattgggcga gaagaccaag atgaatattt ggaagagaag   34440
ttatcgccta aagggttggc ctttggtgca atgggtatga tgagtacaac tgctgtattt   34500
agtctaggtg gagatttctt aggtggccta ggtgttctac cttccgaact cattcaatca   34560
cgctatgaag caggtttcca agtaagggt ctgattgacc aaatacctct ggttggcgtt    34620
ggtgcagatg cagtaaatct ggctaactca atcaagaagt atgcagaagg tgacacagaa   34680
ggtgtagata tcgctaagcg agcactccgt cttgtgccac ttaccaatat aataggtgtc   34740
caaaacgcat tgcgttatgg cttagatgaa ctggaggatt gatgagttat actttcacag   34800
aacatacagc caatggtacg caagtcacct atccttttag ctttgctggt agggataaag   34860
gttatcttcg tgcctcagat gtgatagtgg agtctcttca aggtaacact tggattgaag   34920
ttacatctgg ctggcaacta actggcacgc accagattac ttttgatgta gcaccagttg   34980
caggtttgaa gttccgtatt cgaagggaag tacaaaaaga atatccatac gctgagtttg   35040
```

```
accgtggtgt taccttggat atgaagtctt taaatggttc tttcattcat atactggaga    35100
ttacacagga gttacttgac gggttttatc cagaaggata cttcattaaa cagaatgtaa    35160 gctgggcgg caataagatt actgatttgg ctgatggcac aaatccggga gatgcagtaa     35220
ataaagggca gcttgatgcc atcgacaaga agcatacaga ttggaacgcc aaacaggaca    35280
ttgagattgc tggccttaag gctggtatga cttctggtat tgcgcacaga actgttcctt    35340
ggtacacgat agcccaaggt ggtgagattt ccgtaaaacc accttatgaa tttcaagatg    35400
cactagtttt ccttaatggg gtattgcagc accaaattgt aggcgcatac tctataagca    35460
acaacactat cactttcgca gagccgcttg tggctggtac agaggtgtat gtgctgattg    35520
gtagtcgtgt ggctacatct gaacctaata ttcagttgga gttgaacttt gacttagtag    35580
aaggccaaca agtagtacag attggctctg catttaagta cattgaggtc taccttgatg    35640
gattattaca acctaaactt gcttatcagg tagacggtga cattgttact ttctcagaaa    35700
gagtaccaga atgccggatg actgctaaga ttatcacagc ataaggaggt gggatgatta    35760
actccgaact ggtagatagt ggtgtgaagc ttgcgccacc tgcactcata tcaggtgggt    35820
acttcctcgg tatcagttgg gataattggg tgttaatagc aacattcatt tataccgtgt    35880
tgcaaattgg ggactggttt tataataagt tcaagatttg gagggagaag cgtgagcgta    35940
cacaataaac atgcagctac agaggacgag gttggcattc tgcatggtgc tattaccaaa    36000
atcttcaata agaaagcaca ggcaatactg gacactatag aagaagaccc tgatgcagca    36060
ttacatttag tgtctggtaa ggatattggt gcgatgtgta agtgggttct tgataacggc    36120
attaccgcca cacctgctgc acagcaggaa gagtccaagt tatctaagcg cctcaaggct    36180
atccgagagg catccagtgg taagataatt caattcacta aggaggattg atggctaagg    36240
caagagaatc acaagcggag gctcttgcca gatgggagat gctacaggag ttacagcaga    36300 ccttcctta caccgcggaa ggtttgcttc tctttgcaga tacagttatt cataacttaa    36360
ttgcaggcaa ccctcatctg attcgtatgc aggcggatat cttgaagttc ctattttacg    36420
gacacaagta ccgcctcatc gaagcgcctc gtggtatcgc taagacaaca ctatcagcaa    36480
tctatacggt attccgtatt attcatgaac cgcataagcg tatcatggtt gtgtcccaaa    36540
acgccaagcg agcagaggaa atcgcaggtt gggtagttaa atcttccgt ggcttagact     36600 ttcttgagtt tatgctgccg gatatctacg ctggggaccg tgcatccgtt aaggcgtttg    36660
agattcatta caccctacgt ggtagtgata agtctccttc tgtatcctgt tactcaatcg    36720
aagcaggtat gcagggtgct cgtgctgata ttattctagc ggatgacgta gagtcgatgc    36780
agaatgctcg tacggcagcg ggccgtgcct tgcttgagga gctgactaag gagtttgaat    36840
ctatcaacca gtttggggat atcatttacc ttggtacacc tcagaacgta aactctatct    36900
acaacaacct acctgctcgt ggttactctg ttcgtatctg gactgcgcgt taccctttcag   36960 tagagcaaga gcaatgttat ggcgacttcc ttgcacctat gattgttcaa gatatgaagg    37020
acaacccagc acttcgctca gggtacgggt tggatggtaa tagtggtgca ccttgtgccc    37080
ctgaaatgta tgatgatgaa gtcctgattg agaaggaaat ctctcagggt gctgctaagt    37140
tccagcttca gttcatgctt aacactcgca tgatggatgc tgacagatac ccattacgcc    37200
tgaacaatct aatcttcacc tcgtttggta cagaggaagt ccctgtgatg cctacgtgga    37260
gtaatgattc cataaacatc attggtgatg cacctaagta tggtaacaag cctacggatt    37320
tcatgtacag acctgtagct cgcccatatg aatgggtgtc tgtctcccgc aagattatgt    37380
atattgaccc tgcgggtggt ggtaagaacg gagatgagac gggtgtagcc atcgtattcc    37440
```

```
tgcacggcac attcatttat gtgtatcagt gctttggtgt acctggcgga taccgagagt    37500
cgtccctgaa tcgcattgtg caggccgcaa agcaggcggg tgttaaagag gtattcattg    37560
agaagaactt tggtcatggc gcgtttgagg cggtaattaa gccgtactt gaacgagagt     37620 ggcctgtaac tctggaagag gattacgcca ccggacagaa agagttgcgt atcattgaga    37680
cgctggagcc gctcatggca gcccataggc ttatcttcaa tgcagagatg gtgaagtcag    37740
actttgagtc ggtacagcac tatccgcttg aactacgcat gtcctacagt cttttcaatc    37800
aaatgtcgaa cataacgatt gagaagaaca gcctccggca cgatgaccgc ctagacgccc    37860
tgtatggcgc tatacggcaa ttaacttctc agatagacta tgacgaggtt acacggatta    37920
atcgcctcag agcgcaggag atgcgcgatt acatccatgc tatgaacaca cctcatctac    37980
gcagggcaat gctatatgga gattacggta ctgagcgaag agtgaccaac acttccgtag    38040
cgatgcagca gcgagtttac gggcagaact accgaaataa atcggcaagc agaaatacac    38100
tttctgcaag gatttcaagg acttattaat tactggacac tatagaagga aggcccagat    38160
aataagagaa aataataggt aatatatata taggttaacc taggttatat aggtatgcct    38220
tagtatgggt gtactcctgt acaccctatt ccttactacc ttactatatt tacataatag    38280
gagagagaca atggctaatg attatagtag tcaaccatta acaggtaagt ctaagagaaa    38340
gcaggtacaa cctgtaagtg aagaactaat gcttccggtg ctcaaaaaag aggaagttag    38400
taagaaaagc aatgttatta atgatgccac caaatcaggt aaacagaaag gggccatggt    38460
gtgccttgaa gtgaaaggtg gtgtattgaa gattgctatc gcggttgatg gcaaagaaga    38520
ttcagagtgg aagttagtaa cagtggaacc aactgttaac ccagtttaag ataaggagga    38580
agattacatg gctaaatatg gtactacagg ttctgttact ggtcaggctt ttcgagtaaa    38640
agcagtacaa actattgcaa cggcaatccc gatgcctgtt gttaaagaag aagaccttaa    38700
gagtaaagac caccctatca acatcaaaca tttatcaggt aaacagaaag gtgcaatggt    38760
tgctcttgag aaaggtgaca caaccttaca tattgctgtt gcacgtggta gtgaacccac    38820
agacccttgg gatgtaactg gtatggaaaa ggacgctgtt actccagcag gggtataata    38880
atgcttaata aatacttcaa gcgtaaagag tttgcttgcc gttgtgggtg cggtacatcc    38940
actgttgatg ctgaattact acaggtagtc acagatgtgc gtgagcactt tggttctcct    39000
gtagttatca cttcgggtca tcgctgtgct aagcacaatg ccaatgtagg tggcgctaag    39060
aactccatgc atcttactgg taaggctgct gacattaaag tgtctggcat attaccttct    39120
gaagtgcata agtatcttac tagcaaatac caaggcaagt atggtatagg taagtataac    39180
tccttcactc acatcgatgt acgggatggt tgtgcgcgat ggtaagatgt gttgaatggt    39240
gtgagcgtat ggttgcccaa gctgccgagg atggcaacta tgatgactgg aagaactact    39300
ctgacttgtt agctcaatgg aaagggagat gcaatgaaaa agctgtttaa gtctaagaag    39360
gttgtaggtg cactggttgc acttgttatt gctcttgttt ctgtaggtct tggtgtagac    39420
cttggctctg gcacggaatc ctctgtgaca gatgtggtct gccaagtgat cacctgtgaa    39480
taagtttcta gaagttctgg caggtcttat tggcctgctt gtctctgcta agaagaaaca    39540
agaagagaag gaggcacaaa gtgaagcgaa tcatgttagt gacaaccctt ctgattggtt    39600
cgctgaccac ttccgggtgt cagcaggcgt taccagagaa agcaatggtg aaacctctga    39660
ggccgacgct gacggcagtt tacgaggtag acgataaggt ctgctttagt aagcctgacg    39720
ctacaaaact tggtttgtac attctctcgc tagaacgcgg atacaattaa tacatagctt    39780
```

```
tatgtatcag tgtcttacga tttactggac actatagaag aggtaagata gcgccgttct    39840
tttgagcggc ctattactag ccaatcttca tagggagggt tggaaagtaa taggagatag    39900
catggctaaa ttaaccaaac ctaatactga aggaatcttg cataaaggac aatctttgta    39960
tgagtacctt gatgcgagag ttttaacatc aaagccgttt ggtgctgcag gtgacgccac    40020
tactgatgat acggaggtta tagctgcttc attaaactct cagaaagctg tcacagtctc    40080
agatggtgta ttctctagct ctggtattaa cagtaattac tgtaacttag acggcagggg    40140
tagtggcgtg ctaagtcacc gttcaagtac aggtaactac ttagtattta acaatctacg    40200
tgcaggtcgc ttaagtaata ttacggtaga aagtaataag gcgactgata caactcaggg    40260
acagcaggta tcccttgctg gtggaagtga tgttactgta agtgacgtta acttctcaaa    40320
cgttaaaggt actggtttca gtttaatcgc ataccctaat gatgcgccac ctgatggact    40380
tatgattaaa ggcattcgag gtagctattc cggctatgct actaataagg cagccggatg    40440
cgtacttgct gattcctcag ttaactccct catagataac gtcattgcta agaactaccc    40500
tcagttcgga gcagtagagt tgaaaggtac agccagttac aacatagtca gtaatgttat    40560
agggacagat tgccagcatg taacttacaa cggcactgaa gggccaatag ctccttctaa    40620
taaccttatc aaggggtgta tggctaataa ccctaagtat gcagcggttg ttgcaggcaa    40680
aggaagtacg aacttaatct cagacgtgct cgtagattac tcaacttctg atgctaggca    40740
ggctcatggt gttacagtag agggttctga taacgtcata aataatgtgc ttatgtcagg    40800
atgtgatggt actaactctt taggacaagg gcagactgct acaattgcac gctttatagg    40860
tacagctaat aacaactatg cgtctgtatt tcctagctac agtgctacag gtgttattac    40920
tttcgaatcc ggctctaccc gtaacttcgt agaggtaaag caccctggca ggagaaacga    40980
ccttctcagt tctgctagta ctattgacgg tgcagctact attgacggca ctagtaatag    41040
taacgtagtg cacgcacctg ccttagggca gtacataggt agtatgtcag gtaggttcga    41100
atggcggatt aagtccatgt cactccttc aggcgttctt acttctgctg ataagtacag    41160
aatgcttgga gatggtgctg tgtcattagc tgtaggtggg ggcacttctt ctcaagttcg    41220
cctatttact tctgatggta cttctcggac agtgtccctc accaacggta acgtgcgtct    41280
ttctaccagt agcacaggct ttttgcagtt aggtgctgat gcaatgaccc cagacagtac    41340
tggtacatac gcattaggtt ccgccagccg agcatggtct ggcggtttta ctcaagcagc    41400
attcactgtt acctcagatg ctcggtgtaa aacagaacct cttactatct cagatgcctt    41460 actgatgct tggtctgaag ttgactttgt gcagtttcag tatttggatc gtgttgagga    41520
gaagggtgca gactcagcta gatggcactt cggtatcatc gctcagcgag ctaaggaggc    41580
tttcgaacgt cacggtatag atgcacatcg ctatggcttc ttgtgcttcg acagttggga    41640
tgatgtatac gaggaagatg ccaatggctc tcgtaaactg attacaccag caggttcccg    41700
ctacggtatt cgttacgagg aagtactgat attagaggct gcgttgatgc ggcggactat    41760
taagcgtatg caggaagcac tagcttccct gcctaagtaa gcaacaggca gtgcgtaagc    41820
actgctttta gcgcaacttt tcttaaaggt tatcacggtg gtagccttc agaaaaggag    41880 gttacatgat tcaaagacta ggttcttcat tagttaaatt caagagtaaa atagcaggtg    41940
caatctggcg taacttggat gacaagctca ccgaggttgt atcgcttaaa gattttggag    42000
ccaaaggtga tggtaagaca aacgaccaag atgcagtaaa tgcagcgatg gcttcaggta    42060
agagaattga cggtgctggt gctacttaca agtatcatc tttacctgat atggagcgat    42120
tctataacac ccgcttcgta tgggaacgtt tagcaggtca acctctttac tatgtgagta    42180
```

```
aaggttttat caatggtgaa ctatataaaa tcacggataa cccttattac aatgcttggc    42240
ctcaagacaa agcgtttgta tatgagaacg tgatatatgc accttacatg ggtagtgacc    42300
gtcatggtgt tagtcgtctg catgtatcat gggttaagtc tggtgacgat ggtcaaacat    42360
ggtctactcc agagtggtta actgatctgc atccagatta ccctacagtg aactatcatt    42420
gtatgagtat gggtgtatgt cgcaaccgtc tgtttgccat gattgaaaca cgtactttag    42480
ccaagaacaa actaaccaat tgtgcattgt gggatcgccc tatgtctcgt agtctgcatc    42540
ttactggtgg tatcactaag gctgcaaatc agcaatatgc aacaatacat gtaccagatc    42600
acggactatt cgtgggcgat tttgttaact tctctaattc tgcggtaaca ggtgtatcag    42660
gtgatatgac tgttgcaacg gtaatagata aggacaactt cacggttctt acacctaacc    42720
agcagacttc agatttgaat aacgctggaa agagttggca catgggtact tctttccata    42780
agtctccatg gcgtaagaca gatcttggtc taatccctag tgtcacagag gtgcatagct    42840
ttgctactat tgataacaat ggcttttgtta tgggctatca tcaaggtgat gtagctccac    42900
gagaagttgg tcttttctac ttccctgatg ctttcaatag cccatctaat tatgttcgtc    42960
gtcagatacc atctgagtat gaaccagatg cgtcagagcc atgcatcaag tactatgacg    43020
gtgtattata ccttatcact cgtggcactc ttggtgacag acttggaagc tctttgcatc    43080
gtagtagaga tataggtcag acttgggagt cactgagatt tccacataat gttcatcata    43140
ctaccctacc ttttgctaaa gtaggagatg accttattat gtttggttca gaacgtgcag    43200
aaaatgaatg ggaagcaggt gcaccagatg atcgttacaa ggcatcttat cctcgtacct    43260
tctatgcacg attgaatgta aacaattgga atgcagatga tattgaatgg gttaacatca    43320
cagaccaaat ctatcaaggt gacattgtga actctagtgt aggtgtaggt tcggtagtag    43380
ttaaagacag ctacatttac tatatctttg gtggcgaaaa ccatttcaac ccaatgactt    43440
atggtgacaa caaaggtaaa gacccattta aaggtcatgg acaccctact gatatatact    43500
gctataagat gcagattgca aatgacaatc gtgtatctcg taagtttaca tatggtgcaa    43560
ctccgggtca agctatacct actttcatgg gtactgatgg aatacgaaat atccctgcac    43620 cttttgtattt ctcagataac attgttacag aggatactaa agttggacac ttaacactta    43680
aagcaagcac aagttccaat atacgatctg aagtgcagat ggaaggtgaa tatggctttta    43740 ttggcaagtc tgttccaaag gacaacccaa ctggtcaacg tttgattatt tgtggtggag    43800
aagagacttc gtcctcttca ggtgcacaga taactttgca cggctctaat tcaagtaagg    43860
ctaatcgtat cacttataac ggaaatgagc acctattcca aggtgcacca atcatgcctg    43920
ctgtagataa ccagtttgct gctggtggac ctagtaaccg attcactacc atctacctag    43980
gtagtgaccc tgttacaact tcagatgctg accacaagta cagtatctct agtattaata    44040
ccaaggtgtt aaaggcttgg agcagggttg gttttaaaca gtatggtttg aatagtgaag    44100
cagagaggga ccttgatagc atacacttcg gtgtcttggc tcaggatatt gtagctgctt    44160
ttgaagctga agggttggat gccattaagt atggaattgt gtccttcgaa gaaggtaggt    44220
acggtgtgag gtatagtgaa gttctaatac tagaggctgc ttatactcgt tatcgtttag    44280
acaagttaga ggagatgtat gccactaata aaatcagtta agcaagctgc tgtactccag    44340
aacacagaag agcttattca atcaggacgt gaccctaagc aggcttatgc cattgccaag    44400
gatgttcaac gtcgtgccat gaagaaacct tctgcatctt ctgcgtaagc aggttaatat    44460
cttagtataa acaagggcag acttaggttt gtccttagtg tattccaaag gaggtaacat    44520
```

```
gctgaaagat ggttgggttt catatgaccc tacagaccct aagaattggc tacaggttat    44580
cgctatagct tgtgcaggta gcctattggc tgccctgatg tattcattat ggatgtacac    44640
aaagtaacca aagtcaaaat tttgatgtag gcgtgtgtca gctctctcgc cctcgccctc    44700
gccgggttgt ccccataggg tggcctgagg gaatccgtct tcgacgggca gggctgatgt    44760
actccttgtc tagtacaagg gaggcggagg gaacgcctag ggaggcctag gaatggctta    44820
gtggtggaca aggtgattac cttagtgaag cctcttagtg cattcctgag gccattcagg    44880
gcgtttatga gggattgaca gggtgtgagg gcgtgggcta                          44920

<210> SEQ ID NO 6
<211> LENGTH: 20
<212> TYPE: DNA
<213> ORGANISM: Escherichia virus K1-5

<400> SEQUENCE: 6
actaaatgag gattaaatca                                                  20

<210> SEQ ID NO 7
<211> LENGTH: 20
<212> TYPE: DNA
<213> ORGANISM: Escherichia virus K1-5

<400> SEQUENCE: 7
ttactctgat gcactacatg                                                  20

<210> SEQ ID NO 8
<211> LENGTH: 20
<212> TYPE: DNA
<213> ORGANISM: Escherichia virus K1-5

<400> SEQUENCE: 8
tatattatac cagagaggcg                                                  20

<210> SEQ ID NO 9
<211> LENGTH: 20
<212> TYPE: DNA
<213> ORGANISM: Escherichia virus K1-5

<400> SEQUENCE: 9
gaagttctaa ggagataaca                                                  20

<210> SEQ ID NO 10
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aacctaacta actaaatgag gattaaaaga ggagatatac aatggttttt acgcttgagg    60
acttcgtt                                                              68

<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
```
tgtataacct gaagttctaa agaggagata tacaatggtt tttacgcttg aggac    55

```
<210> SEQ ID NO 12
<211> LENGTH: 23
<212> TYPE: DNA
<213> ORGANISM: Escherichia virus K1-5

<400> SEQUENCE: 12
```
actaaatgag gattaaatca tgg    23

```
<210> SEQ ID NO 13
<211> LENGTH: 23
<212> TYPE: DNA
<213> ORGANISM: Escherichia virus K1-5

<400> SEQUENCE: 13
```
ttactctgat gcactacatg agg    23

```
<210> SEQ ID NO 14
<211> LENGTH: 23
<212> TYPE: DNA
<213> ORGANISM: Escherichia virus K1-5

<400> SEQUENCE: 14
```
tatattatac cagagaggcg agg    23

```
<210> SEQ ID NO 15
<211> LENGTH: 23
<212> TYPE: DNA
<213> ORGANISM: Escherichia virus K1-5

<400> SEQUENCE: 15
```
gaagttctaa ggagataaca tgg    23

```
<210> SEQ ID NO 16
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 16
```
acuaaaugag gauuaaauca guuuuagagc uagaaauagc aaguuaaaau aaggcuaguc    60
cguuaucaac uugaaaaagu ggcaccgagu cggugcuuuu uuu    103

```
<210> SEQ ID NO 17
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 17
```
uuacucugau gcacuacaug guuuuagagc uagaaauagc aaguuaaaau aaggcuaguc    60
cguuaucaac uugaaaaagu ggcaccgagu cggugcuuuu uuu    103

```
<210> SEQ ID NO 18
<211> LENGTH: 103
<212> TYPE: RNA
<213> ORGANISM: Artificial Sequence
<220> FEATURE:
```

```
<223> OTHER INFORMATION: Description of Artificial Sequence: Synthetic
      polynucleotide

<400> SEQUENCE: 18
uauauuauac cagagaggcg guuuuagagc uagaaauagc aaguuaaaau aaggcuaguc      60
cguuaucaac uugaaaaagu ggcaccgagu cggugcuuuu uuu                      103

<210> SEQ ID NO 19
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 19
gaaguucuaa ggagauaaca guuuuagagc uagaaauagc aaguuaaaau aaggcuaguc      60
cguuaucaac uugaaaaagu ggcaccgagu cggugcuuuu uuu                      103

<210> SEQ ID NO 20
<211> LENGTH: 33
<212> TYPE: DNA
<213> ORGANISM: Escherichia virus K1-5
<220> FEATURE:
<221> NAME/KEY: CDS
<222> LOCATION: (1)..(33)

<400> SEQUENCE: 20 gat gat tac tct gat gca cta cat gag gtt gta                           33
Asp Asp Tyr Ser Asp Ala Leu His Glu Val Val
1               5                   10

<210> SEQ ID NO 21
<211> LENGTH: 11
<212> TYPE: PRT
<213> ORGANISM: Escherichia virus K1-5

<400> SEQUENCE: 21

Asp Asp Tyr Ser Asp Ala Leu His Glu Val Val
1               5                   10

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(33)

<400> SEQUENCE: 22 gac gac tat agc gac gcc ctt cat gag gtt gta                           33
Asp Asp Tyr Ser Asp Ala Leu His Glu Val Val
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 23

Asp Asp Tyr Ser Asp Ala Leu His Glu Val Val
1               5                   10
```